(12) United States Patent
Ceccarelli et al.

(10) Patent No.: US 9,284,321 B2
(45) Date of Patent: Mar. 15, 2016

(54) PIPERAZINO[1,2-A]INDOL-1-ONES AND [1,4]DIAZEPINO[1,2-A]INDOL-1-ONE

(71) Applicant: Hoffmann-La Roche Inc., Little Falls, NJ (US)

(72) Inventors: Simona M. Ceccarelli, Basel (CH); Ravi Jagasia, Loerrach (DE); Roland Jakob-Roetne, Inzlingen (DE); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/614,232

(22) Filed: Feb. 4, 2015

(65) Prior Publication Data
US 2015/0246922 A1 Sep. 3, 2015

Related U.S. Application Data

(63) Continuation of application No. PCT/EP2013/066344, filed on Aug. 5, 2013.

(30) Foreign Application Priority Data

Aug. 6, 2012 (EP) .................................. 12179381

(51) Int. Cl.
C07D 487/14 (2006.01)
C07D 487/04 (2006.01)

(52) U.S. Cl.
CPC .................................. C07D 487/04 (2013.01)

(58) Field of Classification Search
CPC .................................................... C07D 487/04
See application file for complete search history.

(56) References Cited

FOREIGN PATENT DOCUMENTS

| EP | WO 2007/065820 | * | 6/2007 |
|---|---|---|---|
| WO | 02/072584 A2 | | 9/2002 |
| WO | 2007/065820 A1 | | 6/2007 |

OTHER PUBLICATIONS

Written Opinion of the International Searching Authority for PCT/EP2013/066344.

* cited by examiner

*Primary Examiner* — Valerie Rodriguez-Garcia
(74) *Attorney, Agent, or Firm* — Brian L. Buckwalter

(57) ABSTRACT

The present invention relates to compounds of general formula I

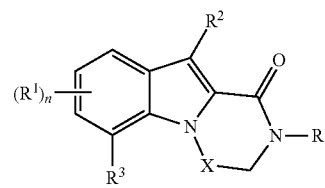

or pharmaceutically acceptable salts thereof, wherein $R^1$, $R^2$, $R^3$, X, R and n are as defined herein.

The compounds may be used for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine.

14 Claims, No Drawings

PIPERAZINO[1,2-A]INDOL-1-ONES AND [1,4]DIAZEPINO[1,2-A]INDOL-1-ONE

CROSS REFERENCE TO RELATED APPLICATIONS

This application is a continuation of PCT/EP2013/066344 filed on Aug. 5, 2013, which is entitled to the priority of EP Application No. 12179381.4 filed on Aug. 6, 2012, the disclosures of which are incorporated herein by reference.

BACKGROUND OF THE INVENTION

Neurogenesis occurs in the developing and adult brain. Conceptually, this process of neurogenesis can be divided into four steps: (i) proliferation of NSCs; (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the subgranular zone (SGZ) in the dentate gyrus of the hippocampus, where new dentate granule cells are generated, 2) the subventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they innervate many interneurons within the dentate gyrus, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072). Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuro-regenerative therapeutic target for normal aging and in particular for a variety of neurodegenerative and neuropsychiatric diseases, including schizophrenia, obsessive-compulsive personality disorder, major depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096).

Hence, chemical stimulation of adult neurogenesis offers new regenerative avenues and opportunities to develop novel drugs for treating neurological diseases and neuropsychiatric disorders.

SUMMARY OF THE INVENTION

The present invention relates to compounds of general formula I

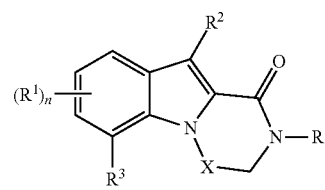

wherein
$R^1$ is hydrogen, halogen, lower alkyl, lower alkoxy, lower alkoxy substituted by halogen or cyano;
$R^2$ is hydrogen, lower alkyl or lower alkyl substituted by halogen;
$R^3$ is phenyl, benzo[1,3]dioxolyl, 2,3-dihydro-benzofuran-5-yl or a 5- and 6-membered heteroaryl, wherein phenyl and the 5- and 6-membered heteroaryl groups may be substituted by one or more substituents, selected from cyano, nitro, amino and lower di-alkylamino, lower alkyl sulfonyl, lower alkoxy, lower alkoxy substituted by halogen, halogen, lower alkyl, lower alkyl substituted by halogen or lower alkyl substituted by hydroxyl;
X is —CH(lower alkyl)-, —CH$_2$—, —CH$_2$CH$_2$— or —CH(lower alkyl)CH$_2$—;
R is hydrogen or lower alkyl;
n is 1 or 2;
or to a pharmaceutically acceptable acid addition salt, to a racemic mixture or to its corresponding enantiomer and/or optical isomers thereof.

Therefore, the object of the present invention was to identify compounds that modulate neurogenesis. It has been found that the compounds of formula I are active in this area and they may therefore be used for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine.

The most preferred indications for compounds of formula I are Alzheimer's disease, depression, anxiety disorders and stroke.

DETAILED DESCRIPTION OF THE INVENTION

The present invention relates to compounds of formula I and to their pharmaceutically acceptable salts, to these compounds as pharmaceutically active substances, to the processes for their production, as well as to the use in the treatment or prevention of disorders, relating to neurogenesis, schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, Parkinson's disease, dementia, Alzheimer's disease, mild cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine, and to pharmaceutical compositions containing the compounds of formula I.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, isopropyl, n-butyl, i-butyl, 2-butyl, t-butyl and the like. Preferred alkyl groups with 1-4 carbon atoms.

The term "alkoxy" denotes a group —O—R' wherein R' is lower alkyl as defined above.

The term "lower alkyl sulfonyl" denotes a group —S(O)$_2$R' wherein R' is lower alkyl as defined above.

The term "halogen" denotes chlorine, bromine, fluorine or iodine.

The term "lower alkyl substituted by halogen" denotes an alkyl group as defined above, wherein at least one hydrogen atoms is replaced by halogen, for example CF$_3$, CH$_2$F, CH$_2$CF$_3$, CH$_2$CH$_2$CF$_3$, CH$_2$CF$_2$CF$_3$ and the like.

The term "lower alkyl substituted by hydroxy" denotes an alkyl group as defined above, wherein at least one hydrogen atom is replaced by hydroxy, for example CH$_2$OH, CH$_2$CH$_2$OH, C(CH$_3$)$_2$OH and the like.

The term "5- and 6-membered heteroaryl" denotes aromatic rings with 5 or 6 ring atoms, containing at least one N, S or O atom, for example pyridinyl, 1,3,4-thiadiazolyl, thiazolyl, thiophenyl, furanyl or pyrimidinyl.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like One embodiment of the invention are compounds of formula

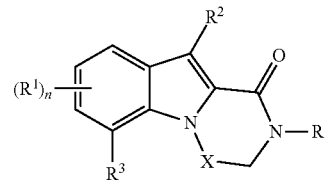

IA $R^1$ is hydrogen, halogen, lower alkyl, lower alkoxy, lower alkoxy substituted by halogen or cyano;
$R^2$ is hydrogen, lower alkyl or lower alkyl substituted by halogen;
$R^3$ is phenyl, which may be substituted by one or more substituents, selected from cyano, nitro, amino and lower dialkylamino, lower alkyl sulfonyl, lower alkoxy, lower alkoxy substituted by halogen, halogen, lower alkyl, lower alkyl substituted by halogen or lower alkyl substituted by hydroxyl;
X is —CH(lower alkyl)-, —CH$_2$—, —CH$_2$CH$_2$— or —CH(lower alkyl)CH$_2$—;
R is hydrogen or lower alkyl;
n is 1 or 2;
or a pharmaceutically acceptable acid addition salt, a racemic mixture or to its corresponding enantiomer and/or optical isomers thereof.

The following examples are encompassed by formula IA:
(R)-4-Methyl-6-phenyl-3,4-dihydro-2H-pyrazino[1,2-a]indol-1-one
(R)-6-(4-Methoxy-phenyl)-4-methyl-3,4-dihydro-2H-pyrazino[1,2-a]indol-1-one
(R)-8-Fluoro-4-methyl-6-phenyl-3,4-dihydro-2H-pyrazino[1,2-a]indol-1-one
(R)-8-Fluoro-6-(4-methoxy-phenyl)-4-methyl-3,4-dihydro-2H-pyrazino[1,2-a]indol-1-one
(R)-8-Fluoro-6-(4-fluoro-phenyl)-4-methyl-3,4-dihydro-2H-pyrazino[1,2-a]indol-1-one
(R)-8-Fluoro-4-methyl-6-p-tolyl-3,4-dihydro-2H-pyrazino[1,2-a]indol-1-one
(R)-6-(3,5-Difluoro-phenyl)-8-fluoro-4-methyl-3,4-dihydro-2H-pyrazino[1,2-a]indol-1-one
(R)-6-(3,4-Difluoro-phenyl)-8-fluoro-4-methyl-3,4-dihydro-2H-pyrazino[1,2-a]indol-1-one
(R)-6-(4-Chloro-phenyl)-8-fluoro-4-methyl-3,4-dihydro-2H-pyrazino[1,2-a]indol-1-one
8-Fluoro-6-phenyl-3,4-dihydro-2H-pyrazino[1,2-a]indol-1-one
(R)-8-Fluoro-4-methyl-6-(4-trifluoromethyl-phenyl)-3,4-dihydro-2H-pyrazino[1,2-a]indol-1-one
(R)-8-Fluoro-6-(3-fluoro-phenyl)-4-methyl-3,4-dihydro-2H-pyrazino[1,2-a]indol-1-one
9-Fluoro-7-phenyl-2,3,4,5-tetrahydro-[1,4]diazepino[1,2-a]indol-1-one
9-Fluoro-7-(4-methoxy-phenyl)-2,3,4,5-tetrahydro-[1,4]diazepino[1,2-a]indol-1-one
9-Fluoro-7-(4-fluoro-phenyl)-2,3,4,5-tetrahydro-[1,4]diazepino[1,2-a]indol-1-one
8-Fluoro-6-(4-fluoro-phenyl)-3,4-dihydro-2H-pyrazino[1,2-a]indol-1-one
8-Fluoro-6-(4-methoxy-phenyl)-3,4-dihydro-2H-pyrazino[1,2-a]indol-1-one
6-(3,4-Difluoro-phenyl)-8-fluoro-3,4-dihydro-2H-pyrazino[1,2-a]indol-1-one
6-(4-Chloro-phenyl)-8-fluoro-3,4-dihydro-2H-pyrazino[1,2-a]indol-1-one 8-Fluoro-6-p-tolyl-3,4-dihydro-2H-pyrazino[1,2-a]indol-1-one
8-Fluoro-6-(4-trifluoromethyl-phenyl)-3,4-dihydro-2H-pyrazino[1,2-a]indol-1-one
(RS)-9-Fluoro-5-methyl-7-phenyl-2,3,4,5-tetrahydro-[1,4]diazepino[1,2-a]indol-1-one
(RS)-9-Fluoro-7-(4-fluoro-phenyl)-5-methyl-2,3,4,5-tetrahydro-[1,4]diazepino[1,2-a]indol-1-one
7-(3,4-Difluoro-phenyl)-9-fluoro-2,3,4,5-tetrahydro-[1,4]diazepino[1,2-a]indol-1-one
7-(4-Chloro-phenyl)-9-fluoro-2,3,4,5-tetrahydro-[1,4]diazepino[1,2-a]indol-1-one
9-Fluoro-7-p-tolyl-2,3,4,5-tetrahydro-[1,4]diazepino[1,2-a]indol-1-one
9-Fluoro-7-(4-trifluoromethyl-phenyl)-2,3,4,5-tetrahydro-[1,4]diazepino[1,2-a]indol-1-one
8,9-Difluoro-6-(4-fluoro-phenyl)-3,4-dihydro-2H-pyrazino[1,2-a]indol-1-one
8,9-Difluoro-6-(4-methoxy-phenyl)-3,4-dihydro-2H-pyrazino[1,2-a]indol-1-one
6-(4-Chloro-phenyl)-8,9-difluoro-3,4-dihydro-2H-pyrazino[1,2-a]indol-1-one
6-(3,4-Difluoro-phenyl)-8,9-difluoro-3,4-dihydro-2H-pyrazino[1,2-a]indol-1-one
9,10-Difluoro-7-(4-fluoro-phenyl)-2,3,4,5-tetrahydro-[1,4]diazepino[1,2-a]indol-1-one
9,10-Difluoro-7-(4-methoxy-phenyl)-2,3,4,5-tetrahydro-[1,4]diazepino[1,2-a]indol-1-one
7,8-Difluoro-6-(4-fluoro-phenyl)-3,4-dihydro-2H-pyrazino[1,2-a]indol-1-one
7,8-Difluoro-6-(4-methoxy-phenyl)-3,4-dihydro-2H-pyrazino[1,2-a]indol-1-one
8,9-Difluoro-7-(4-fluoro-phenyl)-2,3,4,5-tetrahydro-[1,4]diazepino[1,2-a]indol-1-one
8,9-Difluoro-7-(4-methoxy-phenyl)-2,3,4,5-tetrahydro-[1,4]diazepino[1,2-a]indol-1-one
7-(3,4-Difluoro-phenyl)-8,9-difluoro-2,3,4,5-tetrahydro-[1,4]diazepino[1,2-a]indol-1-one
7-(4-Chloro-phenyl)-8,9-difluoro-2,3,4,5-tetrahydro-[1,4]diazepino[1,2-a]indol-1-one
6-(3,4-Difluoro-phenyl)-7,8-difluoro-3,4-dihydro-2H-pyrazino[1,2-a]indol-1-one
6-(4-Chloro-phenyl)-7,8-difluoro-3,4-dihydro-2H-pyrazino[1,2-a]indol-1-one
9-Chloro-7-(3,4-difluoro-phenyl)-2,3,4,5-tetrahydro-[1,4]diazepino[1,2-a]indol-1-one
9-Chloro-7-p-tolyl-2,3,4,5-tetrahydro-[1,4]diazepino[1,2-a]indol-1-one
9-Chloro-7-(4-fluoro-phenyl)-2,3,4,5-tetrahydro-[1,4]diazepino[1,2-a]indol-1-one
8-Chloro-6-(4-chloro-phenyl)-3,4-dihydro-2H-pyrazino[1,2-a]indol-1-one
8-Chloro-6-(3,4-difluoro-phenyl)-3,4-dihydro-2H-pyrazino[1,2-a]indol-1-one
8-Chloro-6-(4-fluoro-phenyl)-3,4-dihydro-2H-pyrazino[1,2-a]indol-1-one
8-Chloro-6-(4-methoxy-phenyl)-3,4-dihydro-2H-pyrazino[1,2-a]indol-1-one
9-Chloro-7-(4-chloro-phenyl)-2,3,4,5-tetrahydro-[1,4]diazepino[1,2-a]indol-1-one
9-Chloro-7-(4-methoxy-phenyl)-2,3,4,5-tetrahydro-[1,4]diazepino[1,2-a]indol-1-one
7-(3,4-Difluoro-phenyl)-9-methyl-2,3,4,5-tetrahydro-[1,4]diazepino[1,2-a]indol-1-one
7-(4-Methoxy-phenyl)-9-methyl-2,3,4,5-tetrahydro-[1,4]diazepino[1,2-a]indol-1-one
7-(4-Fluoro-phenyl)-9-methyl-2,3,4,5-tetrahydro-[1,4]diazepino[1,2-a]indol-1-one
7-(4-Chloro-phenyl)-9-methyl-2,3,4,5-tetrahydro-[1,4]diazepino[1,2-a]indol-1-one
6-(4-Chloro-phenyl)-8-methyl-3,4-dihydro-2H-pyrazino[1,2-a]indol-1-one
6-(3,4-Difluoro-phenyl)-8-methyl-3,4-dihydro-2H-pyrazino[1,2-a]indol-1-one
6-(4-Methoxy-phenyl)-8-methyl-3,4-dihydro-2H-pyrazino[1,2-a]indol-1-one
6-(4-Fluoro-phenyl)-8-methyl-3,4-dihydro-2H-pyrazino[1,2-a]indol-1-one
8-Fluoro-6-(4-fluoro-phenyl)-2-methyl-3,4-dihydro-2H-pyrazino[1,2-a]indol-1-one
8-Chloro-6-(3,4-difluoro-phenyl)-10-methyl-3,4-dihydro-2H-pyrazino[1,2-a]indol-1-one
8-Chloro-6-(4-chloro-phenyl)-10-methyl-3,4-dihydro-2H-pyrazino[1,2-a]indol-1-one
8-Chloro-6-(4-fluoro-phenyl)-10-methyl-3,4-dihydro-2H-pyrazino[1,2-a]indol-1-one
8-Chloro-6-(4-methoxy-phenyl)-10-methyl-3,4-dihydro-2H-pyrazino[1,2-a]indol-1-one
9-Chloro-7-(3,4-difluoro-phenyl)-11-methyl-2,3,4,5-tetrahydro-[1,4]diazepino[1,2-a]indol-1-one
9-Chloro-7-(4-chloro-phenyl)-11-methyl-2,3,4,5-tetrahydro-[1,4]diazepino[1,2-a]indol-1-one
9-Chloro-7-(4-fluoro-phenyl)-11-methyl-2,3,4,5-tetrahydro-[1,4]diazepino[1,2-a]indol-1-one
9-Chloro-7-(4-methoxy-phenyl)-11-methyl-2,3,4,5-tetrahydro-[1,4]diazepino[1,2-a]indol-1-one
6-(3,4-Difluoro-phenyl)-8-fluoro-10-methyl-3,4-dihydro-2H-pyrazino[1,2-a]indol-1-one
6-(4-Chloro-phenyl)-8-fluoro-10-methyl-3,4-dihydro-2H-pyrazino[1,2-a]indol-1-one
8-Fluoro-6-(4-fluoro-phenyl)-10-methyl-3,4-dihydro-2H-pyrazino[1,2-a]indol-1-one
8-Fluoro-6-(4-methoxy-phenyl)-10-methyl-3,4-dihydro-2H-pyrazino[1,2-a]indol-1-one
8-Fluoro-10-methyl-6-phenyl-3,4-dihydro-2H-pyrazino[1,2-a]indol-1-one
6-(4-Chloro-phenyl)-1-oxo-1,2,3,4-tetrahydro-pyrazino[1,2-a]indole-8-carbonitrile
6-(4-Fluoro-phenyl)-1-oxo-1,2,3,4-tetrahydro-pyrazino[1,2-a]indole-8-carbonitrile
6-(4-Methoxy-phenyl)-1-oxo-1,2,3,4-tetrahydro-pyrazino[1,2-a]indole-8-carbonitrile
6-(3,4-Difluoro-phenyl)-1-oxo-1,2,3,4-tetrahydro-pyrazino[1,2-a]indole-8-carbonitrile
8-Fluoro-10-methyl-6-p-tolyl-3,4-dihydro-2H-pyrazino[1,2-a]indol-1-one
8-Fluoro-10-methyl-6-(4-trifluoromethyl-phenyl)-3,4-dihydro-2H-pyrazino[1,2-a]indol-1-one
6-(3,5-Difluoro-phenyl)-8-fluoro-10-methyl-3,4-dihydro-2H-pyrazino[1,2-a]indol-1-one
6-(4-Chloro-3-fluoro-phenyl)-8-fluoro-10-methyl-3,4-dihydro-2H-pyrazino[1,2-a]indol-1-one
6-(3,4-Dichloro-phenyl)-8-fluoro-10-methyl-3,4-dihydro-2H-pyrazino[1,2-a]indol-1-one
8-Fluoro-6-(3-fluoro-phenyl)-10-methyl-3,4-dihydro-2H-pyrazino[1,2-a]indol-1-one
8-Chloro-10-methyl-6-phenyl-3,4-dihydro-2H-pyrazino[1,2-a]indol-1-one
8-Chloro-10-methyl-6-p-tolyl-3,4-dihydro-2H-pyrazino[1,2-a]indol-1-one
8-Chloro-10-methyl-6-(4-trifluoromethyl-phenyl)-3,4-dihydro-2H-pyrazino[1,2-a]indol-1-one 1-Oxo-6-phenyl-1,2,3,4-tetrahydro-pyrazino[1,2-a]indole-8-carbonitrile
1-Oxo-6-p-tolyl-1,2,3,4-tetrahydro-pyrazino[1,2-a]indole-8-carbonitrile
1-Oxo-6-(4-trifluoromethyl-phenyl)-1,2,3,4-tetrahydro-pyrazino[1,2-a]indole-8-carbonitrile
8-Chloro-6-(3-fluoro-phenyl)-10-methyl-3,4-dihydro-2H-pyrazino[1,2-a]indol-1-one
8-Chloro-6-(3,4-dichloro-phenyl)-10-methyl-3,4-dihydro-2H-pyrazino[1,2-a]indol-1-one
8-Chloro-6-(4-chloro-3-fluoro-phenyl)-10-methyl-3,4-dihydro-2H-pyrazino[1,2-a]indol-1-one
8-Chloro-6-(3,5-difluoro-phenyl)-10-methyl-3,4-dihydro-2H-pyrazino[1,2-a]indol-1-one
8-Chloro-6-(2,4-difluoro-phenyl)-10-methyl-3,4-dihydro-2H-pyrazino[1,2-a]indol-1-one
8-Chloro-6-(4-chloro-2-fluoro-phenyl)-10-methyl-3,4-dihydro-2H-pyrazino[1,2-a]indol-1-one
8-Chloro-6-(2,4-dichloro-phenyl)-10-methyl-3,4-dihydro-2H-pyrazino[1,2-a]indol-1-one
4-(8-Chloro-10-methyl-1-oxo-1,2,3,4-tetrahydro-pyrazino[1,2-a]indol-6-yl)-benzonitrile
8-Chloro-6-(3-fluoro-4-methyl-phenyl)-10-methyl-3,4-dihydro-2H-pyrazino[1,2-a]indol-1-one
8-Chloro-6-(4-isopropyl-phenyl)-10-methyl-3,4-dihydro-2H-pyrazino[1,2-a]indol-1-one
8-Chloro-6-(4-methanesulfonyl-phenyl)-10-methyl-3,4-dihydro-2H-pyrazino[1,2-a]indol-1-one
8-Chloro-10-methyl-6-(4-nitro-phenyl)-3,4-dihydro-2H-pyrazino[1,2-a]indol-1-one
8-Chloro-6-(4-hydroxymethyl-phenyl)-10-methyl-3,4-dihydro-2H-pyrazino[1,2-a]indol-1-one
8-Chloro-6-(4-dimethylamino-phenyl)-10-methyl-3,4-dihydro-2H-pyrazino[1,2-a]indol-1-one
8-Chloro-6-(3-chloro-phenyl)-10-methyl-3,4-dihydro-2H-pyrazino[1,2-a]indol-1-one
3-(8-Chloro-10-methyl-1-oxo-1,2,3,4-tetrahydro-pyrazino[1,2-a]indol-6-yl)-benzonitrile
6-(4-tert-Butyl-phenyl)-8-chloro-10-methyl-3,4-dihydro-2H-pyrazino[1,2-a]indol-1-one
6-(2,4-Dichloro-phenyl)-8-fluoro-10-methyl-3,4-dihydro-2H-pyrazino[1,2-a]indol-1-one
6-(4-Chloro-2-fluoro-phenyl)-8-fluoro-10-methyl-3,4-dihydro-2H-pyrazino[1,2-a]indol-1-one
6-(2,4-Difluoro-phenyl)-8-fluoro-10-methyl-3,4-dihydro-2H-pyrazino[1,2-a]indol-1-one
4-(8-Fluoro-10-methyl-1-oxo-1,2,3,4-tetrahydro-pyrazino[1,2-a]indol-6-yl)-benzonitrile
8-Fluoro-6-(4-methanesulfonyl-phenyl)-10-methyl-3,4-dihydro-2H-pyrazino[1,2-a]indol-1-one
8-Fluoro-10-methyl-6-(4-nitro-phenyl)-3,4-dihydro-2H-pyrazino[1,2-a]indol-1-one
8-Fluoro-6-(4-isopropyl-phenyl)-10-methyl-3,4-dihydro-2H-pyrazino[1,2-a]indol-1-one
6-(3-Chloro-phenyl)-8-fluoro-10-methyl-3,4-dihydro-2H-pyrazino[1,2-a]indol-1-one
8-Fluoro-6-(4-hydroxymethyl-phenyl)-10-methyl-3,4-dihydro-2H-pyrazino[1,2-a]indol-1-one
3-(8-Fluoro-10-methyl-1-oxo-1,2,3,4-tetrahydro-pyrazino[1,2-a]indol-6-yl)-benzonitrile
6-(4-tert-Butyl-phenyl)-8-fluoro-10-methyl-3,4-dihydro-2H-pyrazino[1,2-a]indol-1-one
8-Chloro-10-methyl-6-(4-trifluoromethoxy-phenyl)-3,4-dihydro-2H-pyrazino[1,2-a]indol-1-one
8-Chloro-6-(4-fluoro-3-methyl-phenyl)-10-methyl-3,4-dihydro-2H-pyrazino[1,2-a]indol-1-one
8-Chloro-6-(4-chloro-3-trifluoromethyl-phenyl)-10-methyl-3,4-dihydro-2H-pyrazino[1,2-a]indol-1-one
8-Chloro-10-methyl-6-(3,4,5-trifluoro-phenyl)-3,4-dihydro-2H-pyrazino[1,2-a]indol-1-one
6-(4-Dimethylamino-phenyl)-8-fluoro-10-methyl-3,4-dihydro-2H-pyrazino[1,2-a]indol-1-one
8-Fluoro-6-(3-fluoro-4-methyl-phenyl)-10-methyl-3,4-dihydro-2H-pyrazino[1,2-a]indol-1-one
8-Fluoro-6-(4-fluoro-3-methyl-phenyl)-10-methyl-3,4-dihydro-2H-pyrazino[1,2-a]indol-1-one
8-Fluoro-10-methyl-6-(4-trifluoromethoxy-phenyl)-3,4-dihydro-2H-pyrazino[1,2-a]indol-1-one
6-(4-Chloro-3-trifluoromethyl-phenyl)-8-fluoro-10-methyl-3,4-dihydro-2H-pyrazino[1,2-a]indol-1-one
8-Fluoro-10-methyl-6-(2,3,4-trifluoro-phenyl)-3,4-dihydro-2H-pyrazino[1,2-a]indol-1-one
8-Fluoro-10-methyl-6-(3,4,5-trifluoro-phenyl)-3,4-dihydro-2H-pyrazino[1,2-a]indol-1-one
6-(4-Fluoro-phenyl)-10-methyl-1-oxo-1,2,3,4-tetrahydro-pyrazino[1,2-a]indole-8-carbonitrile
6-(4-Chloro-phenyl)-10-methyl-1-oxo-1,2,3,4-tetrahydro-pyrazino[1,2-a]indole-8-carbonitrile
6-(3,4-Difluoro-phenyl)-10-methyl-1-oxo-1,2,3,4-tetrahydro-pyrazino[1,2-a]indole-8-carbonitrile
10-Methyl-1-oxo-6-(4-trifluoromethyl-phenyl)-1,2,3,4-tetrahydro-pyrazino[1,2-a]indole-8-carbonitrile
6-(4-Cyano-phenyl)-10-methyl-1-oxo-1,2,3,4-tetrahydro-pyrazino[1,2-a]indole-8-carbonitrile
6-(2,4-Dichloro-phenyl)-10-methyl-1-oxo-1,2,3,4-tetrahydro-pyrazino[1,2-a]indole-8-carbonitrile
10-Methyl-1-oxo-6-(4-trifluoromethoxy-phenyl)-1,2,3,4-tetrahydro-pyrazino[1,2-a]indole-8-carbonitrile
6-(4-Chloro-3-fluoro-phenyl)-1-oxo-1,2,3,4-tetrahydro-pyrazino[1,2-a]indole-8-carbonitrile
6-(2,4-Difluoro-phenyl)-1-oxo-1,2,3,4-tetrahydro-pyrazino[1,2-a]indole-8-carbonitrile
6-(4-Chloro-2-fluoro-phenyl)-1-oxo-1,2,3,4-tetrahydro-pyrazino[1,2-a]indole-8-carbonitrile
6-(2,4-Dichloro-phenyl)-1-oxo-1,2,3,4-tetrahydro-pyrazino[1,2-a]indole-8-carbonitrile
6-(4-Cyano-phenyl)-1-oxo-1,2,3,4-tetrahydro-pyrazino[1,2-a]indole-8-carbonitrile
6-(4-Chloro-3-fluoro-phenyl)-10-methyl-1-oxo-1,2,3,4-tetrahydro-pyrazino[1,2-a]indole-8-carbonitrile
6-(2,4-Difluoro-phenyl)-10-methyl-1-oxo-1,2,3,4-tetrahydro-pyrazino[1,2-a]indole-8-carbonitrile
6-(4-Chloro-2-fluoro-phenyl)-10-methyl-1-oxo-1,2,3,4-tetrahydro-pyrazino[1,2-a]indole-8-carbonitrile
8-Fluoro-6-(4-fluoro-phenyl)-10-trifluoromethyl-3,4-dihydro-2H-pyrazino[1,2-a]indol-1-one
6-(3,4-Difluoro-phenyl)-1-oxo-10-trifluoromethyl-1,2,3,4-tetrahydro-pyrazino[1,2-a]indole-8-carbonitrile
8-Chloro-6-(4-chlorophenyl)-10-(trifluoromethyl)-3,4-dihydro-2H-pyrazino[1,2-a]indol-1-one
1-Oxo-6-(3,4,5-trifluorophenyl)-3,4-dihydro-2H-pyrazino[1,2-a]indole-8-carbonitrile
1-Oxo-6-[4-(trifluoromethoxy)phenyl]-3,4-dihydro-2H-pyrazino[1,2-a]indole-8-carbonitrile
6-(4-Methylsulfonylphenyl)-1-oxo-3,4-dihydro-2H-pyrazino[1,2-a]indole-8-carbonitrile
6-(3,4-Dichlorophenyl)-1-oxo-3,4-dihydro-2H-pyrazino[1,2-a]indole-8-carbonitrile
6-(3-Chlorophenyl)-1-oxo-3,4-dihydro-2H-pyrazino[1,2-a]indole-8-carbonitrile
6-(3-Cyanophenyl)-1-oxo-3,4-dihydro-2H-pyrazino[1,2-a]indole-8-carbonitrile 1-Oxo-6-[3-(trifluoromethyl)phenyl]-3,4-dihydro-2H-pyrazino[1,2-a]indole-8-carbonitrile 7-(3,4-Difluorophenyl)-11-methyl-1-oxo-2,3,4,5-tetrahydro-[1,4]diazepino[1,2-a]indole-9-carbonitrile 11-Methyl-1-oxo-7-[4-(trifluoromethyl)phenyl]-2,3,4,5-tetrahydro-[1,4]diazepino[1,2-a]indole-9-carbonitrile 7-(4-Fluorophenyl)-11-methyl-1-oxo-2,3,4,5-tetrahydro-[1,4]diazepino[1,2-a]indole-9-carbonitrile 7-(4-Chlorophenyl)-11-methyl-1-oxo-2,3,4,5-tetrahydro-[1,4]diazepino[1,2-a]indole-9-carbonitrile 7-(4-Cyanophenyl)-11-methyl-1-oxo-2,3,4,5-tetrahydro-[1,4]diazepino[1,2-a]indole-9-carbonitrile 11-Methyl-1-oxo-7-[4-(trifluoromethoxy)-phenyl]-2,3,4,5-tetrahydro-[1,4]diazepino[1,2-a]indole-9-carbonitrile 1-Oxo-6-(2,3,4-trifluorophenyl)-3,4-dihydro-2H-pyrazino[1,2-a]indole-8-carbonitrile 6-[4-Chloro-3-(trifluoromethyl)phenyl]-1-oxo-3,4-dihydro-2H-pyrazino[1,2-a]indole-8-carbonitrile 7-(2,4-Difluorophenyl)-11-methyl-1-oxo-2,3,4,5-tetrahydro-[1,4]diazepino[1,2-a]indole-9-carbonitrile 7-(2,4-Dichlorophenyl)-11-methyl-1-oxo-2,3,4,5-tetrahydro-[1,4]diazepino[1,2-a]indole-9-carbonitrile 7-(4-Chloro-2-fluorophenyl)-11-methyl-1-oxo-2,3,4,5-tetrahydro-[1,4]diazepino[1,2-a]indole-9-carbonitrile 6-(4-Fluorophenyl)-8-methoxy-3,4-dihydro-2H-pyrazino[1,2-a]indol-1-one 6-(4-Chlorophenyl)-8-methoxy-3,4-dihydro-2H-pyrazino[1,2-a]indol-1-one 6-(3,4-Difluorophenyl)-8-methoxy-3,4-dihydro-2H-pyrazino[1,2-a]indol-1-one 8-Methoxy-6-[4-(trifluoromethyl)-phenyl]-3,4-dihydro-2H-pyrazino[1,2-a]indol-1-one 7-(4-Chlorophenyl)-1-oxo-2,3,4,5-tetrahydro-[1,4]diazepino[1,2-a]indole-9-carbonitrile 7-(4-Fluorophenyl)-1-oxo-2,3,4,5-tetrahydro-[1,4]diazepino[1,2-a]indole-9-carbonitrile 8-(Trifluoromethoxy)-6-[4-(trifluoromethyl)-phenyl]-3,4-dihydro-2H-pyrazino[1,2-a]indol-1-one 7-(3,4-Difluorophenyl)-1-oxo-2,3,4,5-tetrahydro-[1,4]diazepino[1,2-a]indole-9-carbonitrile 1-Oxo-7-[4-(trifluoromethyl)-phenyl]-2,3,4,5-tetrahydro-[1,4]diazepino[1,2-a]indole-9-carbonitrile 7-(4-Chloro-2-fluorophenyl)-1-oxo-2,3,4,5-tetrahydro-[1,4]diazepino[1,2-a]indole-9-carbonitrile 7-(2,4-Difluorophenyl)-1-oxo-2,3,4,5-tetrahydro-[1,4]diazepino[1,2-a]indole-9-carbonitrile 6-(3,5-Difluorophenyl)-1-oxo-3,4-dihydro-2H-pyrazino[1,2-a]indole-8-carbonitrile 6-(3-Fluorophenyl)-1-oxo-3,4-dihydro-2H-pyrazino[1,2-a]indole-8-carbonitrile 6-[4-(Hydroxymethyl)-phenyl]-1-oxo-3,4-dihydro-2H-pyrazino[1,2-a]indole-8-carbonitrile 6-(4-tert-Butylphenyl)-1-oxo-3,4-dihydro-2H-pyrazino[1,2-a]indole-8-carbonitrile 6-(4-Fluoro-3-methylphenyl)-1-oxo-3,4-dihydro-2H-pyrazino[1,2-a]indole-8-carbonitrile 6-(4-Nitrophenyl)-1-oxo-3,4-dihydro-2H-pyrazino[1,2-a]indole-8-carbonitrile 6-(3-Fluoro-4-methylphenyl)-1-oxo-3,4-dihydro-2H-pyrazino[1,2-a]indole-8-carbonitrile 7-(4-Nitrophenyl)-1-oxo-2,3,4,5-tetrahydro-[1,4]diazepino[1,2-a]indole-9-carbonitrile 7-(4-Fluoro-3-methylphenyl)-1-oxo-2,3,4,5-tetrahydro-[1,4]diazepino[1,2-a]indole-9-carbonitrile 7-(2,4-Dichlorophenyl)-1-oxo-2,3,4,5-tetrahydro-[1,4]diazepino[1,2-a]indole-9-carbonitrile 7-(4-Cyanophenyl)-1-oxo-2,3,4,5-tetrahydro-[1,4]diazepino[1,2-a]indole-9-carbonitrile 7-(3,5-Difluorophenyl)-1-oxo-2,3,4,5-tetrahydro-[1,4]diazepino[1,2-a]indole-9-carbonitrile 7-(3-Fluorophenyl)-1-oxo-2,3,4,5-tetrahydro-[1,4]diazepino[1,2-a]indole-9-carbonitrile 10-Methyl-1-oxo-6-(3,4,5-trifluorophenyl)-3,4-dihydro-2H-pyrazino[1,2-a]indole-8-carbonitrile 10-Methyl-1-oxo-6-phenyl-3,4-dihydro-2H-pyrazino[1,2-a]indole-8-carbonitrile 11-Methyl-1-oxo-7-(3,4,5-trifluorophenyl)-2,3,4,5-tetrahydro-[1,4]diazepino[1,2-a]indole-9-carbonitrile 11-Methyl-1-oxo-7-phenyl-2,3,4,5-tetrahydro-[1,4]diazepino[1,2-a]indole-9-carbonitrile 10-Methyl-1-oxo-6-(2,3,4-trifluorophenyl)-3,4-dihydro-2H-pyrazino[1,2-a]indole-8-carbonitrile 6-(4-Methoxyphenyl)-10-methyl-1-oxo-3,4-dihydro-2H-pyrazino[1,2-a]indole-8-carbonitrile 1-Oxo-7-(3,4,5-trifluorophenyl)-2,3,4,5-tetrahydro-[1,4]diazepino[1,2-a]indole-9-carbonitrile 7-(3,4-Dichlorophenyl)-1-oxo-2,3,4,5-tetrahydro-[1,4]diazepino[1,2-a]indole-9-carbonitrile 7-(4-Chloro-3-fluorophenyl)-1-oxo-2,3,4,5-tetrahydro-[1,4]diazepino[1,2-a]indole-9-carbonitrile 7-(3-Fluoro-4-methylphenyl)-1-oxo-2,3,4,5-tetrahydro-[1,4]diazepino[1,2-a]indole-9-carbonitrile 7-[4-Chloro-3-(trifluoromethyl)phenyl]-1-oxo-2,3,4,5-tetrahydro-[1,4]diazepino[1,2-a]indole-9-carbonitrile 1-Oxo-7-[4-(trifluoromethoxy)phenyl]-2,3,4,5-tetrahydro-[1,4]diazepino[1,2-a]indole-9-carbonitrile 7-(4-Methylsulfonylphenyl)-1-oxo-2,3,4,5-tetrahydro-[1,4]diazepino[1,2-a]indole-9-carbonitrile 10-Methyl-6-(4-methylphenyl)-1-oxo-3,4-dihydro-2H-pyrazino[1,2-a]indole-8-carbonitrile 6-(3-Fluorophenyl)-10-methyl-1-oxo-3,4-dihydro-2H-pyrazino[1,2-a]indole-8-carbonitrile 6-(3,4-Dichlorophenyl)-10-methyl-1-oxo-3,4-dihydro-2H-pyrazino[1,2-a]indole-8-carbonitrile 6-(3,5-Difluorophenyl)-10-methyl-1-oxo-3,4-dihydro-2H-pyrazino[1,2-a]indole-8-carbonitrile 7-(4-Methoxyphenyl)-11-methyl-1-oxo-2,3,4,5-tetrahydro-[1,4]diazepino[1,2-a]indole-9-carbonitrile 7-[4-(Hydroxymethyl)phenyl]-1-oxo-2,3,4,5-tetrahydro-[1,4]diazepino[1,2-a]indole-9-carbonitrile 6-(3-Fluoro-4-methylphenyl)-10-methyl-1-oxo-3,4-dihydro-2H-pyrazino[1,2-a]indole-8-carbonitrile 6-(3-Chlorophenyl)-10-methyl-1-oxo-3,4-dihydro-2H-pyrazino[1,2-a]indole-8-carbonitrile 7-(3-Cyanophenyl)-1-oxo-2,3,4,5-tetrahydro-[1,4]diazepino[1,2-a]indole-9-carbonitrile 7-(4-tert-Butylphenyl)-1-oxo-2,3,4,5-tetrahydro-[1,4]diazepino[1,2-a]indole-9-carbonitrile 1-Oxo-7-phenyl-2,3,4,5-tetrahydro-[1,4]diazepino[1,2-a]indole-9-carbonitrile 7-(4-Methoxyphenyl)-1-oxo-2,3,4,5-tetrahydro-[1,4]diazepino[1,2-a]indole-9-carbonitrile 10-Methyl-6-(4-nitrophenyl)-1-oxo-3,4-dihydro-2H-pyrazino[1,2-a]indole-8-carbonitrile 6-[4-(Hydroxymethyl)phenyl]-10-methyl-1-oxo-3,4-dihydro-2H-pyrazino[1,2-a]indole-8-carbonitrile 6-(3-Cyanophenyl)-10-methyl-1-oxo-3,4-dihydro-2H-pyrazino[1,2-a]indole-8-carbonitrile 6-(4-tert-Butylphenyl)-10-methyl-1-oxo-3,4-dihydro-2H-pyrazino[1,2-a]indole-8-carbonitrile 1-Oxo-7-(2,3,4-trifluorophenyl)-2,3,4,5-tetrahydro-[1,4]diazepino[1,2-a]indole-9-carbonitrile 7-(3-Chlorophenyl)-1-oxo-2,3,4,5-tetrahydro-[1,4]diaz-
epino[1,2-a]indole-9-carbonitrile
7-(3,5-Dichlorophenyl)-1-oxo-2,3,4,5-tetrahydro-[1,4]diaz-
epino[1,2-a]indole-9-carbonitrile
7-(4-Methylphenyl)-1-oxo-2,3,4,5-tetrahydro-[1,4]diaz-
epino[1,2-a]indole-9-carbonitrile
11-Methyl-7-(4-methylphenyl)-1-oxo-2,3,4,5-tetrahydro-[1,
4]diazepino[1,2-a]indole-9-carbonitrile
7-(3-Fluorophenyl)-11-methyl-1-oxo-2,3,4,5-tetrahydro-[1,
4]diazepino[1,2-a]indole-9-carbonitrile
7-(3,5-Difluorophenyl)-11-methyl-1-oxo-2,3,4,5-tetrahy-
dro-[1,4]diazepino[1,2-a]indole-9-carbonitrile
7-(3-Fluoro-4-methylphenyl)-11-methyl-1-oxo-2,3,4,5-tet-
rahydro-[1,4]diazepino[1,2-a]indole-9-carbonitrile
6-(4-Fluoro-3-methylphenyl)-10-methyl-1-oxo-3,4-dihy-
dro-2H-pyrazino[1,2-a]indole-8-carbonitrile
6-(3,5-Dichlorophenyl)-10-methyl-1-oxo-3,4-dihydro-2H-
pyrazino[1,2-a]indole-8-carbonitrile
10-Methyl-6-(4-methylsulfonylphenyl)-1-oxo-3,4-dihydro-
2H-pyrazino[1,2-a]indole-8-carbonitrile
6-[4-Chloro-3-(trifluoromethyl)phenyl]-10-methyl-1-oxo-3,
4-dihydro-2H-pyrazino[1,2-a]indole-8-carbonitrile
7-(3,4-Dichlorophenyl)-11-methyl-1-oxo-2,3,4,5-tetrahy-
dro-[1,4]diazepino[1,2-a]indole-9-carbonitrile or
7-(4-Chloro-3-fluorophenyl)-11-methyl-1-oxo-2,3,4,5-tet-
rahydro-[1,4]diazepino[1,2-a]indole-9-carbonitrile.

A further object of the present invention are compounds of formula

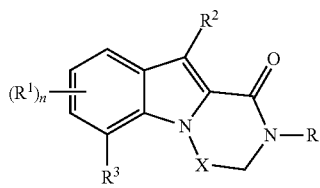

IB wherein
$R^1$ is hydrogen, halogen, lower alkyl, lower alkoxy, lower alkoxy substituted by halogen or cyano;
$R^2$ is hydrogen, lower alkyl or lower alkyl substituted by halogen;
$R^3$ is pyridinyl or pyrimidinyl, which may be substituted by one or more substituents, selected from cyano, nitro, amino and lower di-alkylamino, lower alkyl sulfonyl, lower alkoxy, lower alkoxy substituted by halogen, halogen, lower alkyl, lower alkyl substituted by halogen or lower alkyl substituted by hydroxyl;
X is —CH(lower alkyl)-, —CH$_2$—, —CH$_2$CH$_2$— or —CH (lower alkyl)CH$_2$—;
R is hydrogen or lower alkyl;
n is 1 or 2;
or a pharmaceutically acceptable acid addition salt, a racemic mixture or to its corresponding enantiomer and/or optical isomers thereof.

The following examples are encompassed by formula IB:
(R)-4-Methyl-6-pyridin-4-yl-3,4-dihydro-2H-pyrazino[1,2-
a]indol-1-one
(R)-8-Fluoro-4-methyl-6-pyridin-4-yl-3,4-dihydro-2H-
pyrazino[1,2-a]indol-1-one
9-Fluoro-7-pyridin-4-yl-2,3,4,5-tetrahydro-[1,4]diazepino
[1,2-a]indol-1-one
8-Fluoro-6-pyridin-4-yl-3,4-dihydro-2H-pyrazino[1,2-a]in-
dol-1-one
8-Fluoro-10-methyl-6-pyridin-4-yl-3,4-dihydro-2H-
pyrazino[1,2-a]indol-1-one
8-Chloro-10-methyl-6-pyridin-4-yl-3,4-dihydro-2H-
pyrazino[1,2-a]indol-1-one
1-Oxo-6-pyridin-4-yl-1,2,3,4-tetrahydro-pyrazino[1,2-a]in-
dole-8-carbonitrile
8-Chloro-6-(2-fluoro-pyridin-4-yl)-10-methyl-3,4-dihydro-
2H-pyrazino[1,2-a]indol-1-one
8-Chloro-6-(6-methoxy-pyridin-3-yl)-10-methyl-3,4-dihy-
dro-2H-pyrazino[1,2-a]indol-1-one
8-Chloro-6-(6-chloro-pyridin-3-yl)-10-methyl-3,4-dihydro-
2H-pyrazino[1,2-a]indol-1-one
8-Chloro-6-(6-fluoro-pyridin-3-yl)-10-methyl-3,4-dihydro-
2H-pyrazino[1,2-a]indol-1-one
8-Chloro-6-(2-chloro-pyridin-4-yl)-10-methyl-3,4-dihydro-
2H-pyrazino[1,2-a]indol-1-one
8-Chloro-10-methyl-6-pyridin-3-yl-3,4-dihydro-2H-
pyrazino[1,2-a]indol-1-one
8-Fluoro-6-(2-fluoro-pyridin-4-yl)-10-methyl-3,4-dihydro-
2H-pyrazino[1,2-a]indol-1-one
6-(2-Chloro-pyridin-4-yl)-8-fluoro-10-methyl-3,4-dihydro-
2H-pyrazino[1,2-a]indol-1-one
8-Fluoro-6-(6-fluoro-pyridin-3-yl)-10-methyl-3,4-dihydro-
2H-pyrazino[1,2-a]indol-1-one
6-(6-Chloro-pyridin-3-yl)-8-fluoro-10-methyl-3,4-dihydro-
2H-pyrazino[1,2-a]indol-1-one
8-Fluoro-6-(6-methoxy-pyridin-3-yl)-10-methyl-3,4-dihy-
dro-2H-pyrazino[1,2-a]indol-1-one
8-Fluoro-10-methyl-6-pyridin-3-yl-3,4-dihydro-2H-
pyrazino[1,2-a]indol-1-one
8-Chloro-6-(6-dimethylamino-pyridin-3-yl)-10-methyl-3,4-
dihydro-2H-pyrazino[1,2-a]indol-1-one
6-(6-Dimethylamino-pyridin-3-yl)-8-fluoro-10-methyl-3,4-
dihydro-2H-pyrazino[1,2-a]indol-1-one
6-(6-Amino-pyridin-3-yl)-8-fluoro-10-methyl-3,4-dihydro-
2H-pyrazino[1,2-a]indol-1-one
6-(6-Amino-pyridin-3-yl)-8-chloro-10-methyl-3,4-dihydro-
2H-pyrazino[1,2-a]indol-1-one
6-(2-Fluoro-pyridin-4-yl)-10-methyl-1-oxo-1,2,3,4-tetrahy-
dro-pyrazino[1,2-a]indole-8-carbonitrile
6-(6-Fluoro-pyridin-3-yl)-10-methyl-1-oxo-1,2,3,4-tetrahy-
dro-pyrazino[1,2-a]indole-8-carbonitrile
6-(2-Fluoro-pyridin-4-yl)-1-oxo-1,2,3,4-tetrahydro-
pyrazino[1,2-a]indole-8-carbonitrile
6-(6-Fluoropyridin-3-yl)-1-oxo-3,4-dihydro-2H-pyrazino[1,
2-a]indole-8-carbonitrile
7-(2-Fluoropyridin-4-yl)-11-methyl-1-oxo-2,3,4,5-tetrahy-
dro-[1,4]diazepino[1,2-a]indole-9-carbonitrile
7-(6-Fluoropyridin-3-yl)-11-methyl-1-oxo-2,3,4,5-tetrahy-
dro-[1,4]diazepino[1,2-a]indole-9-carbonitrile
7-(2-Fluoropyridin-4-yl)-1-oxo-2,3,4,5-tetrahydro-[1,4]di-
azepino[1,2-a]indole-9-carbonitrile
6-(6-Aminopyridin-3-yl)-1-oxo-3,4-dihydro-2H-pyrazino
[1,2-a]indole-8-carbonitrile
6-(6-Chloropyridin-3-yl)-1-oxo-3,4-dihydro-2H-pyrazino
[1,2-a]indole-8-carbonitrile
6-(2-Chloropyridin-4-yl)-1-oxo-3,4-dihydro-2H-pyrazino
[1,2-a]indole-8-carbonitrile
1-Oxo-6-pyridin-3-yl-3,4-dihydro-2H-pyrazino[1,2-a]in-
dole-8-carbonitrile
6-(6-Aminopyridin-3-yl)-10-methyl-1-oxo-3,4-dihydro-2H-
pyrazino[1,2-a]indole-8-carbonitrile
10-Methyl-oxo-6-pyridin-4-yl-3,4-dihydro-2H-pyrazino
[1,2-a]indole-8-carbonitrile
11-Methyl-1-oxo-7-pyridin-4-yl-2,3,4,5-tetrahydro-[1,4]di-
azepino[1,2-a]indole-9-carbonitrile 7-(6-Aminopyridin-3-yl)-11-methyl-1-oxo-2,3,4,5-tetrahydro-[1,4]diazepino[1,2-a]indole-9-carbonitrile
7-(2-Chloropyridin-4-yl)-1-oxo-2,3,4,5-tetrahydro-[1,4]diazepino[1,2-a]indole-9-carbonitrile
1-Oxo-7-pyridin-3-yl-2,3,4,5-tetrahydro-[1,4]diazepino[1,2-a]indole-9-carbonitrile
7-(6-Aminopyridin-3-yl)-1-oxo-2,3,4,5-tetrahydro-[1,4]diazepino[1,2-a]indole-9-carbonitrile
7-(6-Chloropyridin-3-yl)-1-oxo-2,3,4,5-tetrahydro-[1,4]diazepino[1,2-a]indole-9-carbonitrile
1-Oxo-7-pyridin-4-yl-2,3,4,5-tetrahydro-[1,4]diazepino[1,2-a]indole-9-carbonitrile
7-(6-Fluoropyridin-3-yl)-1-oxo-2,3,4,5-tetrahydro-[1,4]diazepino[1,2-a]indole-9-carbonitrile
6-(6-Chloropyridin-3-yl)-10-methyl-1-oxo-3,4-dihydro-2H-pyrazino[1,2-a]indole-8-carbonitrile
10-Methyl-1-oxo-6-pyridin-3-yl-3,4-dihydro-2H-pyrazino[1,2-a]indole-8-carbonitrile
11-Methyl-1-oxo-7-pyridin-3-yl-2,3,4,5-tetrahydro-[1,4]diazepino[1,2-a]indole-9-carbonitrile
8-Chloro-10-methyl-6-pyrimidin-5-yl-3,4-dihydro-2H-pyrazino[1,2-a]indol-1-one
8-Chloro-6-(2-methoxy-pyrimidin-5-yl)-10-methyl-3,4-dihydro-2H-pyrazino[1,2-a]indol-1-one
6-(2-Amino-pyrimidin-5-yl)-8-chloro-10-methyl-3,4-dihydro-2H-pyrazino[1,2-a]indol-1-one
8-Fluoro-10-methyl-6-pyrimidin-5-yl-3,4-dihydro-2H-pyrazino[1,2-a]indol-1-one
8-Fluoro-6-(2-methoxy-pyrimidin-5-yl)-10-methyl-3,4-dihydro-2H-pyrazino[1,2-a]indol-1-one
6-(2-Amino-pyrimidin-5-yl)-8-fluoro-10-methyl-3,4-dihydro-2H-pyrazino[1,2-a]indol-1-one
1-Oxo-6-pyrimidin-5-yl-3,4-dihydro-2H-pyrazino[1,2-a]indole-8-carbonitrile
1-Oxo-7-pyrimidin-5-yl-2,3,4,5-tetrahydro-[1,4]diazepino[1,2-a]indole-9-carbonitrile
10-Methyl-1-oxo-6-pyrimidin-5-yl-3,4-dihydro-2H-pyrazino[1,2-a]indole-8-carbonitrile or
11-Methyl-1-oxo-7-pyrimidin-5-yl-2,3,4,5-tetrahydro-[1,4]diazepino[1,2-a]indole-9-carbonitrile.

A further object of the present invention are compounds of formula

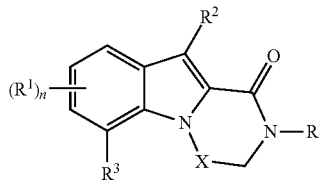

wherein
R¹ is hydrogen, halogen, lower alkyl, lower alkoxy, lower alkoxy substituted by halogen or cyano;
R² is hydrogen, lower alkyl or lower alkyl substituted by halogen;
R³ is benzo[1,3]dioxolyl or 2,3-dihydro-benzofuranyl;
X is —CH(lower alkyl)-, —CH₂—, —CH₂CH₂— or —CH(lower alkyl)CH₂—,
R is hydrogen;
n is 1;
or a pharmaceutically acceptable acid addition salt, a racemic mixture or its corresponding enantiomer and/or optical isomers thereof.

The following example is encompassed by formula IC:
6-Benzo[1,3]dioxol-5-yl-8-chloro-10-methyl-3,4-dihydro-2H-pyrazino[1,2-a]indol-1-one
6-Benzo[1,3]dioxol-5-yl-8-fluoro-10-methyl-3,4-dihydro-2H-pyrazino[1,2-a]indol-1-one
8-Chloro-6-(2,3-dihydro-benzofuran-5-yl)-10-methyl-3,4-dihydro-2H-pyrazino[1,2-a]indol-1-one or
6-(2,3-Dihydro-benzofuran-5-yl)-8-fluoro-10-methyl-3,4-dihydro-2H-pyrazino[1,2-a]indol-1-one.

A further object of the present invention are compounds of formula

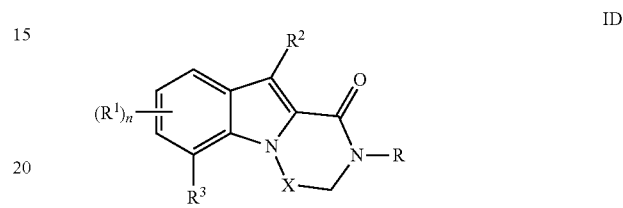

wherein
R¹ is hydrogen, halogen, lower alkyl, lower alkoxy, lower alkoxy substituted by halogen or cyano;
R² is hydrogen, lower alkyl or lower alkyl substituted by halogen;
R³ is a 5-membered heteroaryl, which may be substituted by one or more substituents, selected from cyano, nitro, amino and lower di-alkylamino, lower alkyl sulfonyl, lower alkoxy, lower alkoxy substituted by halogen, halogen, lower alkyl, lower alkyl substituted by halogen or lower alkyl substituted by hydroxyl;
X is —CH(lower alkyl)-, —CH₂—, —CH₂CH₂— or —CH(lower alkyl)CH₂—;
R is hydrogen or lower alkyl;
n is 1 or 2;
or a pharmaceutically acceptable acid addition salt, a racemic mixture or to its corresponding enantiomer and/or optical isomers thereof, for example the following compounds
8-Fluoro-10-methyl-6-thiazol-2-yl-3,4-dihydro-2H-pyrazino[1,2-a]indol-1-one
6-(5-Chloro-thiophen-2-yl)-8-fluoro-10-methyl-3,4-dihydro-2H-pyrazino[1,2-a]indol-1-one
8-Fluoro-10-methyl-6-[5-(trifluoromethyl)-1,3,4-thiadiazol-2-yl]-3,4-dihydro-2H-pyrazino[1,2-a]indol-1-one
5-(8-Fluoro-10-methyl-1-oxo-3,4-dihydro-2H-pyrazino indol-6-yl)thiophene-2-carbonitrile
8-Fluoro-10-methyl-6-[5-(trifluoromethyl)-1,3-thiazol-2-yl]-3,4-dihydro-2H-pyrazino[1,2-a]indol-1-one or
8-Fluoro-6-(furan-2-yl)-10-methyl-3,4-dihydro-2H-pyrazino[1,2-a]indol-1-one.

A further embodiment of the invention are compounds of formula I, wherein X is —CH(lower alkyl)-.
A further embodiment of the invention are compounds of formula I, wherein X is —CH₂—.
A further embodiment of the invention are compounds of formula I, wherein X is —CH₂CH₂—.
A further embodiment of the invention are compounds of formula I, wherein X is —CH(lower alkyl)CH₂—.

The present compounds of formula I and their pharmaceutically acceptable salts can be prepared by methods known in the art, for example, by processes described below, which process comprises reacting a compound of formula

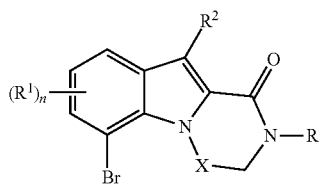

with a compound of formula

R$_3$B(OH)$_2$     2 to a compound of formula

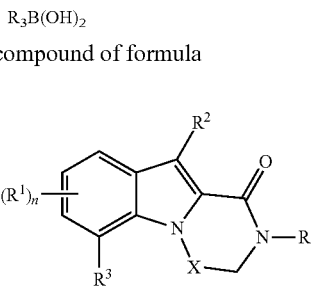

wherein the substituents are as described above and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

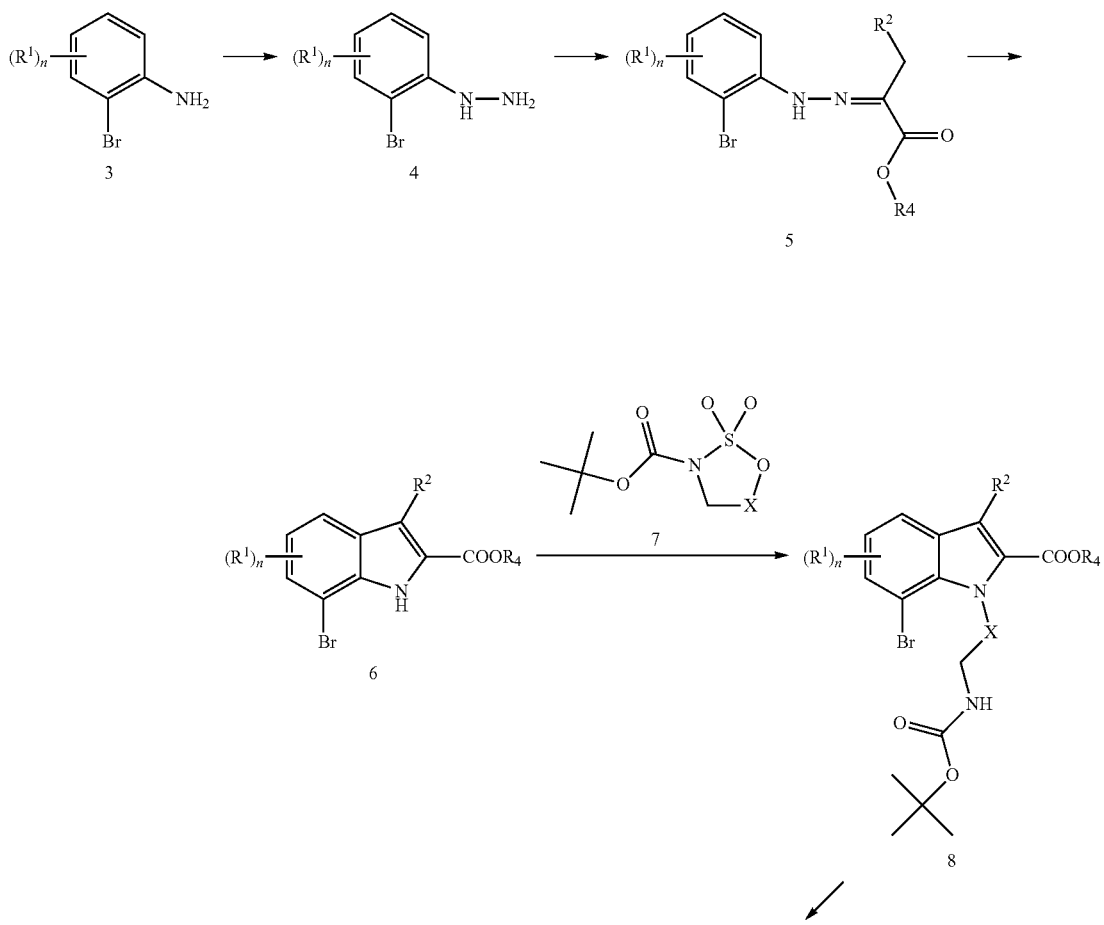

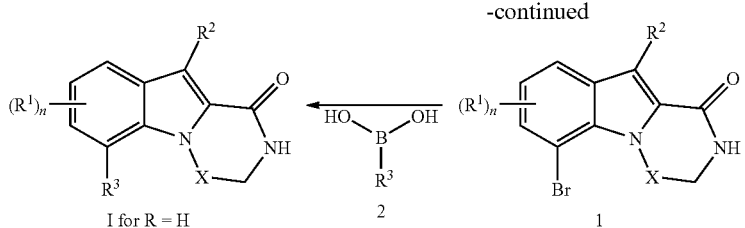

I for R = H wherein the substituents are as described above and $R_4$ is lower alkyl.

Starting from the anilines of formula 3 the corresponding hydrazines of formula 4 were prepared. These derivatives were the starting points for a classical indole synthesis yielding the indole-2-carboxylates of formula 6 via the intermediates of formula 5. N-alkylation using the commercially available reagents of formula 7 gave rise to the N-Boc protected precursors of formula 8 which were after cleavage of the protecting group converted into the building blocks of formula 1. Reaction with e.g. commercially available boronic acids yielded the final compounds of formula I.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009. 27(3): p. 275-80.)

Compounds respond is measured by the increase in cells based on ATP levels (Promega:CellTiterGlo®) after an incubation period of 4 days.

NSCs are thawed and expanded over 3 passages. On the $14^{th}$ day, NSCs are seeded in Polyornithin/Laminin coated 384 well plates at a cell density of 21'000 cells/cm² in a media volume of 38 µl.

4 hours after cell seeding, compound solutions are added at a volume of 2 µl. Stock solutions of the compounds (water, 5% DMSO) are diluted to obtain a dose response (11 points, dilution factor is 2), ranging from 8 µM to 8 nM. Controls are run to consistently determine the neurogenic properties of the cells:

Negative (neutral) control is cell culture Media (final DMSO concentration: 0.25%).

Positive controls are:
1. cell culture Media+100 ng/ml FGF2 (final DMSO concentration: 0.1%)
2. cell culture Media+20 ng/ml EGF (final DMSO concentration: 0.1%)
3. cell culture Media+100 ng/ml Wnt3a (final DMSO concentration: 0.1%)

After 4 days incubation at 37° C., 5% $CO_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (Ultra-Glo™ recombinant luciferase), magnesium and luciferin. Luciferin reacts with ATP producing oxyluciferin, AMP and light. The luminescence signal is proportional to the ATP content.

The value of negative (neutral) control is determined for each assay plate by taking the average of 16 negative control wells. The neurogenic compound response is calculated for each compound as (compound/Negative Control)*100.

The values of $EC_{150}$ from the dose response curve are determined for each test compound. The EC150 is the compound concentration at which 150% activity of control (100%) is reached. The preferred compounds show a $EC_{150}$ (µM) in the range of <4.0 µM as shown in the table below.

List of Examples and EC$_{150}$ Data

| Ex. | Structure | Name | EC$_{150}$ (uM) |
|---|---|---|---|
| 1 | 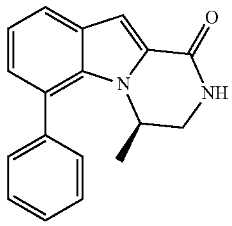 [SMILES: C[C@@H]1CNC(=O)c2cc3cccc(-c4ccccc4)c3n21] | (R)-4-Methyl-6-phenyl-3,4-dihydro-2H-pyrazino[1,2-a]indol-1-one | 3.97 |
| 2 | 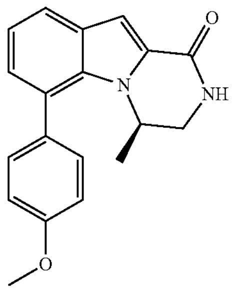 [SMILES: COc1ccc(-c2cccc3cc4n(c23)[C@H](C)CNC4=O)cc1] | (R)-6-(4-Methoxy-phenyl)-4-methyl-3,4-dihydro-2H-pyrazino[1,2-a]indol-1-one | 0.85 |
| 3 | 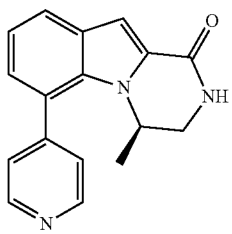 [SMILES: C[C@@H]1CNC(=O)c2cc3cccc(-c4ccncc4)c3n21] | (R)-4-Methyl-6-pyridin-4-yl-3,4-dihydro-2H-pyrazino[1,2-a]indol-1-one | 2.31 |
| 4 | 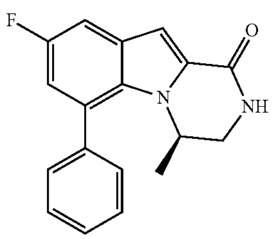 [SMILES: C[C@@H]1CNC(=O)c2cc3cc(F)cc(-c4ccccc4)c3n21] | (R)-8-Fluoro-4-methyl-6-phenyl-3,4-dihydro-2H-pyrazino[1,2-a]indol-1-one | 0.37 |
| 5 | 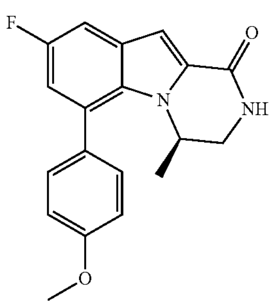 [SMILES: COc1ccc(-c2cc(F)cc3cc4n(c23)[C@H](C)CNC4=O)cc1] | (R)-8-Fluoro-6-(4-methoxy-phenyl)-4-methyl-3,4-dihydro-2H-pyrazino[1,2-a]indol-1-one | 0.034 |

-continued

| Ex. | Structure | Name | EC$_{150}$ (uM) |
|---|---|---|---|
| 6 | 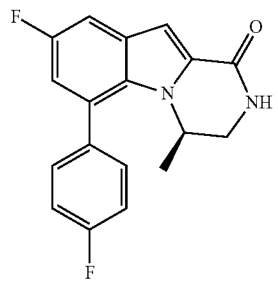 [SMILES: C[C@@H]1CNC(=O)c2cc3cc(F)cc(-c4ccc(F)cc4)c3n21] | (R)-8-Fluoro-6-(4-fluoro-phenyl)-4-methyl-3,4-dihydro-2H-pyrazino[1,2-a]indol-1-one | 0.22 |
| 7 | 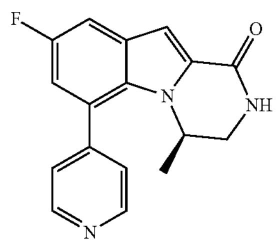 [SMILES: C[C@@H]1CNC(=O)c2cc3cc(F)cc(-c4ccncc4)c3n21] | (R)-8-Fluoro-4-methyl-6-pyridin-4-yl-3,4-dihydro-2H-pyrazino[1,2-a]indol-1-one | 0.4 |
| 8 | 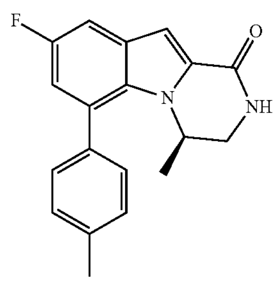 [SMILES: Cc1ccc(-c2cc(F)cc3cc4n(c23)[C@H](C)CNC4=O)cc1] | (R)-8-Fluoro-4-methyl-6-p-tolyl-3,4-dihydro-2H-pyrazino[1,2-a]indol-1-one | 0.048 |
| 9 | 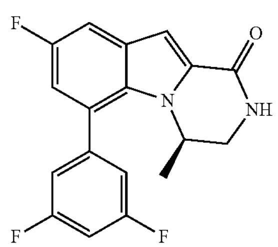 [SMILES: C[C@@H]1CNC(=O)c2cc3cc(F)cc(-c4cc(F)cc(F)c4)c3n21] | (R)-6-(3,5-Difluoro-phenyl)-8-fluoro-4-methyl-3,4-dihydro-2H-pyrazino[1,2-a]indol-1-one | 0.37 |
| 10 | 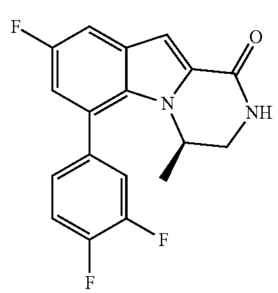 [SMILES: C[C@@H]1CNC(=O)c2cc3cc(F)cc(-c4ccc(F)c(F)c4)c3n21] | (R)-6-(3,4-Difluoro-phenyl)-8-fluoro-4-methyl-3,4-dihydro-2H-pyrazino[1,2-a]indol-1-one | 0.22 |

-continued

| Ex. | Structure | Name | EC$_{150}$ (uM) |
|---|---|---|---|
| 11 | 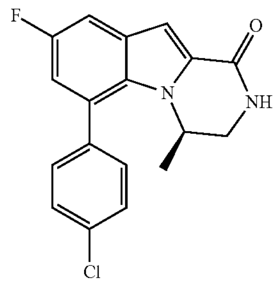 [SMILES: C[C@@H]1CNC(=O)c2cc3cc(F)cc(-c4ccc(Cl)cc4)c3n21] | (R)-6-(4-Chloro-phenyl)-8-fluoro-4-methyl-3,4-dihydro-2H-pyrazino[1,2-a]indol-1-one | 0.1 |
| 12 | 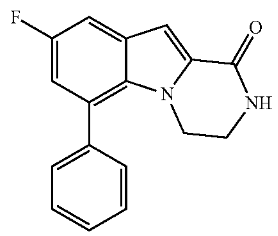 [SMILES: O=C1NCCn2c1cc1cc(F)cc(-c3ccccc3)c12] | 8-Fluoro-6-phenyl-3,4-dihydro-2H-pyrazino[1,2-a]indol-1-one | 0.037 |
| 13 | 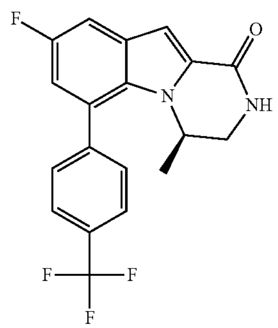 [SMILES: C[C@@H]1CNC(=O)c2cc3cc(F)cc(-c4ccc(C(F)(F)F)cc4)c3n21] | (R)-8-Fluoro-4-methyl-6-(4-trifluoromethyl-phenyl)-3,4-dihydro-2H-pyrazino[1,2-a]indol-1-one | 0.16 |
| 14 | 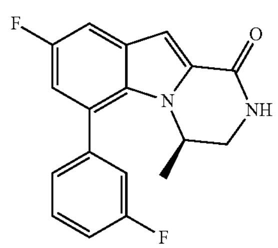 [SMILES: C[C@@H]1CNC(=O)c2cc3cc(F)cc(-c4cccc(F)c4)c3n21] | (R)-8-Fluoro-6-(3-fluoro-phenyl)-4-methyl-3,4-dihydro-2H-pyrazino[1,2-a]indol-1-one | 0.34 |
| 15 | 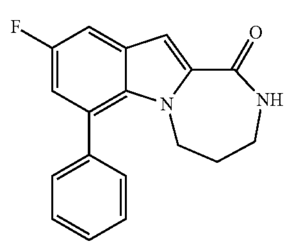 [SMILES: O=C1NCCCn2c1cc1cc(F)cc(-c3ccccc3)c12] | 9-Fluoro-7-phenyl-2,3,4,5-tetrahydro-[1,4]diazepino[1,2-a]indol-1-one | 0.084 |

-continued
| Ex. | Structure | Name | EC$_{150}$ (uM) |
|---|---|---|---|
| 16 | 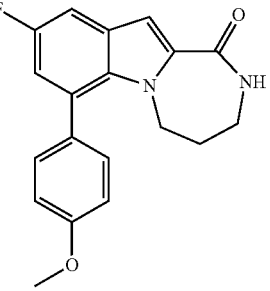 | 9-Fluoro-7-(4-methoxy-phenyl)-2,3,4,5-tetrahydro-[1,4]diazepino[1,2-a]indol-1-one | 0.009 |
| 17 | 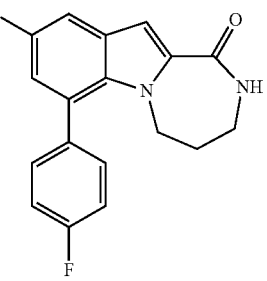 | 9-Fluoro-7-(4-fluoro-phenyl)-2,3,4,5-tetrahydro-[1,4]diazepino[1,2-a]indol-1-one | 0.05 |
| 18 | 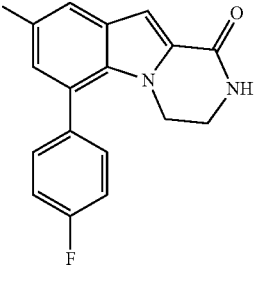 | 8-Fluoro-6-(4-fluoro-phenyl)-3,4-dihydro-2H-pyrazino[1,2-a]indol-1-one | 0.026 |
| 19 | 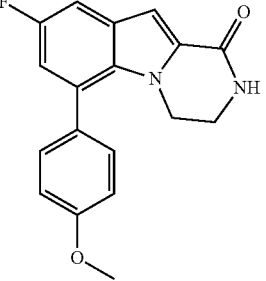 | 8-Fluoro-6-(4-methoxy-phenyl)-3,4-dihydro-2H-pyrazino[1,2-a]indol-1-one- | 0.007 |
| 20 | 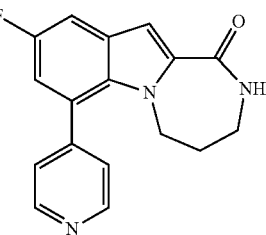 | 9-Fluoro-7-pyridin-4-yl-2,3,4,5-tetrahydro-[1,4]diazepino[1,2-a]indol-1-one | 0.037 |

-continued

| Ex. | Structure | Name | EC$_{150}$ (uM) |
|---|---|---|---|
| 21 | 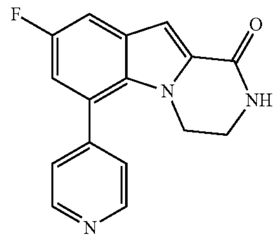 [SMILES: O=C1NCCn2c1cc1cc(F)cc(-c3ccncc3)c12] | 8-Fluoro-6-pyridin-4-yl-3,4-dihydro-2H-pyrazino[1,2-a]indol-1-one | 0.036 |
| 22 | 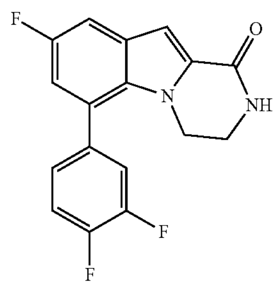 [SMILES: O=C1NCCn2c1cc1cc(F)cc(-c3ccc(F)c(F)c3)c12] | 6-(3,4-Difluoro-phenyl)-8-fluoro-3,4-dihydro-2H-pyrazino[1,2-a]indol-1-one | 0.037 |
| 23 | 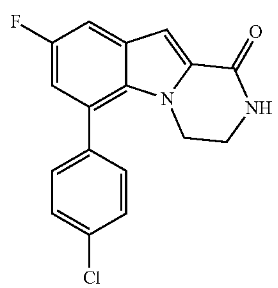 | 6-(4-Chloro-phenyl)-8-fluoro-3,4-dihydro-2H-pyrazino[1,2-a]indol-1-one | 0.019 |
| 24 | 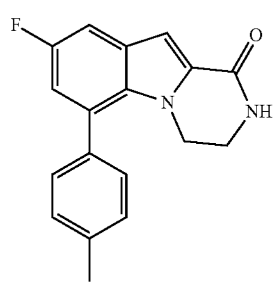 [SMILES: Cc1ccc(-c2cc(F)cc3cc4n(c23)CCNC4=O)cc1] | 8-Fluoro-6-p-tolyl-3,4-dihydro-2H-pyrazino[1,2-a]indol-1-one | 0.017 |
| 25 | 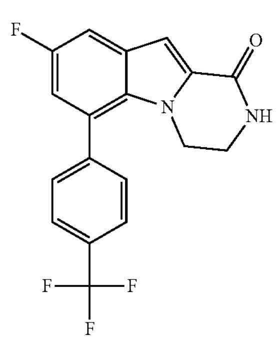 [SMILES: O=C1NCCn2c1cc1cc(F)cc(-c3ccc(C(F)(F)F)cc3)c12] | 8-Fluoro-6-(4-trifluoromethyl-phenyl)-3,4-dihydro-2H-pyrazino[1,2-a]indol-1-one | 0.023 |

-continued

| Ex. | Structure | Name | EC$_{150}$ (uM) |
|---|---|---|---|
| 26 | 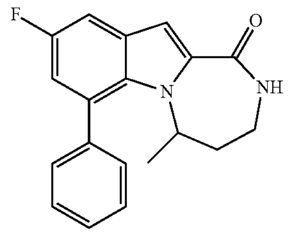 [SMILES: CC1CCNC(=O)c2cc3cc(F)cc(-c4ccccc4)c3n21] | (RS)-9-Fluoro-5-methyl-7-phenyl-2,3,4,5-tetrahydro-[1,4]diazepino[1,2-a]indol-1-one | 0.24 |
| 27 | 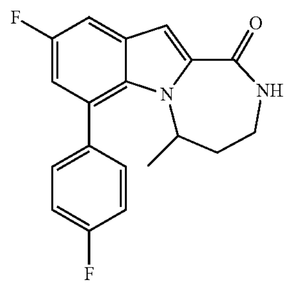 [SMILES: CC1CCNC(=O)c2cc3cc(F)cc(-c4ccc(F)cc4)c3n21] | (RS)-9-Fluoro-7-(4-fluoro-phenyl)-5-methyl-2,3,4,5-tetrahydro-[1,4]diazepino[1,2-a]indol-1-one | 0.18 |
| 28 | 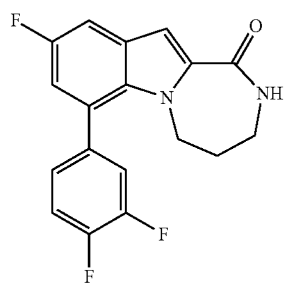 [SMILES: O=C1NCCCn2c1cc1cc(F)cc(-c3ccc(F)c(F)c3)c12] | 7-(3,4-Difluoro-phenyl)-9-fluoro-2,3,4,5-tetrahydro-[1,4]diazepino[1,2-a]indol-1-one | 0.1 |
| 29 | 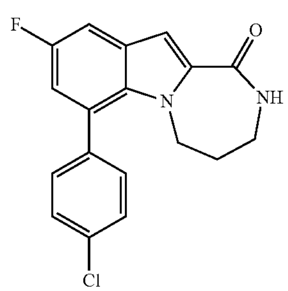 [SMILES: O=C1NCCCn2c1cc1cc(F)cc(-c3ccc(Cl)cc3)c12] | 7-(4-Chloro-phenyl)-9-fluoro-2,3,4,5-tetrahydro-[1,4]diazepino[1,2-a]indol-1-one | 0.03 |
| 30 | 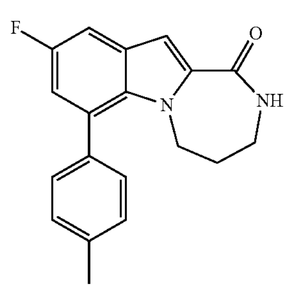 [SMILES: Cc1ccc(-c2cc(F)cc3cc4n(c23)CCCNC4=O)cc1] | 9-Fluoro-7-p-tolyl-2,3,4,5-tetrahydro-[1,4]diazepino[1,2-a]indol-1-one | 0.036 |

| Ex. | Structure | Name | EC$_{150}$ (uM) |
|---|---|---|---|
| 31 | 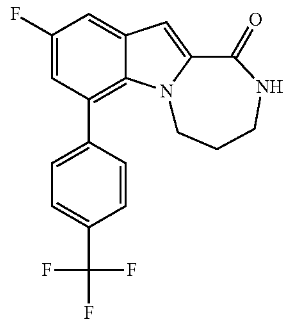 [SMILES: O=C1NCCCn2c1cc1cc(F)cc(-c3ccc(C(F)(F)F)cc3)c12] | 9-Fluoro-7-(4-trifluoromethyl-phenyl)-2,3,4,5-tetrahydro-[1,4]diazepino[1,2-a]indol-1-one | 0.056 |
| 32 | 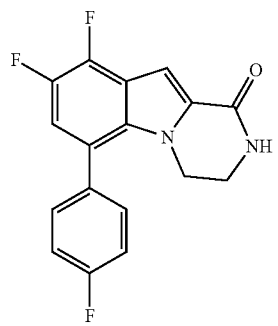 [SMILES: O=C1NCCn2c1cc1c(F)c(F)cc(-c3ccc(F)cc3)c12] | 8,9-Difluoro-6-(4-fluoro-phenyl)-3,4-dihydro-2H-pyrazino[1,2-a]indol-1-one | 2.6 |
| 33 | 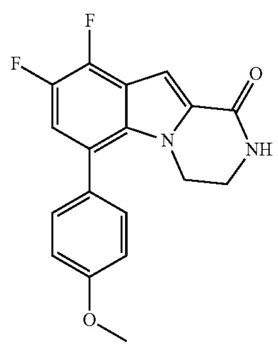 [SMILES: COc1ccc(-c2cc(F)c(F)c3cc4n(c23)CCNC4=O)cc1] | 8,9-Difluoro-6-(4-methoxy-phenyl)-3,4-dihydro-2H-pyrazino[1,2-a]indol-1-one | 0.22 |
| 34 | 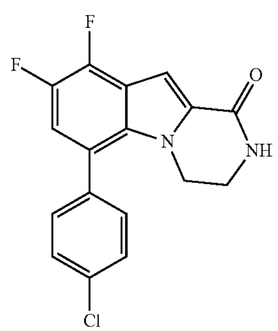 [SMILES: O=C1NCCn2c1cc1c(F)c(F)cc(-c3ccc(Cl)cc3)c12] | 6-(4-Chloro-phenyl)-8,9-difluoro-3,4-dihydro-2H-pyrazino[1,2-a]indol-1-one | 1.4 |

-continued

| Ex. | Structure | Name | EC$_{150}$ (uM) |
|---|---|---|---|
| 35 | 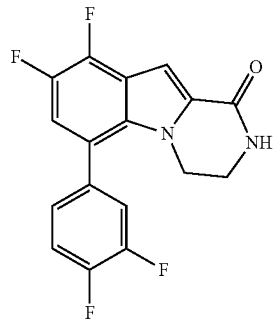 [SMILES: O=C1NCCn2c1cc1c(F)c(F)cc(-c3ccc(F)c(F)c3)c12] | 6-(3,4-Difluoro-phenyl)-8,9-difluoro-3,4-dihydro-2H-pyrazino[1,2-a]indol-1-one | 2.6 |
| 36 | 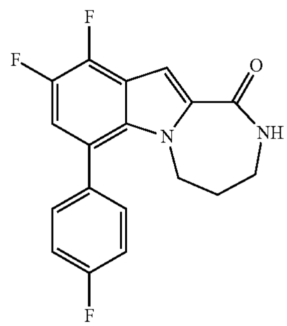 [SMILES: O=C1NCCCn2c1cc1c(F)c(F)cc(-c3ccc(F)cc3)c12] | 9,10-Difluoro-7-(4-fluoro-phenyl)-2,3,4,5-tetrahydro-[1,4]diazepino[1,2-a]indol-1-one | 3.9 |
| 37 | 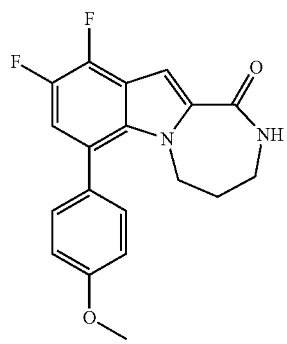 [SMILES: COc1ccc(-c2cc(F)c(F)c3cc4n(c23)CCCNC4=O)cc1] | 9,10-Difluoro-7-(4-methoxy-phenyl)-2,3,4,5-tetrahydro-[1,4]diazepino[1,2-a]indol-1-one | 0.45 |
| 38 | 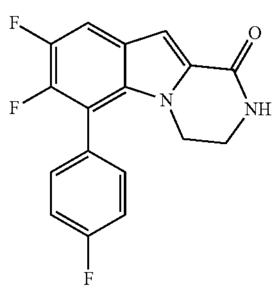 [SMILES: O=C1NCCn2c1cc1cc(F)c(F)c(-c3ccc(F)cc3)c12] | 7,8-Difluoro-6-(4-fluoro-phenyl)-3,4-dihydro-2H-pyrazino[1,2-a]indol-1-one | 0.03 |
| 39 | 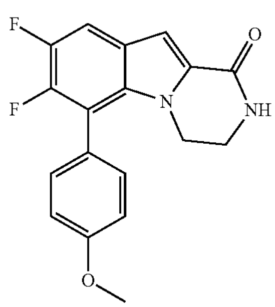 [SMILES: COc1ccc(-c2c(F)c(F)cc3cc4n(c23)CCNC4=O)cc1] | 7,8-Difluoro-6-(4-methoxy-phenyl)-3,4-dihydro-2H-pyrazino[1,2-a]indol-1-one | 0.005 |

-continued
| Ex. | Structure | Name | EC$_{150}$ (uM) |
|---|---|---|---|
| 40 | 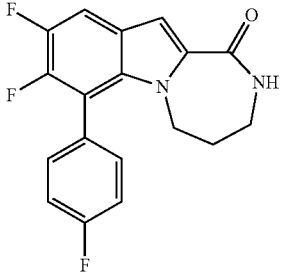 [SMILES: O=C1NCCCn2c1cc1cc(F)c(F)c(-c3ccc(F)cc3)c12] | 8,9-Difluoro-7-(4-fluoro-phenyl)-2,3,4,5-tetrahydro-[1,4]diazepino[1,2-a]indol-1-one | 0.024 |
| 41 | 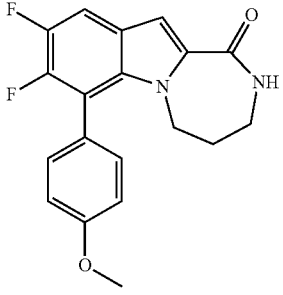 [SMILES: COc1ccc(-c2c(F)c(F)cc3cc4n(c23)CCCNC4=O)cc1] | 8,9-Difluoro-7-(4-methoxy-phenyl)-2,3,4,5-tetrahydro-[1,4]diazepino[1,2-a]indol-1-one | 0.006 |
| 42 | 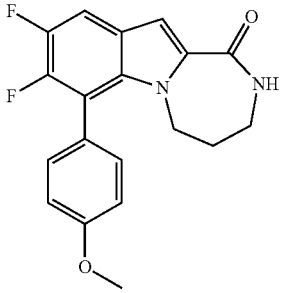 [SMILES: COc1ccc(-c2c(F)c(F)cc3cc4n(c23)CCCNC4=O)cc1] | 7-(3,4-Difluoro-phenyl)-8,9-difluoro-2,3,4,5-tetrahydro-[1,4]diazepino[1,2-a]indol-1-one | 0.21 |
| 43 | 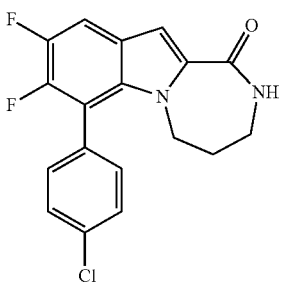 | 7-(4-Chloro-phenyl)-8,9-difluoro-2,3,4,5-tetrahydro-[1,4]diazepino[1,2-a]indol-1-one | 0.08 |
| 44 | 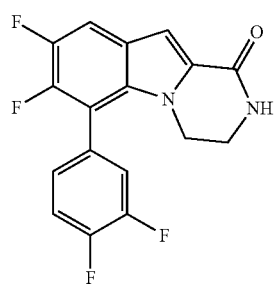 [SMILES: O=C1NCCn2c1cc1cc(F)c(F)c(-c3ccc(F)c(F)c3)c12] | 6-(3,4-Difluoro-phenyl)-7,8-difluoro-3,4-dihydro-2H-pyrazino[1,2-a]indol-1-one | 0.3 |

-continued
| Ex. | Structure | Name | EC₁₅₀ (uM) |
|---|---|---|---|
| 45 | 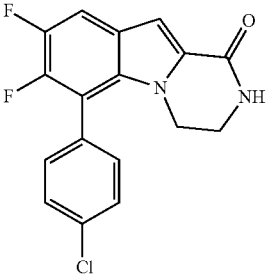 [SMILES: O=C1NCCn2c1cc1cc(F)c(F)c(-c3ccc(Cl)cc3)c12] | 6-(4-Chloro-phenyl)-7,8-difluoro-3,4-dihydro-2H-pyrazino[1,2-a]indol-1-one | 0.076 |
| 46 | 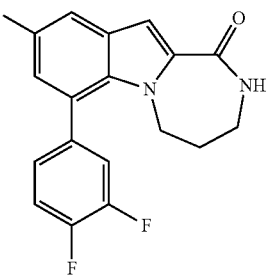 | 9-Chloro-7-(3,4-difluoro-phenyl)-2,3,4,5-tetrahydro-[1,4]diazepino[1,2-a]indol-1-one | 0.69 |
| 47 | 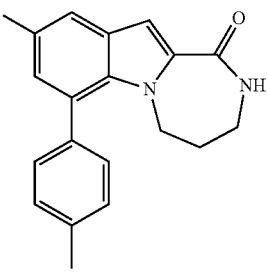 | 9-Chloro-7-p-tolyl-2,3,4,5-tetrahydro-[1,4]diazepino[1,2-a]indol-1-one | 0.6 |
| 48 | 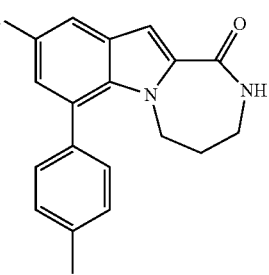 | 9-Chloro-7-(4-fluoro-phenyl)-2,3,4,5-tetrahydro-[1,4]diazepino[1,2-a]indol-1-one | 0.43 |
| 49 | 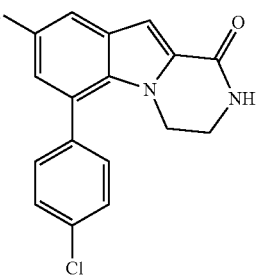 | 8-Chloro-6-(4-chloro-phenyl)-3,4-dihydro-2H-pyrazino[1,2-a]indol-1-one | 0.045 |

-continued

| Ex. | Structure | Name | EC$_{150}$ (uM) |
|---|---|---|---|
| 50 | 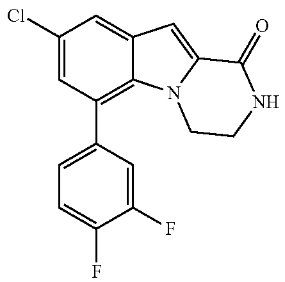 [SMILES: O=C1NCCn2c1cc1cc(Cl)cc(-c3ccc(F)c(F)c3)c12] | 8-Chloro-6-(3,4-difluoro-phenyl)-3,4-dihydro-2H-pyrazino[1,2-a]indol-1-one | 0.13 |
| 51 | 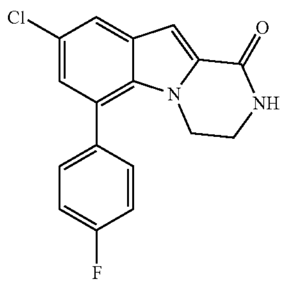 [SMILES: O=C1NCCn2c1cc1cc(Cl)cc(-c3ccc(F)cc3)c12] | 8-Chloro-6-(4-fluoro-phenyl)-3,4-dihydro-2H-pyrazino[1,2-a]indol-1-one | 0.098 |
| 52 | 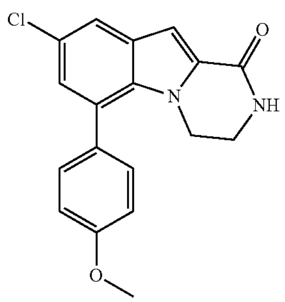 [SMILES: COc1ccc(-c2cc(Cl)cc3cc4n(c23)CCNC4=O)cc1] | 8-Chloro-6-(4-methoxy-phenyl)-3,4-dihydro-2H-pyrazino[1,2-a]indol-1-one | 0.022 |
| 53 | 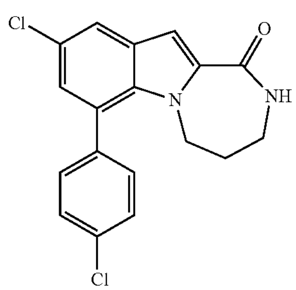 [SMILES: O=C1NCCCn2c1cc1cc(Cl)cc(-c3ccc(Cl)cc3)c12] | 9-Chloro-7-(4-chloro-phenyl)-2,3,4,5-tetrahydro-[1,4]diazepino[1,2-a]indol-1-one | 0.15 |
| 54 | 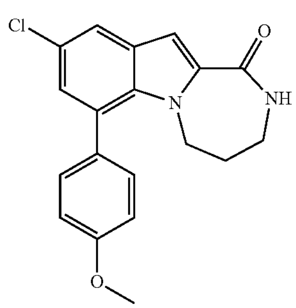 [SMILES: COc1ccc(-c2cc(Cl)cc3cc4n(c23)CCCNC4=O)cc1] | 9-Chloro-7-(4-methoxy-phenyl)-2,3,4,5-tetrahydro-[1,4]diazepino[1,2-a]indol-1-one | 0.07 |

-continued

| Ex. | Structure | Name | EC$_{150}$ (uM) |
|---|---|---|---|
| 55 | 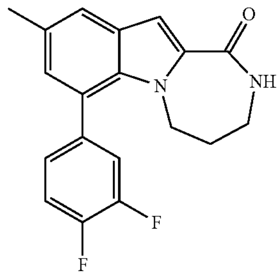 [SMILES: Cc1cc(-c2ccc(F)c(F)c2)c2c(c1)cc1n2CCCNC1=O] | 7-(3,4-Difluoro-phenyl)-9-methyl-2,3,4,5-tetrahydro-[1,4]diazepino[1,2-a]indol-1-one | 2.8 |
| 56 | 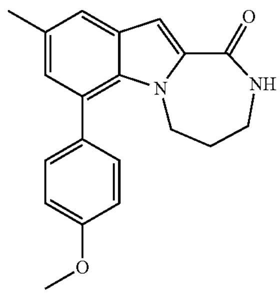 [SMILES: COc1ccc(-c2cc(C)cc3cc4n(c23)CCCNC4=O)cc1] | 7-(4-Methoxy-phenyl)-9-methyl-2,3,4,5-tetrahydro-[1,4]diazepino[1,2-a]indol-1-one | 0.35 |
| 57 | 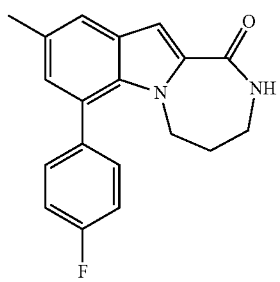 [SMILES: Cc1cc(-c2ccc(F)cc2)c2c(c1)cc1n2CCCNC1=O] | 7-(4-Fluoro-phenyl)-9-methyl-2,3,4,5-tetrahydro-[1,4]diazepino[1,2-a]indol-1-one | 1.44 |
| 58 | 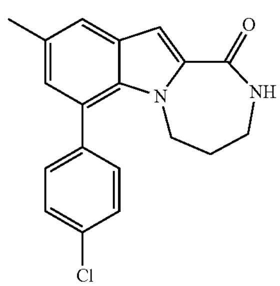 [SMILES: Cc1cc(-c2ccc(Cl)cc2)c2c(c1)cc1n2CCCNC1=O] | 7-(4-Chloro-phenyl)-9-methyl-2,3,4,5-tetrahydro-[1,4]diazepino[1,2-a]indol-1-one | 1.51 |
| 59 | 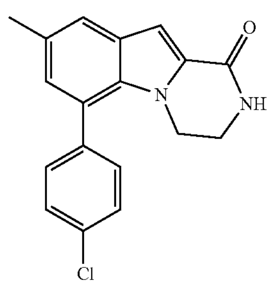 [SMILES: Cc1cc(-c2ccc(Cl)cc2)c2c(c1)cc1n2CCNC1=O] | 6-(4-Chloro-phenyl)-8-methyl-3,4-dihydro-2H-pyrazino[1,2-a]indol-1-one | 0.18 |

-continued

| Ex. | Structure | Name | EC$_{150}$ (uM) |
|---|---|---|---|
| 60 | 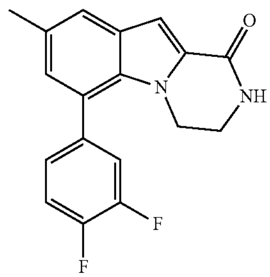 [SMILES: Cc1cc(-c2ccc(F)c(F)c2)c2c(c1)cc1n2CCNC1=O] | 6-(3,4-Difluoro-phenyl)-8-methyl-3,4-dihydro-2H-pyrazino[1,2-a]indol-1-one | 0.71 |
| 61 | 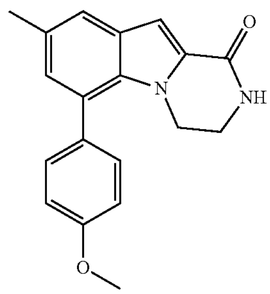 [SMILES: COc1ccc(-c2cc(C)cc3cc4n(c23)CCNC4=O)cc1] | 6-(4-Methoxy-phenyl)-8-methyl-3,4-dihydro-2H-pyrazino[1,2-a]indol-1-one | 0.059 |
| 62 | 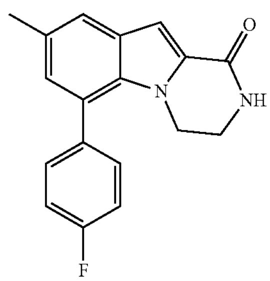 [SMILES: Cc1cc(-c2ccc(F)cc2)c2c(c1)cc1n2CCNC1=O] | 6-(4-Fluoro-phenyl)-8-methyl-3,4-dihydro-2H-pyrazino[1,2-a]indol-1-one | 0.32 |
| 63 | 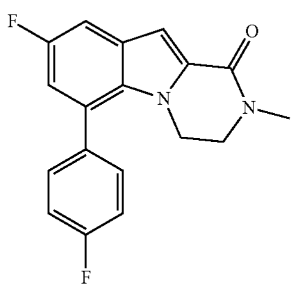 [SMILES: CN1CCn2c(cc3cc(F)cc(-c4ccc(F)cc4)c32)C1=O] | 8-Fluoro-6-(4-fluoro-phenyl)-2-methyl-3,4-dihydro-2H-pyrazino[1,2-a]indol-1-one | 0.6 |
| 64 | 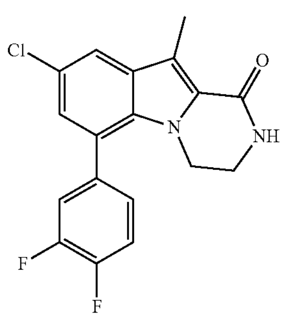 [SMILES: Cc1c2n(c3c(-c4ccc(F)c(F)c4)cc(Cl)cc13)CCNC2=O] | 8-Chloro-6-(3,4-difluoro-phenyl)-10-methyl-3,4-dihydro-2H-pyrazino[1,2-a]indol-1-one | 0.12 |

-continued

| Ex. | Structure | Name | EC$_{150}$ (uM) |
|---|---|---|---|
| 65 | 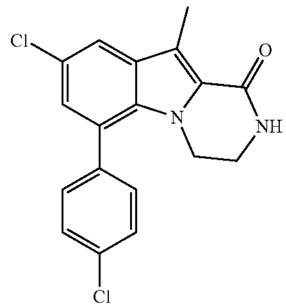 [SMILES: Cc1c2n(c3c(-c4ccc(Cl)cc4)cc(Cl)cc13)CCNC2=O] | 8-Chloro-6-(4-chloro-phenyl)-10-methyl-3,4-dihydro-2H-pyrazino[1,2-a]indol-1-one | 0.019 |
| 66 | 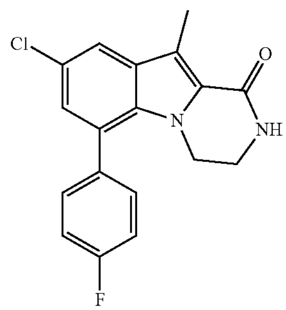 [SMILES: Cc1c2n(c3c(-c4ccc(F)cc4)cc(Cl)cc13)CCNC2=O] | 8-Chloro-6-(4-fluoro-phenyl)-10-methyl-3,4-dihydro-2H-pyrazino[1,2-a]indol-1-one | 0.047 |
| 67 | 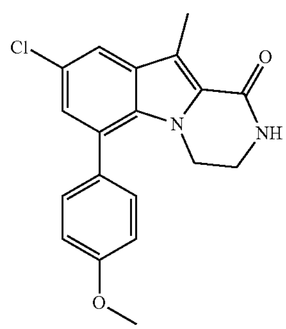 [SMILES: COc1ccc(-c2cc(Cl)cc3c(C)c4n(c23)CCNC4=O)cc1] | 8-Chloro-6-(4-methoxy-phenyl)-10-methyl-3,4-dihydro-2H-pyrazino[1,2-a]indol-1-one | 0.008 |
| 68 | 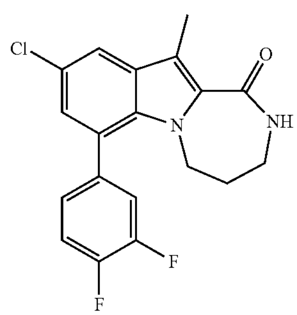 [SMILES: Cc1c2n(c3c(-c4ccc(F)c(F)c4)cc(Cl)cc13)CCCNC2=O] | 9-Chloro-7-(3,4-difluoro-phenyl)-11-methyl-2,3,4,5-tetrahydro-[1,4]diazepino[1,2-a]indol-1-one | 0.12 |
| 69 | 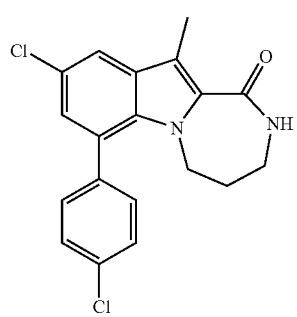 [SMILES: Cc1c2n(c3c(-c4ccc(Cl)cc4)cc(Cl)cc13)CCCNC2=O] | 9-Chloro-7-(4-chloro-phenyl)-11-methyl-2,3,4,5-tetrahydro-[1,4]diazepino[1,2-a]indol-1-one | 0.061 |

-continued
| Ex. | Structure | Name | EC$_{150}$ (uM) |
|---|---|---|---|
| 70 | 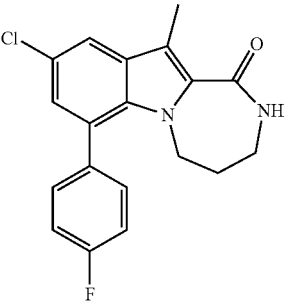 [SMILES: Cc1c2n(c3c(-c4ccc(F)cc4)cc(Cl)cc13)CCCNC2=O] | 9-Chloro-7-(4-fluoro-phenyl)-11-methyl-2,3,4,5-tetrahydro-[1,4]diazepino[1,2-a]indol-1-one | 0.063 |
| 71 | 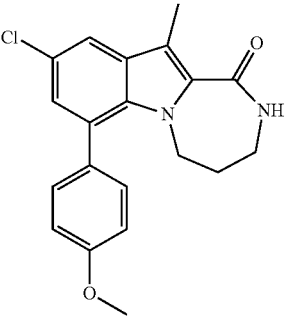 [SMILES: COc1ccc(-c2cc(Cl)cc3c(C)c4n(c23)CCCNC4=O)cc1] | 9-Chloro-7-(4-methoxy-phenyl)-11-methyl-2,3,4,5-tetrahydro-[1,4]diazepino[1,2-a]indol-1-one | 0.021 |
| 72 | 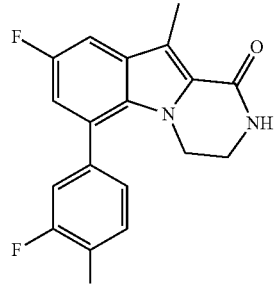 | 6-(3,4-Difluoro-phenyl)-8-fluoro-10-methyl-3,4-dihydro-2H-pyrazino[1,2-a]indol-1-one | 0.12 |
| 73 | 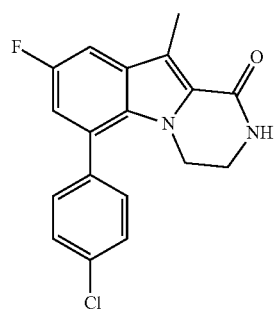 [SMILES: Cc1c2n(c3c(-c4ccc(Cl)cc4)cc(F)cc13)CCNC2=O] | 6-(4-Chloro-phenyl)-8-fluoro-10-methyl-3,4-dihydro-2H-pyrazino[1,2-a]indol-1-one | 0.017 |
| 74 | 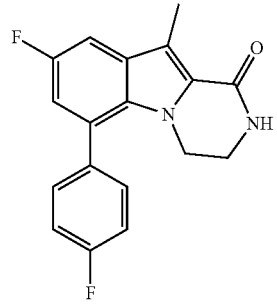 | 8-Fluoro-6-(4-fluoro-phenyl)-10-methyl-3,4-dihydro-2H-pyrazino[1,2-a]indol-1-one | 0.072 |

| Ex. | Structure | Name | EC$_{150}$ (uM) |
|---|---|---|---|
| 75 | 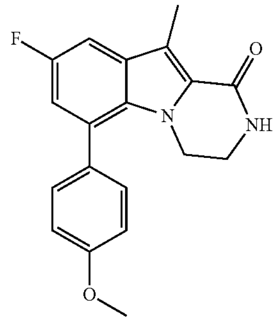 [SMILES: COc1ccc(-c2cc(F)cc3c(C)c4n(c23)CCNC4=O)cc1] | 8-Fluoro-6-(4-methoxy-phenyl)-10-methyl-3,4-dihydro-2H-pyrazino[1,2-a]indol-1-one | 0.005 |
| 76 | 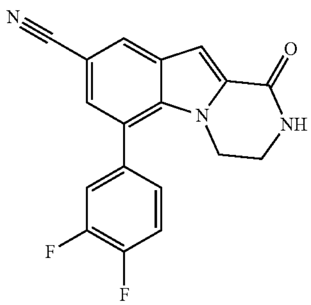 [SMILES: N#Cc1cc(-c2ccc(F)c(F)c2)c2c(c1)cc1n2CCNC1=O] | 6-(3,4-Difluoro-phenyl)-1-oxo-1,2,3,4-tetrahydro-pyrazino[1,2-a]indole-8-carbonitrile | 0.02 |
| 77 | 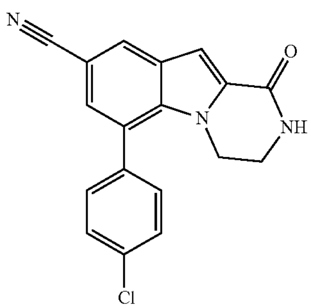 | 6-(4-Chloro-phenyl)-1-oxo-1,2,3,4-tetrahydro-pyrazino[1,2-a]indole-8-carbonitrile | 0.02 |
| 78 | 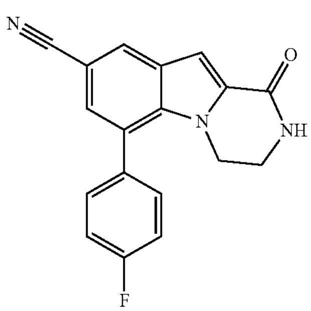 [SMILES: N#Cc1cc(-c2ccc(F)cc2)c2c(c1)cc1n2CCNC1=O] | 6-(4-Fluoro-phenyl)-1-oxo-1,2,3,4-tetrahydro-pyrazino[1,2-a]indole-8-carbonitrile | 0.012 |
| 79 | 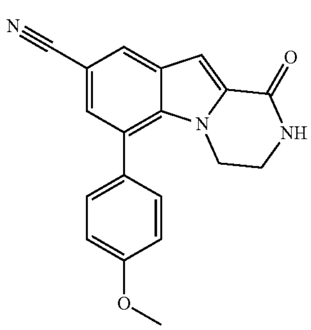 [SMILES: COc1ccc(-c2cc(C#N)cc3cc4n(c23)CCNC4=O)cc1] | 6-(4-Methoxy-phenyl)-1-oxo-1,2,3,4-tetrahydro-pyrazino[1,2-a]indole-8-carbonitrile | 0.004 |

| Ex. | Structure | Name | EC$_{150}$ (uM) |
|---|---|---|---|
| 80 | 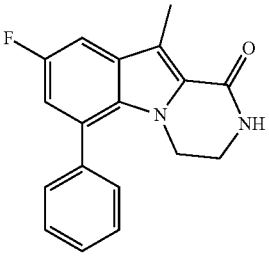 [SMILES: Cc1c2n(c3c(-c4ccccc4)cc(F)cc13)CCNC2=O] | 8-Fluoro-10-methyl-6-phenyl-3,4-dihydro-2H-pyrazino[1,2-a]indol-1-one | 0.098 |
| 81 | 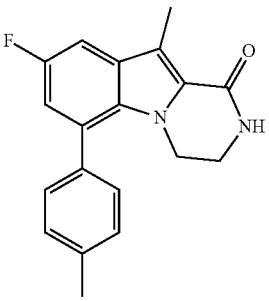 [SMILES: Cc1ccc(-c2cc(F)cc3c(C)c4n(c23)CCNC4=O)cc1] | 8-Fluoro-10-methyl-6-p-tolyl-3,4-dihydro-2H-pyrazino[1,2-a]indol-1-one | 0.014 |
| 82 | 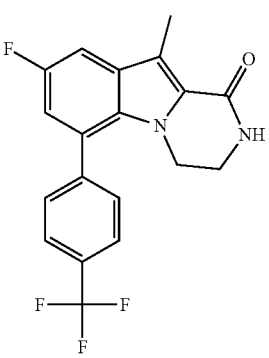 [SMILES: Cc1c2n(c3c(-c4ccc(C(F)(F)F)cc4)cc(F)cc13)CCNC2=O] | 8-Fluoro-10-methyl-6-(4-trifluoromethyl-phenyl)-3,4-dihydro-2H-pyrazino[1,2-a]indol-1-one | 0.036 |
| 83 | 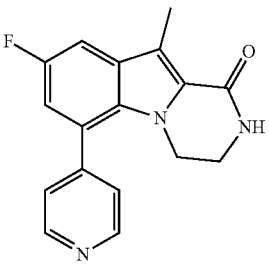 | 8-Fluoro-10-methyl-6-pyridin-4-yl-3,4-dihydro-2H-pyrazino[1,2-a]indol-1-one | 0.039 |
| 84 | 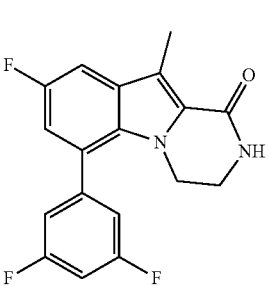 [SMILES: Cc1c2n(c3c(-c4cc(F)cc(F)c4)cc(F)cc13)CCNC2=O] | 6-(3,5-Difluoro-phenyl)-8-fluoro-10-methyl-3,4-dihydro-2H-pyrazino[1,2-a]indol-1-one | 0.15 |

-continued

| Ex. | Structure | Name | EC$_{150}$ (uM) |
|---|---|---|---|
| 85 | 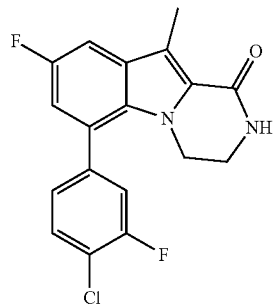 [SMILES: Cc1c2n(c3c(-c4ccc(Cl)c(F)c4)cc(F)cc13)CCNC2=O] | 6-(4-Chloro-3-fluoro-phenyl)-8-fluoro-10-methyl-3,4-dihydro-2H-pyrazino[1,2-a]indol-1-one | 0.04 |
| 86 | 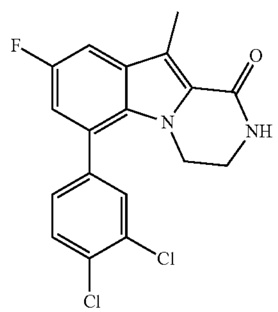 [SMILES: Cc1c2n(c3c(-c4ccc(Cl)c(Cl)c4)cc(F)cc13)CCNC2=O] | 6-(3,4-Dichloro-phenyl)-8-fluoro-10-methyl-3,4-dihydro-2H-pyrazino[1,2-a]indol-1-one | 0.05 |
| 87 | 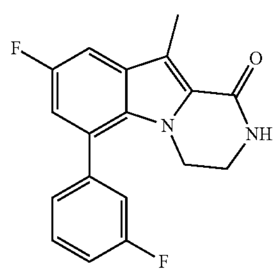 [SMILES: Cc1c2n(c3c(-c4cccc(F)c4)cc(F)cc13)CCNC2=O] | 8-Fluoro-6-(3-fluoro-phenyl)-10-methyl-3,4-dihydro-2H-pyrazino[1,2-a]indol-1-one | 0.1 |
| 88 | 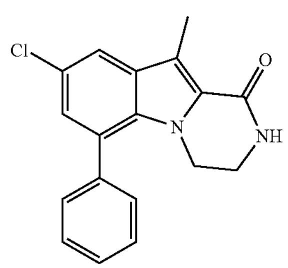 [SMILES: Cc1c2n(c3c(-c4ccccc4)cc(Cl)cc13)CCNC2=O] | 8-Chloro-10-methyl-6-phenyl-3,4-dihydro-2H-pyrazino[1,2-a]indol-1-one | 0.053 |
| 89 | 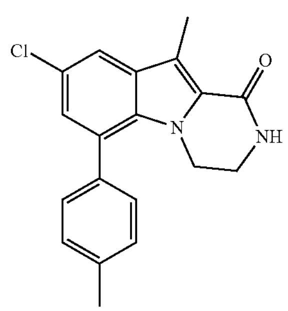 [SMILES: Cc1ccc(-c2cc(Cl)cc3c(C)c4n(c23)CCNC4=O)cc1] | 8-Chloro-10-methyl-6-p-tolyl-3,4-dihydro-2H-pyrazino[1,2-a]indol-1-one | 0.01 |

-continued

| Ex. | Structure | Name | EC$_{150}$ (uM) |
|---|---|---|---|
| 90 | 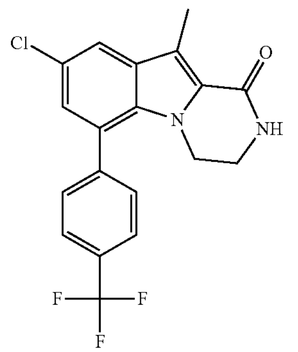 [SMILES: Cc1c2n(c3c(-c4ccc(C(F)(F)F)cc4)cc(Cl)cc13)CCNC2=O] | 8-Chloro-10-methyl-6-(4-trifluoromethyl-phenyl)-3,4-dihydro-2H-pyrazino[1,2-a]indol-1-one | 0.017 |
| 91 | 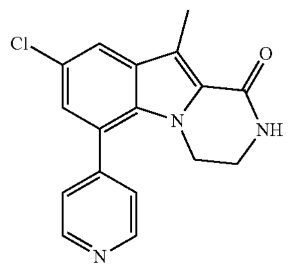 [SMILES: Cc1c2n(c3c(-c4ccncc4)cc(Cl)cc13)CCNC2=O] | 8-Chloro-10-methyl-6-pyridin-4-yl-3,4-dihydro-2H-pyrazino[1,2-a]indol-1-one | 0.017 |
| 92 | 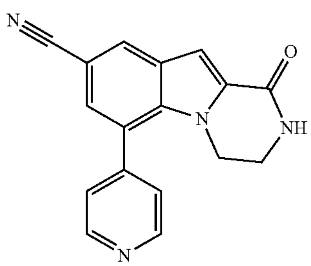 [SMILES: N#Cc1cc(-c2ccncc2)c2c(c1)cc1n2CCNC1=O] | 1-Oxo-6-pyridin-4-yl-1,2,3,4-tetrahydro-pyrazino[1,2-a]indole-8-carbonitrile | 0.047 |
| 93 | 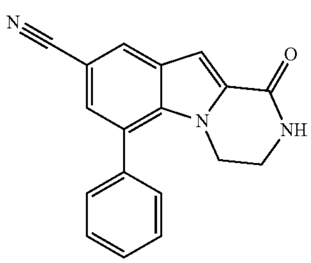 [SMILES: N#Cc1cc(-c2ccccc2)c2c(c1)cc1n2CCNC1=O] | 1-Oxo-6-phenyl-1,2,3,4-tetrahydro-pyrazino[1,2-a]indole-8-carbonitrile | 0.035 |
| 94 | 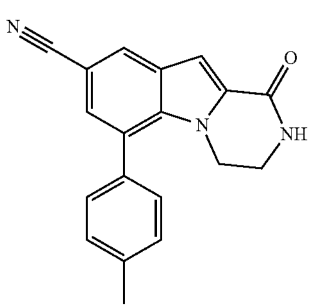 [SMILES: Cc1ccc(-c2cc(C#N)cc3cc4n(c23)CCNC4=O)cc1] | 1-Oxo-6-p-tolyl-1,2,3,4-tetrahydro-pyrazino[1,2-a]indole-8-carbonitrile | 0.011 |

-continued

| Ex. | Structure | Name | EC$_{150}$ (uM) |
|---|---|---|---|
| 95 | 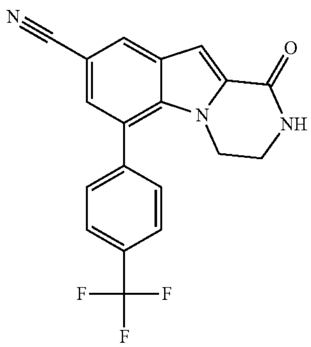 [SMILES: N#Cc1cc(-c2ccc(C(F)(F)F)cc2)c2c(c1)cc1n2CCNC1=O] | 1-Oxo-6-(4-trifluoromethyl-phenyl)-1,2,3,4-tetrahydro-pyrazino[1,2-a]indole-8-carbonitrile | 0.018 |
| 96 | 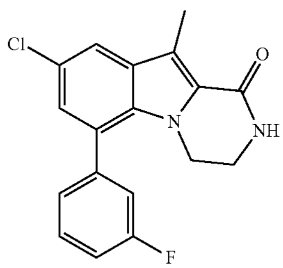 [SMILES: Cc1c2n(c3c(-c4cccc(F)c4)cc(Cl)cc13)CCNC2=O] | 8-Chloro-6-(3-fluoro-phenyl)-10-methyl-3,4-dihydro-2H-pyrazino[1,2-a]indol-1-one | 0.15 |
| 97 | 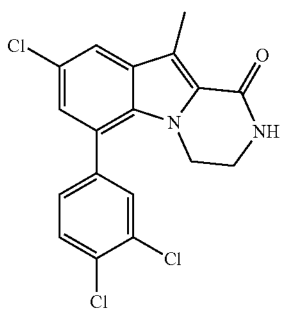 [SMILES: Cc1c2n(c3c(-c4ccc(Cl)c(Cl)c4)cc(Cl)cc13)CCNC2=O] | 8-Chloro-6-(3,4-dichloro-phenyl)-10-methyl-3,4-dihydro-2H-pyrazino[1,2-a]indol-1-one | 0.056 |
| 98 | 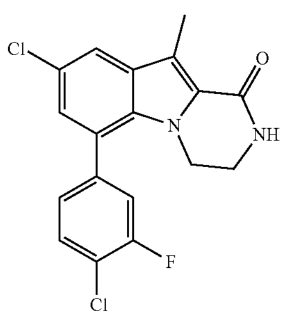 [SMILES: Cc1c2n(c3c(-c4ccc(Cl)c(F)c4)cc(Cl)cc13)CCNC2=O] | 8-Chloro-6-(4-chloro-3-fluoro-phenyl)-10-methyl-3,4-dihydro-2H-pyrazino[1,2-a]indol-1-one | 0.019 |
| 99 | 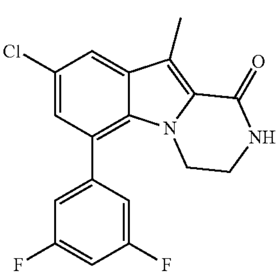 [SMILES: Cc1c2n(c3c(-c4cc(F)cc(F)c4)cc(Cl)cc13)CCNC2=O] | 8-Chloro-6-(3,5-difluoro-phenyl)-10-methyl-3,4-dihydro-2H-pyrazino[1,2-a]indol-1-one | 0.12 |

-continued

| Ex. | Structure | Name | EC$_{150}$ (uM) |
|---|---|---|---|
| 100 | 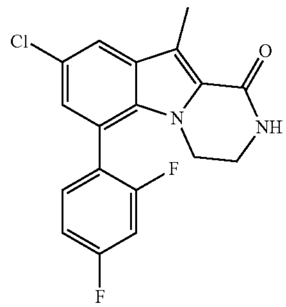 [SMILES: Cc1c2n(c3c(-c4ccc(F)cc4F)cc(Cl)cc13)CCNC2=O] | 8-Chloro-6-(2,4-difluoro-phenyl)-10-methyl-3,4-dihydro-2H-pyrazino[1,2-a]indol-1-one | 0.009 |
| 101 | 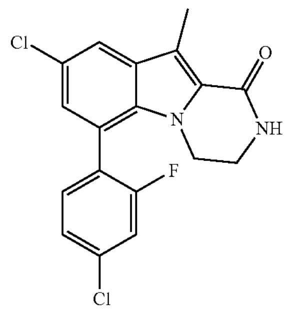 [SMILES: Cc1c2n(c3c(-c4ccc(Cl)cc4F)cc(Cl)cc13)CCNC2=O] | 8-Chloro-6-(4-chloro-2-fluoro-phenyl)-10-methyl-3,4-dihydro-2H-pyrazino[1,2-a]indol-1-one | 0.006 |
| 102 | 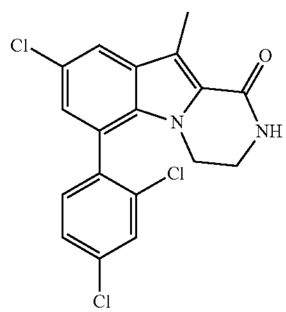 [SMILES: Cc1c2n(c3c(-c4ccc(Cl)cc4Cl)cc(Cl)cc13)CCNC2=O] | 8-Chloro-6-(2,4-dichloro-phenyl)-10-methyl-3,4-dihydro-2H-pyrazino[1,2-a]indol-1-one | 0.009 |
| 103 | 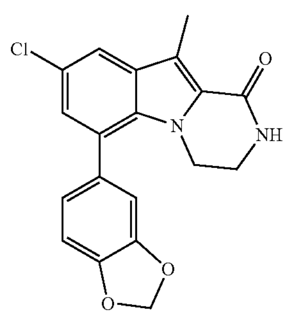 [SMILES: Cc1c2n(c3c(-c4ccc5c(c4)OCO5)cc(Cl)cc13)CCNC2=O] | 6-Benzo[1,3]dioxol-5-yl-8-chloro-10-methyl-3,4-dihydro-2H-pyrazino[1,2-a]indol-1-one | 0.018 |
| 104 | 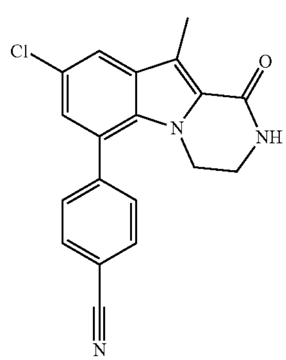 [SMILES: Cc1c2n(c3c(-c4ccc(C#N)cc4)cc(Cl)cc13)CCNC2=O] | 4-(8-Chloro-10-methyl-1-oxo-1,2,3,4-tetrahydro-pyrazino[1,2-a]indol-6-yl)-benzonitrile | 0.015 |

-continued

| Ex. | Structure | Name | EC$_{150}$ (uM) |
|---|---|---|---|
| 105 | 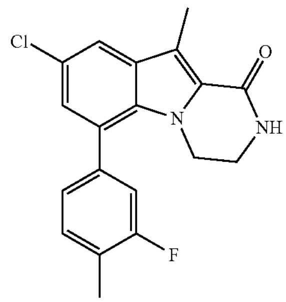 [SMILES: Cc1ccc(-c2cc(Cl)cc3c(C)c4n(c23)CCNC4=O)cc1F] | 8-Chloro-6-(3-fluoro-4-methyl-phenyl)-10-methyl-3,4-dihydro-2H-pyrazino[1,2-a]indol-1-one | 0.029 |
| 106 | 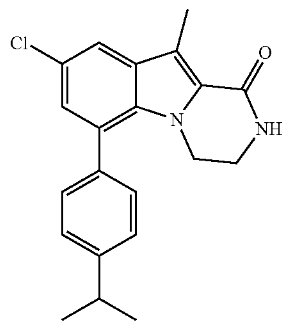 [SMILES: Cc1c2n(c3c(-c4ccc(C(C)C)cc4)cc(Cl)cc13)CCNC2=O] | 8-Chloro-6-(4-isopropyl-phenyl)-10-methyl-3,4-dihydro-2H-pyrazino[1,2-a]indol-1-one | 0.05 |
| 107 | 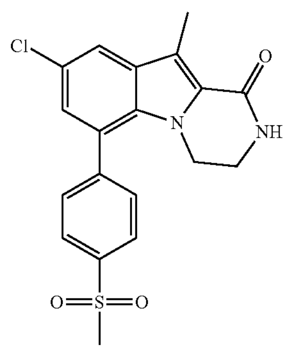 [SMILES: Cc1c2n(c3c(-c4ccc(S(C)(=O)=O)cc4)cc(Cl)cc13)CCNC2=O] | 8-Chloro-6-(4-methanesulfonyl-phenyl)-10-methyl-3,4-dihydro-2H-pyrazino[1,2-a]indol-1-one | 0.027 |
| 108 | 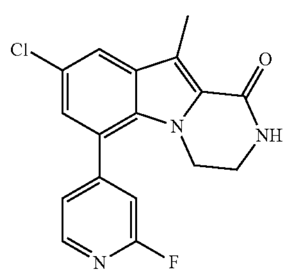 [SMILES: Cc1c2n(c3c(-c4ccnc(F)c4)cc(Cl)cc13)CCNC2=O] | 8-Chloro-6-(2-fluoro-pyridin-4-yl)-10-methyl-3,4-dihydro-2H-pyrazino[1,2-a]indol-1-one | 0.021 |
| 109 | 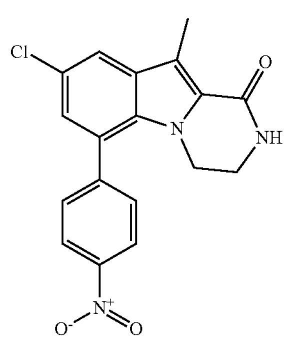 [SMILES: Cc1c2n(c3c(-c4ccc([N+](=O)[O-])cc4)cc(Cl)cc13)CCNC2=O] | 8-Chloro-10-methyl-6-(4-nitro-phenyl)-3,4-dihydro-2H-pyrazino[1,2-a]indol-1-one | 0.007 |

-continued

| Ex. | Structure | Name | EC₁₅₀ (uM) |
|---|---|---|---|
| 110 | 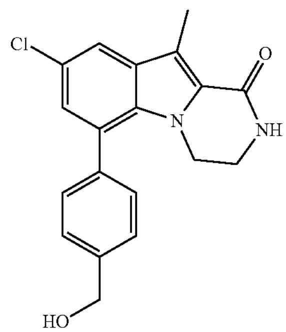 [SMILES: Cc1c2n(c3c(-c4ccc(CO)cc4)cc(Cl)cc13)CCNC2=O] | 8-Chloro-6-(4-hydroxymethyl-phenyl)-10-methyl-3,4-dihydro-2H-pyrazino[1,2-a]indol-1-one | 0.014 |
| 111 | 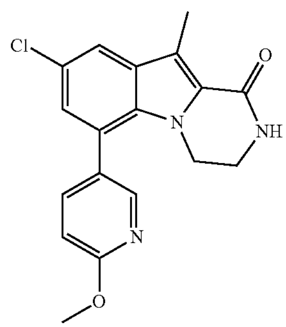 [SMILES: COc1ccc(-c2cc(Cl)cc3c(C)c4n(c23)CCNC4=O)cn1] | 8-Chloro-6-(6-methoxy-pyridin-3-yl)-10-methyl-3,4-dihydro-2H-pyrazino[1,2-a]indol-1-one- | 0.015 |
| 112 | 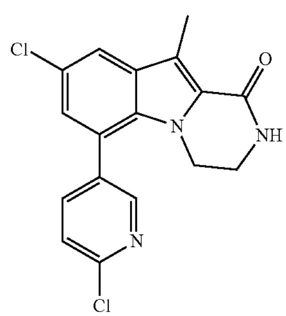 [SMILES: Cc1c2n(c3c(-c4ccc(Cl)nc4)cc(Cl)cc13)CCNC2=O] | 8-Chloro-6-(6-chloro-pyridin-3-yl)-10-methyl-3,4-dihydro-2H-pyrazino[1,2-a]indol-1-one | 0.012 |
| 113 | 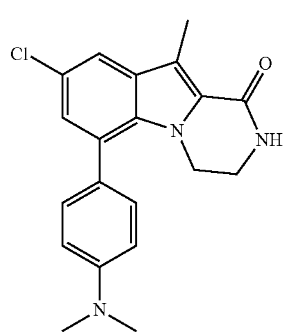 [SMILES: Cc1c2n(c3c(-c4ccc(N(C)C)cc4)cc(Cl)cc13)CCNC2=O] | 8-Chloro-6-(4-dimethylamino-phenyl)-10-methyl-3,4-dihydro-2H-pyrazino[1,2-a]indol-1-one | 0.01 |

| Ex. | Structure | Name | EC$_{150}$ (uM) |
|---|---|---|---|
| 114 | 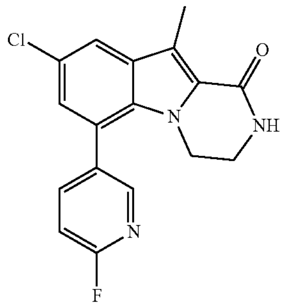 [SMILES: Cc1c2n(c3c(-c4ccc(F)nc4)cc(Cl)cc13)CCNC2=O] | 8-Chloro-6-(6-fluoro-pyridin-3-yl)-10-methyl-3,4-dihydro-2H-pyrazino[1,2-a]indol-1-one | 0.04 |
| 115 | 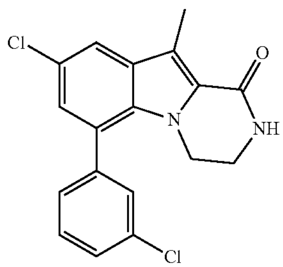 [SMILES: Cc1c2n(c3c(-c4cccc(Cl)c4)cc(Cl)cc13)CCNC2=O] | 8-Chloro-6-(3-chloro-phenyl)-10-methyl-3,4-dihydro-2H-pyrazino[1,2-a]indol-1-one | 0.43 |
| 116 | 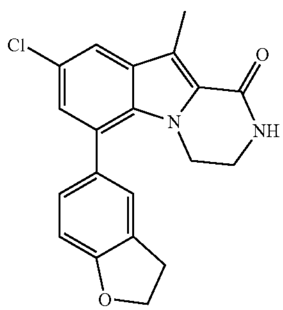 [SMILES: Cc1c2n(c3c(-c4ccc5c(c4)CCO5)cc(Cl)cc13)CCNC2=O] | 8-Chloro-6-(2,3-dihydro-benzofuran-5-yl)-10-methyl-3,4-dihydro-2H-pyrazino[1,2-a]indol-1-one | 0.055 |
| 117 | 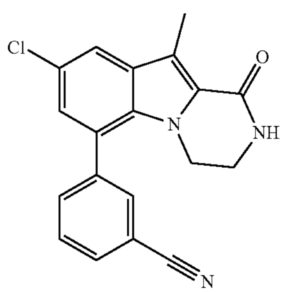 [SMILES: Cc1c2n(c3c(-c4cccc(C#N)c4)cc(Cl)cc13)CCNC2=O] | 3-(8-Chloro-10-methyl-1-oxo-1,2,3,4-tetrahydro-pyrazino[1,2-a]indol-6-yl)-benzonitrile | 0.4 |
| 118 | 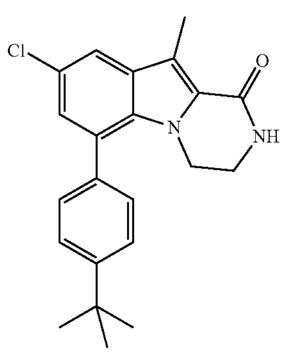 [SMILES: Cc1c2n(c3c(-c4ccc(C(C)(C)C)cc4)cc(Cl)cc13)CCNC2=O] | 6-(4-tert-Butyl-phenyl)-8-chloro-10-methyl-3,4-dihydro-2H-pyrazino[1,2-a]indol-1-one | 0.15 |

| Ex. | Structure | Name | EC₁₅₀ (uM) |
|---|---|---|---|
| 119 | 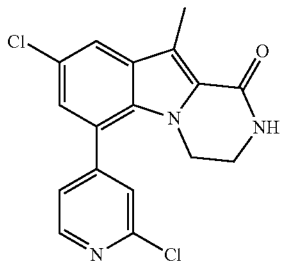 [SMILES: Cc1c2n(c3c(-c4ccnc(Cl)c4)cc(Cl)cc13)CCNC2=O] | 8-Chloro-6-(2-chloro-pyridin-4-yl)-10-methyl-3,4-dihydro-2H-pyrazino[1,2-a]indol-1-one | 0.16 |
| 120 | 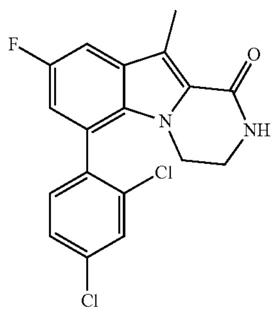 [SMILES: Cc1c2n(c3c(-c4ccc(Cl)cc4Cl)cc(F)cc13)CCNC2=O] | 6-(2,4-Dichloro-phenyl)-8-fluoro-10-methyl-3,4-dihydro-2H-pyrazino[1,2-a]indol-1-one | 0.01 |
| 121 | 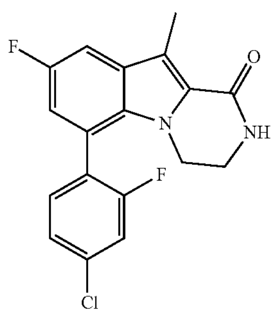 [SMILES: Cc1c2n(c3c(-c4ccc(Cl)cc4F)cc(F)cc13)CCNC2=O] | 6-(4-Chloro-2-fluoro-phenyl)-8-fluoro-10-methyl-3,4-dihydro-2H-pyrazino[1,2-a]indol-1-one | 0.01 |
| 122 | 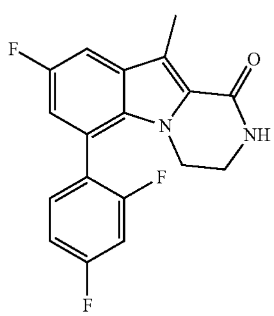 [SMILES: Cc1c2n(c3c(-c4ccc(F)cc4F)cc(F)cc13)CCNC2=O] | 6-(2,4-Difluoro-phenyl)-8-fluoro-10-methyl-3,4-dihydro-2H-pyrazino[1,2-a]indol-1-one | 0.013 |
| 123 | 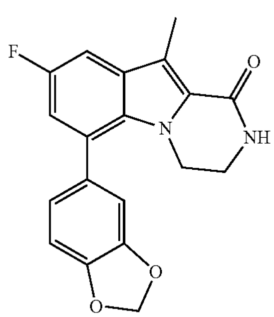 [SMILES: Cc1c2n(c3c(-c4ccc5c(c4)OCO5)cc(F)cc13)CCNC2=O] | 6-Benzo[1,3]dioxol-5-yl-8-fluoro-10-methyl-3,4-dihydro-2H-pyrazino[1,2-a]indol-1-one | 0.031 |

| Ex. | Structure | Name | EC$_{150}$ (uM) |
|---|---|---|---|
| 124 | 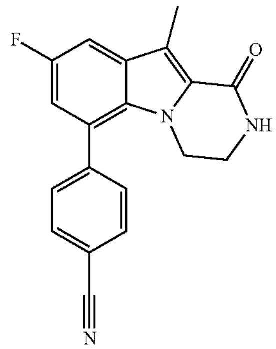 [SMILES: Cc1c2n(c3c(-c4ccc(C#N)cc4)cc(F)cc13)CCNC2=O] | 4-(8-Fluoro-10-methyl-1-oxo-1,2,3,4-tetrahydro-pyrazino[1,2-a]indol-6-yl)-benzonitrile | 0.023 |
| 125 | 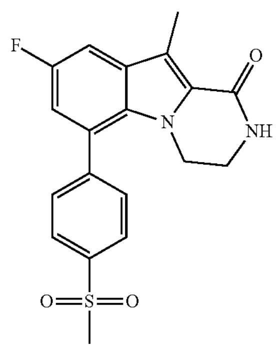 [SMILES: Cc1c2n(c3c(-c4ccc(S(C)(=O)=O)cc4)cc(F)cc13)CCNC2=O] | 8-Fluoro-6-(4-methanesulfonyl-phenyl)-10-methyl-3,4-dihydro-2H-pyrazino[1,2-a]indol-1-one | 0.015 |
| 126 | 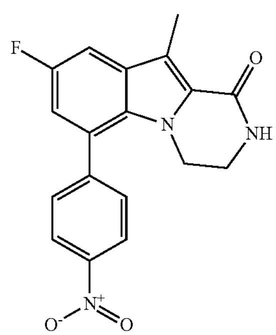 [SMILES: Cc1c2n(c3c(-c4ccc([N+](=O)[O-])cc4)cc(F)cc13)CCNC2=O] | 8-Fluoro-10-methyl-6-(4-nitro-phenyl)-3,4-dihydro-2H-pyrazino[1,2-a]indol-1-one | 0.01 |
| 127 | 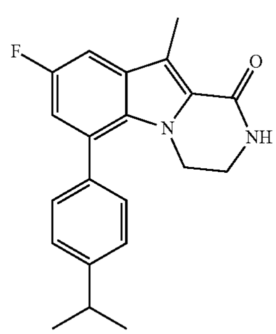 [SMILES: Cc1c2n(c3c(-c4ccc(C(C)C)cc4)cc(F)cc13)CCNC2=O] | 8-Fluoro-6-(4-isopropyl-phenyl)-10-methyl-3,4-dihydro-2H-pyrazino[1,2-a]indol-1-one | 0.025 |

-continued

| Ex. | Structure | Name | EC$_{150}$ (uM) |
|---|---|---|---|
| 128 | 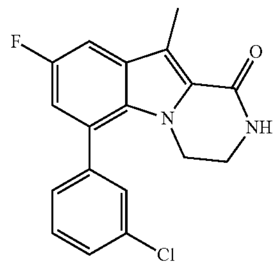 [SMILES: Cc1c2n(c3c(-c4cccc(Cl)c4)cc(F)cc13)CCNC2=O] | 6-(3-Chloro-phenyl)-8-fluoro-10-methyl-3,4-dihydro-2H-pyrazino[1,2-a]indol-1-one | 0.22 |
| 129 | 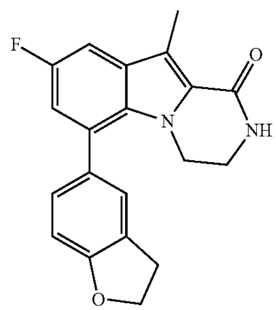 [SMILES: Cc1c2n(c3c(-c4ccc5c(c4)CCO5)cc(F)cc13)CCNC2=O] | 6-(2,3-Dihydro-benzofuran-5-yl)-8-fluoro-10-methyl-3,4-dihydro-2H-pyrazino[1,2-a]indol-1-one | 0.022 |
| 130 | 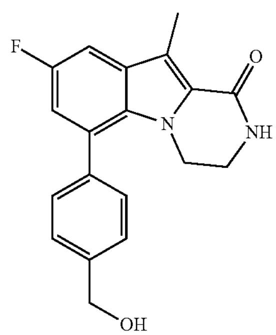 [SMILES: Cc1c2n(c3c(-c4ccc(CO)cc4)cc(F)cc13)CCNC2=O] | 8-Fluoro-6-(4-hydroxymethyl-phenyl)-10-methyl-3,4-dihydro-2H-pyrazino[1,2-a]indol-1-one | 0.011 |
| 131 | 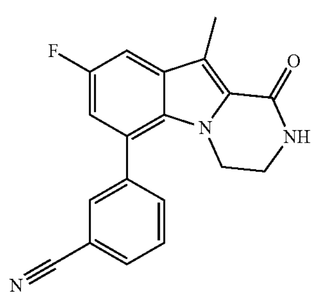 [SMILES: Cc1c2n(c3c(-c4cccc(C#N)c4)cc(F)cc13)CCNC2=O] | 3-(8-Fluoro-10-methyl-1-oxo-1,2,3,4-tetrahydro-pyrazino[1,2-a]indol-6-yl)-benzonitrile | 0.33 |
| 132 | 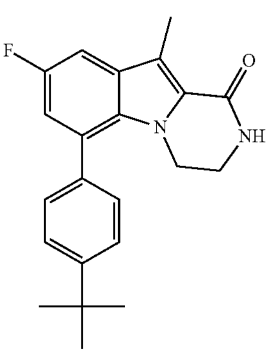 [SMILES: Cc1c2n(c3c(-c4ccc(C(C)(C)C)cc4)cc(F)cc13)CCNC2=O] | 6-(4-tert-Butyl-phenyl)-8-fluoro-10-methyl-3,4-dihydro-2H-pyrazino[1,2-a]indol-1-one | 0.046 |

-continued

| Ex. | Structure | Name | EC$_{150}$ (uM) |
|---|---|---|---|
| 133 | 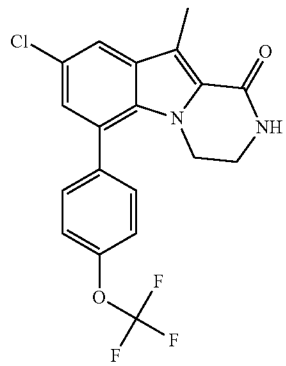 [SMILES: Cc1c2n(c3c(-c4ccc(OC(F)(F)F)cc4)cc(Cl)cc13)CCNC2=O] | 8-Chloro-10-methyl-6-(4-trifluoromethoxy-phenyl)-3,4-dihydro-2H-pyrazino[1,2-a]indol-1-one | 0.004 |
| 134 | 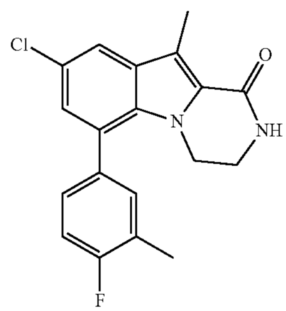 [SMILES: Cc1cc(-c2cc(Cl)cc3c(C)c4n(c23)CCNC4=O)ccc1F] | 8-Chloro-6-(4-fluoro-3-methyl-phenyl)-10-methyl-3,4-dihydro-2H-pyrazino[1,2-a]indol-1-one | 0.083 |
| 135 | 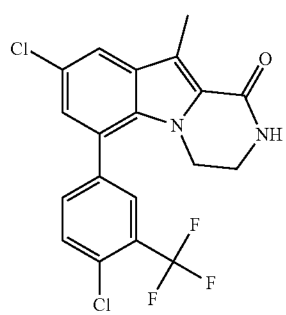 [SMILES: Cc1c2n(c3c(-c4ccc(Cl)c(C(F)(F)F)c4)cc(Cl)cc13)CCNC2=O] | 8-Chloro-6-(4-chloro-3-trifluoromethyl-phenyl)-10-methyl-3,4-dihydro-2H-pyrazino[1,2-a]indol-1-one | 0.036 |
| 136 | 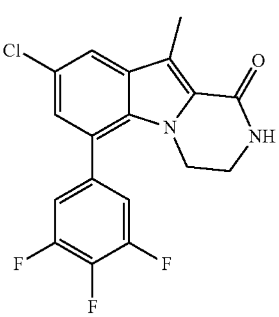 [SMILES: Cc1c2n(c3c(-c4cc(F)c(F)c(F)c4)cc(Cl)cc13)CCNC2=O] | 8-Chloro-10-methyl-6-(3,4,5-trifluoro-phenyl)-3,4-dihydro-2H-pyrazino[1,2-a]indol-1-one | 0.021 |
| 137 | 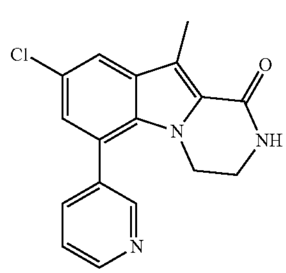 [SMILES: Cc1c2n(c3c(-c4cccnc4)cc(Cl)cc13)CCNC2=O] | 8-Chloro-10-methyl-6-pyridin-3-yl-3,4-dihydro-2H-pyrazino[1,2-a]indol-1-one | 0.088 |

-continued

| Ex. | Structure | Name | EC₁₅₀ (uM) |
|---|---|---|---|
| 138 | 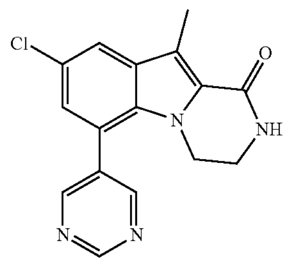 [SMILES: Cc1c2n(c3c(-c4cncnc4)cc(Cl)cc13)CCNC2=O] | 8-Chloro-10-methyl-6-pyrimidin-5-yl-3,4-dihydro-2H-pyrazino[1,2-a]indol-1-one | 0.21 |
| 139 | 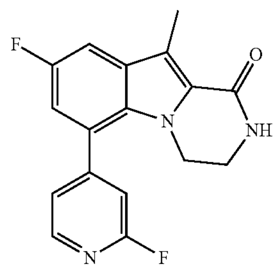 [SMILES: Cc1c2n(c3c(-c4ccnc(F)c4)cc(F)cc13)CCNC2=O] | 8-Fluoro-6-(2-fluoro-pyridin-4-yl)-10-methyl-3,4-dihydro-2H-pyrazino[1,2-a]indol-1-one | 0.027 |
| 140 | 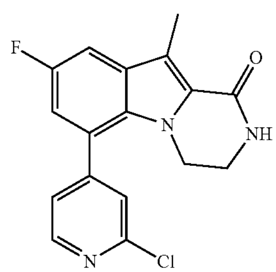 [SMILES: Cc1c2n(c3c(-c4ccnc(Cl)c4)cc(F)cc13)CCNC2=O] | 6-(2-Chloro-pyridin-4-yl)-8-fluoro-10-methyl-3,4-dihydro-2H-pyrazino[1,2-a]indol-1-one | 0.12 |
| 141 | 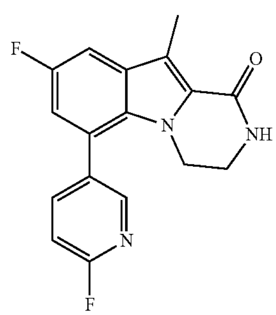 | 8-Fluoro-6-(6-fluoro-pyridin-3-yl)-10-methyl-3,4-dihydro-2H-pyrazino[1,2-a]indol-1-one | 0.13 |
| 142 | 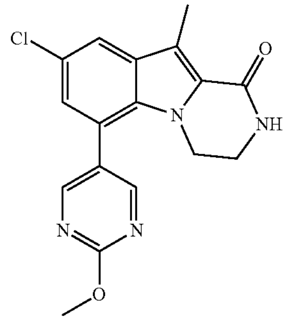 | 8-Chloro-6-(2-methoxy-pyrimidin-5-yl)-10-methyl-3,4-dihydro-2H-pyrazino[1,2-a]indol-1-one | 0.039 |

| Ex. | Structure | Name | EC$_{150}$ (uM) |
|---|---|---|---|
| 143 | 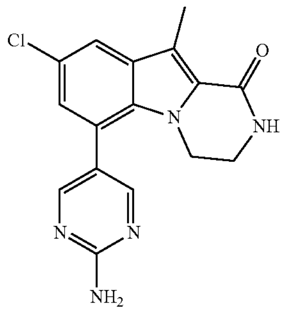 | 6-(2-Amino-pyrimidin-5-yl)-8-chloro-10-methyl-3,4-dihydro-2H-pyrazino[1,2-a]indol-1-one | 0.32 |
| 144 | 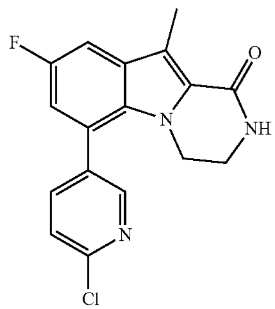 [SMILES: Cc1c2n(c3c(-c4ccc(F)nc4)cc(F)cc13)CCNC2=O] | 6-(6-Chloro-pyridin-3-yl)-8-fluoro-10-methyl-3,4-dihydro-2H-pyrazino[1,2-a]indol-1-one | 0.081 |
| 145 | 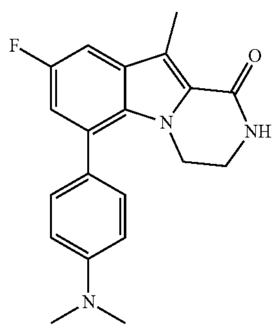 [SMILES: Cc1c2n(c3c(-c4ccc(N(C)C)cc4)cc(F)cc13)CCNC2=O] | 6-(4-Dimethylamino-phenyl)-8-fluoro-10-methyl-3,4-dihydro-2H-pyrazino[1,2-a]indol-1-one | 0.017 |
| 146 | 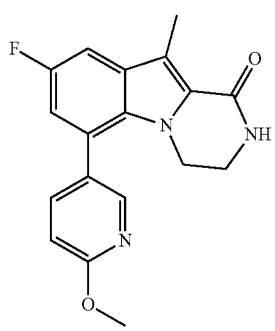 [SMILES: COc1ccc(-c2cc(F)cc3c(C)c4n(c23)CCNC4=O)cn1] | 8-Fluoro-6-(6-methoxy-pyridin-3-yl)-10-methyl-3,4-dihydro-2H-pyrazino[1,2-a]indol-1-one | 0.02 |
| 147 | 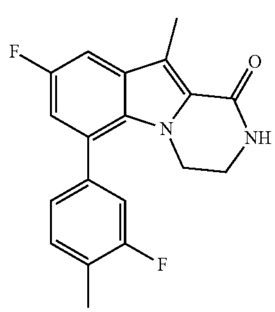 [SMILES: Cc1ccc(-c2cc(F)cc3c(C)c4n(c23)CCNC4=O)cc1F] | 8-Fluoro-6-(3-fluoro-4-methyl-phenyl)-10-methyl-3,4-dihydro-2H-pyrazino[1,2-a]indol-1-one | 0.039 |

| Ex. | Structure | Name | EC$_{150}$ (uM) |
|---|---|---|---|
| 148 | 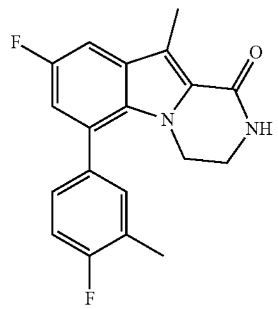 [SMILES: Cc1cc(-c2cc(F)cc3c(C)c4n(c23)CCNC4=O)ccc1F] | 8-Fluoro-6-(4-fluoro-3-methyl-phenyl)-10-methyl-3,4-dihydro-2H-pyrazino[1,2-a]indol-1-one | 0.078 |
| 149 | 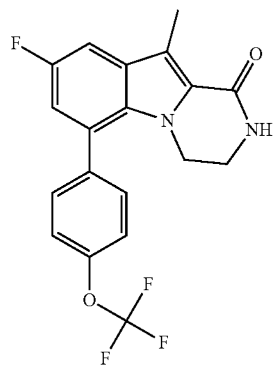 [SMILES: Cc1c2n(c3c(-c4ccc(OC(F)(F)F)cc4)cc(F)cc13)CCNC2=O] | 8-Fluoro-10-methyl-6-(4-trifluoromethoxy-phenyl)-3,4-dihydro-2H-pyrazino[1,2-a]indol-1-one | 0.016 |
| 150 | 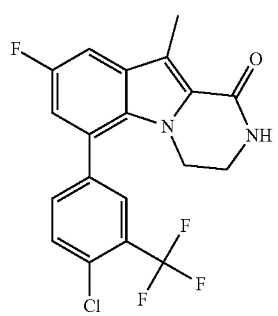 [SMILES: Cc1c2n(c3c(-c4ccc(Cl)c(C(F)(F)F)c4)cc(F)cc13)CCNC2=O] | 6-(4-Chloro-3-trifluoromethyl-phenyl)-8-fluoro-10-methyl-3,4-dihydro-2H-pyrazino[1,2-a]indol-1-one | 0.61 |
| 151 | 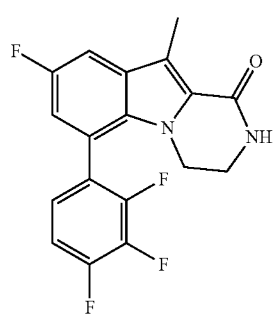 [SMILES: Cc1c2n(c3c(-c4ccc(F)c(F)c4F)cc(F)cc13)CCNC2=O] | 8-Fluoro-10-methyl-6-(2,3,4-trifluoro-phenyl)-3,4-dihydro-2H-pyrazino[1,2-a]indol-1-one | 0.035 |
| 152 | 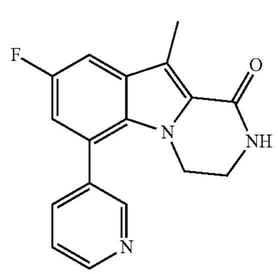 [SMILES: Cc1c2n(c3c(-c4cccnc4)cc(F)cc13)CCNC2=O] | 8-Fluoro-10-methyl-6-pyridin-3-yl-3,4-dihydro-2H-pyrazino[1,2-a]indol-1-one | 0.13 |

-continued
| Ex. | Structure | Name | EC$_{150}$ (uM) |
|---|---|---|---|
| 153 | 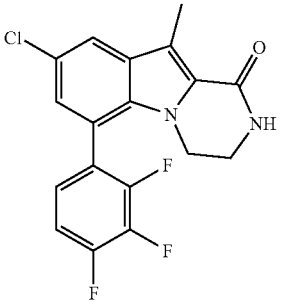 [SMILES: Cc1c2n(c3c(-c4ccc(F)c(F)c4F)cc(Cl)cc13)CCNC2=O] | 8-Chloro-10-methyl-6-(2,3,4-trifluoro-phenyl)-3,4-dihydro-2H-pyrazino[1,2-a]indol-1-one | 0.029 |
| 154 | 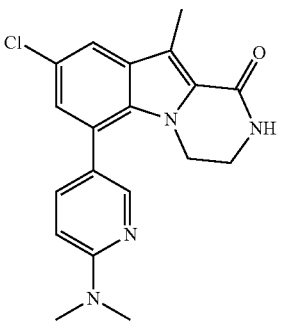 [SMILES: Cc1c2n(c3c(-c4ccc(N(C)C)nc4)cc(Cl)cc13)CCNC2=O] | 8-Chloro-6-(6-dimethylamino-pyridin-3-yl)-10-methyl-3,4-dihydro-2H-pyrazino[1,2-a]indol-1-one | 0.022 |
| 155 | 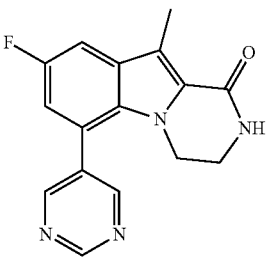 [SMILES: Cc1c2n(c3c(-c4cncnc4)cc(F)cc13)CCNC2=O] | 8-Fluoro-10-methyl-6-pyrimidin-5-yl-3,4-dihydro-2H-pyrazino[1,2-a]indol-1-one | 0.57 |
| 156 | 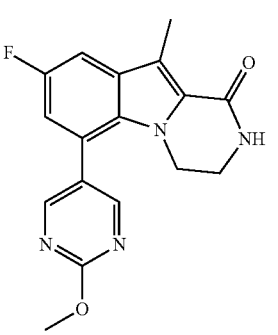 [SMILES: COc1ncc(-c2cc(F)cc3c(C)c4n(c23)CCNC4=O)cn1] | 8-Fluoro-6-(2-methoxy-pyrimidin-5-yl)-10-methyl-3,4-dihydro-2H-pyrazino[1,2-a]indol-1-one | 0.11 |
| 157 | 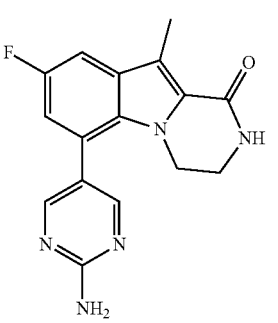 [SMILES: Cc1c2n(c3c(-c4cnc(N)nc4)cc(F)cc13)CCNC2=O] | 6-(2-Amino-pyrimidin-5-yl)-8-fluoro-10-methyl-3,4-dihydro-2H-pyrazino[1,2-a]indol-1-one | 0.19 |

| Ex. | Structure | Name | EC$_{150}$ (uM) |
|---|---|---|---|
| 158 | 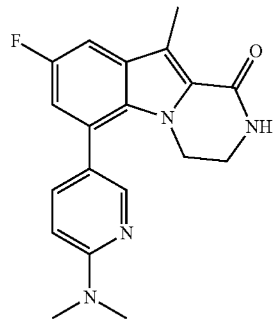 [SMILES: Cc1c2n(c3c(-c4ccc(N(C)C)nc4)cc(F)cc13)CCNC2=O] | 6-(6-Dimethylamino-pyridin-3-yl)-8-fluoro-10-methyl-3,4-dihydro-2H-pyrazino[1,2-a]indol-1-one | 0.012 |
| 159 | 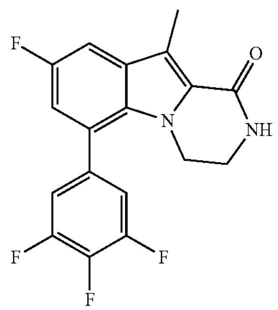 [SMILES: Cc1c2n(c3c(-c4cc(F)c(F)c(F)c4)cc(F)cc13)CCNC2=O] | 8-Fluoro-10-methyl-6-(3,4,5-trifluoro-phenyl)-3,4-dihydro-2H-pyrazino[1,2-a]indol-1-one | 0.22 |
| 160 | 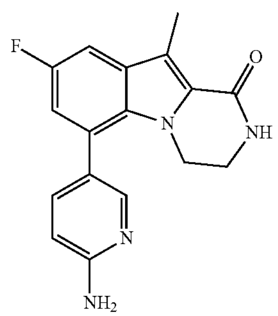 [SMILES: Cc1c2n(c3c(-c4ccc(N)nc4)cc(F)cc13)CCNC2=O] | 6-(6-Amino-pyridin-3-yl)-8-fluoro-10-methyl-3,4-dihydro-2H-pyrazino[1,2-a]indol-1-one | 0.18 |
| 161 | 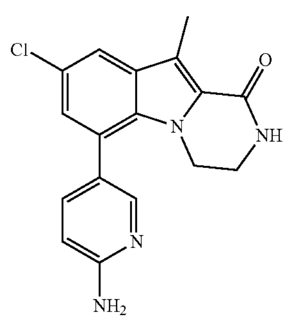 [SMILES: Cc1c2n(c3c(-c4ccc(N)nc4)cc(Cl)cc13)CCNC2=O] | 6-(6-Amino-pyridin-3-yl)-8-chloro-10-methyl-3,4-dihydro-2H-pyrazino[1,2-a]indol-1-one | 0.27 |
| 162 | 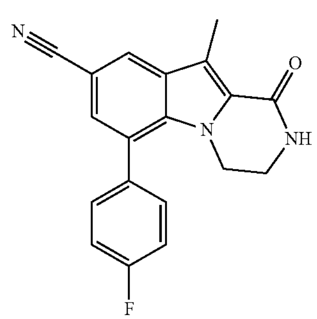 [SMILES: Cc1c2n(c3c(-c4ccc(F)cc4)cc(C#N)cc13)CCNC2=O] | 6-(4-Fluoro-phenyl)-10-methyl-1-oxo-1,2,3,4-tetrahydro-pyrazino[1,2-a]indole-8-carbonitrile | 0.021 |

| Ex. | Structure | Name | EC$_{150}$ (uM) |
|---|---|---|---|
| 163 | 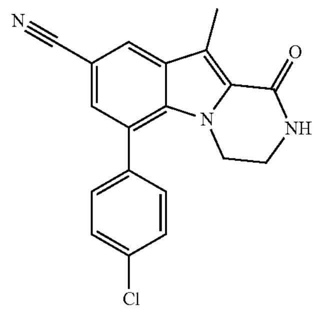 [SMILES: Cc1c2n(c3c(-c4ccc(Cl)cc4)cc(C#N)cc13)CCNC2=O] | 6-(4-Chloro-phenyl)-10-methyl-1-oxo-1,2,3,4-tetrahydro-pyrazino[1,2-a]indole-8-carbonitrile | 0.013 |
| 164 | 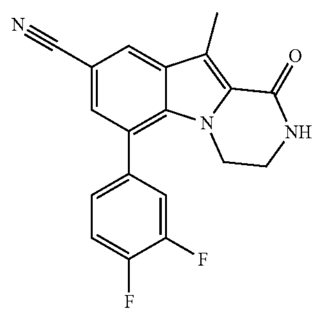 [SMILES: Cc1c2n(c3c(-c4ccc(F)c(F)c4)cc(C#N)cc13)CCNC2=O] | 6-(3,4-Difluoro-phenyl)-10-methyl-1-oxo-1,2,3,4-tetrahydro-pyrazino[1,2-a]indole-8-carbonitrile | 0.045 |
| 165 | 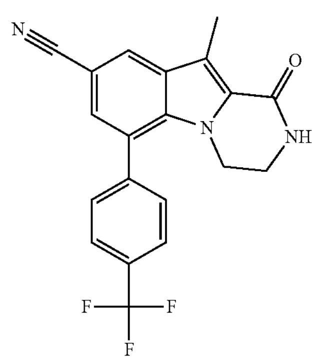 [SMILES: Cc1c2n(c3c(-c4ccc(C(F)(F)F)cc4)cc(C#N)cc13)CCNC2=O] | 10-Methyl-1-oxo-6-(4-trifluoromethyl-phenyl)-1,2,3,4-tetrahydro-pyrazino[1,2-a]indole-8-carbonitrile | 0.018 |
| 166 | 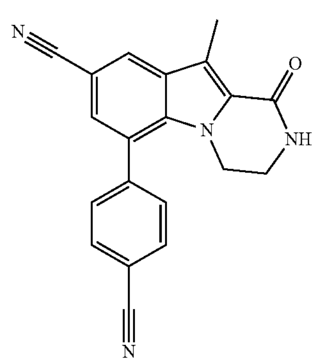 [SMILES: Cc1c2n(c3c(-c4ccc(C#N)cc4)cc(C#N)cc13)CCNC2=O] | 6-(4-Cyano-phenyl)-10-methyl-1-oxo-1,2,3,4-tetrahydro-pyrazino[1,2-a]indole-8-carbonitrile | 0.028 |

-continued

| Ex. | Structure | Name | EC$_{150}$ (uM) |
|---|---|---|---|
| 167 | 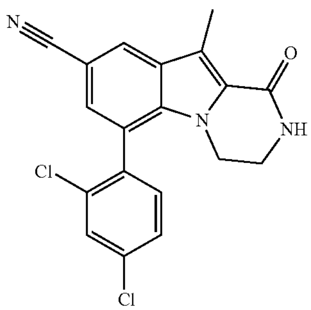 [SMILES: Cc1c2n(c3c(-c4ccc(Cl)cc4Cl)cc(C#N)cc13)CCNC2=O] | 6-(2,4-Dichloro-phenyl)-10-methyl-1-oxo-1,2,3,4-tetrahydro-pyrazino[1,2-a]indole-8-carbonitrile | 0.002 |
| 168 | 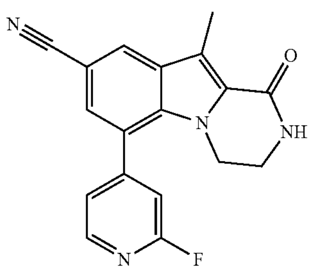 | 6-(2-Fluoro-pyridin-4-yl)-10-methyl-1-oxo-1,2,3,4-tetrahydro-pyrazino[1,2-a]indole-8-carbonitrile | 0.064 |
| 169 | 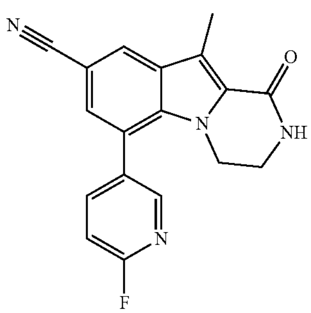 [SMILES: Cc1c2n(c3c(-c4ccc(F)nc4)cc(C#N)cc13)CCNC2=O] | 6-(6-Fluoro-pyridin-3-yl)-10-methyl-1-oxo-1,2,3,4-tetrahydro-pyrazino[1,2-a]indole-8-carbonitrile | 0.066 |
| 170 | 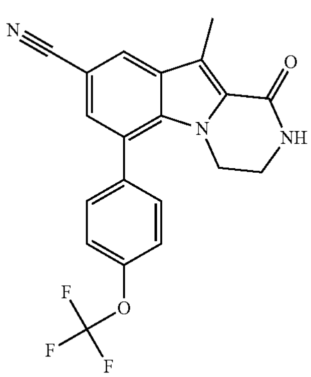 [SMILES: Cc1c2n(c3c(-c4ccc(OC(F)(F)F)cc4)cc(C#N)cc13)CCNC2=O] | 10-Methyl-1-oxo-6-(4-trifluoromethoxy-phenyl)-1,2,3,4-tetrahydro-pyrazino[1,2-a]indole-8-carbonitrile | 0.014 |
| 171 | 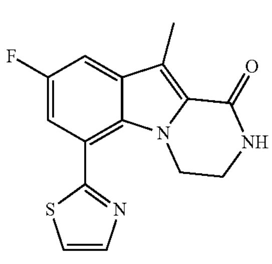 [SMILES: Cc1c2n(c3c(-c4nccs4)cc(F)cc13)CCNC2=O] | 8-Fluoro-10-methyl-6-thiazol-2-yl-3,4-dihydro-2H-pyrazino[1,2-a]indol-1-one | 0.36 |

-continued

| Ex. | Structure | Name | EC$_{150}$ (uM) |
|---|---|---|---|
| 172 | 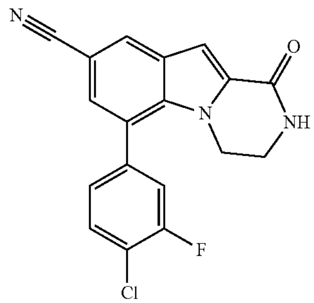 [SMILES: N#Cc1cc(-c2ccc(Cl)c(F)c2)c2c(c1)cc1n2CCNC1=O] | 6-(4-Chloro-3-fluoro-phenyl)-1-oxo-1,2,3,4-tetrahydro-pyrazino[1,2-a]indole-8-carbonitrile | 0.045 |
| 173 | 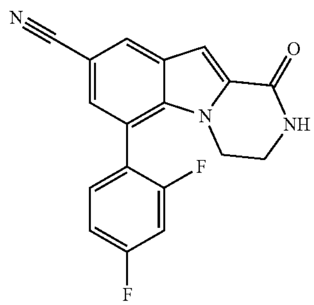 [SMILES: N#Cc1cc(-c2ccc(F)cc2F)c2c(c1)cc1n2CCNC1=O] | 6-(2,4-Difluoro-phenyl)-1-oxo-1,2,3,4-tetrahydro-pyrazino[1,2-a]indole-8-carbonitrile | 0.01 |
| 174 | 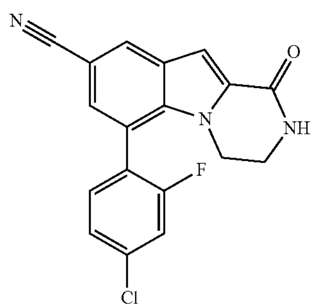 [SMILES: N#Cc1cc(-c2ccc(Cl)cc2F)c2c(c1)cc1n2CCNC1=O] | 6-(4-Chloro-2-fluoro-phenyl)-1-oxo-1,2,3,4-tetrahydro-pyrazino[1,2-a]indole-8-carbonitrile | 0.019 |
| 175 | 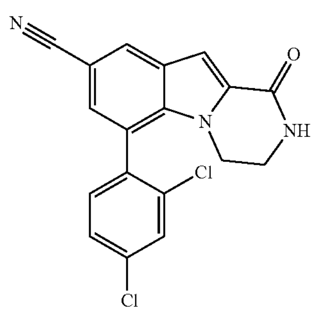 [SMILES: N#Cc1cc(-c2ccc(Cl)cc2Cl)c2c(c1)cc1n2CCNC1=O] | 6-(2,4-Dichloro-phenyl)-1-oxo-1,2,3,4-tetrahydro-pyrazino[1,2-a]indole-8-carbonitrile | 0.034 |
| 176 | 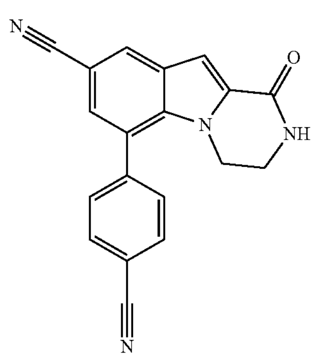 [SMILES: N#Cc1ccc(-c2cc(C#N)cc3cc4n(c23)CCNC4=O)cc1] | 6-(4-Cyano-phenyl)-1-oxo-1,2,3,4-tetrahydro-pyrazino[1,2-a]indole-8-carbonitrile | 0.17 |

| Ex. | Structure | Name | EC$_{150}$ (uM) |
|---|---|---|---|
| 177 | 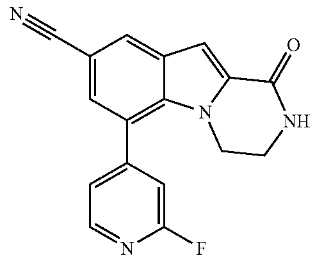 [SMILES: N#Cc1cc(-c2ccnc(F)c2)c2c(c1)cc1n2CCNC1=O] | 6-(2-Fluoro-pyridin-4-yl)-1-oxo-1,2,3,4-tetrahydro-pyrazino[1,2-a]indole-8-carbonitrile | 0.68 |
| 178 | 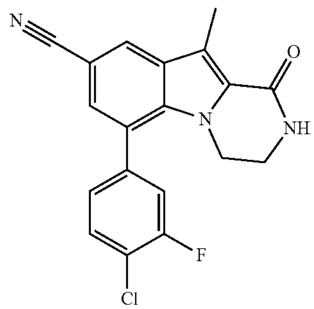 | 6-(4-Chloro-3-fluoro-phenyl)-10-methyl-1-oxo-1,2,3,4-tetrahydro-pyrazino[1,2-a]indole-8-carbonitrile | 0.048 |
| 179 | 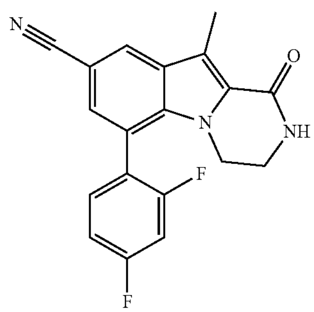 [SMILES: Cc1c2n(c3c(-c4ccc(F)cc4F)cc(C#N)cc13)CCNC2=O] | 6-(2,4-Difluoro-phenyl)-10-methyl-1-oxo-1,2,3,4-tetrahydro-pyrazino[1,2-a]indole-8-carbonitrile | 0.013 |
| 180 | 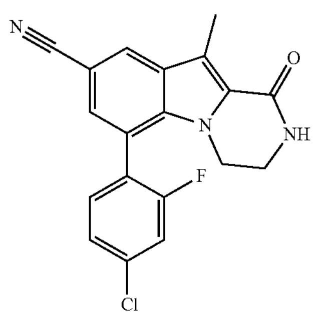 [SMILES: Cc1c2n(c3c(-c4ccc(Cl)cc4F)cc(C#N)cc13)CCNC2=O] | 6-(4-Chloro-2-fluoro-phenyl)-10-methyl-1-oxo-1,2,3,4-tetrahydro-pyrazino[1,2-a]indole-8-carbonitrile | 0.008 |
| 181 | 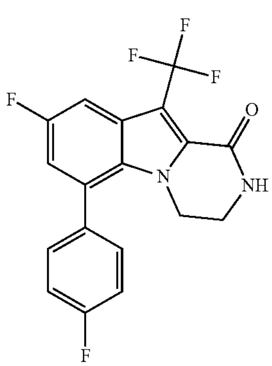 [SMILES: O=C1NCCn2c1c(C(F)(F)F)c1cc(F)cc(-c3ccc(F)cc3)c12] | 8-Fluoro-6-(4-fluoro-phenyl)-10-trifluoromethyl-3,4-dihydro-2H-pyrazino[1,2-a]indol-1-one | 0.62 |

-continued

| Ex. | Structure | Name | EC$_{150}$ (uM) |
|---|---|---|---|
| 182 | 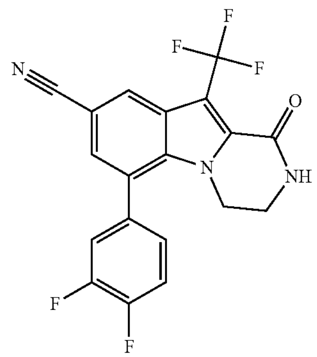 [SMILES: N#Cc1cc(-c2ccc(F)c(F)c2)c2c(c1)c(C(F)(F)F)c1n2CCNC1=O] | 6-(3,4-Difluoro-phenyl)-1-oxo-10-trifluoromethyl-1,2,3,4-tetrahydro-pyrazino[1,2-a]indole-8-carbonitrile | 0.29 |
| 183 | 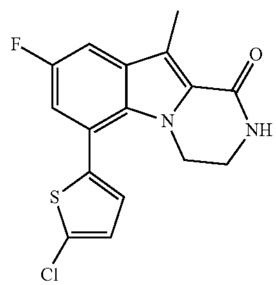 [SMILES: Cc1c2n(c3c(-c4ccc(Cl)s4)cc(F)cc13)CCNC2=O] | 6-(5-Chloro-thiophen-2-yl)-8-fluoro-10-methyl-3,4-dihydro-2H-pyrazino[1,2-a]indol-1-one | 0.19 |
| 184 | 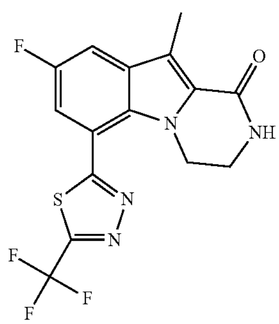 [SMILES: Cc1c2n(c3c(-c4nnc(C(F)(F)F)s4)cc(F)cc13)CCNC2=O] | 8-Fluoro-10-methyl-6-[5-(trifluoromethyl)-1,3,4-thiadiazol-2-yl]-3,4-dihydro-2H-pyrazino[1,2-a]indol-1-one | 1.11 |
| 185 | 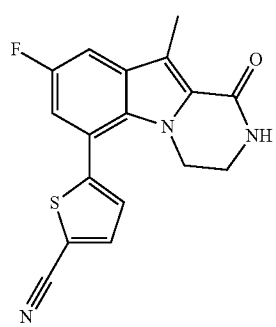 [SMILES: Cc1c2n(c3c(-c4ccc(C#N)s4)cc(F)cc13)CCNC2=O] | 5-(8-Fluoro-10-methyl-1-oxo-3,4-dihydro-2H-pyrazino[1,2-a]indol-6-yl)thiophene-2-carbonitrile | 0.11 |
| 186 | 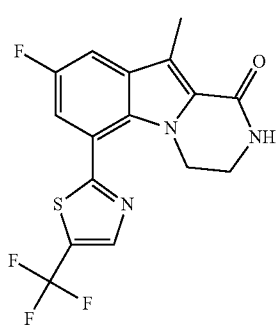 [SMILES: Cc1c2n(c3c(-c4ncc(C(F)(F)F)s4)cc(F)cc13)CCNC2=O] | 8-Fluoro-10-methyl-6-[5-(trifluoromethyl)-1,3-thiazol-2-yl]-3,4-dihydro-2H-pyrazino[1,2-a]indol-1-one | 0.33 |

| Ex. | Structure | Name | EC$_{150}$ (uM) |
|---|---|---|---|
| 187 | 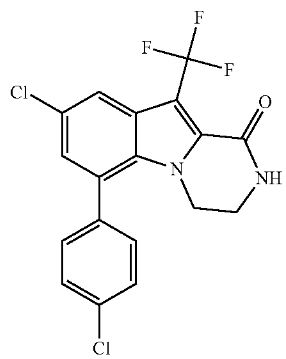 [SMILES: O=C1NCCn2c1c(C(F)(F)F)c1cc(Cl)cc(-c3ccc(Cl)cc3)c12] | 8-Chloro-6-(4-chlorophenyl)-10-(trifluoromethyl)-3,4-dihydro-2H-pyrazino[1,2-a]indol-1-one | 0.088 |
| 188 | 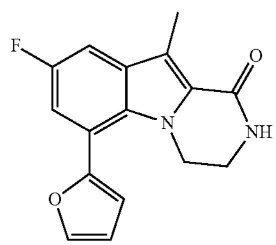 [SMILES: Cc1c2n(c3c(-c4ccco4)cc(F)cc13)CCNC2=O] | 8-Fluoro-6-(furan-2-yl)-10-methyl-3,4-dihydro-2H-pyrazino[1,2-a]indol-1-one | 0.1 |
| 189 | 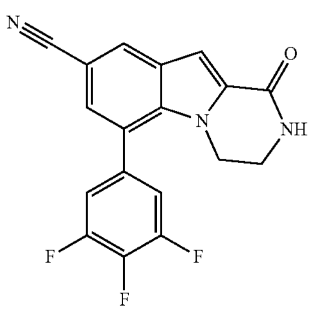 [SMILES: N#Cc1cc(-c2cc(F)c(F)c(F)c2)c2c(c1)cc1n2CCNC1=O] | 1-Oxo-6-(3,4,5-trifluorophenyl)-3,4-dihydro-2H-pyrazino[1,2-a]indole-8-carbonitrile | 0.22 |
| 190 | 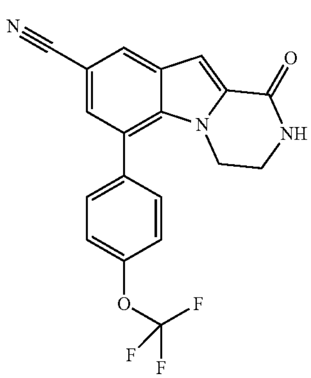 [SMILES: N#Cc1cc(-c2ccc(OC(F)(F)F)cc2)c2c(c1)cc1n2CCNC1=O] | 1-Oxo-6-[4-(trifluoromethoxy)phenyl]-3,4-dihydro-2H-pyrazino[1,2-a]indole-8-carbonitrile | 0.037 |

-continued

| Ex. | Structure | Name | EC$_{150}$ (uM) |
|---|---|---|---|
| 191 | 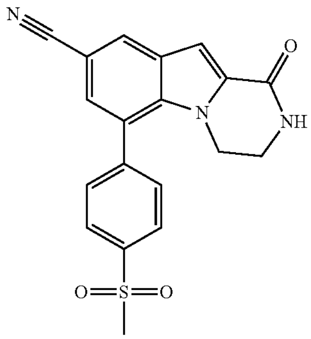 [SMILES: CS(=O)(=O)c1ccc(-c2cc(C#N)cc3cc4n(c23)CCNC4=O)cc1] | 6-(4-Methylsulfonylphenyl)-1-oxo-3,4-dihydro-2H-pyrazino[1,2-a]indole-8-carbonitrile | 0.24 |
| 192 | 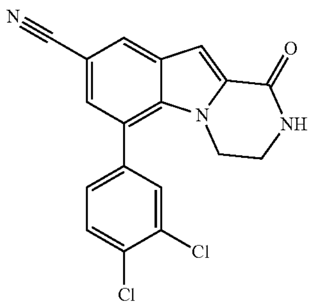 [SMILES: N#Cc1cc(-c2ccc(Cl)c(Cl)c2)c2c(c1)cc1n2CCNC1=O] | 6-(3,4-Dichlorophenyl)-1-oxo-3,4-dihydro-2H-pyrazino[1,2-a]indole-8-carbonitrile | 0.13 |
| 193 | 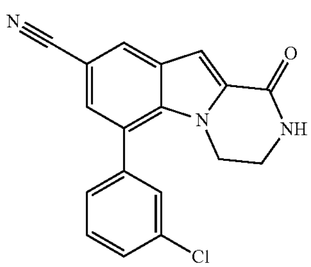 [SMILES: N#Cc1cc(-c2cccc(Cl)c2)c2c(c1)cc1n2CCNC1=O] | 6-(3-Chlorophenyl)-1-oxo-3,4-dihydro-2H-pyrazino[1,2-a]indole-8-carbonitrile | 0.32 |
| 194 | 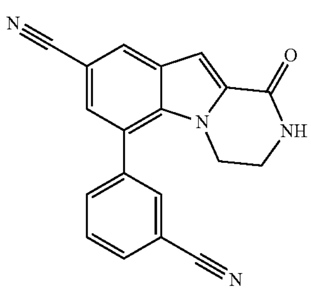 [SMILES: N#Cc1cccc(-c2cc(C#N)cc3cc4n(c23)CCNC4=O)c1] | 6-(3-Cyanophenyl)-1-oxo-3,4-dihydro-2H-pyrazino[1,2-a]indole-8-carbonitrile | 1.08 |
| 195 | 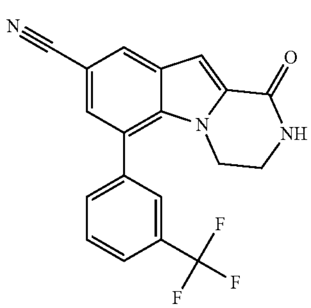 [SMILES: N#Cc1cc(-c2cccc(C(F)(F)F)c2)c2c(c1)cc1n2CCNC1=O] | 1-Oxo-6-[3-(trifluoromethyl)phenyl]-3,4-dihydro-2H-pyrazino[1,2-a]indole-8-carbonitrile | 1.4 |

-continued

| Ex. | Structure | Name | EC$_{150}$ (uM) |
|---|---|---|---|
| 196 | 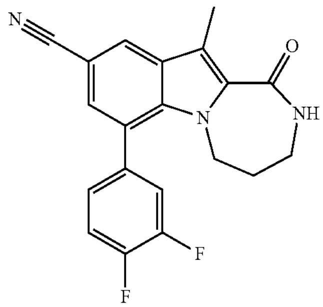 [SMILES: Cc1c2n(c3c(-c4ccc(F)c(F)c4)cc(C#N)cc13)CCCNC2=O] | 7-(3,4-Difluorophenyl)-11-methyl-1-oxo-2,3,4,5-tetrahydro-[1,4]diazepino[1,2-a]indole-9-carbonitrile | 0.086 |
| 197 | 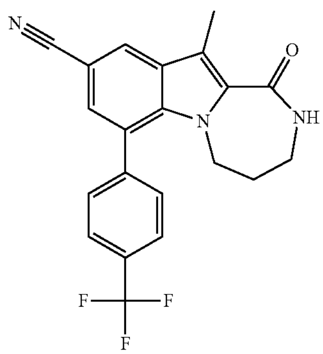 [SMILES: Cc1c2n(c3c(-c4ccc(C(F)(F)F)cc4)cc(C#N)cc13)CCCNC2=O] | 11-Methyl-1-oxo-7-[4-(trifluoromethyl)phenyl]-2,3,4,5-tetrahydro-[1,4]diazepino[1,2-a]indole-9-carbonitrile | 0.14 |
| 198 | 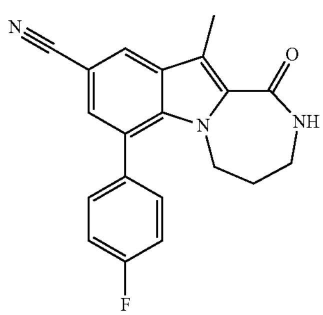 [SMILES: Cc1c2n(c3c(-c4ccc(F)cc4)cc(C#N)cc13)CCCNC2=O] | 7-(4-Fluorophenyl)-11-methyl-1-oxo-2,3,4,5-tetrahydro-[1,4]diazepino[1,2-a]indole-9-carbonitrile | 0.033 |
| 199 | 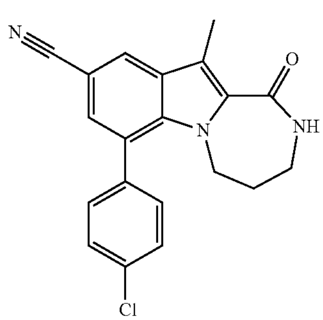 [SMILES: Cc1c2n(c3c(-c4ccc(Cl)cc4)cc(C#N)cc13)CCCNC2=O] | 7-(4-Chlorophenyl)-11-methyl-1-oxo-2,3,4,5-tetrahydro-[1,4]diazepino[1,2-a]indole-9-carbonitrile | 0.053 |

-continued

| Ex. | Structure | Name | EC$_{150}$ (uM) |
|---|---|---|---|
| 200 | 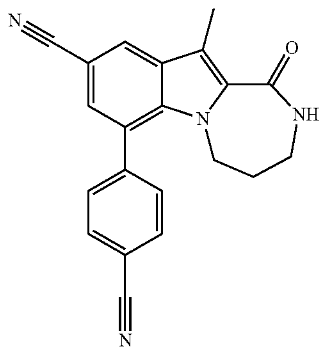 [SMILES: Cc1c2n(c3c(-c4ccc(C#N)cc4)cc(C#N)cc13)CCCNC2=O] | 7-(4-Cyanophenyl)-11-methyl-1-oxo-2,3,4,5-tetrahydro-[1,4]diazepino[1,2-a]indole-9-carbonitrile | 0.041 |
| 201 | 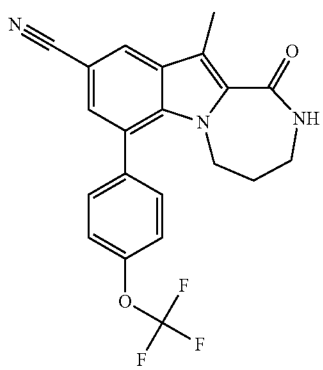 [SMILES: Cc1c2n(c3c(-c4ccc(OC(F)(F)F)cc4)cc(C#N)cc13)CCCNC2=O] | 11-Methyl-1-oxo-7-[4-(trifluoromethoxy)-phenyl]-2,3,4,5-tetrahydro-[1,4]diazepino[1,2-a]indole-9-carbonitrile | 0.048 |
| 202 | 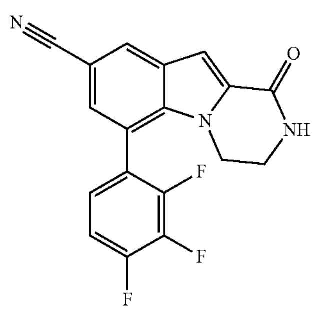 [SMILES: N#Cc1cc(-c2ccc(F)c(F)c2F)c2c(c1)cc1n2CCNC1=O] | 1-Oxo-6-(2,3,4-trifluorophenyl)-3,4-dihydro-[1,2-a]indole-8-carbonitrile | 0.046 |
| 203 | 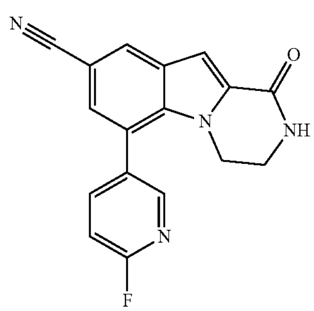 | 6-(6-Fluoropyridin-3-yl)-1-oxo-3,4-dihydro-2H-pyrazino[1,2-a]indole-8-carbonitrile | 0.36 |

-continued

| Ex. | Structure | Name | EC$_{150}$ (uM) |
|---|---|---|---|
| 204 | 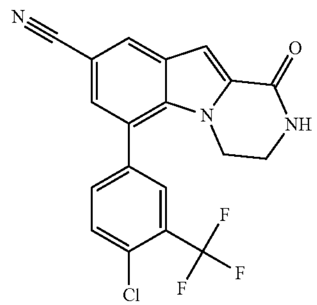 [SMILES: N#Cc1cc(-c2ccc(Cl)c(C(F)(F)F)c2)c2c(c1)cc1n2CCNC1=O] | 6-[4-Chloro-3-(trifluoromethyl)phenyl]-1-oxo-3,4-dihydro-2H-pyrazino[1,2-a]indole-8-carbonitrile | 1.28 |
| 205 | 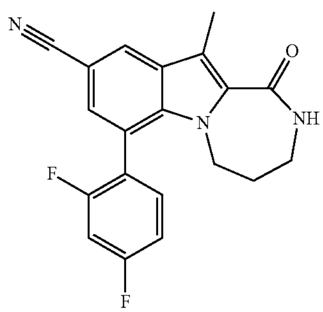 [SMILES: Cc1c2n(c3c(-c4ccc(F)cc4F)cc(C#N)cc13)CCCNC2=O] | 7-(2,4-Difluorophenyl)-11-methyl-1-oxo-2,3,4,5-tetrahydro-[1,4]diazepino[1,2-a]indole-9-carbonitrile | 0.031 |
| 206 | 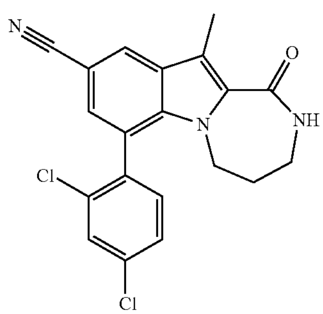 [SMILES: Cc1c2n(c3c(-c4ccc(Cl)cc4Cl)cc(C#N)cc13)CCCNC2=O] | 7-(2,4-Dichlorophenyl)-11-methyl-1-oxo-2,3,4,5-tetrahydro-diazepino[1,2-a]indole-9-carbonitrile | 0.031 |
| 207 | 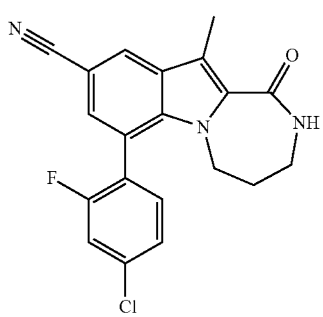 [SMILES: Cc1c2n(c3c(-c4ccc(Cl)cc4F)cc(C#N)cc13)CCCNC2=O] | 7-(4-Chloro-2-fluorophenyl)-11-methyl-1-oxo-2,3,4,5-tetrahydro-[1,4]diazepino[1,2-a]indole-9-carbonitrile | 0.019 |
| 208 | 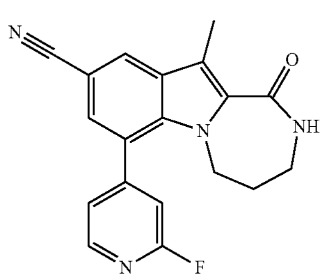 [SMILES: Cc1c2n(c3c(-c4ccnc(F)c4)cc(C#N)cc13)CCCNC2=O] | 7-(2-Fluoropyridin-4-yl)-11-methyl-1-oxo-2,3,4,5-tetrahydro-[1,4]diazepino[1,2-a]indole-9-carbonitrile | 0.049 |

| Ex. | Structure | Name | EC$_{150}$ (uM) |
|---|---|---|---|
| 209 | 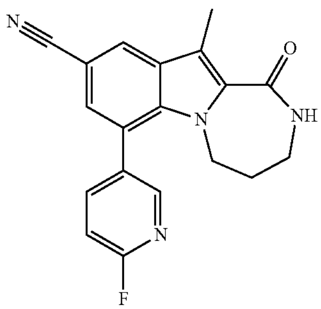 [SMILES: Cc1c2n(c3c(-c4ccc(F)nc4)cc(C#N)cc13)CCCNC2=O] | 7-(6-Fluoropyridin-3-yl)-11-methyl-1-oxo-2,3,4,5-tetrahydro-[1,4]diazepino[1,2-a]indole-9-carbonitrile | 0.16 |
| 210 | 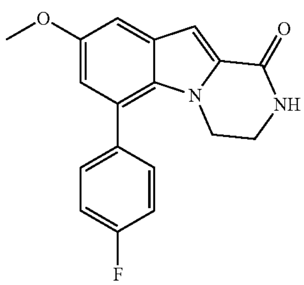 [SMILES: COc1cc(-c2ccc(F)cc2)c2c(c1)cc1n2CCNC1=O] | 6-(4-Fluorophenyl)-8-methoxy-3,4-dihydro-2H-pyrazino[1,2-a]indol-1-one | 2.29 |
| 211 | 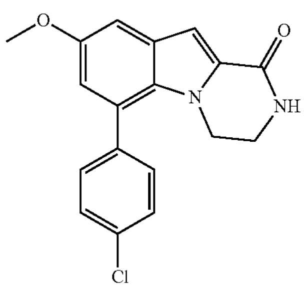 [SMILES: COc1cc(-c2ccc(Cl)cc2)c2c(c1)cc1n2CCNC1=O] | 6-(4-Chlorophenyl)-8-methoxy-3,4-dihydro-2H-pyrazino[1,2-a]indol-1-one | 1.54 |
| 212 | 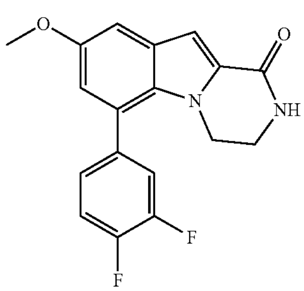 [SMILES: COc1cc(-c2ccc(F)c(F)c2)c2c(c1)cc1n2CCNC1=O] | 6-(3,4-Difluorophenyl)-8-methoxy-3,4-dihydro-2H-pyrazino[1,2-a]indol-1-one | 1.24 |
| 213 | 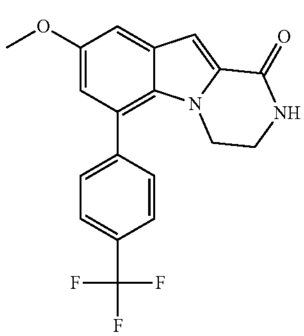 [SMILES: COc1cc(-c2ccc(C(F)(F)F)cc2)c2c(c1)cc1n2CCNC1=O] | 8-Methoxy-6-[4-(trifluoromethyl)-phenyl]-3,4-dihydro-2H-pyrazino[1,2-a]indol-1-one | 0.8 |

-continued

| Ex. | Structure | Name | EC$_{150}$ (uM) |
|---|---|---|---|
| 214 | 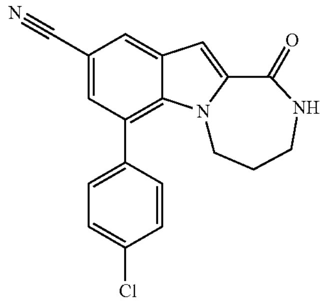 [SMILES: N#Cc1cc(-c2ccc(Cl)cc2)c2c(c1)cc1n2CCCNC1=O] | 7-(4-Chlorophenyl)-1-oxo-2,3,4,5-tetrahydro-[1,4]diazepino[1,2-a]indole-9-carbonitrile | 0.14 |
| 215 | 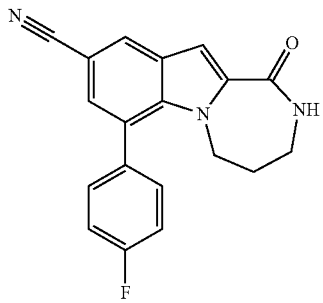 [SMILES: N#Cc1cc(-c2ccc(F)cc2)c2c(c1)cc1n2CCCNC1=O] | 7-(4-Fluorophenyl)-1-oxo-2,3,4,5-tetrahydro-[1,4]diazepino[1,2-a]indole-9-carbonitrile | 0.09 |
| 216 | 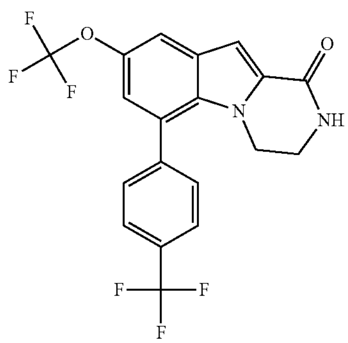 [SMILES: O=C1NCCn2c1cc1cc(OC(F)(F)F)cc(-c3ccc(C(F)(F)F)cc3)c12] | 8-(Trifluoromethoxy)-6-[4-(trifluoromethyl)-phenyl]-3,4-dihydro-2H-pyrazino[1,2-a]indol-1-one | 0.022 |
| 217 | 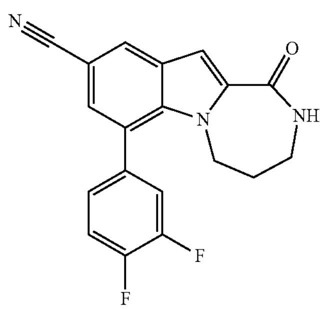 | 7-(3,4-Difluorophenyl)-1-oxo-2,3,4,5-tetrahydro-[1,4]diazepino[1,2-a]indole-9-carbonitrile | 0.51 |
| 218 | 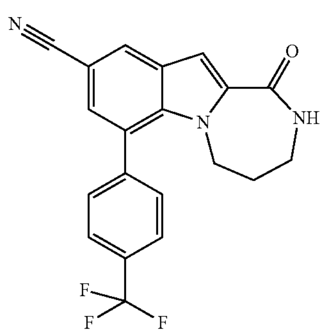 [SMILES: N#Cc1cc(-c2ccc(C(F)(F)F)cc2)c2c(c1)cc1n2CCCNC1=O] | 1-Oxo-7-[4-(trifluoromethyl)-phenyl]-2,3,4,5-tetrahydro-[1,4]diazepino[1,2-a]indole-9-carbonitrile | 0.45 |

-continued

| Ex. | Structure | Name | EC$_{150}$ (uM) |
|---|---|---|---|
| 219 | 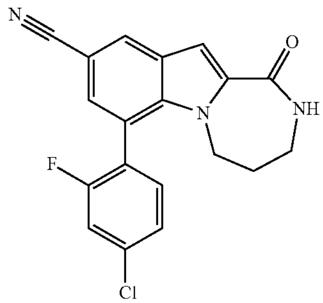 [SMILES: N#Cc1cc(-c2ccc(Cl)cc2F)c2c(c1)cc1n2CCCNC1=O] | 7-(4-Chloro-2-fluorophenyl)-1-oxo-2,3,4,5-tetrahydro-[1,4]diazepino[1,2-a]indole-9-carbonitrile | 0.08 |
| 220 | 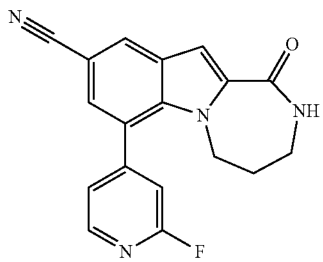 | 7-(2-Fluoropyridin-4-yl)-1-oxo-2,3,4,5-tetrahydro-[1,4]diazepino[1,2-a]indole-9-carbonitrile | 0.5 |
| 221 | 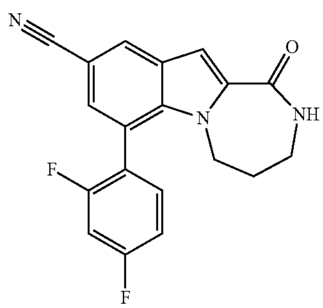 [SMILES: N#Cc1cc(-c2ccc(F)cc2F)c2c(c1)cc1n2CCCNC1=O] | 7-(2,4-Difluorophenyl)-1-oxo-2,3,4,5-tetrahydro-[1,4]diazepino[1,2-a]indole-9-carbonitrile | 0.073 |
| 222 | 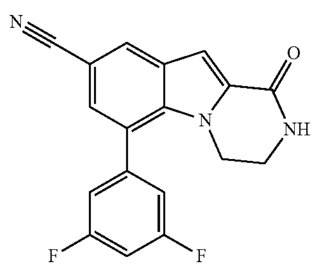 [SMILES: N#Cc1cc(-c2cc(F)cc(F)c2)c2c(c1)cc1n2CCNC1=O] | 6-(3,5-Difluorophenyl)-1-oxo-3,4-dihydro-2H-pyrazino[1,2-a]indole-8-carbonitrile | 0.22 |
| 223 | 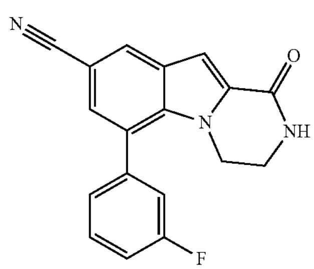 [SMILES: N#Cc1cc(-c2cccc(F)c2)c2c(c1)cc1n2CCNC1=O] | 6-(3-Fluorophenyl)-1-oxo-3,4-dihydro-2H-pyrazino[1,2-a]indole-8-carbonitrile | 0.076 |

| Ex. | Structure | Name | EC$_{150}$ (uM) |
|---|---|---|---|
| 224 | 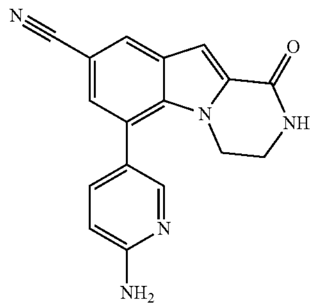 [SMILES: N#Cc1cc(-c2ccc(N)nc2)c2c(c1)cc1n2CCNC1=O] | 6-(6-Aminopyridin-3-yl)-1-oxo-3,4-dihydro-2H-pyrazino[1,2-a]indole-8-carbonitrile | 0.76 |
| 225 | 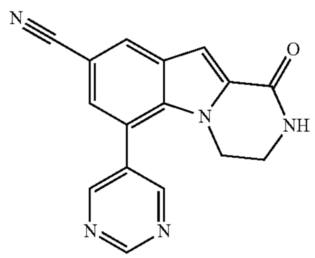 [SMILES: N#Cc1cc(-c2cncnc2)c2c(c1)cc1n2CCNC1=O] | 1-Oxo-6-pyrimidin-5-yl-3,4-dihydro-2H-pyrazino[1,2-a]indole-8-carbonitrile | 1.75 |
| 226 | 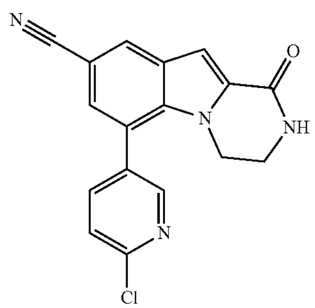 | 6-(6-Chloropyridin-3-yl)-1-oxo-3,4-dihydro-2H-pyrazino[1,2-a]indole-8-carbonitrile | 2.2 |
| 227 | 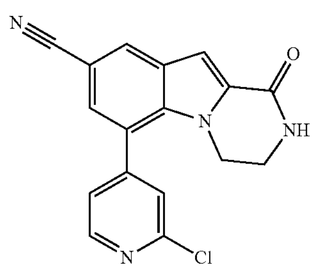 [SMILES: N#Cc1cc(-c2ccnc(Cl)c2)c2c(c1)cc1n2CCNC1=O] | 6-(2-Chloropyridin-4-yl)-1-oxo-3,4-dihydro-2H-pyrazino[1,2-a]indole-8-carbonitrile | 0.55 |
| 228 | 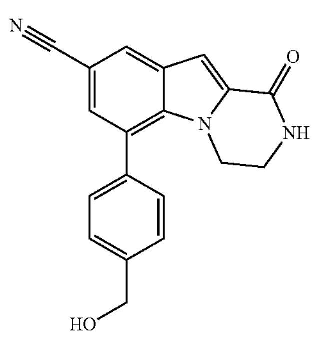 [SMILES: N#Cc1cc(-c2ccc(CO)cc2)c2c(c1)cc1n2CCNC1=O] | 6-[4-(Hydroxymethyl)-phenyl]-1-oxo-3,4-dihydro-2H-pyrazino[1,2-a]indole-8-carbonitrile | 0.041 |

-continued

| Ex. | Structure | Name | EC$_{150}$ (uM) |
|---|---|---|---|
| 229 | 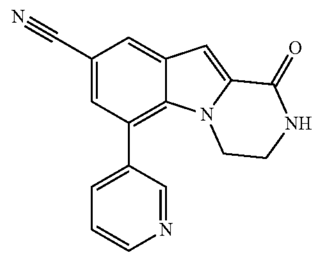 | 1-Oxo-6-pyridin-3-yl-3,4-dihydro-2H-pyrazino[1,2-a]indole-8-carbonitrile | 0.94 |
| 230 | 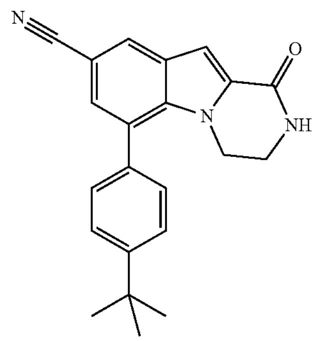 [SMILES: CC(C)(C)c1ccc(-c2cc(C#N)cc3cc4n(c23)CCNC4=O)cc1] | 6-(4-tert-Butylphenyl)-1-oxo-3,4-dihydro-2H-pyrazino[1,2-a]indole-8-carbonitrile | 0.14 |
| 231 | 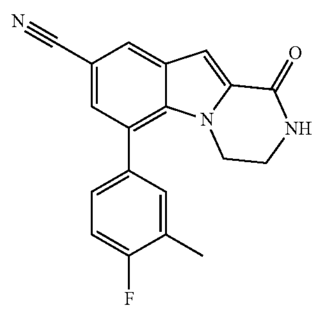 [SMILES: Cc1cc(-c2cc(C#N)cc3cc4n(c23)CCNC4=O)ccc1F] | 6-(4-Fluoro-3-methylphenyl)-1-oxo-3,4-dihydro-2H-pyrazino[1,2-a]indole-8-carbonitrile | 0.058 |
| 232 | 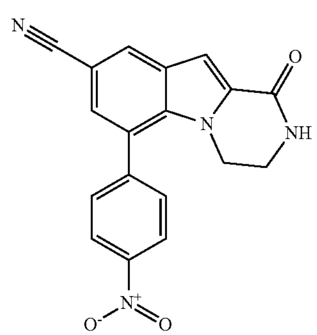 [SMILES: N#Cc1cc(-c2ccc([N+](=O)[O-])cc2)c2c(c1)cc1n2CCNC1=O] | 6-(4-Nitrophenyl)-1-oxo-3,4-dihydro-2H-pyrazino[1,2-a]indole-8-carbonitrile | 0.02 |
| 233 | 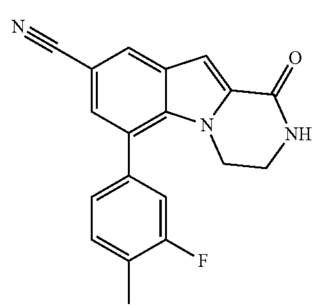 [SMILES: Cc1ccc(-c2cc(C#N)cc3cc4n(c23)CCNC4=O)cc1F] | 6-(3-Fluoro-4-methylphenyl)-1-oxo-3,4-dihydro-2H-pyrazino[1,2-a]indole-8-carbonitrile | 0.052 |

-continued

| Ex. | Structure | Name | EC$_{150}$ (uM) |
|---|---|---|---|
| 234 | 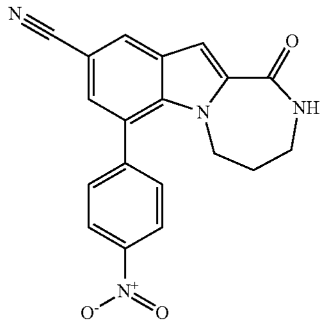 [SMILES: N#Cc1cc(-c2ccc([N+](=O)[O-])cc2)c2c(c1)cc1n2CCCNC1=O] | 7-(4-Nitrophenyl)-1-oxo-2,3,4,5-tetrahydro-[1,4]diazepino[1,2-a]indole-9-carbonitrile | 0.21 |
| 235 | 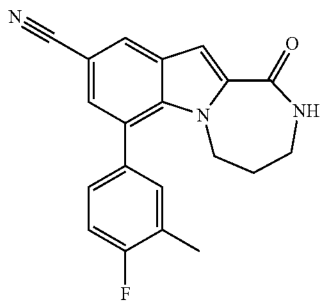 | 7-(4-Fluoro-3-methylphenyl)-1-oxo-2,3,4,5-tetrahydro-[1,4]diazepino[1,2-a]indole-9-carbonitrile | 0.77 |
| 236 | 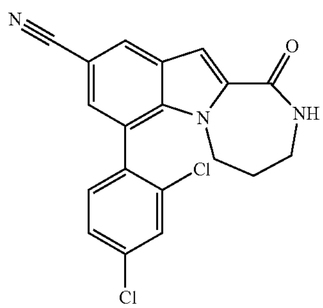 [SMILES: N#Cc1cc(-c2ccc(Cl)cc2Cl)c2c(c1)cc1n2CCCNC1=O] | 7-(2,4-Dichlorophenyl)-1-oxo-2,3,4,5-tetrahydro-[1,4]diazepino[1,2-a]indole-9-carbonitrile | 0.13 |
| 237 | 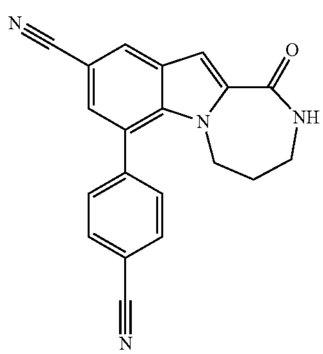 [SMILES: N#Cc1ccc(-c2cc(C#N)cc3cc4n(c23)CCCNC4=O)cc1] | 7-(4-Cyanophenyl)-1-oxo-2,3,4,5-tetrahydro-[1,4]diazepino[1,2-a]indole-9-carbonitrile | 0.22 |
| 238 | 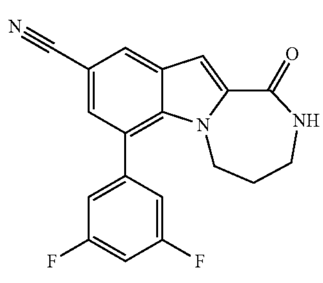 [SMILES: N#Cc1cc(-c2cc(F)cc(F)c2)c2c(c1)cc1n2CCCNC1=O] | 7-(3,5-Difluorophenyl)-1-oxo-2,3,4,5-tetrahydro-[1,4]diazepino[1,2-a]indole-9-carbonitrile | 1 |

| Ex. | Structure | Name | EC$_{150}$ (uM) |
|---|---|---|---|
| 239 | 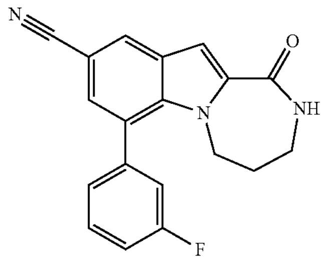 [SMILES: N#Cc1cc(-c2cccc(F)c2)c2c(c1)cc1n2CCCNC1=O] | 7-(3-Fluorophenyl)-1-oxo-2,3,4,5-tetrahydro-[1,4]diazepino[1,2-a]indole-9-carbonitrile | 0.61 |
| 240 | 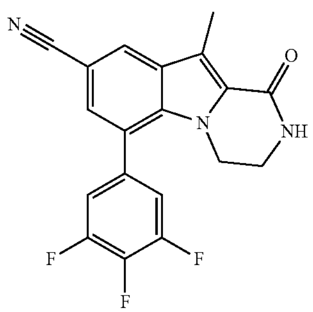 [SMILES: Cc1c2n(c3c(-c4cc(F)c(F)c(F)c4)cc(C#N)cc13)CCNC2=O] | 10-Methyl-1-oxo-6-(3,4,5-trifluorophenyl)-3,4-dihydro-2H-pyrazino[1,2-a]indole-8-carbonitrile | 0.11 |
| 241 | 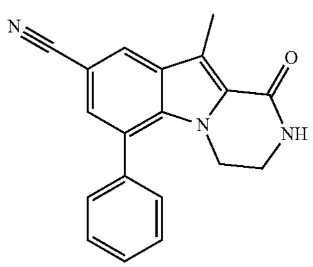 [SMILES: Cc1c2n(c3c(-c4ccccc4)cc(C#N)cc13)CCNC2=O] | 10-Methyl-1-oxo-6-phenyl-3,4-dihydro-2H-pyrazino[1,2-a]indole-8-carbonitrile | 0.062 |
| 242 | 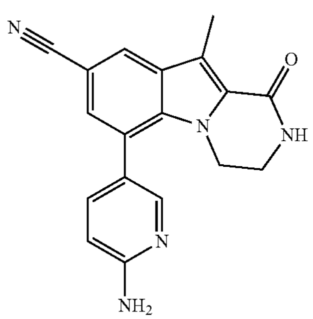 [SMILES: Cc1c2n(c3c(-c4ccc(N)nc4)cc(C#N)cc13)CCNC2=O] | 6-(6-Aminopyridin-3-yl)-10-methyl-1-oxo-3,4-dihydro-2H-pyrazino[1,2-a]indole-8-carbonitrile- | 0.68 |
| 243 | 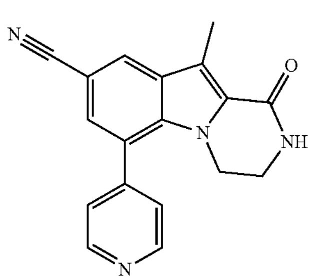 [SMILES: Cc1c2n(c3c(-c4ccncc4)cc(C#N)cc13)CCNC2=O] | 10-Methyl-1-oxo-6-pyridin-4-yl-3,4-dihydro-2H-pyrazino[1,2-a]indole-8-carbonitrile | 0.09 |

| Ex. | Structure | Name | EC$_{150}$ (uM) |
|---|---|---|---|
| 244 | 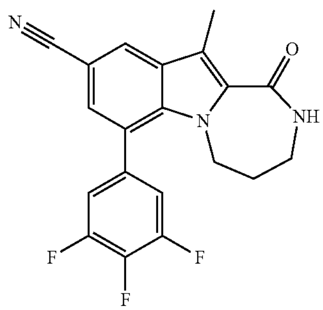 [SMILES: Cc1c2n(c3c(-c4cc(F)c(F)c(F)c4)cc(C#N)cc13)CCCNC2=O] | 11-Methyl-1-oxo-7-(3,4,5-trifluorophenyl)-2,3,4,5-tetrahydro-[1,4]diazepino[1,2-a]indole-9-carbonitrile | 0.47 |
| 245 | 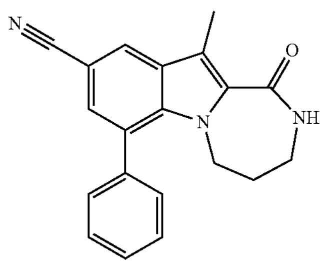 [SMILES: Cc1c2n(c3c(-c4ccccc4)cc(C#N)cc13)CCCNC2=O] | 11-Methyl-1-oxo-7-phenyl-2,3,4,5-tetrahydro-[1,4]diazepino[1,2-a]indole-9-carbonitrile | 0.095 |
| 246 | 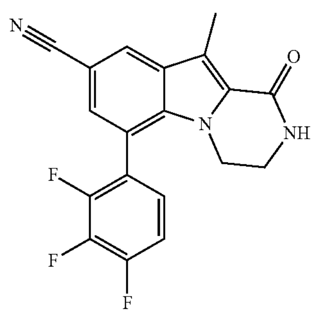 [SMILES: Cc1c2n(c3c(-c4ccc(F)c(F)c4F)cc(C#N)cc13)CCNC2=O] | 10-Methyl-1-oxo-6-(2,3,4-trifluorophenyl)-3,4-dihydro-2H-pyrazino[1,2-a]indole-8-carbonitrile | 0.084 |
| 247 | 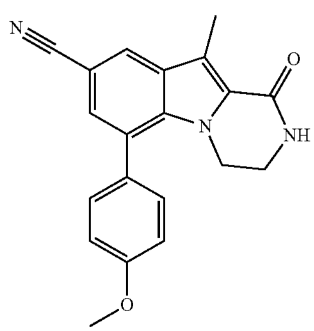 [SMILES: COc1ccc(-c2cc(C#N)cc3c(C)c4n(c23)CCNC4=O)cc1] | 6-(4-Methoxyphenyl)-10-methyl-1-oxo-3,4-dihydro-2H-pyrazino[1,2-a]indole-8-carbonitrile | 0.03 |
| 248 | 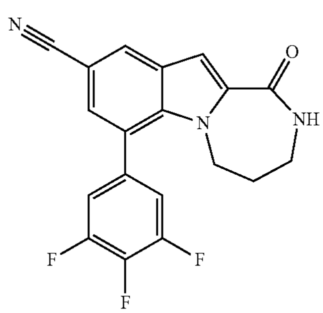 [SMILES: N#Cc1cc(-c2cc(F)c(F)c(F)c2)c2c(c1)cc1n2CCCNC1=O] | 1-Oxo-7-(3,4,5-trifluorophenyl)-2,3,4,5-tetrahydro-[1,4]diazepino[1,2-a]indole-9-carbonitrile | 0.62 |

-continued

| Ex. | Structure | Name | EC$_{150}$ (uM) |
|---|---|---|---|
| 249 | 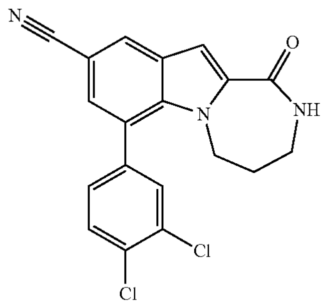 | 7-(3,4-Dichlorophenyl)-1-oxo-2,3,4,5-tetrahydro-[1,4]diazepino[1,2-a]indole-9-carbonitrile | 0.31 |
| 250 | 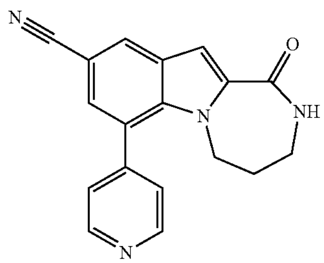 [SMILES: N#Cc1cc(-c2ccncc2)c2c(c1)cc1n2CCCNC1=O] | 11-Methyl-1-oxo-7-pyridin-4-yl-2,3,4,5-tetrahydro-[1,4]diazepino[1,2-a]indole-9-carbonitrile | 0.15 |
| 251 | 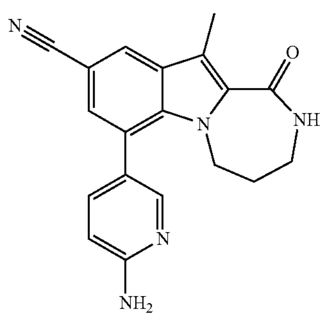 [SMILES: Cc1c2n(c3c(-c4ccc(N)nc4)cc(C#N)cc13)CCCNC2=O] | 7-(6-Aminopyridin-3-yl)-11-methyl-1-oxo-2,3,4,5-tetrahydro-[1,4]diazepino[1,2-a]indole-9-carbonitrile | 0.29 |
| 252 | 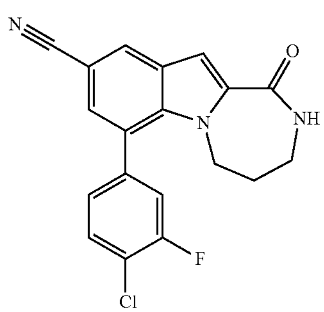 | 7-(4-Chloro-3-fluorophenyl)-1-oxo-2,3,4,5-tetrahydro-[1,4]diazepino[1,2-a]indole-9-carbonitrile | 1.38 |
| 253 | 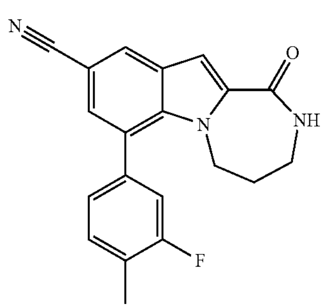 [SMILES: Cc1ccc(-c2cc(C#N)cc3cc4n(c23)CCCNC4=O)cc1F] | 7-(3-Fluoro-4-methylphenyl)-1-oxo-2,3,4,5-tetrahydro-[1,4]diazepino[1,2-a]indole-9-carbonitrile | 0.65 |

-continued

| Ex. | Structure | Name | EC$_{150}$ (uM) |
|---|---|---|---|
| 254 | 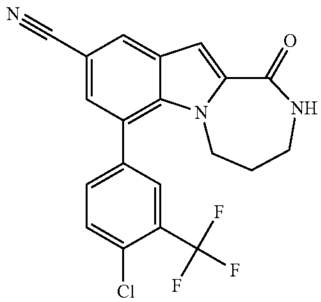 [SMILES: N#Cc1cc(-c2ccc(Cl)c(C(F)(F)F)c2)c2c(c1)cc1n2CCCNC1=O] | 7-[4-Chloro-3-trifluoromethyl)phenyl]-1-oxo-2,3,4,5-tetrahydro-[1,4]diazepino[1,2-a]indole-9-carbonitrile | |
| 255 | 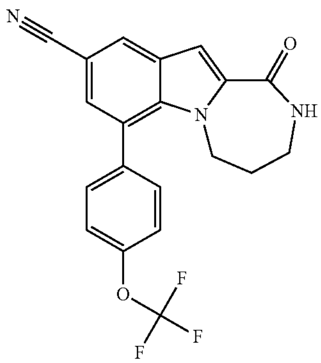 [SMILES: N#Cc1cc(-c2ccc(OC(F)(F)F)cc2)c2c(c1)cc1n2CCCNC1=O] | 1-Oxo-7-[4-(trifluoromethoxy)phenyl]-2,3,4,5-tetrahydro-[1,4]diazepino[1,2-a]indole-9-carbonitrile | 0.3 |
| 256 | 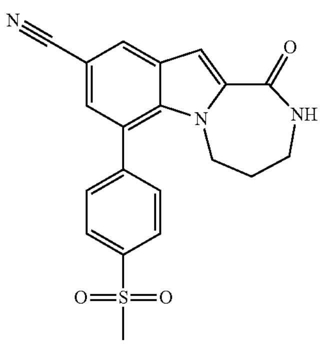 [SMILES: CS(=O)(=O)c1ccc(-c2cc(C#N)cc3cc4n(c23)CCCNC4=O)cc1] | 7-(4-Methylsulfonylphenyl)-1-oxo-2,3,4,5-tetrahydro-[1,4]diazepino[1,2-a]indole-9-carbonitrile | 1.42 |
| 257 | 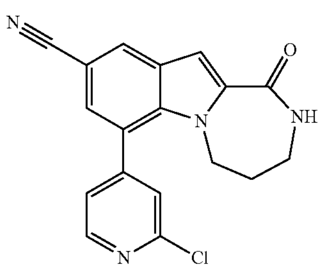 | 7-(2-Chloropyridin-4-yl)-1-oxo-2,3,4,5-tetrahydro-[1,4]diazepino[1,2-a]indole-9-carbonitrile | 0.54 |
| 258 | 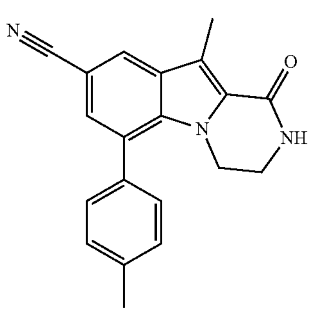 [SMILES: Cc1ccc(-c2cc(C#N)cc3c(C)c4n(c23)CCNC4=O)cc1] | 10-Methyl-6-(4-methylphenyl)-1-oxo-3,4-dihydro-2H-pyrazino[1,2-a]indole-8-carbonitrile | 0.035 |

-continued

| Ex. | Structure | Name | EC$_{150}$ (uM) |
|---|---|---|---|
| 259 | 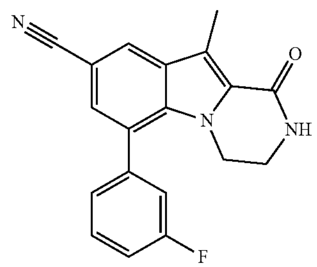 [SMILES: Cc1c2n(c3c(-c4cccc(F)c4)cc(C#N)cc13)CCNC2=O] | 6-(3-Fluorophenyl)-10-methyl-1-oxo-3,4-dihydro-2H-pyrazino[1,2-a]indole-8-carbonitrile | 0.06 |
| 260 | 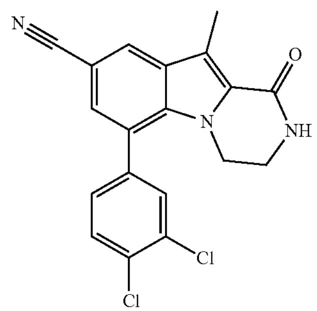 [SMILES: Cc1c2n(c3c(-c4ccc(Cl)c(Cl)c4)cc(C#N)cc13)CCNC2=O] | 6-(3,4-Dichlorophenyl)-10-methyl-1-oxo-3,4-dihydro-2H-pyrazino[1,2-a]indole-8-carbonitrile | 0.12 |
| 261 | 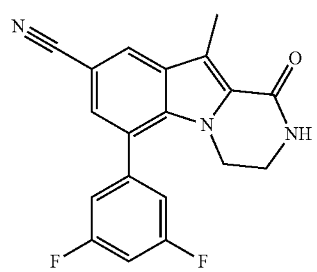 [SMILES: Cc1c2n(c3c(-c4cc(F)cc(F)c4)cc(C#N)cc13)CCNC2=O] | 6-(3,5-Difluorophenyl)-10-methyl-1-oxo-3,4-dihydro-2H-pyrazino[1,2-a]indole-8-carbonitrile | 0.091 |
| 262 | 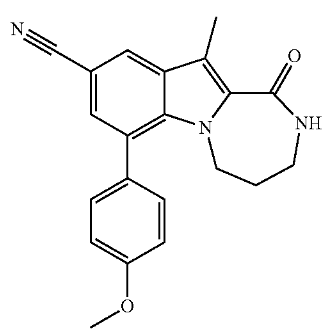 [SMILES: COc1ccc(-c2cc(C#N)cc3c(C)c4n(c23)CCCNC4=O)cc1] | 7-(4-Methoxyphenyl)-11-methyl-1-oxo-2,3,4,5-tetrahydro-[1,4]diazepino[1,2-a]indole-9-carbonitrile | 0.029 |
| 263 | 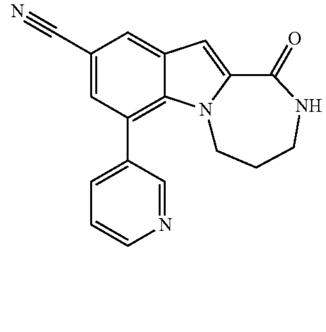 [SMILES: N#Cc1cc(-c2cccnc2)c2c(c1)cc1n2CCCNC1=O] | 1-Oxo-7-pyridin-3-yl-2,3,4,5-tetrahydro-[1,4]diazepino[1,2-a]indole-9-carbonitrile | |

| Ex. | Structure | Name | EC$_{150}$ (uM) |
|---|---|---|---|
| 264 | 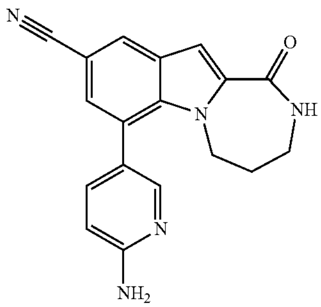 [SMILES: N#Cc1cc(-c2ccc(N)nc2)c2c(c1)cc1n2CCCNC1=O] | 7-(6-Aminopyridin-3-yl)-1-oxo-2,3,4,5-tetrahydro-[1,4]diazepino[1,2-a]indole-9-carbonitrile | |
| 265 | 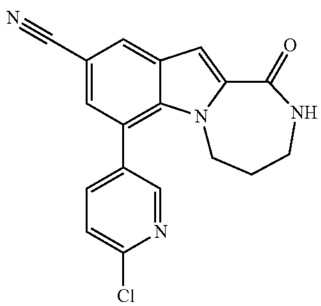 [SMILES: N#Cc1cc(-c2ccc(Cl)nc2)c2c(c1)cc1n2CCCNC1=O] | 7-(6-Chloropyridin-3-yl)-1-oxo-2,3,4,5-tetrahydro-[1,4]diazepino[1,2-a]indole-9-carbonitrile | |
| 266 | 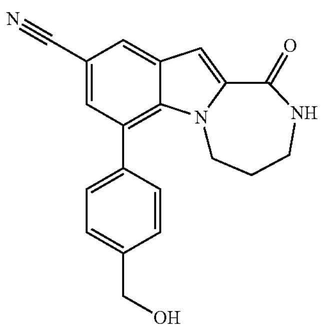 [SMILES: N#Cc1cc(-c2ccc(CO)cc2)c2c(c1)cc1n2CCCNC1=O] | 7-[4-(Hydroxymethyl)phenyl]-1-oxo-2,3,4,5-tetrahydro-[1,4]diazepino[1,2-a]indole-9-carbonitrile | 0.93 |
| 267 | 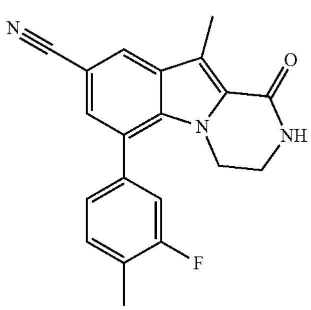 [SMILES: Cc1ccc(-c2cc(C#N)cc3c(C)c4n(c23)CCNC4=O)cc1F] | 6-(3-Fluoro-4-methylphenyl)-10-methyl-1-oxo-3,4-dihydro-2H-pyrazino[1,2-a]indole-8-carbonitrile | 0.71 |
| 268 | 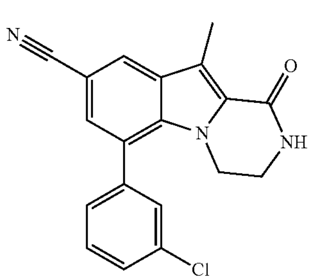 [SMILES: Cc1c2n(c3c(-c4cccc(Cl)c4)cc(C#N)cc13)CCNC2=O] | 6-(3-Chlorophenyl)-10-methyl-1-oxo-3,4-dihydro-2H-pyrazino[1,2-a]indole-8-carbonitrile | |

-continued

| Ex. | Structure | Name | EC$_{150}$ (uM) |
|---|---|---|---|
| 269 | 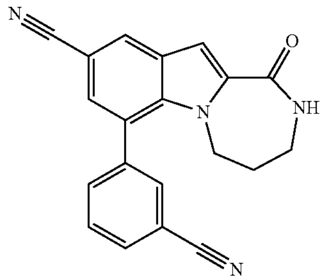 [SMILES: N#Cc1cccc(-c2cc(C#N)cc3cc4n(c23)CCCNC4=O)c1] | 7-(3-Cyanophenyl)-1-oxo-2,3,4,5-tetrahydro-[1,4]diazepino[1,2-a]indole-9-carbonitrile | 1.09 |
| 270 | 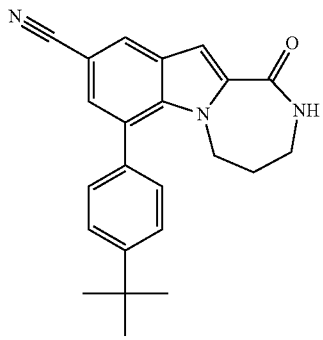 [SMILES: CC(C)(C)c1ccc(-c2cc(C#N)cc3cc4n(c23)CCCNC4=O)cc1] | 7-(4-tert-Butylphenyl)-1-oxo-2,3,4,5-tetrahydro-[1,4]diazepino[1,2-a]indole-9-carbonitrile | |
| 271 | 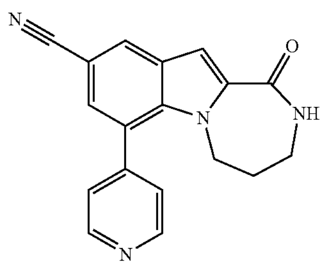 [SMILES: N#Cc1cc(-c2ccncc2)c2c(c1)cc1n2CCCNC1=O] | 1-Oxo-7-pyridin-4-yl-2,3,4,5-tetrahydro-[1,4]diazepino[1,2-a]indole-9-carbonitrile | 0.65 |
| 272 | 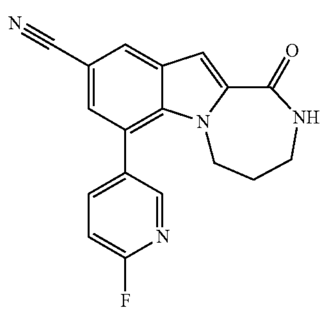 [SMILES: N#Cc1cc(-c2ccc(F)nc2)c2c(c1)cc1n2CCCNC1=O] | 7-(6-Fluoropyridin-3-yl)-1-oxo-2,3,4,5-tetrahydro-[1,4]diazepino[1,2-a]indole-9-carbonitrile | |
| 273 | 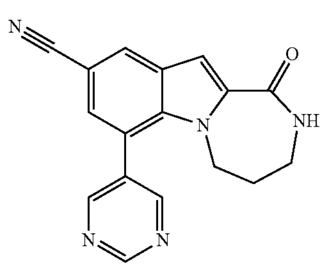 | 1-Oxo-7-pyrimidin-5-yl-2,3,4,5-tetrahydro-[1,4]diazepino[1,2-a]indole-9-carbonitrile | |

| Ex. | Structure | Name | EC$_{150}$ (uM) |
|---|---|---|---|
| 274 | 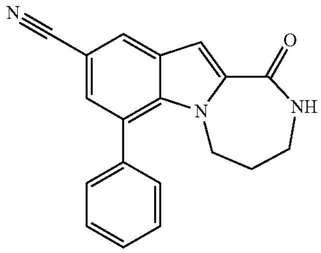 | 1-Oxo-7-phenyl-2,3,4,5-tetrahydro-[1,4]diazepino[1,2-a]indole-9-carbonitrile | 1.1 |
| 275 | 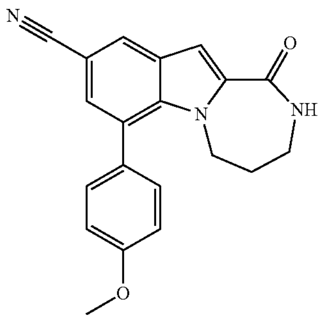 [SMILES: COc1ccc(-c2cc(C#N)cc3cc4n(c23)CCCNC4=O)cc1] | 7-(4-Methoxyphenyl)-1-oxo-2,3,4,5-tetrahydro-[1,4]diazepino[1,2-a]indole-9-carbonitrile | 1.11 |
| 276 | 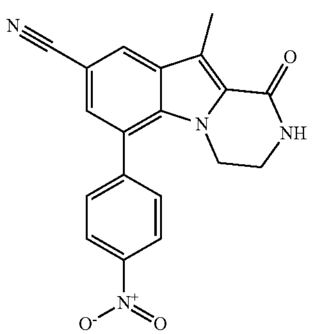 [SMILES: Cc1c2n(c3c(-c4ccc([N+](=O)[O-])cc4)cc(C#N)cc13)CCNC2=O] | 10-Methyl-6-(4-nitrophenyl)-1-oxo-3,4-dihydro-2H-pyrazino[1,2-a]indole-8-carbonitrile | 0.11 |
| 277 | 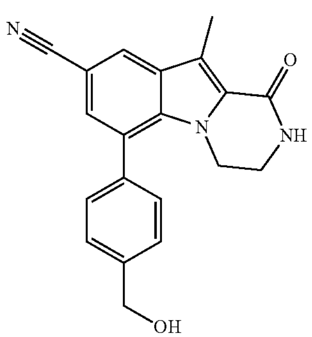 [SMILES: Cc1c2n(c3c(-c4ccc(CO)cc4)cc(C#N)cc13)CCNC2=O] | 6-[4-(Hydroxymethyl)phenyl]-10-methyl-1-oxo-3,4-dihydro-2H-pyrazino[1,2-a]indole-8-carbonitrile | 0.025 |
| 278 | 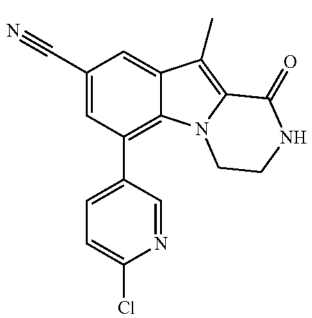 [SMILES: Cc1c2n(c3c(-c4ccc(Cl)nc4)cc(C#N)cc13)CCNC2=O] | 6-(6-Chloropyridin-3-yl)-10-methyl-1-oxo-3,4-dihydro-2H-pyrazino[1,2-a]indole-8-carbonitrile | 0.44 |

| Ex. | Structure | Name | EC$_{150}$ (uM) |
|---|---|---|---|
| 279 | 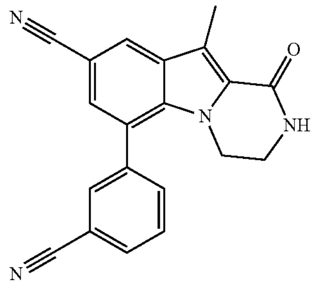 [SMILES: Cc1c2n(c3c(-c4cccc(C#N)c4)cc(C#N)cc13)CCNC2=O] | 6-(3-Cyanophenyl)-10-methyl-1-oxo-3,4-dihydro-2H-pyrazino[1,2-a]indole-8-carbonitrile | 0.31 |
| 280 | 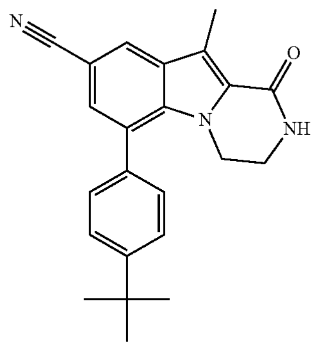 [SMILES: Cc1c2n(c3c(-c4ccc(C(C)(C)C)cc4)cc(C#N)cc13)CCNC2=O] | 6-(4-tert-Butylphenyl)-10-methyl-1-oxo-3,4-dihydro-2H-pyrazino[1,2-a]indole-8-carbonitrile | 0.14 |
| 281 | 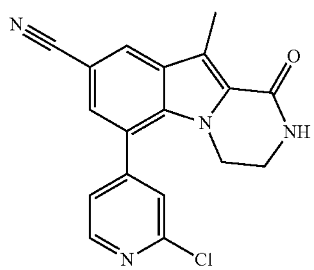 | 6-(2-Chloropyridin-4-yl)-10-methyl-1-oxo-3,4-dihydro-2H-pyrazino[1,2-a]indole-8-carbonitrile | 0.22 |
| 282 | 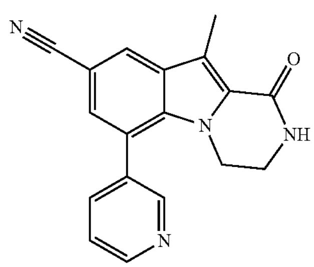 [SMILES: Cc1c2n(c3c(-c4cccnc4)cc(C#N)cc13)CCNC2=O] | 10-Methyl-1-oxo-6-pyridin-3-yl-3,4-dihydro-2H-pyrazino[1,2-a]indole-8-carbonitrile | 0.96 |
| 283 | 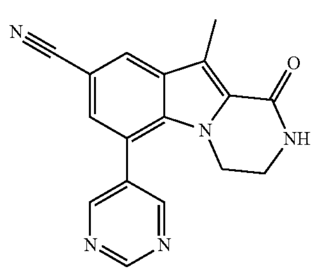 [SMILES: Cc1c2n(c3c(-c4cncnc4)cc(C#N)cc13)CCNC2=O] | 10-Methyl-1-oxo-6-pyrimidin-5-yl-3,4-dihydro-2H-pyrazino[1,2-a]indole-8-carbonitrile | 1.61 |

-continued

| Ex. | Structure | Name | EC$_{150}$ (uM) |
|---|---|---|---|
| 284 | 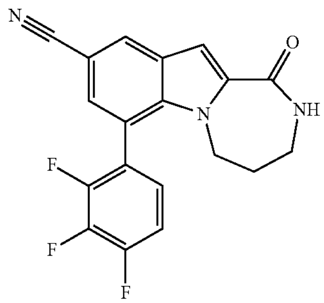 [SMILES: N#Cc1cc(-c2ccc(F)c(F)c2F)c2c(c1)cc1n2CCCNC1=O] | 1-Oxo-7-(2,3,4-trifluorophenyl)-2,3,4,5-tetrahydro-[1,4]diazepino[1,2-a]indole-9-carbonitrile | 0.16 |
| 285 | 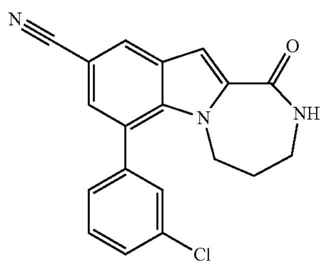 | 7-(3-Chlorophenyl)-1-oxo-2,3,4,5-tetrahydro-[1,4]diazepino[1,2-a]indole-9-carbonitrile | 3.12 |
| 286 | 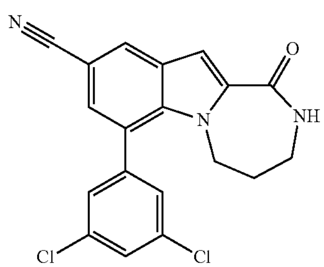 [SMILES: N#Cc1cc(-c2cc(Cl)cc(Cl)c2)c2c(c1)cc1n2CCCNC1=O] | 7-(3,5-Dichlorophenyl)-1-oxo-2,3,4,5-tetrahydro-[1,4]diazepino[1,2-a]indole-9-carbonitrile | |
| 287 | 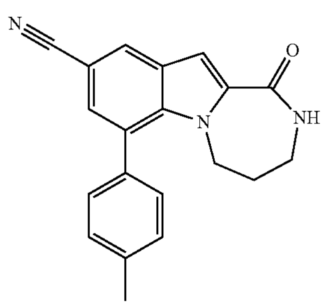 [SMILES: Cc1ccc(-c2cc(C#N)cc3cc4n(c23)CCCNC4=O)cc1] | 7-(4-Methylphenyl)-1-oxo-2,3,4,5-tetrahydro-[1,4]diazepino[1,2-a]indole-9-carbonitrile | 0.22 |
| 288 | 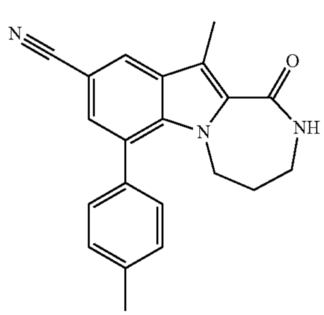 [SMILES: Cc1ccc(-c2cc(C#N)cc3c(C)c4n(c23)CCCNC4=O)cc1] | 11-Methyl-7-(4-methylphenyl)-1-oxo-2,3,4,5-tetrahydro-[1,4]diazepino[1,2-a]indole-9-carbonitrile | 0.04 |

-continued

| Ex. | Structure | Name | EC$_{150}$ (uM) |
|---|---|---|---|
| 289 | 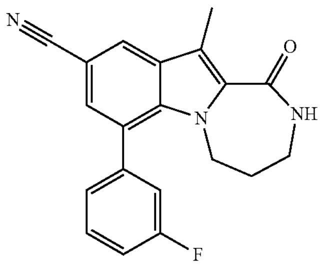 [SMILES: Cc1c2n(c3c(-c4cccc(F)c4)cc(C#N)cc13)CCCNC2=O] | 7-(3-Fluorophenyl)-11-methyl-1-oxo-2,3,4,5-tetrahydro-[1,4]diazepino[1,2-a]indole-9-carbonitrile | 0.035 |
| 290 | 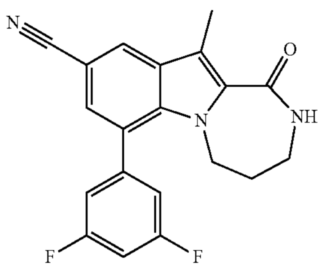 [SMILES: Cc1c2n(c3c(-c4cc(F)cc(F)c4)cc(C#N)cc13)CCCNC2=O] | 7-(3,5-Difluorophenyl)-11-methyl-1-oxo-2,3,4,5-tetrahydro-[1,4]diazepino[1,2-a]indole-9-carbonitrile | 0.29 |
| 291 | 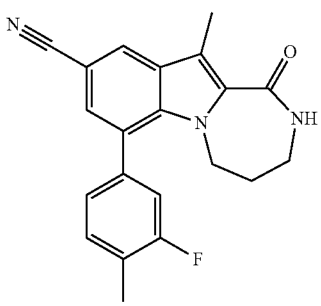 [SMILES: Cc1ccc(-c2cc(C#N)cc3c(C)c4n(c23)CCCNC4=O)cc1F] | 7-(3-Fluoro-4-methylphenyl)-11-methyl-1-oxo-2,3,4,5-tetrahydro-[1,4]diazepino[1,2-a]indole-9-carbonitrile | 0.16 |
| 292 | 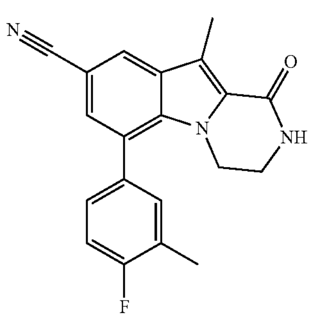 [SMILES: Cc1cc(-c2cc(C#N)cc3c(C)c4n(c23)CCNC4=O)ccc1F] | 6-(4-Fluoro-3-methylphenyl)-10-methyl-1-oxo-3,4-dihydro-2H-pyrazino[1,2-a]indole-8-carbonitrile | 0.089 |
| 293 | 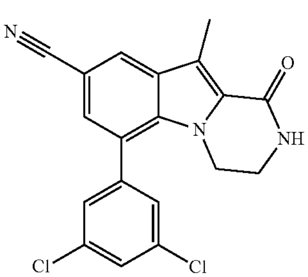 [SMILES: Cc1c2n(c3c(-c4cc(Cl)cc(Cl)c4)cc(C#N)cc13)CCNC2=O] | 6-(3,5-Dichlorophenyl)-10-methyl-1-oxo-3,4-dihydro-2H-pyrazino[1,2-a]indole-8-carbonitrile | |

-continued

| Ex. | Structure | Name | EC$_{150}$ (uM) |
|---|---|---|---|
| 294 | 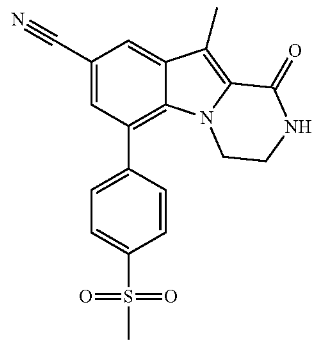 [SMILES: Cc1c2n(c3c(-c4ccc(S(C)(=O)=O)cc4)cc(C#N)cc13)CCNC2=O] | 10-Methyl-6-(4-methylsulfonylphenyl)-1-oxo-3,4-dihydro-2H-pyrazino[1,2-a]indole-8-carbonitrile | 0.27 |
| 295 | 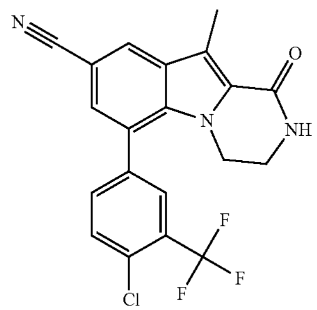 [SMILES: Cc1c2n(c3c(-c4ccc(Cl)c(C(F)(F)F)c4)cc(C#N)cc13)CCNC2=O] | 6-[4-Chloro-3-(trifluoromethyl)phenyl]-10-methyl-1-oxo-3,4-dihydro-2H-pyrazino[1,2-a]indole-8-carbonitrile | 0.3 |
| 296 | 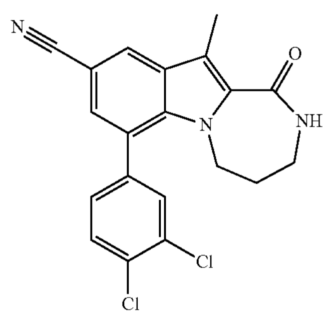 [SMILES: Cc1c2n(c3c(-c4ccc(Cl)c(Cl)c4)cc(C#N)cc13)CCCNC2=O] | 7-(3,4-Dichlorophenyl)-11-methyl-1-oxo-2,3,4,5-tetrahydro-[1,4]diazepino[1,2-a]indole-9-carbonitrile | 0.2 |
| 297 | 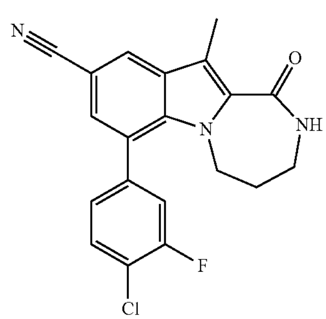 [SMILES: Cc1c2n(c3c(-c4ccc(Cl)c(F)c4)cc(C#N)cc13)CCCNC2=O] | 7-(4-Chloro-3-fluorophenyl)-11-methyl-1-oxo-2,3,4,5-tetrahydro-[1,4]diazepino[1,2-a]indole-9-carbonitrile | 0.096 |
| 298 | 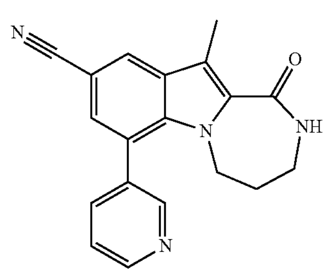 [SMILES: Cc1c2n(c3c(-c4cccnc4)cc(C#N)cc13)CCCNC2=O] | 11-Methyl-1-oxo-7-pyridin-3-yl-2,3,4,5-tetrahydro-[1,4]diazepino[1,2-a]indole-9-carbonitrile | 1 |

| Ex. | Structure | Name | $EC_{150}$ (uM) |
|---|---|---|---|
| 299 | 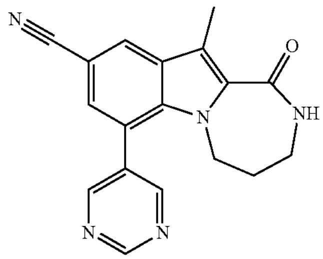 [SMILES: Cc1c2n(c3c(-c4cncnc4)cc(C#N)cc13)CCCNC2=O] | 11-Methyl-1-oxo-7-pyrimidin-5-yl-2,3,4,5-tetrahydro-[1,4]diazepino[1,2-a]indole-9-carbonitrile | |

The 299 compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula (I) or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Pharmaceutical Compositions Comprising Compounds of the Invention

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

Experimental Part

Intermediates

Intermediate 1: 6-Bromo-8-fluoro-3,4-dihydro-2H-pyrazino[1,2-a]indol-1-one

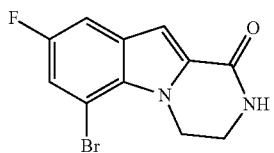 [SMILES: O=C1NCCn2c1cc1cc(F)cc(Br)c12]

Step A

To a stirred mixture of sodium hydride [disp. 55-65%] (175 mg, 4.37 mmol) in DMF (5.6 ml) was added drop wise at room temperature under argon atmosphere a solution of commercially available ethyl 7-bromo-5-fluoro-1H-indole-2-carboxylate [CAS No. 396076-60-1] (1.04 g, 3.64 mmol) in DMF (2.8 ml). Afterwards the mixture was allowed to stir for 5 min at room temperature, then commercially available 2,2-dioxo-[1,2,3]oxathiazolidine-3-carboxylic acid tert-butyl ester [CAS No. 459817-82-4] (975 mg, 4.37 mmol) was added and the solution was allowed to stir at room temperature for 15 h. The solution was cooled in an ice bath, and citric acid (10%, 62 ml) was added drop wise. The mixture was allowed to stir at room temperature for 1 h, and was afterwards extracted with ethyl acetate (2×70 ml). The combined organic layers were washed with brine (80 ml), dried (MgSO$_4$) and evaporated. The crude material (2.04 g) was purified by flash chromatography on silica gel (heptan/ethyl acetate 0-80%) to yield 7-bromo-1-(2-tert-butoxycarbonylamino-ethyl)-5-fluoro-1H-indole-2-carboxylic acid ethyl ester as a light yellow oil (1.37 g, 88%), MS (ISN) m/z=431.2 [(M+H)$^+$].

Step B

To a stirred solution of ethyl 7-bromo-1-(2-(tert-butoxycarbonylamino)ethyl)-5-fluoro-1H-indole-2-carboxylate (step A) (1.43 g, 3.33 mmol) in dichloromethane (15.2 ml) was added drop wise at 0° C. trifluoroacetic acid (4.79 g, 3.23 ml, 42.0 mmol). Afterwards the solution was allowed to stir for 15 min at 0° C., and for 30 min at room temperature. The reaction mixture was evaporated and the remaining material was solved in methanol (15.2 ml). Potassium carbonate (1.83 g, 13.3 mmol) was added and the mixture was allowed to stir at room temperature for 17 h. The mixture was evaporated, water (50 ml) was added and the mixture was extracted with dichloromethane (2×40 ml). The combined organic layers were washed with brine (50 ml), dried (MgSO$_4$) and evaporated. The crude product (0.86 g) was purified by trituration with dichloromethane (3 ml) and heptane (15 ml) to yield the title compound as an off-white solid (0.85 g, 90%), MS (ISN) m/z=283.2 [(M+H)$^+$], mp 253.5° C.

Intermediate 2: 7-Bromo-9-fluoro-2,3,4,5-tetrahydro-[1,4]diazepino[1,2-a]indol-1-one

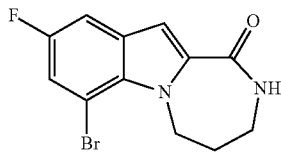

Step A

7-Bromo-1-(3-tert-butoxycarbonylamino-propyl)-5-fluoro-1H-indole-2-carboxylic acid ethyl ester, yellow oil (0.29 g, 74%), MS (ISP) m/z=443.2 [(M+H)$^+$], was prepared in accordance with the general method of intermediate 1, step A, from commercially available ethyl 7-bromo-5-fluoro-1H-indole-2-carboxylate [CAS No. 396076-60-1] (0.25 g, 0.88 mmol) and commercially available 2,2-dioxo-2λ'-[1,2,3]oxathiazinane-3-carboxylic acid tert-butyl ester [CAS No. 521267-18-5] (0.25 g, 1.06 mmol).

Step B

The title compound, off-white solid (0.14 g, 71%), MS (ISP) m/z=297.2 [(M+H)$^+$], mp 249° C., was prepared in accordance with the general method of intermediate 1, step B, from 7-bromo-1-(3-tert-butoxycarbonylamino-propyl)-5-fluoro-1H-indole-2-carboxylic acid ethyl ester (step A) (0.29 g, 0.66 mmol).

Intermediate 3: (RS)-7-Bromo-9-fluoro-5-methyl-2,3,4,5-tetrahydro-[1,4]diazepino[1,2-a]indol-1-one

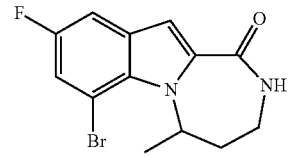 [SMILES: CC1CCNC(=O)c2cc3cc(F)cc(Br)c3n21]

Step A

7-Bromo-1-(3-tert-butoxycarbonylamino-1-methyl-propyl)-5-fluoro-1H-indole-2-carboxylic acid ethyl ester, yellow oil (0.38 g, 19%), MS (ISP) m/z=457.2 [(M+H)$^+$], was prepared in accordance with the general method of intermediate 1, step A, from commercially available ethyl 7-bromo-5-fluoro-1H-indole-2-carboxylate [CAS No. 396076-60-1] (1.25 g, 4.38 mmol) and 2,2-dioxo-6-methyl-2λ'-[1,2,3]oxathiazinane-3-carboxylic acid tert-butyl ester [CAS No. 1311368-91-8] (1.32 g, 5.25 mmol).

Step B

The title compound, light yellow solid (0.2 g, 77%), MS (ISP) m/z=313.1 [(M+H)$^+$], mp 152.5° C., was prepared in accordance with the general method of intermediate 1, step B, from 7-bromo-1-(3-tert-butoxycarbonylamino-1-methyl-propyl)-5-fluoro-1H-indole-2-carboxylic acid ethyl ester (step A) (0.38 g, 0.83 mmol).

Intermediate 4: 6-Bromo-8,9-difluoro-3,4-dihydro-2H-pyrazino[1,2-a]indol-1-one

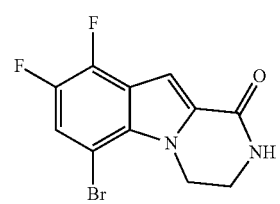 [SMILES: O=C1NCCn2c1cc1c(F)c(F)cc(Br)c12]

Step A

A stirred mixture of commercially available 2-bromo-4,5-difluoro-aniline (5 g, 24.0 mmol) and hydrochloric acid (25%, 22.9 ml) was cooled to 0° C., a solution of sodium nitrite (1.91 g, 27.6 mmol) in water (15 ml) was added drop wise over 15 min (the temperature should not rise above 10° C.). After the mixture was allowed to stir at 0° C. for 1 h, a solution of tin (II) chloride (20.5 g, 108 mmol) in hydrochloric acid (25%, 34.2 ml) was added drop wise at 0° C. (the temperature not rise above 10° C.). After the reaction mixture was allowed to stir for 1 hr at 0° C., the formed precipitate was collected by filtration and washed with water and heptane. Water (46 ml) and sodium hydroxide solution (37%, 25 ml) was added to the crude product, and the mixture was extracted with dichloromethane (3×70 ml). The combined organic layers were washed with brine (100 ml), dried (MgSO4) and evaporated.

The crude product (4.75 g) was further purified by trituration with heptane (25 ml) to yield (2-bromo-4,5-difluoro-phenyl)-hydrazine as a light brown solid (4.29 g, 80%), MS (EI) m/z=222.0 [(M)$^+$], mp 98° C.

Step B

A stirred solution of (2-bromo-4,5-difluoro-phenyl)-hydrazine (step A) (4.29 g, 19.2 mmol) in ethanol (13.8 ml) was cooled to 0° C. and a solution of ethyl pyruvate (2.39 g, 2.3 ml, 20.0 mmol) in ethanol (4 ml) was added drop wise at 0° C. for 15 min. After the mixture was allowed to stir at room temperature for 22 h it was evaporated to give crude (Z)-ethyl 2-[2-(2-bromo-4,5-difluoro-phenyl)-hydrazono]-propanoate (6.18 g, 100%) as light brown solid, MS (ISP) m/z=323.0 [(M+H)$^+$], mp 78° C., which was used without further purification.

Step C

A mixture of (Z)-ethyl 2-[2-(2-bromo-4,5-difluoro-phenyl)-hydrazono]-propanoate (step B) (6.18 g, 19.2 mmol) and commercially available Eaton's reagent (7.7 wt % phosphorus pentoxide solution in methanesulfonic acid) (46.6 ml) was allowed to stir for 2 h at 50° C. Afterwards the reaction mixture was carefully poured into saturated sodium carbonate solution (200 ml), and sodium bicarbonate was added to reach pH 8-9. The reaction mixture was extracted with dichloromethane (3×70 ml). The combined organic layers were washed with brine (100 ml), dried (MgSO$_4$) and evaporated. The crude product (5.76 g) was further purified by column chromatography on silica gel (heptane/ethyl acetate 4:1) and trituration with diethyl ether and heptane to yield ethyl 7-bromo-4,5-difluoro-1H-indole-2-carboxylate as a light brown solid, MS (ISP) m/z=304.0 [(M+H)$^+$], mp 214° C.

Step D

7-Bromo-1-(2-tert-butoxycarbonylamino-ethyl)-4,5-difluoro-1H-indole-2-carboxylic acid ethyl ester, light yellow solid (1.6 g, 94%), MS (ISP) m/z=449.0 [(M+H)$^+$], mp 127° C., was prepared in accordance with the general method of intermediate 1, step A, from ethyl 7-bromo-4,5-difluoro-1H-indole-2-carboxylate (step C) (1.16 g, 3.8 mmol) and commercially available 2,2-dioxo-[1,2,3]oxathiazolidine-3-carboxylic acid tert-butyl ester [CAS No. 459817-82-4] (1.02 g, 4.56 mmol).

Step E

The title compound, white solid (1.05 g, 98%), MS (ISP) m/z=303.1 [(M+H)$^+$], mp 242.5° C., was prepared in accordance with the general method of intermediate 1, step B, from 7-bromo-1-(2-tert-butoxycarbonylamino-ethyl)-4,5-difluoro-1H-indole-2-carboxylic acid ethyl ester (step D) (1.59 g, 3.55 mmol).

Intermediate 5: 7-Bromo-9,10-difluoro-2,3,4,5-tetrahydro-[1,4]diazepino[1,2-a]indol-1-one

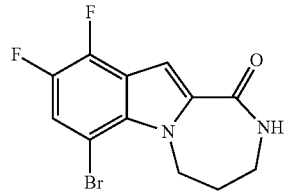 [SMILES: O=C1NCCCn2c1cc1c(F)c(F)cc(Br)c12]

Step A

7-Bromo-1-(3-tert-butoxycarbonylamino-propyl)-4,5-difluoro-1H-indole-2-carboxylic acid ethyl ester, light yellow solid (1.64 g, 94%), MS (ISP) m/z=462.1 [(M+H)$^+$], mp 124° C. was prepared in accordance with the general method of intermediate 1, step A, from ethyl 7-bromo-4,5-difluoro-1H-indole-2-carboxylate (intermediate 4, step C) (1.16 g, 3.8 mmol) and commercially available 2,2-dioxo-2λ'-[1,2,3]oxathiazinane-3-carboxylic acid tert-butyl ester [CAS No. 521267-18-5] (1.08 g, 4.56 mmol).

Step B

The title compound, white solid (0.97 g, 87%), MS (ISP) m/z=315.0 [(M+H)$^+$], mp 209.5° C., was prepared in accordance with the general method of intermediate 1, step B, from 7-bromo-1-(3-tert-butoxycarbonylamino-propyl)-4,5-difluoro-1H-indole-2-carboxylic acid ethyl ester (step A) (1.64 g, 3.56 mmol).

Intermediate 6: 6-Bromo-7,8-difluoro-3,4-dihydro-2H-pyrazino[1,2-a]indol-1-one

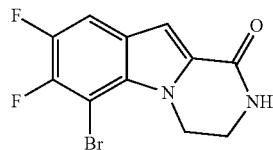 [SMILES: O=C1NCCn2c1cc1cc(F)c(F)c(Br)c12]

Step A (2-Bromo-3,4-difluoro-phenyl)-hydrazine, brown solid (2.12 g, 66%), MS (EI) m/z=222.0 [(M)$^+$], mp 116.5° C., was prepared in accordance with the general method of intermediate 4, step A, from commercially available 2-bromo-3,4-difluoro-aniline (3 g, 14.4 mmol).

Step B (Z)-Ethyl 2-[2-(2-bromo-3,4-difluoro-phenyl)-hydrazono]-propanoate, brown solid (3.05 g, 100%), MS (ISP) m/z=323.2 [(M+H)$^+$], mp 87° C., was prepared in accordance with the general method of intermediate 4, step B, from (2-bromo-3,4-difluoro-phenyl)-hydrazine (step A) (2.12 g, 9.51 mmol).

Step C

Ethyl 7-bromo-5,6-difluoro-1H-indole-2-carboxylate, off-white solid (2.45 g, 85%), MS (ISP) m/z=304.2 [(M+H)$^+$], mp 140° C., was prepared in accordance with the general method of intermediate 4, step C, from (Z)-ethyl 2-[2-(2-bromo-3,4-difluoro-phenyl)-hydrazono]-propanoate (step B) (3.05 g, 9.5 mmol).

Step D

7-Bromo-1-(2-tert-butoxycarbonylamino-ethyl)-5,6-difluoro-1H-indole-2-carboxylic acid ethyl ester, light yellow solid (1.55 g, 91%), MS (ISP) m/z=449.0 [(M+H)⁺], mp 103° C., was prepared in accordance with the general method of intermediate 1, step A, from ethyl 7-bromo-5,6-difluoro-1H-indole-2-carboxylate (step C) (1.16 g, 3.8 mmol) and commercially available 2,2-dioxo-[1,2,3]oxathiazolidine-3-carboxylic acid tert-butyl ester [CAS No. 459817-82-4] (1.02 g, 4.56 mmol).

Step E

The title compound, white solid (0.89 g, 88%), MS (ISP) m/z=302.9 [(M+H)⁺], mp 265.5° C., was prepared in accordance with the general method of intermediate 1, step B, from 7-bromo-1-(2-tert-butoxycarbonylamino-ethyl)-5,6-difluoro-1H-indole-2-carboxylic acid ethyl ester (step D) (1.51 g, 3.38 mmol).

Intermediate 7: 7-Bromo-8,9-difluoro-2,3,4,5-tetrahydro-[1,4]diazepino[1,2-a]indol-1-one

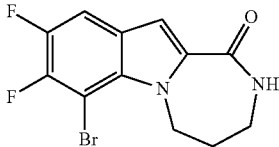

Step A

7-Bromo-1-(3-tert-butoxycarbonylamino-propyl)-5,6-difluoro-1H-indole-2-carboxylic acid ethyl ester, light yellow solid (1.4 g, 80%), MS (ISP) m/z=462.1 [(M+H)⁺], mp 95.5° C. was prepared in accordance with the general method of intermediate 1, step A, from ethyl 7-bromo-5,6-difluoro-1H-indole-2-carboxylate (intermediate 6, step C) (1.16 g, 3.8 mmol) and commercially available 2,2-dioxo-2λ'-[1,2,3]oxathiazinane-3-carboxylic acid tert-butyl ester [CAS No. 521267-18-5] (1.08 g, 4.56 mmol).

Step B

The title compound, white solid (0.78 g, 85%), MS (ISP) m/z=316.9 [(M+H)⁺], mp 249° C., was prepared in accordance with the general method of intermediate 1, step B, from 7-bromo-1-(3-tert-butoxycarbonylamino-propyl)-5,6-difluoro-1H-indole-2-carboxylic acid ethyl ester (step A) (1.34 g, 2.9 mmol).

Intermediate 8: 7-Bromo-9-chloro-2,3,4,5-tetrahydro-[1,4]diazepino[1,2-a]indol-1-one

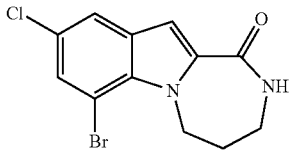 [SMILES: O=C1NCCCn2c1cc1cc(Cl)cc(Br)c12]

Step A

7-Bromo-1-(3-tert-butoxycarbonylamino-propyl)-5-chloro-1H-indole-2-carboxylic acid ethyl ester, light yellow solid (1.48 g, 85%), MS (ISP) m/z=461.2 [(M+H)⁺], mp 115.5° C., was prepared in accordance with the general method of intermediate 1, step A, from commercially available ethyl 7-bromo-5-chloro-1H-indole-2-carboxylate [CAS No. 1352896-41-3] (1.15 g, 3.8 mmol) and commercially available 2,2-dioxo-2λ'-[1,2,3]oxathiazinane-3-carboxylic acid tert-butyl ester [CAS No. 521267-18-5] (1.08 g, 4.56 mmol).

Step B

The title compound, light yellow solid (0.88 g, 88%), MS (ISP) m/z=314.9 [(M+H)⁺], mp 219° C., was prepared in accordance with the general method of intermediate 1, step B, from 7-bromo-1-(3-tert-butoxycarbonylamino-propyl)-5-chloro-1H-indole-2-carboxylic acid ethyl ester (step A) (1.47 g, 3.2 mmol).

Intermediate 9: 6-Bromo-8-chloro-3,4-dihydro-2H-pyrazino[1,2-a]indol-1-one

Step A

7-Bromo-1-(2-tert-butoxycarbonylamino-ethyl)-5-chloro-1H-indole-2-carboxylic acid ethyl ester, yellow oil (1.36 g, 80%), MS (ISP) m/z=447.0 [(M+H)⁺], was prepared in accordance with the general method of intermediate 1, step A, from commercially available ethyl 7-bromo-5-chloro-1H-indole-2-carboxylate [CAS No. 1352896-41-3] (1.15 g, 3.8 mmol) and commercially available 2,2-dioxo-[1,2,3]oxathiazolidine-3-carboxylic acid tert-butyl ester [CAS No. 459817-82-4] (1.02 g, 4.56 mmol).

Step B

The title compound, white solid (0.74 g, 82%), MS (ISP) m/z=301.0 [(M+H)⁺], mp 247° C., was prepared in accordance with the general method of intermediate 1, step B, from 7-bromo-1-(2-tert-butoxycarbonylamino-ethyl)-5-chloro-1H-indole-2-carboxylic acid ethyl ester (step A) (1.35 g, 3.03 mmol).

Intermediate 10: 6-Bromo-8-methyl-3,4-dihydro-2H-pyrazino[1,2-a]indol-1-one

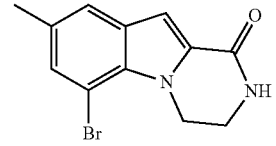 [SMILES: Cc1cc(Br)c2c(c1)cc1n2CCNC1=O]

Step A

7-Bromo-1-(2-tert-butoxycarbonylamino-ethyl)-5-methyl-1H-indole-2-carboxylic acid ethyl ester, orange solid (0.41 g, 85%), MS (ISP) m/z=426.4 [(M+H)⁺], mp 92.5° C., was prepared in accordance with the general method of intermediate 1, step A, from commercially available ethyl 7-bromo-5-methyl-1H-indole-2-carboxylate [CAS No. 15936-72-8] (0.32 g, 1.12 mmol) and commercially available 2,2-dioxo-[1,2,3]oxathiazolidine-3-carboxylic acid tert-butyl ester [CAS No. 459817-82-4] (0.3 g, 1.35 mmol).

Step B

The title compound, white solid (0.23 g, 86%), MS (ISP) m/z=279.3 [(M+H)⁺], mp 243° C., was prepared in accordance with the general method of intermediate 1, step B, from 7-bromo-1-(2-tert-butoxycarbonylamino-ethyl)-5-methyl-1H-indole-2-carboxylic acid ethyl ester (step A) (0.4 g, 0.95 mmol).

Intermediate 11: 7-Bromo-9-methyl-2,3,4,5-tetrahydro-[1,4]diazepino[1,2-a]indol-1-one

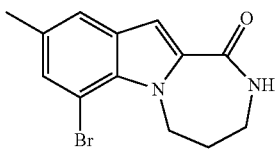 [SMILES: Cc1cc(Br)c2c(c1)cc1n2CCCNC1=O]

Step A

7-Bromo-1-(3-tert-butoxycarbonylamino-propyl)-5-methyl-1H-indole-2-carboxylic acid ethyl ester, off-white solid (0.38 g, 78%), MS (ISP) m/z=440.4 [(M+H)+], mp 107.5° C., was prepared in accordance with the general method of intermediate 1, step A, from commercially available ethyl 7-bromo-5-methyl-1H-indole-2-carboxylate [CAS No. 1352896-41-3] (0.32 g, 1.12 mmol) and commercially available 2,2-dioxo-2λ'-[1,2,3]oxathiazinane-3-carboxylic acid tert-butyl ester [CAS No. 521267-18-5] (0.32 g, 1.35 mmol).

Step B

The title compound, white solid (0.22 g, 86%), MS (ISP) m/z=293.4 [(M+H)+], mp 232° C., was prepared in accordance with the general method of intermediate 1, step B, from 7-bromo-1-(3-tert-butoxycarbonylamino-propyl)-5-methyl-1H-indole-2-carboxylic acid ethyl ester (step A) (0.38 g, 0.86 mmol).

Intermediate 12: 6-Bromo-8-chloro-10-methyl-3,4-dihydro-2H-pyrazino[1,2-a]indol-1-one

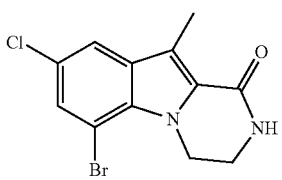 [SMILES: Cc1c2n(c3c(Br)cc(Cl)cc13)CCNC2=O]

Step A (2-Bromo-4-chloro-phenyl)-hydrazine, off-white solid (1.98 g, 60%), MS (ISP) m/z=223.3 [(M+H)+], mp 102° C., was prepared in accordance with the general method of intermediate 4, step A, from commercially available 2-bromo-4-chloro-aniline (3.1 g, 15.0 mmol).

Step B

A stirred solution of (2-bromo-4-chloro-phenyl)-hydrazine (step A) (1.98 g, 8.94 mmol) in ethanol (6.5 ml) was cooled to 0° C. and a solution of commercially available methyl 2-ketobutyrate (1.08 g, 1.04 ml, 9.3 mmol) in ethanol (2 ml) was added drop wise at 0° C. for 15 min. After the mixture was allowed to stir at room temperature for 3 h it was evaporated. The crude material (3.01 g) was purified by flash chromatography on silica gel (heptane/ethyl acetate 0-20%) to yield (Z)-2-[(2-bromo-4-chloro-phenyl)-hydrazono]-butyric acid methyl ester (2.67 g, 94%) as a light yellow solid, MS (ISP) m/z=321.3 [(M+H)+], mp 67° C.

Step C

To a stirred solution of (Z)-2-[(2-bromo-4-chloro-phenyl)-hydrazono]-butyric acid methyl ester (step B) (2.67 g, 8.35 mmol) in acetic acid (30 ml) was added at room temperature zinc chloride (6.26 g, 46.0 mmol) and the mixture was allowed to stir for 1 h under reflux conditions. Afterwards the reaction mixture was poured into ice/water (50 ml) and extracted with ethyl acetate (2×50 ml). The combined organic layers were washed with brine (50 ml), dried (MgSO4) and evaporated. The crude product (2.5 g) was further purified by flash chromatography on silica gel (heptane/ethyl acetate 0-20%) and trituration with diethyl ether (5 ml) and heptane (15 ml) to yield methyl 7-bromo-5-chloro-3-methyl-1H-indole-2-carboxylate as an off-white solid (2.02 g, 80%), MS (ISN) m/z=302.3 [(M−H)+], mp 163.5° C.

Step D

7-Bromo-1-(2-tert-butoxycarbonylamino-ethyl)-5-chloro-3-methyl-1H-indole-2-carboxylic acid ethyl ester, light yellow oil (1.45 g, 97%), MS (ISP) m/z=447.3 [(M+H)+], was prepared in accordance with the general method of intermediate 1, step A, from methyl 7-bromo-5-chloro-3-methyl-1H-indole-2-carboxylate (step C) (1.01 g, 3.34 mmol) and commercially available 2,2-dioxo-[1,2,3]oxathiazolidine-3-carboxylic acid tert-butyl ester [CAS No. 459817-82-4] (0.895 g, 4.01 mmol).

Step E

The title compound, white solid (0.9 g, 88%), MS (ISP) m/z=315.2 [(M+H)+], mp 261° C., was prepared in accordance with the general method of intermediate 1, step B, from 7-bromo-1-(2-tert-butoxycarbonylamino-ethyl)-5-chloro-3-methyl-1H-indole-2-carboxylic acid ethyl ester (step D) (1.45 g, 3.25 mmol).

Intermediate 13: 7-Bromo-9-chloro-11-methyl-2,3,4,5-tetrahydro-[1,4]diazepino[1,2-a]indol-1-one

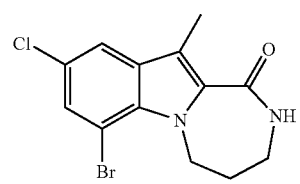 [SMILES: Cc1c2n(c3c(Br)cc(Cl)cc13)CCCNC2=O]

Step A

7-Bromo-1-(3-tert-butoxycarbonylamino-propyl)-5-chloro-3-methyl-1H-indole-2-carboxylic acid methyl ester, light yellow oil (1.4 g, 91%), MS (ISP) m/z=461.3 [(M+H)+], was prepared in accordance with the general method of intermediate 1, step A, from methyl 7-bromo-5-chloro-3-methyl-1H-indole-2-carboxylate (intermediate 12, step C) (1.01 g, 3.34 mmol) and commercially available 2,2-dioxo-2λ'-[1,2,3]oxathiazinane-3-carboxylic acid tert-butyl ester [CAS No. 521267-18-5] (0.95 g, 4.01 mmol).

Step B

The title compound, white solid (0.85 g, 85%), MS (ISP) m/z=329.3 [(M+H)+], mp 232° C., was prepared in accordance with the general method of intermediate 1, step B, from 7-bromo-1-(3-tert-butoxycarbonylamino-propyl)-5-chloro-3-methyl-1H-indole-2-carboxylic acid methyl ester (step A) (1.4 g, 3.05 mmol).

Intermediate 14: 6-Bromo-8-fluoro-10-methyl-3,4-dihydro-2H-pyrazino[1,2-a]indol-1-one

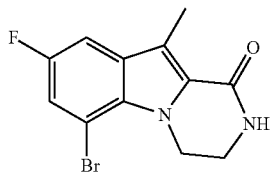 [SMILES: Cc1c2n(c3c(Br)cc(F)cc13)CCNC2=O]

Step A (2-Bromo-4-fluoro-phenyl)-hydrazine, white solid (1.63 g, 89%), MS (ISP) m/z=205.1 [(M+H)+], mp 76° C., was prepared in accordance with the general method of intermediate 4, step A, from commercially available 2-bromo-4-fluoro-aniline (1.7 g, 8.95 mmol).

Step B (Z)-2-[(2-bromo-4-fluoro-phenyl)-hydrazono]-butyric acid methyl ester (2.03 g, 85%) as a orange solid, MS (ISP) m/z=303.3 [(M+H)+], mp 44° C., was prepared in accordance with the general method of intermediate 12, step B, from (2-bromo-4-fluoro-phenyl)-hydrazine (step A) (1.62 g, 7.9 mmol).

Step C

Methyl 7-bromo-5-chloro-3-methyl-1H-indole-2-carboxylate, light yellow solid (1.62 g, 85%), MS (ISN) m/z=286.3 [(M−H)+], mp 127° C., was prepared in accordance with the general method of intermediate 12, step C, from (Z)-2-[(2-bromo-4-fluoro-phenyl)-hydrazono]-butyric acid methyl ester (step B) (2.02 g, 6.66 mmol).

Step D

7-Bromo-1-(2-tert-butoxycarbonylamino-ethyl)-5-fluoro-3-methyl-1H-indole-2-carboxylic acid ethyl ester, light yellow solid (1.41 g, 98%), MS (ISP) m/z=429.3 [(M+H)+], mp 110° C., was prepared in accordance with the general method of intermediate 1, step A, from methyl 7-bromo-5-fluoro-3-methyl-1H-indole-2-carboxylate (step C) (0.956 g, 3.34 mmol) and commercially available 2,2-dioxo-[1,2,3]oxathiazolidine-3-carboxylic acid tert-butyl ester [CAS No. 459817-82-4] (0.895 g, 4.01 mmol).

Step E

The title compound, white solid (0.91 g, 95%), MS (ISP) m/z=299.3 [(M+H)+], mp 229° C., was prepared in accordance with the general method of intermediate 1, step B, from 7-bromo-1-(2-tert-butoxycarbonylamino-ethyl)-5-fluoro-3-methyl-1H-indole-2-carboxylic acid ethyl ester (step D) (1.39 g, 3.24 mmol).

Intermediate 15: 6-Bromo-1-oxo-1,2,3,4-tetrahydro-pyrazino[1,2-a]indole-8-carbonitrile

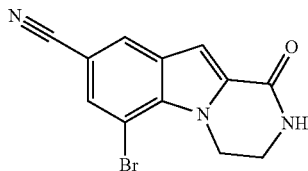 [SMILES: N#Cc1cc(Br)c2c(c1)cc1n2CCNC1=O]

Step A

To a stirred solution of commercially available 4-amino-3-bromo-5-iodobenzonitrile (0.5 g, 1.55 mmol) in THF (7.7 ml) was added Boc-anhydride (0.71 g, 755 µl, 3.25 mmol) and 4-dimethylaminopyridine (18.9 mg, 155 µmol), and the solution was allowed to stir for 3 h at room temperature. The reaction mixture was evaporated and purified by flash chromatography on silica gel (heptane/ethyl acetate 0-50%) to yield a light yellow solid (0.74 g) which was subsequently solved in dichloromethane (2.2 ml) and cooled to 0° C. Afterwards trifluoroacetic acid (318 mg, 215 µl, 2.79 mmol) was added, and the solution was allowed to stir for 3 h at 0° C. Saturated sodium carbonate solution (5 ml) was added and the mixture was extracted with dichloromethane (2×20 ml). The combined organic layers were washed with brine (30 ml), dried (MgSO4) and evaporated. The crude product (0.69 g) was further purified by flash chromatography on silica gel (heptane/ethyl acetate 0-20%) and crystallization (heptane) to yield (2-bromo-4-cyano-6-iodo-phenyl)-carbamic acid tert-butyl ester (0.42 g, 64%) as an off-white solid, MS (ISN) m/z=421.3 [(M−H)+], mp 117.5° C.

Step B

A mixture of (2-bromo-4-cyano-6-iodo-phenyl)-carbamic acid tert-butyl ester (step A) (413 mg, 0.98 mmol), 3,3-diethoxyprop-1-yne (125 mg, 140 µl, 0.98 mmol), triethylamine (395 mg, 544 µl, 3.9 mmol), copper(I)iodide (5.58 mg, 29.3 µmol) and bis(triphenylphosphine)-palladium(II)chloride (34.3 mg, 48.8 µmol) was allowed to stir for 3 h at room temperature. Afterwards 2,3,4,6,7,8,9,10-octahydropyrimido [1,2-a]azepine (297 mg, 292 µl, 1.95 mmol) and DMF (1.58 ml) were added, and the reaction mixture was allowed to stir for 17 h at room temperature, poured into water (10 ml) and extracted with ethyl acetate (2×20 ml). The combined organic layers were washed with brine, dried (MgSO4) and evaporated. The crude product (0.51 g) was further purified by flash chromatography on silica gel (heptane/ethyl acetate 0-20%) to yield 7-bromo-5-cyano-2-diethoxymethyl-indole-1-carboxylic acid tert-butyl ester (0.29 g, 64%) as a light yellow oil, MS (EI) m/z=422 [(M)+].

Step C 7-bromo-5-cyano-2-diethoxymethyl-indole-1-carboxylic acid tert-butyl ester (0.29 g, 685 µmol) was solved in THF (2 ml) and cooled to 0° C. Afterwards hydrochloric acid (37%, 1.35 g, 1.14 ml, 13.7 mmol) was added quickly, and the mixture was allowed to stir for 15 min at 0° C. and for 5 h at room temperature. The mixture was cooled (ice bath), saturated sodium carbonate solution (10 ml) was added and the mixture was extracted with ethyl acetate (2×25 ml). The combined organic layers were washed with brine (30 ml), dried (MgSO4) and evaporated. The crude product (0.18 g) was further purified by flash chromatography on silica gel (heptane/ethyl acetate 0-20%) to yield 7-bromo-2-formyl-1H-indole-5-carbonitrile (0.17 g, 100%) as an orange solid, MS (ISN) m/z=247.4 [(M−H)+], mp 117.5° C.

Step D

To a stirred solution of 7-bromo-2-formyl-1H-indole-5-carbonitrile (0.17 g, 683 µmol) in MeOH (6.03 ml) was added sodium cyanide (167 mg, 3.41 mmol) and manganese dioxide (297 mg, 3.41 mmol) and the reaction mixture was allowed to stir for 17 h at room temperature. The mixture was evaporated, water (20 ml) was added and the mixture was extracted with ethyl acetate (2×15 ml). The combined organic layers were washed with brine, dried (MgSO4) and evaporated. The crude product (0.11 g) was further purified by flash chromatography on silica gel (heptane/ethyl acetate 0-20%) to yield methyl 7-bromo-5-cyano-1H-indole-2-carboxylate (0.105 g, 55%) as an orange solid, MS (ISN) m/z=279.3 [(M−H)+], mp 248° C.

Step E

7-Bromo-1-(2-tert-butoxycarbonylamino-ethyl)-5-cyano-1H-indole-2-carboxylic acid methyl ester, light yellow oil (1.74 g, 95%), MS (ISP) m/z=423.3 [(M+H)⁺], was prepared in accordance with the general method of intermediate 1, step A, from methyl 7-bromo-5-cyano-1H-indole-2-carboxylate (step D) (1.21 g, 4.34 mmol) and commercially available 2,2-dioxo-[1,2,3]oxathiazolidine-3-carboxylic acid tert-butyl ester [CAS No. 459817-82-4] (1.16 g, 5.2 mmol).

Step F

The title compound, light brown solid (0.93 g, 78%), MS (ISP) m/z=288.4 [(M+H)⁺], mp 279° C., was prepared in accordance with the general method of intermediate 1, step B, from 7-bromo-1-(2-tert-butoxycarbonylamino-ethyl)-5-cyano-1H-indole-2-carboxylic acid methyl ester (step A) (1.74 g, 4.12 mmol).

Intermediate 16: 6-Bromo-10-methyl-1-oxo-1,2,3,4-tetrahydro-pyrazino[1,2-a]indole-8-carbonitrile

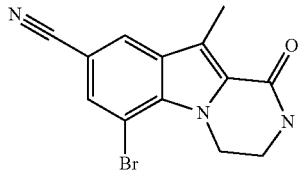 [SMILES: Cc1c2n(c3c(Br)cc(C#N)cc13)CCNC2=O]

Step A (2-Bromo-4-cyano-phenyl)-hydrazine, white solid (5.05 g, 47%), MS (ISN) m/z=210.1 [(M−H)⁻], mp 115° C., was prepared in accordance with the general method of intermediate 4, step A, from commercially available 2-bromo-4-cyano-aniline (10.0 g, 50.8 mmol).

Step B (Z)-2-[(2-bromo-4-cyano-phenyl)-hydrazono]-butyric acid methyl ester (7.33 g, 99%) as a brown solid, MS (ISN) m/z=310.3 [(M−H)⁻], mp 103° C., was prepared in accordance with the general method of intermediate 12, step B, from (2-bromo-4-cyano-phenyl)-hydrazine (step A) (5.04 g, 23.8 mmol).

Step C

Methyl 7-bromo-5-cyano-3-methyl-1H-indole-2-carboxylate, off-white solid (3.44 g, 50%), MS (ISN) m/z=293.4 [(M−H)⁻], mp 248° C., was prepared in accordance with the general method of intermediate 12, step C, from (Z)-2-[(2-bromo-4-cyano-phenyl)-hydrazono]-butyric acid methyl ester (step B) (7.22 g, 23.3 mmol).

Step D

7-Bromo-1-(2-tert-butoxycarbonylamino-ethyl)-5-cyano-3-methyl-1H-indole-2-carboxylic acid ethyl ester, light brown foam (3.88 g, 77%), MS (ISP) m/z=436.5 [(M+H)⁺], was prepared in accordance with the general method of intermediate 1, step A, from methyl 7-bromo-5-cyano-3-methyl-1H-indole-2-carboxylate (step C) (3.40 g, 11.6 mmol) and commercially available 2,2-dioxo-[1,2,3]oxathiazolidine-3-carboxylic acid tert-butyl ester [CAS No. 459817-82-4] (3.11 g, 13.9 mmol).

Step E

The title compound, off-white solid (2.42 g, 91%), MS (ISN) m/z=302.5 [(M−H)⁻], mp 313° C., was prepared in accordance with the general method of intermediate 1, step B, from 7-bromo-1-(2-tert-butoxycarbonylamino-ethyl)-5-cyano-3-methyl-1H-indole-2-carboxylic acid ethyl ester (step D) (3.8 g, 8.71 mmol).

Intermediate 17: 7-Bromo-11-methyl-1-oxo-2,3,4,5-tetrahydro-[1,4]diazepino[1,2-a]indole-9-carbonitrile

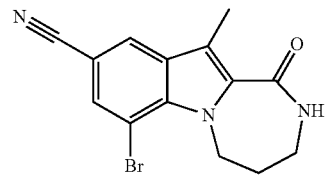 [SMILES: Cc1c2n(c3c(Br)cc(C#N)cc13)CCCNC2=O]

Step A

Methyl 7-bromo-5-cyano-3-methyl-1-[3-[(2-methylpropan-2-yl)-oxycarbonylamino]propyl]-indole-2-carboxylate, white solid (5.61 g, 98%), MS (ISP) m/z=451.3 [(M+H)⁺], mp 136° C., was prepared in accordance with the general method of intermediate 1, step A, from methyl 7-bromo-5-cyano-3-methyl-1H-indole-2-carboxylate (intermediate 16, step C) (3.71 g, 12.7 mmol) and commercially available 2,2-dioxo-2λ'-[1,2,3]oxathiazinane-3-carboxylic acid tert-butyl ester [CAS No. 521267-18-5] (3.6 g, 15.2 mmol).

Step B

The title compound, white solid (2.8 g, 71%), MS (ISP) m/z=318.4 [(M+H)⁺], mp 249° C., was prepared in accordance with the general method of intermediate 1, step B, from methyl 7-bromo-5-cyano-3-methyl-1-[3-[(2-methylpropan-2-yl)-oxycarbonylamino]propyl]-indole-2-carboxylate (step A) (5.61 g, 12.5 mmol).

Intermediate 18: 6-Bromo-8-methoxy-3,4-dihydro-2H-pyrazino[1,2-a]indol-1-one

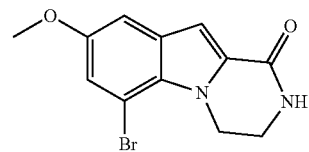 [SMILES: COc1cc(Br)c2c(c1)cc1n2CCNC1=O]

Step A (2-Bromo-4-methoxy-phenyl)-hydrazine, brown solid (4.34 g, 84%), MS (ISN) m/z=216.1 PI-M, mp 70° C., was prepared in accordance with the general method of intermediate 4, step A, from commercially available 2-bromo-4-methoxy-aniline (4.79 g, 23.7 mmol).

Step B

Ethyl(2Z)-2-[(2-bromo-4-methoxyphenyl)-hydrazinylidene]-propanoate, brown solid (6.28 g, 99%), MS (ISP) m/z=317.4 [(M+H)⁺], mp 69° C., was prepared in accordance with the general method of intermediate 4, step B, from (2-bromo-4-methoxy-phenyl)-hydrazine (step A) (4.33 g, 15.9 mmol).

Step C

Ethyl 7-bromo-5-methoxy-1H-indole-2-carboxylate, light yellow solid (1.73 g, 31%), MS (ISP) m/z=298.4 [(M+H)⁺], mp 121.5° C., was prepared in accordance with the general method of intermediate 12, step C, from ethyl(2Z)-2-[(2-bromo-4-methoxyphenyl)-hydrazinylidene]-propanoate (step B) (5.9 g, 18.7 mmol).

Step D

Ethyl 7-bromo-5-methoxy-1-{2-[(2-methylpropan-2-yl)-oxycarbonylamino]-ethyl}-indole-2-carboxylate, light yellow oil (1.48 g, 100%), MS (ISP) m/z=442.4 [(M+H)+], was prepared in accordance with the general method of intermediate 1, step A, from ethyl 7-bromo-5-methoxy-1H-indole-2-carboxylate (step C) (1.0 g, 3.35 mmol) and commercially available 2,2-dioxo-[1,2,3]oxathiazolidine-3-carboxylic acid tert-butyl ester [CAS No. 459817-82-4] (0.9 g, 4.03 mmol).

Step E

The title compound, off-white solid (0.91 g, 92%), MS (ISP) m/z=295.5 [(M+H)+], mp 261° C., was prepared in accordance with the general method of intermediate 1, step B, from ethyl 7-bromo-5-methoxy-1-{2-[(2-methylpropan-2-yl)-oxycarbonylamino]-ethyl}-indole-2-carboxylate (step D) (1.48 g, 3.35 mmol).

Intermediate 19: 6-Bromo-8-(trifluoromethoxy)-3,4-dihydro-2H-pyrazino[1,2-a]indol-1-one

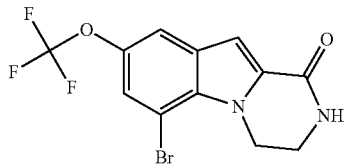 [SMILES: O=C1NCCn2c1cc1cc(OC(F)(F)F)cc(Br)c12]

Step A (2-Bromo-4-trifluoromethoxy-phenyl)-hydrazine, brown oil (2.64 g, 50%), MS (ISP) m/z=271.1 [(M+H)+], was prepared in accordance with the general method of intermediate 4, step A, from commercially available 2-bromo-4-trifluoromethoxy-aniline (5.0 g, 19.5 mmol).

Step B

Ethyl(2Z)-2-[(2-bromo-4-trifluoromethoxy-phenyl)-hydrazinylidene]-propanoate, light brown solid (3.61 g, 100%), MS (ISP) m/z=369.4 [(M+H)+], mp 65° C., was prepared in accordance with the general method of intermediate 4, step B, from (2-bromo-3,4-difluoro-phenyl)-hydrazine (step A) (2.65 g, 9.78 mmol).

Step C

Ethyl 7-bromo-5-trifluoromethoxy-1H-indole-2-carboxylate, off-white solid (2.53 g, 77%), MS (ISN) m/z=350.4 [(M−H)−], mp 117° C., was prepared in accordance with the general method of intermediate 4, step C, from ethyl(2Z)-2-[(2-bromo-4-trifluoromethoxy-phenyl)-hydrazinylidene]-propanoate (step B) (3.44 g, 9.32 mmol).

Step D

Ethyl 7-bromo-1-{2-[(2-methylpropan-2-yl)-oxycarbonylamino]-ethyl}-5-(trifluoromethoxy)-indole-2-carboxylate, light yellow oil (1.66 g, 100%), MS (ISP) m/z=496.5 [(M+H)+], was prepared in accordance with the general method of intermediate 1, step A, from ethyl 7-bromo-5-trifluoromethoxy-1H-indole-2-carboxylate (step C) (1.18 g, 3.35 mmol) and commercially available 2,2-dioxo-[1,2,3]oxathiazolidine-3-carboxylic acid tert-butyl ester [CAS No. 459817-82-4] (0.9 g, 4.02 mmol).

Step E

The title compound, off-white solid (1.04 g, 89%), MS (ISN) m/z=349.4 [(M+H)+], mp 214° C., was prepared in accordance with the general method of intermediate 1, step B, from ethyl 7-bromo-1-{2-[(2-methylpropan-2-yl)-oxycarbonylamino]-ethyl}-5-(trifluoromethoxy)-indole-2-carboxylate (step D) (1.66 g, 3.35 mmol).

Intermediate 20: 7-Bromo-1-oxo-2,3,4,5-tetrahydro-[1,4]diazepino[1,2-a]indole-9-carbonitrile

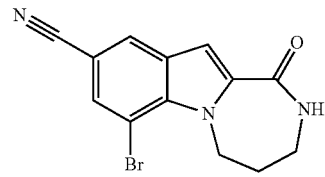 [SMILES: N#Cc1cc(Br)c2c(c1)cc1n2CCCNC1=O]

Step A

Methyl 7-bromo-5-cyano-1-{3-[(2-methylpropan-2-yl)-oxycarbonylamino]-propyl}-indole-2-carboxylate, white solid (1.15 g, 57%), MS (ISP) m/z=438.3 [(M+H)+], mp 144° C., was prepared in accordance with the general method of intermediate 1, step A, from methyl 7-bromo-5-cyano-1H-indole-2-carboxylate (intermediate 15, step D) (1.3 g, 4.66 mmol) and commercially available 2,2-dioxo-2λ'-[1,2,3]oxathiazinane-3-carboxylic acid tert-butyl ester [CAS No. 521267-18-5] (1.33 g, 5.59 mmol).

Step B

The title compound, off-white solid (0.65 g, 81%), MS (ISP) m/z=306.3 [(M+H)+], mp 256.5° C., was prepared in accordance with the general method of intermediate 1, step B, from methyl 7-bromo-5-cyano-1-{3-[(2-methylpropan-2-yl)-oxycarbonylamino]-propyl}-indole-2-carboxylate (step A) (1.15 g, 2.64 mmol).

Example 1

(R)-4-Methyl-6-phenyl-3,4-dihydro-2H-pyrazino[1,2-a]indol-1-one

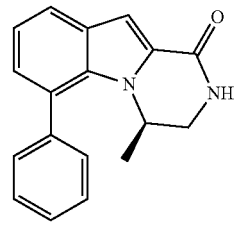 [SMILES: C[C@@H]1CNC(=O)c2cc3cccc(-c4ccccc4)c3n21]

A mixture of (R)-6-bromo-4-methyl-3,4-dihydropyrazino[1,2-a]indol-1(2H)-one [CAS No. 396075-75-5] (69.8 mg, 0.25 mmol) and commercially available phenylboronic acid (39.6 mg, 0.325 mmol) in 1,2-dimethoxyethane (1.67 ml) and 2M sodium carbonate solution (416 μl, 832 μmol) was purged with argon in an ultrasonic bath for 5 min. Then triphenylphosphine (13.1 mg, 50.0 μmol) and palladium(II)acetate (5.61 mg, 25.0 μmol) were added at room temperature, and afterwards the reaction mixture was allowed to stir for 2 h at 85° C. The reaction mixture was cooled to room temperature, poured into water (20 ml) and extracted with dichloromethane (2×20 ml). The combined organic layers were washed with brine (1×20 ml), dried (MgSO4) and evaporated. The crude material (70 mg) was purified by flash chromatography on silica gel [dichloromethane-dichloromethane/MeOH 9:1 (20-80%)] and subsequent trituration with diethyl ether (0.5 ml) and heptane (10 ml) to yield the title compound as a grey solid (60 mg, 87%), MS (ISN) m/z=277.2 [(M+H)+], mp 239° C.

Example 2

(R)-6-(4-Methoxy-phenyl)-4-methyl-3,4-dihydro-2H-pyrazino[1,2-a]indol-1-one

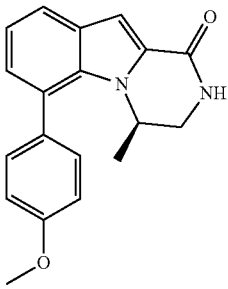 [SMILES: COc1ccc(-c2cccc3cc4n(c23)[C@H](C)CNC4=O)cc1]

The title compound, grey solid (74 mg, 97%), MS (ISP) m/z=307.3 [(M+H)$^+$], mp 247° C., was prepared in accordance with the general method of example 1 from (R)-6-bromo-4-methyl-3,4-dihydropyrazino[1,2-a]indol-1(2H)-one [CAS No. 396075-75-5] (69.8 mg, 0.25 mmol) and commercially available 4-methoxy-phenylboronic acid (49.4 mg, 0.325 mmol).

Example 3

(R)-4-Methyl-6-pyridin-4-yl-3,4-dihydro-2H-pyrazino[1,2-a]indol-1-one

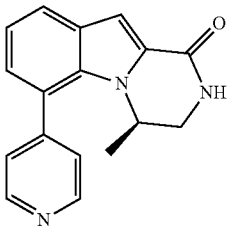 [SMILES: C[C@@H]1CNC(=O)c2cc3cccc(-c4ccncc4)c3n21]

The title compound, white solid (20 mg, 29%), MS (ISP) m/z=278.2 [(M+H)$^+$], mp 264° C., was prepared in accordance with the general method of example 1 from (R)-6-bromo-4-methyl-3,4-dihydropyrazino[1,2-a]indol-1(2H)-one [CAS No. 396075-75-5] (69.8 mg, 0.25 mmol) and commercially available pyridine-4-ylboronic acid (39.3 mg, 0.325 mmol).

Example 4

(R)-8-Fluoro-4-methyl-6-phenyl-3,4-dihydro-2H-pyrazino[1,2-a]indol-1-one

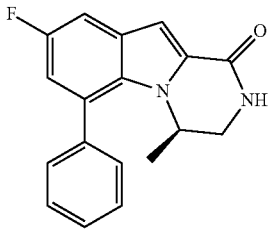 [SMILES: C[C@@H]1CNC(=O)c2cc3cc(F)cc(-c4ccccc4)c3n21]

The title compound, grey solid (67 mg, 91%), MS (ISP) m/z=295.3 [(M+H)$^+$], mp 243.5° C., was prepared in accordance with the general method of example 1 from (R)-6-bromo-8-fluoro-4-methyl-3,4-dihydropyrazino[1,2-a]indol-1(2H)-one [CAS No. 396076-62-3] (74.3 mg, 0.25 mmol) and commercially available phenylboronic acid (39.6 mg, 0.325 mmol).

Example 5

(R)-8-Fluoro-6-(4-methoxy-phenyl)-4-methyl-3,4-dihydro-2H-pyrazino[1,2-a]indol-1-one

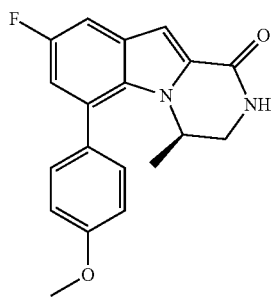 [SMILES: COc1ccc(-c2cc(F)cc3cc4n(c23)[C@H](C)CNC4=O)cc1]

The title compound, grey solid (74 mg, 91%), MS (ISP) m/z=325.3 [(M+H)$^+$], mp 228.5° C., was prepared in accordance with the general method of example 1 from (R)-6-bromo-8-fluoro-4-methyl-3,4-dihydropyrazino[1,2-a]indol-1(2H)-one [CAS No. 396076-62-3] (74.3 mg, 0.25 mmol) and commercially available 4-methoxy-phenylboronic acid (49.4 mg, 0.325 mmol).

Example 6

(R)-8-Fluoro-6-(4-fluoro-phenyl)-4-methyl-3,4-dihydro-2H-pyrazino[1,2-a]indol-1-one

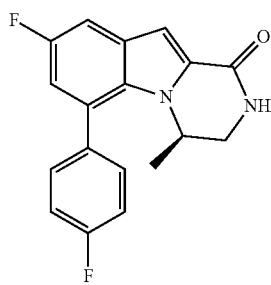 [SMILES: C[C@@H]1CNC(=O)c2cc3cc(F)cc(-c4ccc(F)cc4)c3n21]

The title compound, grey solid (75 mg, 96%), MS (ISP) m/z=313.3 [(M+H)$^+$], mp 276° C., was prepared in accordance with the general method of example 1 from (R)-6-bromo-8-fluoro-4-methyl-3,4-dihydropyrazino[1,2-a]indol-1(2H)-one [CAS No. 396076-62-3] (74.3 mg, 0.25 mmol) and commercially available 4-fluoro-phenylboronic acid (45.4 mg, 0.325 mmol).

Example 7

(R)-8-Fluoro-4-methyl-6-pyridin-4-yl-3,4-dihydro-2H-pyrazino[1,2-a]indol-1-one

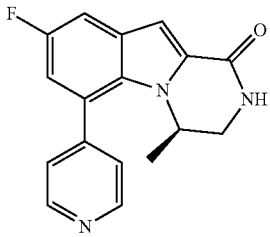 [SMILES: C[C@@H]1CNC(=O)c2cc3cc(F)cc(-c4ccncc4)c3n21]

The title compound, white solid (26 mg, 35%), MS (ISP) m/z=296.3 [(M+H)$^+$], mp 294.5° C., was prepared in accordance with the general method of example 1 from (R)-6-bromo-8-fluoro-4-methyl-3,4-dihydropyrazino[1,2-a]indol-1(2H)-one [CAS No. 396076-62-3] (74.3 mg, 0.25 mmol) and commercially available pyridine-4-ylboronic acid (39.9 mg, 0.325 mmol).

Example 8

(R)-8-Fluoro-4-methyl-6-p-tolyl-3,4-dihydro-2H-pyrazino[1,2-a]indol-1-one

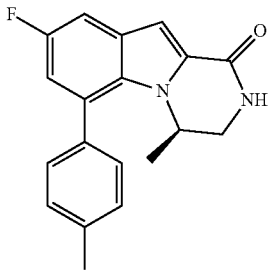 [SMILES: Cc1ccc(-c2cc(F)cc3cc4n(c23)[C@H](C)CNC4=O)cc1]

The title compound, brown solid (64.5 mg, 84%), MS (ISP) m/z=309.4 [(M+H)$^+$], mp 294.5° C., was prepared in accordance with the general method of example 1 from (R)-6-bromo-8-fluoro-4-methyl-3,4-dihydropyrazino[1,2-a]indol-1(2H)-one [CAS No. 396076-62-3] (74.3 mg, 0.25 mmol) and commercially available p-tolylboronic acid (44.2 mg, 0.325 mmol).

Example 9

(R)-6-(3,5-Difluoro-phenyl)-8-fluoro-4-methyl-3,4-dihydro-2H-pyrazino[1,2-a]indol-1-one

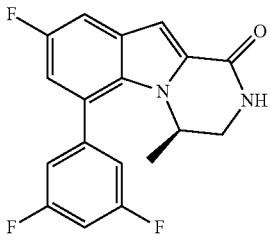 [SMILES: C[C@@H]1CNC(=O)c2cc3cc(F)cc(-c4cc(F)cc(F)c4)c3n21]

The title compound, grey solid (59 mg, 71%), MS (ISP) m/z=331.1 [(M+H)$^+$], mp 229.5° C., was prepared in accordance with the general method of example 1 from (R)-6-bromo-8-fluoro-4-methyl-3,4-dihydropyrazino[1,2-a]indol-1(2H)-one [CAS No. 396076-62-3] (74.3 mg, 0.25 mmol) and commercially available 3,5-difluoro-phenylboronic acid (51.3 mg, 0.325 mmol).

Example 10

(R)-6-(3,4-Difluoro-phenyl)-8-fluoro-4-methyl-3,4-dihydro-2H-pyrazino[1,2-a]indol-1-one

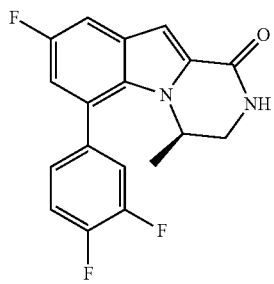 [SMILES: C[C@@H]1CNC(=O)c2cc3cc(F)cc(-c4ccc(F)c(F)c4)c3n21]

The title compound, white solid (76 mg, 92%), MS (ISP) m/z=331.1 [(M+H)$^+$], mp 267° C., was prepared in accordance with the general method of example 1 from (R)-6-bromo-8-fluoro-4-methyl-3,4-dihydropyrazino[1,2-a]indol-1(2H)-one [CAS No. 396076-62-3] (74.3 mg, 0.25 mmol) and commercially available 3,4-difluoro-phenylboronic acid (51.3 mg, 0.325 mmol).

Example 11

(R)-6-(4-Chloro-phenyl)-8-fluoro-4-methyl-3,4-dihydro-2H-pyrazino[1,2-a]indol-1-one

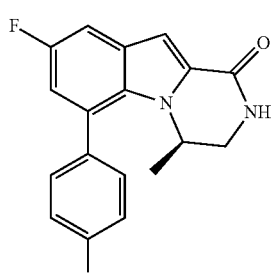

The title compound, light brown solid (80 mg, 97%), MS (ISP) m/z=329.3 [(M+H)$^+$], mp 282.5° C., was prepared in accordance with the general method of example 1 from (R)-6-bromo-8-fluoro-4-methyl-3,4-dihydropyrazino[1,2-a]indol-1(2H)-one [CAS No. 396076-62-3] (74.3 mg, 0.25 mmol) and commercially available 4-chloro-phenylboronic acid (50.8 mg, 0.325 mmol).

Example 12

8-Fluoro-6-phenyl-3,4-dihydro-2H-pyrazino[1,2-a]indol-1-one

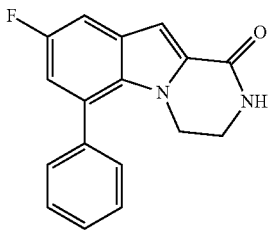 [SMILES: O=C1NCCn2c1cc1cc(F)cc(-c3ccccc3)c12]

The title compound, grey solid (52 mg, 74%), MS (ISP) m/z=281.3 [(M+H)⁺], mp 236.5° C., was prepared in accordance with the general method of example 1 from 6-bromo-8-fluoro-3,4-dihydro-2H-pyrazino[1,2-a]indol-1-one (intermediate 1) (70.8 mg, 0.25 mmol) and commercially available phenylboronic acid (39.6 mg, 0.325 mmol).

Example 13

(R)-8-Fluoro-4-methyl-6-(4-trifluoromethyl-phenyl)-3,4-dihydro-2H-pyrazino[1,2-a]indol-1-one

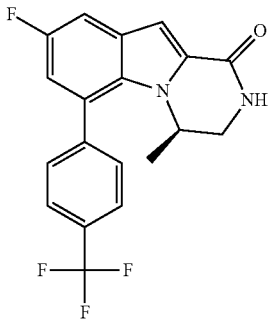 [SMILES: C[C@@H]1CNC(=O)c2cc3cc(F)cc(-c4ccc(C(F)(F)F)cc4)c3n21]

The title compound, light brown solid (81 mg, 89%), MS (ISP) m/z=363.3 [(M+H)⁺], mp 307° C., was prepared in accordance with the general method of example 1 from (R)-6-bromo-8-fluoro-4-methyl-3,4-dihydropyrazino[1,2-a]indol-1(2H)-one [CAS No. 396076-62-3] (74.3 mg, 0.25 mmol) and commercially available 4-trifluoromethyl-phenylboronic acid (61.7 mg, 0.325 mmol).

Example 14

(R)-8-Fluoro-6-(3-fluoro-phenyl)-4-methyl-3,4-dihydro-2H-pyrazino[1,2-a]indol-1-one

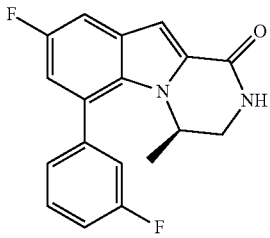 [SMILES: C[C@@H]1CNC(=O)c2cc3cc(F)cc(-c4cccc(F)c4)c3n21]

The title compound, white solid (59 mg, 76%), MS (ISP) m/z=313.3 [(M+H)⁺], mp 232° C., was prepared in accordance with the general method of example 1 from (R)-6-bromo-8-fluoro-4-methyl-3,4-dihydropyrazino[1,2-a]indol-1(2H)-one [CAS No. 396076-62-3] (74.3 mg, 0.25 mmol) and commercially available 3-fluoro-phenylboronic acid (45.5 mg, 0.325 mmol).

Example 15

9-Fluoro-7-phenyl-2,3,4,5-tetrahydro-[1,4]diazepino[1,2-a]indol-1-one

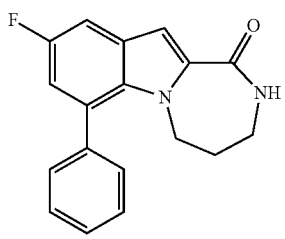

The title compound, light grey solid (62 mg, 84%), MS (ISP) m/z=295.2 [(M+H)⁺], mp 277° C., was prepared in accordance with the general method of example 1 from 7-bromo-9-fluoro-2,3,4,5-tetrahydro-[1,4]diazepino[1,2-a]indol-1-one (intermediate 2) (74.3 mg, 0.25 mmol) and commercially available phenylboronic acid (39.6 mg, 0.325 mmol).

Example 16

9-Fluoro-7-(4-methoxy-phenyl)-2,3,4,5-tetrahydro-[1,4]diazepino[1,2-a]indol-1-one

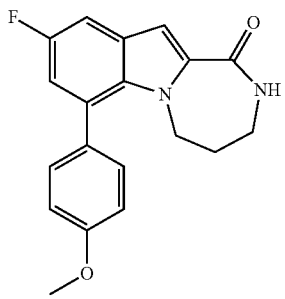 [SMILES: COc1ccc(-c2cc(F)cc3cc4n(c23)CCCNC4=O)cc1]

The title compound, light brown solid (62 mg, 76%), MS (ISP) m/z=325.3 [(M+H)⁺], mp 225.5° C., was prepared in accordance with the general method of example 1 from 7-bromo-9-fluoro-2,3,4,5-tetrahydro-[1,4]diazepino[1,2-a]indol-1-one (intermediate 2) (74.3 mg, 0.25 mmol) and commercially available 4-methoxy-phenylboronic acid (49.4 mg, 0.325 mmol).

Example 17

9-Fluoro-7-(4-fluoro-phenyl)-2,3,4,5-tetrahydro-[1,4]diazepino[1,2-a]indol-1-one

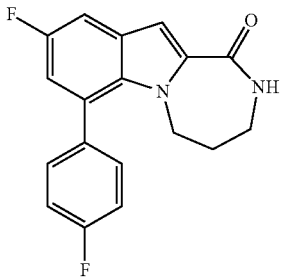

The title compound, light brown solid (54 mg, 69%), MS (ISP) m/z=313.2 [(M+H)+], mp 239.5° C., was prepared in accordance with the general method of example 1 from 7-bromo-9-fluoro-2,3,4,5-tetrahydro-[1,4]diazepino[1,2-a]indol-1-one (intermediate 2) (74.3 mg, 0.25 mmol) and commercially available 4-fluoro-phenylboronic acid (45.5 mg, 0.325 mmol).

Example 18

8-Fluoro-6-(4-fluoro-phenyl)-3,4-dihydro-2H-pyrazino[1,2-a]indol-1-one

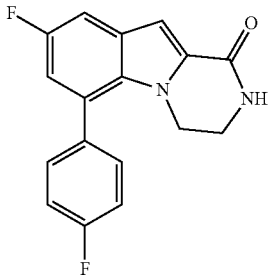 [SMILES: O=C1NCCn2c1cc1cc(F)cc(-c3ccc(F)cc3)c12]

The title compound, off-white solid (59 mg, 79%), MS (ISP) m/z=299.3 [(M+H)+], mp 304° C., was prepared in accordance with the general method of example 1 from 6-bromo-8-fluoro-3,4-dihydro-2H-pyrazino[1,2-a]indol-1-one (intermediate 1) (70.8 mg, 0.25 mmol) and commercially available 4-fluoro-phenylboronic acid (45.5 mg, 0.325 mmol).

Example 19

8-Fluoro-6-(4-methoxy-phenyl)-3,4-dihydro-2H-pyrazino[1,2-a]indol-1-one

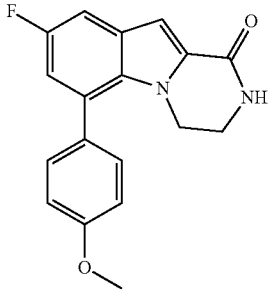 [SMILES: COc1ccc(-c2cc(F)cc3cc4n(c23)CCNC4=O)cc1]

The title compound, white solid (33 mg, 43%), MS (ISP) m/z=311.3 [(M+H)+], mp 274.5° C., was prepared in accordance with the general method of example 1 from 6-bromo-8-fluoro-3,4-dihydro-2H-pyrazino[1,2-a]indol-1-one (intermediate 1) (70.8 mg, 0.25 mmol) and commercially available 4-methoxy-phenylboronic acid (49.4 mg, 0.325 mmol).

Example 20

9-Fluoro-7-pyridin-4-yl-2,3,4,5-tetrahydro-[1,4]diazepino[1,2-a]indol-1-one

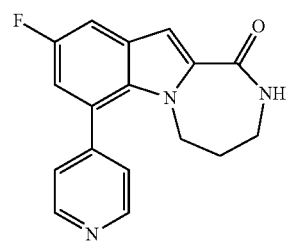 [SMILES: O=C1NCCCn2c1cc1cc(F)cc(-c3ccncc3)c12]

The title compound, white solid (24 mg, 33%), MS (ISP) m/z=296.3 [(M+H)+], mp 309° C., was prepared in accordance with the general method of example 1 from 7-bromo-9-fluoro-2,3,4,5-tetrahydro-[1,4]diazepino[1,2-a]indol-1-one (intermediate 2) (74.3 mg, 0.25 mmol) and commercially available pyridine-4-ylboronic acid (39.9 mg, 0.325 mmol).

Example 21

8-Fluoro-6-pyridin-4-yl-3,4-dihydro-2H-pyrazino[1,2-a]indol-1-one

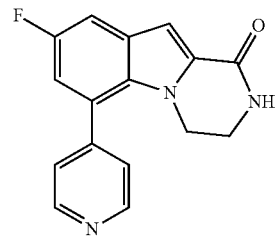

The title compound, white solid (44 mg, 63%), MS (ISP) m/z=282.3 [(M+H)+], mp 323.5° C., was prepared in accordance with the general method of example 1 from 6-bromo-8-fluoro-3,4-dihydro-2H-pyrazino[1,2-a]indol-1-one (intermediate 1) (70.8 mg, 0.25 mmol) and commercially available pyridine-4-ylboronic acid (39.9 mg, 0.325 mmol).

Example 22

6-(3,4-Difluoro-phenyl)-8-fluoro-3,4-dihydro-2H-pyrazino[1,2-a]indol-1-one

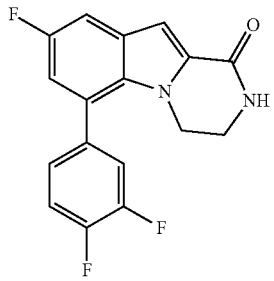

The title compound, light grey solid (72 mg, 91%), MS (ISP) m/z=317.1 [(M+H)+], mp 289.5° C., was prepared in accordance with the general method of example 1 from 6-bromo-8-fluoro-3,4-dihydro-2H-pyrazino[1,2-a]indol-1-one (intermediate 1) (70.8 mg, 0.25 mmol) and commercially available 3,4-difluoro-phenylboronic acid (51.3 mg, 0.325 mmol).

Example 23

6-(4-Chloro-phenyl)-8-fluoro-3,4-dihydro-2H-pyrazino[1,2-a]indol-1-one

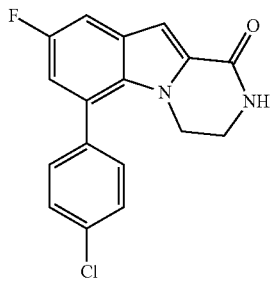

The title compound, light grey solid (75 mg, 95%), MS (ISP) m/z=315.1 [(M+H)+], mp 322° C., was prepared in accordance with the general method of example 1 from 6-bromo-8-fluoro-3,4-dihydro-2H-pyrazino[1,2-a]indol-1-one (intermediate 1) (70.8 mg, 0.25 mmol) and commercially available 4-chloro-phenylboronic acid (50.8 mg, 0.325 mmol).

Example 24

8-Fluoro-6-p-tolyl-3,4-dihydro-2H-pyrazino[1,2-a]indol-1-one

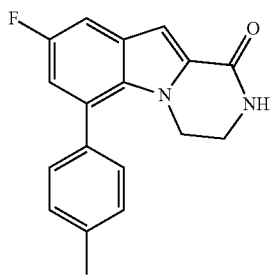

The title compound, light grey solid (70 mg, 95%), MS (ISP) m/z=295.2 [(M+H)+], mp 271.5° C., was prepared in accordance with the general method of example 1 from 6-bromo-8-fluoro-3,4-dihydro-2H-pyrazino[1,2-a]indol-1-one (intermediate 1) (70.8 mg, 0.25 mmol) and commercially available p-tolylboronic acid (44.2 mg, 0.325 mmol).

Example 25

8-Fluoro-6-(4-trifluoromethyl-phenyl)-3,4-dihydro-2H-pyrazino[1,2-a]indol-1-one

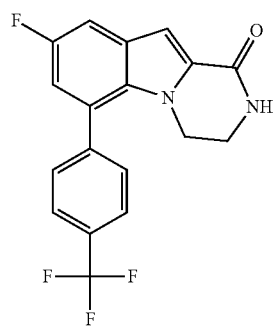 [SMILES: O=C1NCCn2c1cc1cc(F)cc(-c3ccc(C(F)(F)F)cc3)c12]

The title compound, off-white solid (81 mg, 93%), MS (ISP) m/z=349.2 [(M+H)+], mp 346° C., was prepared in accordance with the general method of example 1 from 6-bromo-8-fluoro-3,4-dihydro-2H-pyrazino[1,2-a]indol-1-one (intermediate 1) (70.8 mg, 0.25 mmol) and commercially available 4-trifluoromethyl-phenylboronic acid (61.7 mg, 0.325 mmol).

Example 26

(RS)-9-Fluoro-5-methyl-7-phenyl-2,3,4,5-tetrahydro-[1,4]diazepino[1,2-a]indol-1-one

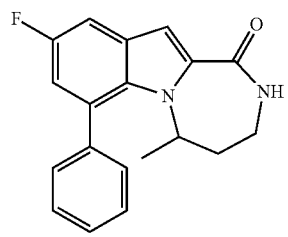 [SMILES: CC1CCNC(=O)c2cc3cc(F)cc(-c4ccccc4)c3n21]

The title compound, grey solid (67 mg, 87%), MS (ISP) m/z=309.4 [(M+H)+], mp 232.5° C., was prepared in accordance with the general method of example 1 from (RS)-7-bromo-9-fluoro-5-methyl-2,3,4,5-tetrahydro-[1,4]diazepino[1,2-a]indol-1-one (intermediate 3) (77.8 mg, 0.25 mmol) and commercially available phenylboronic acid (39.6 mg, 0.325 mmol).

Example 27

(RS)-9-Fluoro-7-(4-fluoro-phenyl)-5-methyl-2,3,4,5-tetrahydro-[1,4]diazepino[1,2-a]indol-1-one

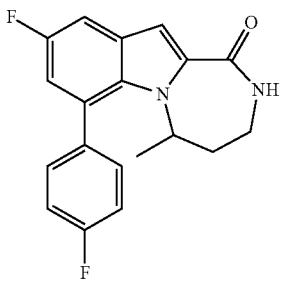 [SMILES: CC1CCNC(=O)c2cc3cc(F)cc(-c4ccc(F)cc4)c3n21]

The title compound, grey solid (79 mg, 97%), MS (ISP) m/z=327.2 [(M+H)$^+$], mp 235.5° C., was prepared in accordance with the general method of example 1 from (RS)-7-bromo-9-fluoro-5-methyl-2,3,4,5-tetrahydro-[1,4]diazepino[1,2-a]indol-1-one (intermediate 3) (77.8 mg, 0.25 mmol) and commercially available 4-fluoro-phenylboronic acid (45.5 mg, 0.325 mmol).

Example 28

7-(3,4-Difluoro-phenyl)-9-fluoro-2,3,4,5-tetrahydro-[1,4]diazepino[1,2-a]indol-1-one

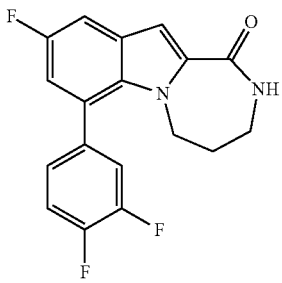

The title compound, light yellow solid (79 mg, 96%), MS (ISP) m/z=331.1 [(M+H)$^+$], mp 230.5° C., was prepared in accordance with the general method of example 1 from 7-bromo-9-fluoro-2,3,4,5-tetrahydro-[1,4]diazepino[1,2-a]indol-1-one (intermediate 2) (74.3 mg, 0.25 mmol) and commercially available 3,4-difluoro-phenylboronic acid (51.3 mg, 0.325 mmol).

Example 29

7-(4-Chloro-phenyl)-9-fluoro-2,3,4,5-tetrahydro-[1,4]diazepino[1,2-a]indol-1-one

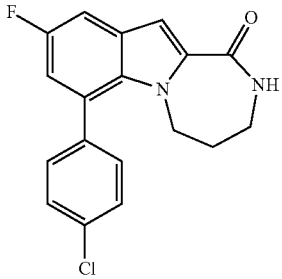

The title compound, light grey solid (78 mg, 95%), MS (ISP) m/z=329.2 [(M+H)$^+$], mp 263.5° C., was prepared in accordance with the general method of example 1 from 7-bromo-9-fluoro-2,3,4,5-tetrahydro-[1,4]diazepino[1,2-a]indol-1-one (intermediate 2) (74.3 mg, 0.25 mmol) and commercially available 4-chloro-phenylboronic acid (50.8 mg, 0.325 mmol).

Example 30

9-Fluoro-7-p-tolyl-2,3,4,5-tetrahydro-[1,4]diazepino[1,2-a]indol-1-one

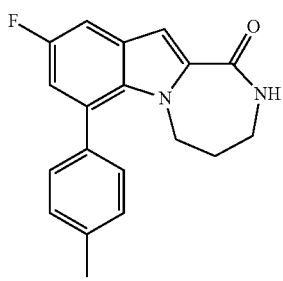

The title compound, light brown solid (69 mg, 90%), MS (ISP) m/z=309.3 [(M+H)$^+$], mp 258.5° C., was prepared in accordance with the general method of example 1 from 7-bromo-9-fluoro-2,3,4,5-tetrahydro-[1,4]diazepino[1,2-a]indol-1-one (intermediate 2) (74.3 mg, 0.25 mmol) and commercially available p-tolylboronic acid (44.2 mg, 0.325 mmol).

Example 31

9-Fluoro-7-(4-trifluoromethyl-phenyl)-2,3,4,5-tetrahydro-[1,4]diazepino[1,2-a]indol-1-one

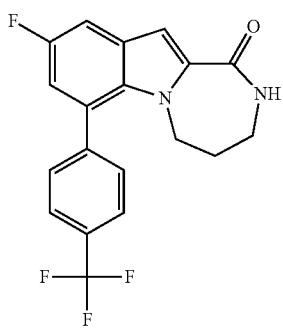 [SMILES: O=C1NCCCn2c1cc1cc(F)cc(-c3ccc(C(F)(F)F)cc3)c12]

The title compound, grey solid (88 mg, 97%), MS (ISP) m/z=363.2 [(M+H)$^+$], mp 257° C., was prepared in accordance with the general method of example 1 from 7-bromo-9-fluoro-2,3,4,5-tetrahydro-[1,4]diazepino[1,2-a]indol-1- one (intermediate 2) (74.3 mg, 0.25 mmol) and commercially available 4-trifluoromethyl-phenylboronic acid (61.7 mg, 0.325 mmol).

Example 32

8,9-Difluoro-6-(4-fluoro-phenyl)-3,4-dihydro-2H-pyrazino[1,2-a]indol-1-one

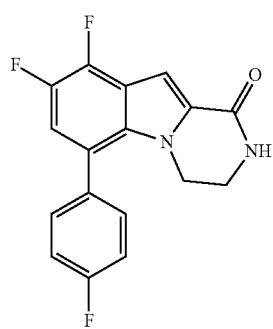

The title compound, grey solid (70 mg, 89%), MS (ISP) m/z=317.1 [(M+H)+], mp 283.5° C., was prepared in accordance with the general method of example 1 from 6-bromo-8,9-difluoro-3,4-dihydro-2H-pyrazino[1,2-a]indol-1-one (intermediate 4) (75.3 mg, 0.25 mmol) and commercially available 4-fluoro-phenylboronic acid (45.5 mg, 0.325 mmol).

Example 33

8,9-Difluoro-6-(4-methoxy-phenyl)-3,4-dihydro-2H-pyrazino[1,2-a]indol-1-one

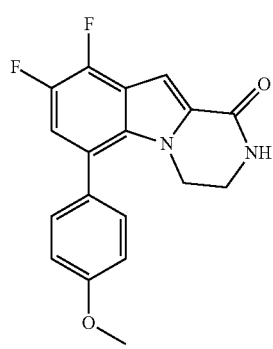 [SMILES: COc1ccc(-c2cc(F)c(F)c3cc4n(c23)CCNC4=O)cc1]

The title compound, off-white solid (77 mg, 94%), MS (ISP) m/z=329.2 [(M+H)+], mp 227.5° C., was prepared in accordance with the general method of example 1 from 6-bromo-8,9-difluoro-3,4-dihydro-2H-pyrazino[1,2-a]in-dol-1-one (intermediate 4) (75.3 mg, 0.25 mmol) and commercially available 4-methoxy-phenylboronic acid (49.4 mg, 0.325 mmol).

Example 34

6-(4-Chloro-phenyl)-8,9-difluoro-3,4-dihydro-2H-pyrazino[1,2-a]indol-1-one

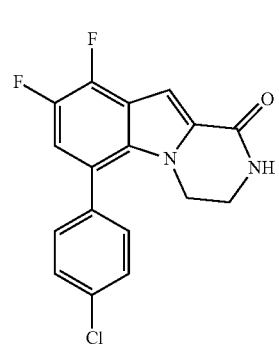 [SMILES: O=C1NCCn2c1cc1c(F)c(F)cc(-c3ccc(Cl)cc3)c12]

The title compound, grey solid (42 mg, 51%), MS (ISP) m/z=333.1 [(M+H)+], mp 327° C., was prepared in accordance with the general method of example 1 from 6-bromo-8,9-difluoro-3,4-dihydro-2H-pyrazino[1,2-a]indol-1-one (intermediate 4) (75.3 mg, 0.25 mmol) and commercially available 4-chloro-phenylboronic acid (50.8 mg, 0.325 mmol).

Example 35

6-(3,4-Difluoro-phenyl)-8,9-difluoro-3,4-dihydro-2H-pyrazino[1,2-a]indol-1-one

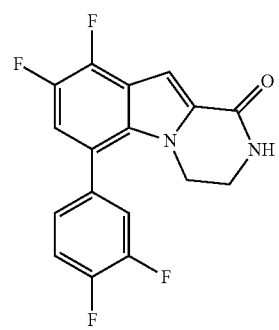 [SMILES: O=C1NCCn2c1cc1c(F)c(F)cc(-c3ccc(F)c(F)c3)c12]

The title compound, white solid (72 mg, 86%), MS (ISP) m/z=335.3 [(M+H)+], mp 317.5° C., was prepared in accordance with the general method of example 1 from 6-bromo-8,9-difluoro-3,4-dihydro-2H-pyrazino[1,2-a]indol-1-one (intermediate 4) (75.3 mg, 0.25 mmol) and commercially available 3,4-difluoro-phenylboronic acid (51.3 mg, 0.325 mmol).

Example 36

9,10-Difluoro-7-(4-fluoro-phenyl)-2,3,4,5-tetrahydro-[1,4]diazepino[1,2-a]indol-1-one

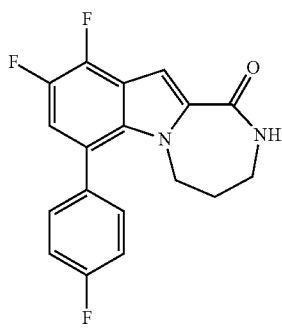

The title compound, light grey solid (79 mg, 96%), MS (ISP) m/z=331.2 [(M+H)⁺], mp 287° C., was prepared in accordance with the general method of example 1 from 7-bromo-9,10-difluoro-2,3,4,5-tetrahydro-[1,4]diazepino[1,2-a]indol-1-one (intermediate 5) (78.8 mg, 0.25 mmol) and commercially available 4-fluoro-phenylboronic acid (45.5 mg, 0.325 mmol).

Example 37

9,10-Difluoro-7-(4-methoxy-phenyl)-2,3,4,5-tetrahydro-[1,4]diazepino[1,2-a]indol-1-one

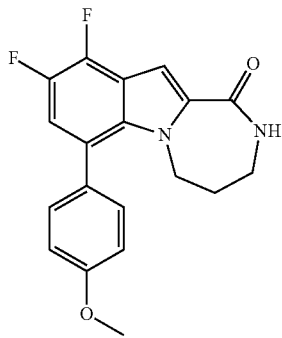

The title compound, grey solid (82 mg, 96%), MS (ISP) m/z=343.2 [(M+H)⁺], mp 207.5° C., was prepared in accordance with the general method of example 1 from 7-bromo-9,10-difluoro-2,3,4,5-tetrahydro-[1,4]diazepino[1,2-a]indol-1-one (intermediate 5) (78.8 mg, 0.25 mmol) and commercially available 4-methoxy-phenylboronic acid (49.4 mg, 0.325 mmol).

Example 38

7,8-Difluoro-6-(4-fluoro-phenyl)-3,4-dihydro-2H-pyrazino[1,2-a]indol-1-one

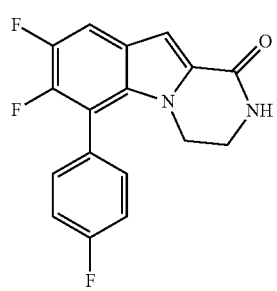 [SMILES: O=C1NCCn2c1cc1cc(F)c(F)c(-c3ccc(F)cc3)c12]

The title compound, off-white solid (69 mg, 87%), MS (ISP) m/z=317.0 [(M+H)⁺], mp 286.5° C., was prepared in accordance with the general method of example 1 from 6-bromo-7,8-difluoro-3,4-dihydro-2H-pyrazino[1,2-a]indol-1-one (intermediate 6) (75.3 mg, 0.25 mmol) and commercially available 4-fluoro-phenylboronic acid (45.5 mg, 0.325 mmol).

Example 39

7,8-Difluoro-6-(4-methoxy-phenyl)-3,4-dihydro-2H-pyrazino[1,2-a]indol-1-one

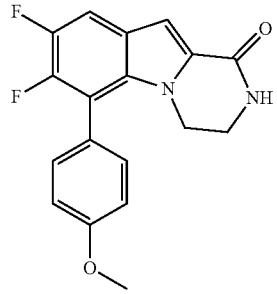 [SMILES: COc1ccc(-c2c(F)c(F)cc3cc4n(c23)CCNC4=O)cc1]

The title compound, off-white solid (65 mg, 79%), MS (ISP) m/z=329.1 [(M+H)⁺], mp 274.5° C., was prepared in accordance with the general method of example 1 from 6-bromo-7,8-difluoro-3,4-dihydro-2H-pyrazino[1,2-a]indol-1-one (intermediate 6) (75.3 mg, 0.25 mmol) and commercially available 4-methoxy-phenylboronic acid (49.4 mg, 0.325 mmol).

Example 40

8,9-Difluoro-7-(4-fluoro-phenyl)-2,3,4,5-tetrahydro-[1,4]diazepino[1,2-a]indol-1-one

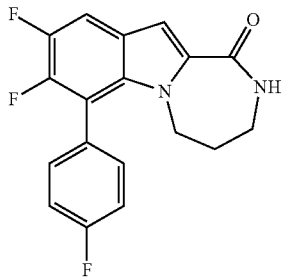 [SMILES: O=C1NCCCn2c1cc1cc(F)c(F)c(-c3ccc(F)cc3)c12]

The title compound, off-white solid (30 mg, 36%), MS (ISP) m/z=331.1 [(M+H)$^+$], mp 223.5° C., was prepared in accordance with the general method of example 1 from 7-bromo-8,9-difluoro-2,3,4,5-tetrahydro-[1,4]diazepino[1,2-a]indol-1-one (intermediate 7) (78.8 mg, 0.25 mmol) and commercially available 4-fluoro-phenylboronic acid (45.5 mg, 0.325 mmol).

Example 41

8,9-Difluoro-7-(4-methoxy-phenyl)-2,3,4,5-tetrahydro-[1,4]diazepino[1,2-a]indol-1-one

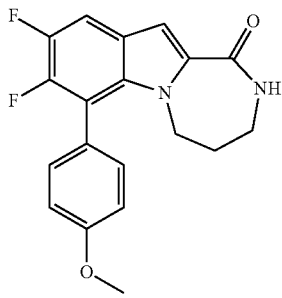 [SMILES: COc1ccc(-c2c(F)c(F)cc3cc4n(c23)CCCNC4=O)cc1]

The title compound, light yellow solid (46 mg, 54%), MS (ISP) m/z=343.2 [(M+H)$^+$], mp 182.5° C., was prepared in accordance with the general method of example 1 from 7-bromo-8,9-difluoro-2,3,4,5-tetrahydro-[1,4]diazepino[1,2-a]indol-1-one (intermediate 7) (78.8 mg, 0.25 mmol) and commercially available 4-methoxy-phenylboronic acid (49.4 mg, 0.325 mmol).

Example 42

7-(3,4-Difluoro-phenyl)-8,9-difluoro-2,3,4,5-tetrahydro-[1,4]diazepino[1,2-a]indol-1-one

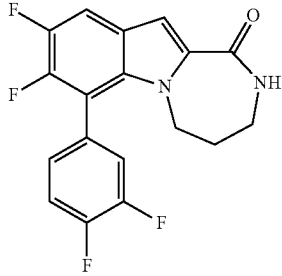 [SMILES: O=C1NCCCn2c1cc1cc(F)c(F)c(-c3ccc(F)c(F)c3)c12]

The title compound, white solid (71 mg, 82%), MS (ISP) m/z=349.3 [(M+H)$^+$], mp 225° C., was prepared in accordance with the general method of example 1 from 7-bromo-8,9-difluoro-2,3,4,5-tetrahydro-[1,4]diazepino[1,2-a]indol-1-one (intermediate 7) (78.8 mg, 0.25 mmol) and commercially available 3,4-difluoro-phenylboronic acid (51.3 mg, 0.325 mmol).

Example 43

7-(4-Chloro-phenyl)-8,9-difluoro-2,3,4,5-tetrahydro-[1,4]diazepino[1,2-a]indol-1-one

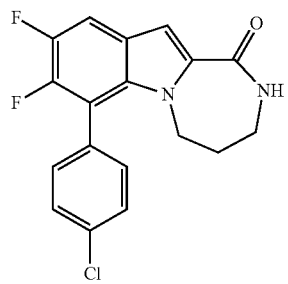 [SMILES: O=C1NCCCn2c1cc1cc(F)c(F)c(-c3ccc(Cl)cc3)c12]

The title compound, off-white solid (73 mg, 84%), MS (ISP) m/z=347.1 [(M+H)$^+$], mp 232.5° C., was prepared in accordance with the general method of example 1 from 7-bromo-8,9-difluoro-2,3,4,5-tetrahydro-[1,4]diazepino[1,2-a]indol-1-one (intermediate 7) (78.8 mg, 0.25 mmol) and commercially available 4-chloro-phenylboronic acid (50.8 mg, 0.325 mmol).

Example 44

6-(3,4-Difluoro-phenyl)-7,8-difluoro-3,4-dihydro-2H-pyrazino[1,2-a]indol-1-one

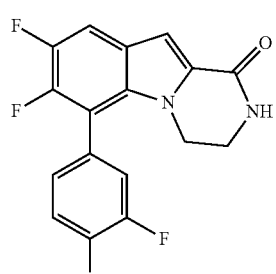

The title compound, white solid (61 mg, 73%), MS (ISP) m/z=335.2 [(M+H)$^+$], mp 305° C., was prepared in accordance with the general method of example 1 from 6-bromo-7,8-difluoro-3,4-dihydro-2H-pyrazino[1,2-a]indol-1-one (intermediate 6) (75.3 mg, 0.25 mmol) and commercially available 3,4-difluoro-phenylboronic acid (51.3 mg, 0.325 mmol).

Example 45

6-(4-Chloro-phenyl)-7,8-difluoro-3,4-dihydro-2H-pyrazino[1,2-a]indol-1-one

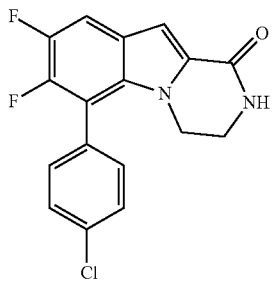 [SMILES: O=C1NCCn2c1cc1cc(F)c(F)c(-c3ccc(Cl)cc3)c12]

The title compound, white solid (60 mg, 72%), MS (ISP) m/z=333.3 [(M+H)$^+$], mp 332.5° C., was prepared in accordance with the general method of example 1 from 6-bromo-7,8-difluoro-3,4-dihydro-2H-pyrazino[1,2-a]indol-1-one (intermediate 6) (75.3 mg, 0.25 mmol) and commercially available 4-chloro-phenylboronic acid (50.8 mg, 0.325 mmol).

Example 46

9-Chloro-7-(3,4-difluoro-phenyl)-2,3,4,5-tetrahydro-[1,4]diazepino[1,2-a]indol-1-one

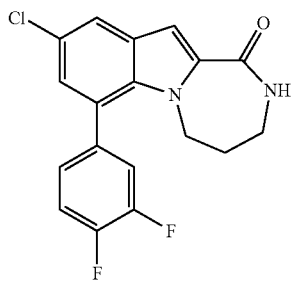 [SMILES: O=C1NCCCn2c1cc1cc(Cl)cc(-c3ccc(F)c(F)c3)c12]

The title compound, light brown solid (75 mg, 87%), MS (ISP) m/z=347.1 [(M+H)$^+$], mp 230.5° C., was prepared in accordance with the general method of example 1 from 7-bromo-9-chloro-2,3,4,5-tetrahydro-[1,4]diazepino[1,2-a]indol-1-one (intermediate 8) (78.4 mg, 0.25 mmol) and commercially available 3,4-difluoro-phenylboronic acid (51.3 mg, 0.325 mmol).

Example 47

9-Chloro-7-p-tolyl-2,3,4,5-tetrahydro-[1,4]diazepino[1,2-a]indol-1-one

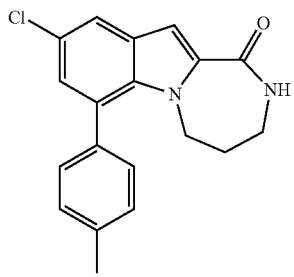 [SMILES: Cc1ccc(-c2cc(Cl)cc3cc4n(c23)CCCNC4=O)cc1]

The title compound, white solid (76 mg, 94%), MS (ISP) m/z=325.2 [(M+H)$^+$], mp 227° C., was prepared in accordance with the general method of example 1 from 7-bromo-9-chloro-2,3,4,5-tetrahydro-[1,4]diazepino[1,2-a]indol-1-one (intermediate 8) (78.4 mg, 0.25 mmol) and commercially available p-tolylboronic acid (44.2 mg, 0.325 mmol).

Example 48

9-Chloro-7-(4-fluoro-phenyl)-2,3,4,5-tetrahydro-[1,4]diazepino[1,2-a]indol-1-one

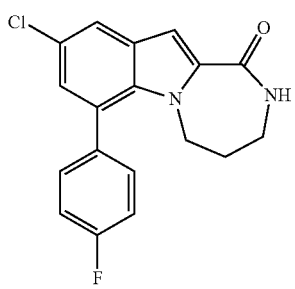 [SMILES: O=C1NCCCn2c1cc1cc(Cl)cc(-c3ccc(F)cc3)c12]

The title compound, white solid (70 mg, 85%), MS (ISP) m/z=329.1 [(M+H)$^+$], mp 260° C., was prepared in accordance with the general method of example 1 from 7-bromo-9-chloro-2,3,4,5-tetrahydro-[1,4]diazepino[1,2-a]indol-1-one (intermediate 8) (78.4 mg, 0.25 mmol) and commercially available 4-fluoro-phenylboronic acid (45.5 mg, 0.325 mmol).

Example 49

8-Chloro-6-(4-chloro-phenyl)-3,4-dihydro-2H-pyrazino[1,2-a]indol-1-one

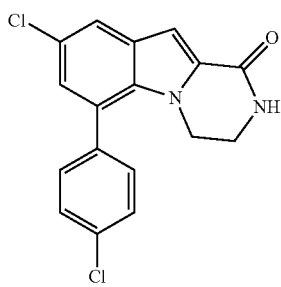 [SMILES: O=C1NCCn2c1cc1cc(Cl)cc(-c3ccc(Cl)cc3)c12]

The title compound, white solid (80 mg, 97%), MS (ISP) m/z=331.1 [(M+H)$^+$], mp 320° C., was prepared in accordance with the general method of example 1 from 6-bromo-8-chloro-3,4-dihydro-2H-pyrazino[1,2-a]indol-1-one (intermediate 9) (74.9 mg, 0.25 mmol) and commercially available 4-chloro-phenylboronic acid (50.8 mg, 0.325 mmol).

Example 50

8-Chloro-6-(3,4-difluoro-phenyl)-3,4-dihydro-2H-pyrazino[1,2-a]indol-1-one

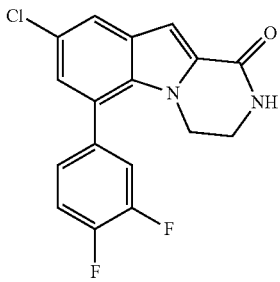 [SMILES: O=C1NCCn2c1cc1cc(Cl)cc(-c3ccc(F)c(F)c3)c12]

The title compound, white solid (72 mg, 86%), MS (ISP) m/z=333.1 [(M+H)+], mp 277.5° C., was prepared in accordance with the general method of example 1 from 6-bromo-8-chloro-3,4-dihydro-2H-pyrazino[1,2-a]indol-1-one (intermediate 9) (74.9 mg, 0.25 mmol) and commercially available 3,4-difluoro-phenylboronic acid (51.3 mg, 0.325 mmol).

Example 51

8-Chloro-6-(4-fluoro-phenyl)-3,4-dihydro-2H-pyrazino[1,2-a]indol-1-one

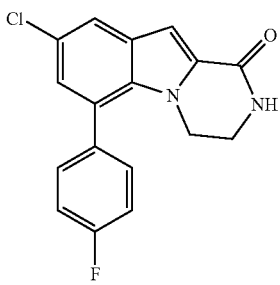 [SMILES: O=C1NCCn2c1cc1cc(Cl)cc(-c3ccc(F)cc3)c12]

The title compound, white solid (70 mg, 89%), MS (ISP) m/z=315.1 [(M+H)+], mp 298° C., was prepared in accordance with the general method of example 1 from 6-bromo-8-chloro-3,4-dihydro-2H-pyrazino[1,2-a]indol-1-one (intermediate 9) (74.9 mg, 0.25 mmol) and commercially available 4-fluoro-phenylboronic acid (45.5 mg, 0.325 mmol).

Example 52

8-Chloro-6-(4-methoxy-phenyl)-3,4-dihydro-2H-pyrazino[1,2-a]indol-1-one

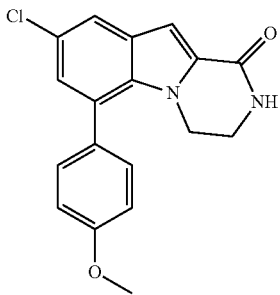 [SMILES: COc1ccc(-c2cc(Cl)cc3cc4n(c23)CCNC4=O)cc1]

The title compound, white solid (74 mg, 91%), MS (ISP) m/z=327.2 [(M+H)+], mp 282.5° C., was prepared in accordance with the general method of example 1 from 6-bromo-8-chloro-3,4-dihydro-2H-pyrazino[1,2-a]indol-1-one (intermediate 9) (74.9 mg, 0.25 mmol) and commercially available 4-methoxy-phenylboronic acid (49.4 mg, 0.325 mmol).

Example 53

9-Chloro-7-(4-chloro-phenyl)-2,3,4,5-tetrahydro-[1,4]diazepino[1,2-a]indol-1-one

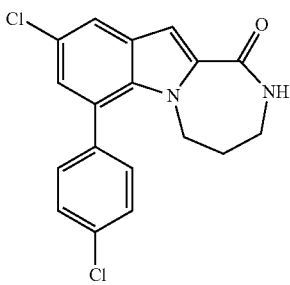 [SMILES: O=C1NCCCn2c1cc1cc(Cl)cc(-c3ccc(Cl)cc3)c12]

The title compound, white solid (17 mg, 19%), MS (ISP) m/z=345.4 [(M+H)+], mp 237° C., was prepared in accordance with the general method of example 1 from 7-bromo-9-chloro-2,3,4,5-tetrahydro-[1,4]diazepino[1,2-a]indol-1-one (intermediate 8) (78.4 mg, 0.25 mmol) and commercially available 4-chloro-phenylboronic acid (50.8 mg, 0.325 mmol).

Example 54

9-Chloro-7-(4-methoxy-phenyl)-2,3,4,5-tetrahydro-[1,4]diazepino[1,2-a]indol-1-one

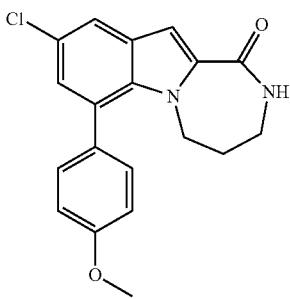 [SMILES: COc1ccc(-c2cc(Cl)cc3cc4n(c23)CCCNC4=O)cc1]

The title compound, white solid (80 mg, 94%), MS (ISP) m/z=341.4 [(M+H)+], mp 218° C., was prepared in accordance with the general method of example 1 from 7-bromo-9-chloro-2,3,4,5-tetrahydro-[1,4]diazepino[1,2-a]indol-1one (intermediate 8) (78.4 mg, 0.25 mmol) and commercially available 4-methoxy-phenylboronic acid (49.4 mg, 0.325 mmol).

Example 55

7-(3,4-Difluoro-phenyl)-9-methyl-2,3,4,5-tetrahydro-[1,4]diazepino[1,2-a]indol-1-one

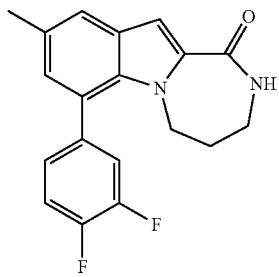 [SMILES: Cc1cc(-c2ccc(F)c(F)c2)c2c(c1)cc1n2CCCNC1=O]

The title compound, white solid (42 mg, 76%), MS (ISP) m/z=327.4 [(M+H)⁺], mp 231° C., was prepared in accordance with the general method of example 1 from 7-bromo-9-methyl-2,3,4,5-tetrahydro-[1,4]diazepino[1,2-a]indol-1-one (intermediate 11) (50 mg, 0.17 mmol) and commercially available 3,4-difluoro-phenylboronic acid (35 mg, 0.22 mmol).

Example 56

7-(4-Methoxy-phenyl)-9-methyl-2,3,4,5-tetrahydro-[1,4]diazepino[1,2-a]indol-1-one

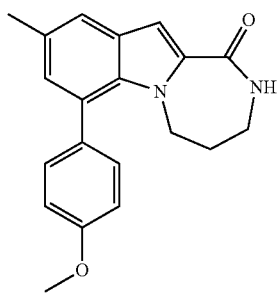 [SMILES: COc1ccc(-c2cc(C)cc3cc4n(c23)CCCNC4=O)cc1]

The title compound, off-white solid (33 mg, 60%), MS (ISP) m/z=321.5 [(M+H)⁺], mp 208° C., was prepared in accordance with the general method of example 1 from 7-bromo-9-methyl-2,3,4,5-tetrahydro-[1,4]diazepino[1,2-a]indol-1-one (intermediate 11) (50 mg, 0.17 mmol) and commercially available 4-methoxy-phenylboronic acid (33.7 mg, 0.22 mmol).

Example 57

7-(4-Fluoro-phenyl)-9-methyl-2,3,4,5-tetrahydro-[1,4]diazepino[1,2-a]indol-1-one

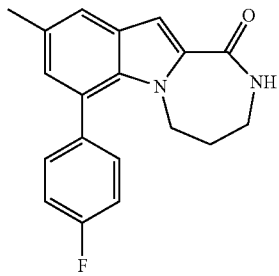 [SMILES: Cc1cc(-c2ccc(F)cc2)c2c(c1)cc1n2CCCNC1=O]

The title compound, white solid (40.5 mg, 77%), MS (ISP) m/z=309.5 [(M+H)⁺], mp 234.5° C., was prepared in accordance with the general method of example 1 from 7-bromo-9-methyl-2,3,4,5-tetrahydro-[1,4]diazepino[1,2-a]indol-1-one (intermediate 11) (50 mg, 0.17 mmol) and commercially available 4-fluoro-phenylboronic acid (31 mg, 0.22 mmol).

Example 58

7-(4-Chloro-phenyl)-9-methyl-2,3,4,5-tetrahydro-[1,4]diazepino[1,2-a]indol-1-one

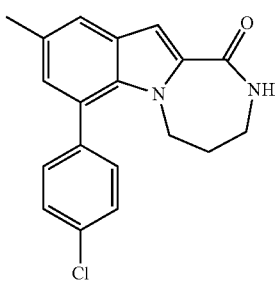 [SMILES: Cc1cc(-c2ccc(Cl)cc2)c2c(c1)cc1n2CCCNC1=O]

The title compound, white solid (43 mg, 77%), MS (ISP) m/z=325.4 [(M+H)⁺], mp 258.5° C., was prepared in accordance with the general method of example 1 from 7-bromo-9-methyl-2,3,4,5-tetrahydro-[1,4]diazepino[1,2-a]indol-1-one (intermediate 11) (50 mg, 0.17 mmol) and commercially available 4-chloro-phenylboronic acid (34.7 mg, 0.22 mmol).

Example 59

6-(4-Chloro-phenyl)-8-methyl-3,4-dihydro-2H-pyrazino[1,2-a]indol-1-one

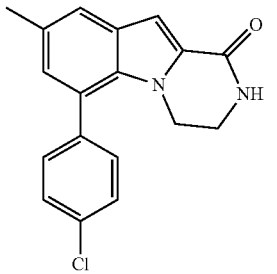 [SMILES: Cc1cc(-c2ccc(Cl)cc2)c2c(c1)cc1n2CCNC1=O]

The title compound, white solid (45 mg, 78%), MS (ISP) m/z=311.4 [(M+H)⁺], mp 269° C., was prepared in accordance with the general method of example 1 from 6-bromo-8-methyl-3,4-dihydro-2H-pyrazino[1,2-a]indol-1-one (intermediate 10) (52 mg, 0.186 mmol) and commercially available 4-chloro-phenylboronic acid (37.9 mg, 0.24 mmol).

Example 60

6-(3,4-Difluoro-phenyl)-8-methyl-3,4-dihydro-2H-pyrazino[1,2-a]indol-1-one

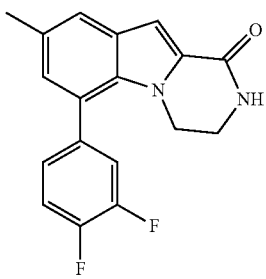 [SMILES: Cc1cc(-c2ccc(F)c(F)c2)c2c(c1)cc1n2CCNC1=O]

The title compound, white solid (46 mg, 79%), MS (ISP) m/z=313.4 [(M+H)$^+$], mp 249.5° C., was prepared in accordance with the general method of example 1 from 6-bromo-8-methyl-3,4-dihydro-2H-pyrazino[1,2-a]indol-1-one (intermediate 10) (52 mg, 0.186 mmol) and commercially available 3,4-difluoro-phenylboronic acid (38.2 mg, 0.24 mmol).

Example 61

6-(4-Methoxy-phenyl)-8-methyl-3,4-dihydro-2H-pyrazino[1,2-a]indol-1-one

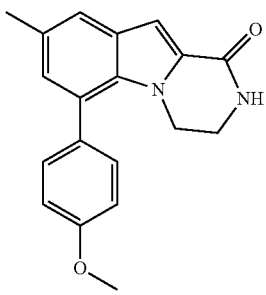 [SMILES: COc1ccc(-c2cc(C)cc3cc4n(c23)CCNC4=O)cc1]

The title compound, grey solid (38 mg, 67%), MS (ISP) m/z=307.5 [(M+H)$^+$], mp 245° C., was prepared in accordance with the general method of example 1 from 6-bromo-8-methyl-3,4-dihydro-2H-pyrazino[1,2-a]indol-1-one (intermediate 10) (52 mg, 0.186 mmol) and commercially available 4-methoxy-phenylboronic acid (36.8 mg, 0.24 mmol).

Example 62

6-(4-Fluoro-phenyl)-8-methyl-3,4-dihydro-2H-pyrazino[1,2-a]indol-1-one

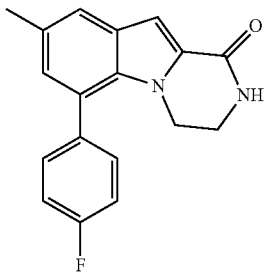 [SMILES: Cc1cc(-c2ccc(F)cc2)c2c(c1)cc1n2CCNC1=O]

The title compound, white solid (43 mg, 78%), MS (ISP) m/z=295.4 [(M+H)$^+$], mp 257° C., was prepared in accordance with the general method of example 1 from 6-bromo-8-methyl-3,4-dihydro-2H-pyrazino[1,2-a]indol-1-one (intermediate 10) (52 mg, 0.186 mmol) and commercially available 4-fluoro-phenylboronic acid (33.9 mg, 0.24 mmol).

Example 63

8-Fluoro-6-(4-fluoro-phenyl)-2-methyl-3,4-dihydro-2H-pyrazino[1,2-a]indol-1-one

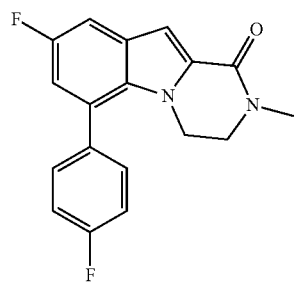 [SMILES: CN1CCn2c(cc3cc(F)cc(-c4ccc(F)cc4)c32)C1=O]

To a stirred solution of 8-fluoro-6-(4-fluoro-phenyl)-3,4-dihydro-2H-pyrazino[1,2-a]indol-1-one (example 18) (0.05 g, 0.17 mmol) in DMF (1.1 ml) was added at room temperature sodium hydride (8.78 mg, 0.2 mmol), and the mixture was allowed to stir at room temperature for 30 min. Afterwards iodomethane (23.8 mg, 10.5 µl, 0.17 mmol) was added and the reaction mixture was allowed to stir at room temperature for 16 h. The mixture was poured into ice/water (30 ml) and extracted with ethyl acetate (2×25 ml). The combined organic layers were washed with brine (25 ml), dried (MgSO4) and evaporated. The crude product (50 mg) was further purified by flash chromatography on silica gel [dichloromethane-dichloromethane/MeOH 9:1 (0-50%)] to yield the title compound as a white solid (21 mg, 40%), MS (ISP) m/z=313.4 [(M+H)$^+$], mp 212° C.

Example 64

8-Chloro-6-(3,4-difluoro-phenyl)-10-methyl-3,4-dihydro-2H-pyrazino[1,2-a]indol-1-one

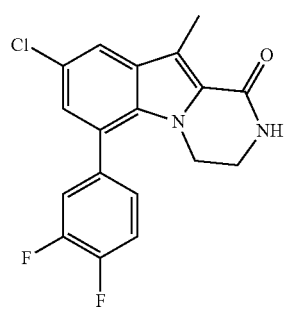 [SMILES: Cc1c2n(c3c(-c4ccc(F)c(F)c4)cc(Cl)cc13)CCNC2=O]

The title compound, white solid (69 mg, 80%), MS (ISP) m/z=347.4 [(M+H)$^+$], mp 235.5° C., was prepared in accordance with the general method of example 1 from 6-bromo-8-chloro-10-methyl-3,4-dihydro-2H-pyrazino[1,2-a]indol- 1-one (intermediate 12) (78.4 mg, 0.25 mmol) and commercially available 3,4-difluoro-phenylboronic acid (51.3 mg, 0.325 mmol).

Example 65

8-Chloro-6-(4-chloro-phenyl)-10-methyl-3,4-dihydro-2H-pyrazino[1,2-a]indol-1-one

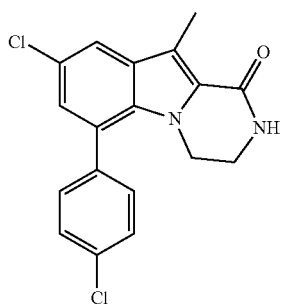 [SMILES: Cc1c2n(c3c(-c4ccc(Cl)cc4)cc(Cl)cc13)CCNC2=O]

The title compound, white solid (74 mg, 86%), MS (ISP) m/z=345.4 [(M+H)$^+$], mp 236.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-chloro-phenylboronic acid (50.8 mg, 0.325 mmol).

Example 66

8-Chloro-6-(4-fluoro-phenyl)-10-methyl-3,4-dihydro-2H-pyrazino[1,2-a]indol-1-one

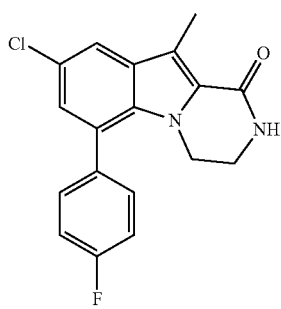 [SMILES: Cc1c2n(c3c(-c4ccc(F)cc4)cc(Cl)cc13)CCNC2=O]

The title compound, off-white solid (71 mg, 86%), MS (ISP) m/z=329.4 [(M+H)$^+$], mp 227.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-fluoro-phenylboronic acid (45.5 mg, 0.325 mmol).

Example 67

8-Chloro-6-(4-methoxy-phenyl)-10-methyl-3,4-dihydro-2H-pyrazino[1,2-a]indol-1-one

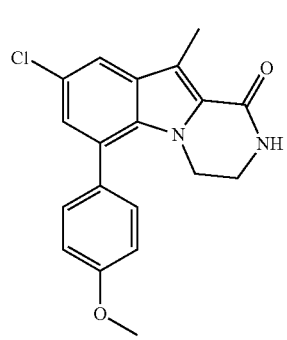 [SMILES: COc1ccc(-c2cc(Cl)cc3c(C)c4n(c23)CCNC4=O)cc1]

The title compound, white solid (80 mg, 94%), MS (ISP) m/z=341.3 [(M+H)$^+$], mp 264° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-methoxy-phenylboronic acid (49.4 mg, 0.325 mmol).

Example 68

9-Chloro-7-(3,4-difluoro-phenyl)-11-methyl-2,3,4,5-tetrahydro-[1,4]diazepino[1,2-a]indol-1-one

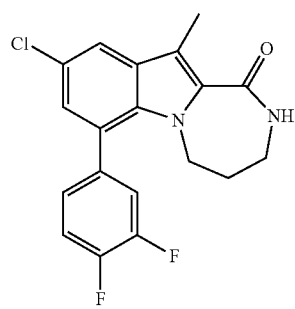 [SMILES: Cc1c2n(c3c(-c4ccc(F)c(F)c4)cc(Cl)cc13)CCCNC2=O]

The title compound, white solid (71 mg, 79%), MS (ISP) m/z=361.4 [(M+H)$^+$], mp 254° C., was prepared in accordance with the general method of example 1 from 7-bromo-9-chloro-11-methyl-2,3,4,5-tetrahydro-[1,4]diazepino[1,2- a]indol-1-one (intermediate 13) (81.9 mg, 0.25 mmol) and commercially available 3,4-difluoro-phenylboronic acid (51.3 mg, 0.325 mmol).

Example 69

9-Chloro-7-(4-chloro-phenyl)-11-methyl-2,3,4,5-tetrahydro-[1,4]diazepino[1,2-a]indol-1-one

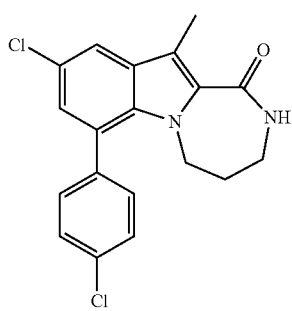 [SMILES: Cc1c2n(c3c(-c4ccc(Cl)cc4)cc(Cl)cc13)CCCNC2=O]

The title compound, white solid (72 mg, 80%), MS (ISP) m/z=359.3 [(M+H)+], mp 271° C., was prepared in accordance with the general method of example 1 from 7-bromo-9-chloro-11-methyl-2,3,4,5-tetrahydro-[1,4]diazepino[1,2-a]indol-1-one (intermediate 13) (81.9 mg, 0.25 mmol) and commercially available 4-chloro-phenylboronic acid (50.8 mg, 0.325 mmol).

Example 70

9-Chloro-7-(4-fluoro-phenyl)-11-methyl-2,3,4,5-tetrahydro-[1,4]diazepino[1,2-a]indol-1-one

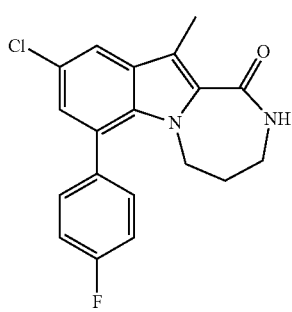 [SMILES: Cc1c2n(c3c(-c4ccc(F)cc4)cc(Cl)cc13)CCCNC2=O]

The title compound, off-white solid (75 mg, 88%), MS (ISP) m/z=343.4 [(M+H)+], mp 260° C., was prepared in accordance with the general method of example 1 from 7-bromo-9-chloro-11-methyl-2,3,4,5-tetrahydro-[1,4]diaz-epino[1,2-a]indol-1-one (intermediate 13) (81.9 mg, 0.25 mmol) and commercially available 4-fluoro-phenylboronic acid (45.5 mg, 0.325 mmol).

Example 71

9-Chloro-7-(4-methoxy-phenyl)-11-methyl-2,3,4,5-tetrahydro-[1,4]diazepino[1,2-a]indol-1-one

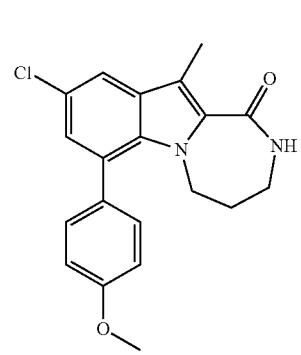 [SMILES: COc1ccc(-c2cc(Cl)cc3c(C)c4n(c23)CCCNC4=O)cc1]

The title compound, off-white solid (81 mg, 91%), MS (ISP) m/z=355.4 [(M+H)+], mp 240.5° C., was prepared in accordance with the general method of example 1 from 7-bromo-9-chloro-11-methyl-2,3,4,5-tetrahydro-[1,4]diaz-epino[1,2-a]indol-1-one (intermediate 13) (81.9 mg, 0.25 mmol) and commercially available 4-methoxy-phenylboronic acid (49.4 mg, 0.325 mmol).

Example 72

6-(3,4-Difluoro-phenyl)-8-fluoro-10-methyl-3,4-dihydro-2H-pyrazino[1,2-a]indol-1-one

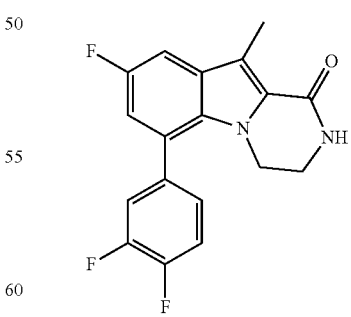

The title compound, light grey solid (71 mg, 86%), MS (ISP) m/z=331.4 [(M+H)+], mp 229.5° C., was prepared in accordance with the general method of example 1 from 6-bromo-8-fluoro-10-methyl-3,4-dihydro-2H-pyrazino[1,2- a]indol-1-one (intermediate 14) (74.3 mg, 0.25 mmol) and commercially available 3,4-difluoro-phenylboronic acid (51.3 mg, 0.325 mmol).

Example 73

6-(4-Chloro-phenyl)-8-fluoro-10-methyl-3,4-dihydro-2H-pyrazino[1,2-a]indol-1-one

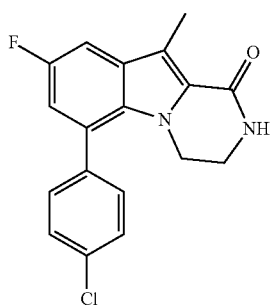 [SMILES: Cc1c2n(c3c(-c4ccc(Cl)cc4)cc(F)cc13)CCNC2=O]

The title compound, white solid (67 mg, 82%), MS (ISP) m/z=329.4 [(M+H)⁺], mp 209.5° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-chloro-phenylboronic acid (50.8 mg, 0.325 mmol).

Example 74

8-Fluoro-6-(4-fluoro-phenyl)-10-methyl-3,4-dihydro-2H-pyrazino[1,2-a]indol-1-one

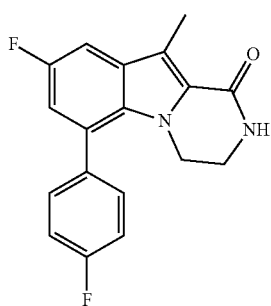 [SMILES: Cc1c2n(c3c(-c4ccc(F)cc4)cc(F)cc13)CCNC2=O]

The title compound, light grey solid (64 mg, 82%), MS (ISP) m/z=313.4 [(M+H)⁺], mp 182° C., was prepared in accordance with the general method of example 1 from 6-bromo-8-fluoro-10-methyl-3,4-dihydro-2H-pyrazino[1,2- a]indol-1-one (intermediate 14) (74.3 mg, 0.25 mmol) and commercially available 4-fluoro-phenylboronic acid (45.5 mg, 0.325 mmol).

Example 75

8-Fluoro-6-(4-methoxy-phenyl)-10-methyl-3,4-dihydro-2H-pyrazino[1,2-a]indol-1-one

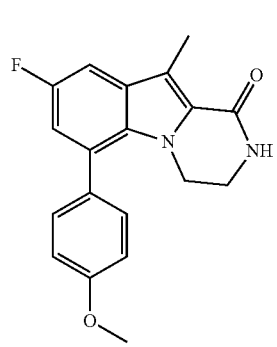 [SMILES: COc1ccc(-c2cc(F)cc3c(C)c4n(c23)CCNC4=O)cc1]

The title compound, light grey solid (74 mg, 91%), MS (ISP) m/z=325.4 [(M+H)⁺], mp 237° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-methoxy-phenylboronic acid (49.4 mg, 0.325 mmol).

Example 76

6-(3,4-Difluoro-phenyl)-1-oxo-1,2,3,4-tetrahydropyrazino[1,2-a]indole-8-carbonitrile

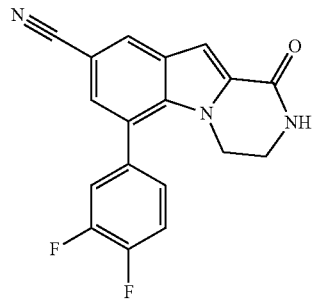 [SMILES: N#Cc1cc(-c2ccc(F)c(F)c2)c2c(c1)cc1n2CCNC1=O]

The title compound, off-white solid (68 mg, 84%), MS (ISP) m/z=324.4 [(M+H)⁺], mp 289.5° C., was prepared in accordance with the general method of example 1 from 6-bromo-1-oxo-1,2,3,4-tetrahydro-pyrazino[1,2-a]indole-8- carbonitrile (intermediate 15) (72.5 mg, 0.25 mmol) and commercially available 3,4-difluoro-phenylboronic acid (51.3 mg, 0.325 mmol).

Example 77

6-(4-Chloro-phenyl)-1-oxo-1,2,3,4-tetrahydro-pyrazino[1,2-a]indole-8-carbonitrile

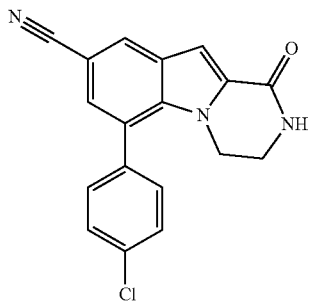 [SMILES: N#Cc1cc(-c2ccc(Cl)cc2)c2c(c1)cc1n2CCNC1=O]

The title compound, off-white solid (68 mg, 85%), MS (ISP) m/z=322.4 [(M+H)$^+$], mp 316.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-chloro-phenylboronic acid (50.8 mg, 0.325 mmol).

Example 78

6-(4-Fluoro-phenyl)-1-oxo-1,2,3,4-tetrahydro-pyrazino[1,2-a]indole-8-carbonitrile

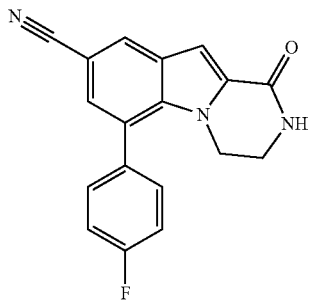

The title compound, off-white solid (65 mg, 85%), MS (ISP) m/z=306.4 [(M+H)$^+$], mp 297.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-fluoro-phenylboronic acid (45.5 mg, 0.325 mmol).

Example 79

6-(4-Methoxy-phenyl)-1-oxo-1,2,3,4-tetrahydro-pyrazino[1,2-a]indole-8-carbonitrile

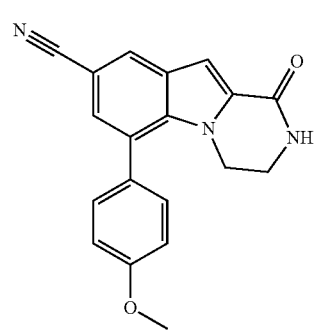 [SMILES: COc1ccc(-c2cc(C#N)cc3cc4n(c23)CCNC4=O)cc1]

The title compound, off-white solid (65 mg, 82%), MS (ISP) m/z=318.4 [(M+H)$^+$], mp 278.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-methoxy-phenylboronic acid (49.4 mg, 0.325 mmol).

Example 80

8-Fluoro-10-methyl-6-phenyl-3,4-dihydro-2H-pyrazino[1,2-a]indol-1-one

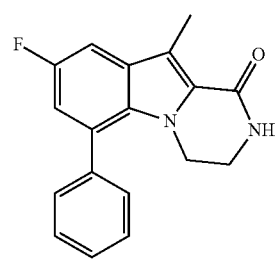

The title compound, off-white solid (66 mg, 90%), MS (ISP) m/z=295.5 [(M+H)$^+$], mp 244° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available phenylboronic acid (39.6 mg, 0.325 mmol).

Example 81

8-Fluoro-10-methyl-6-p-tolyl-3,4-dihydro-2H-pyrazino[1,2-a]indol-1-one

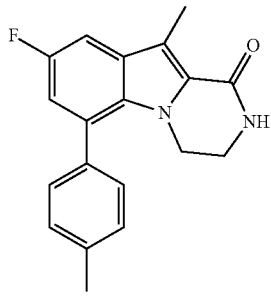 [SMILES: Cc1ccc(-c2cc(F)cc3c(C)c4n(c23)CCNC4=O)cc1]

The title compound, off-white solid (66 mg, 86%), MS (ISP) m/z=309.5 [(M+H)⁺], mp 226° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available p-tolylboronic acid (44.2 mg, 0.325 mmol).

Example 82

8-Fluoro-10-methyl-6-(4-trifluoromethyl-phenyl)-3,4-dihydro-2H-pyrazino[1,2-a]indol-1-one

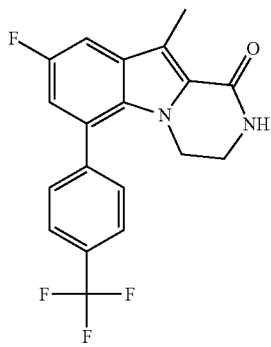 [SMILES: Cc1c2n(c3c(-c4ccc(C(F)(F)F)cc4)cc(F)cc13)CCNC2=O]

The title compound, off-white solid (74 mg, 82%), MS (ISP) m/z=363.4 [(M+H)⁺], mp 269.5° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-trifluoromethyl-phenylboronic acid (61.7 mg, 0.325 mmol).

Example 83

8-Fluoro-10-methyl-6-pyridin-4-yl-3,4-dihydro-2H-pyrazino[1,2-a]indol-1-one

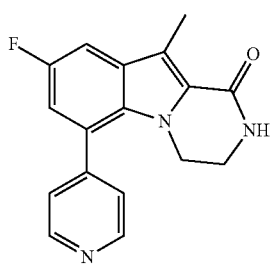 [SMILES: Cc1c2n(c3c(-c4ccncc4)cc(F)cc13)CCNC2=O]

The title compound, light yellow solid (46 mg, 62%), MS (ISP) m/z=296.5 [(M+H)⁺], mp 290° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available pyridine-4-ylboronic acid (39.9 mg, 0.325 mmol).

Example 84

6-(3,5-Difluoro-phenyl)-8-fluoro-10-methyl-3,4-dihydro-2H-pyrazino[1,2-a]indol-1-one

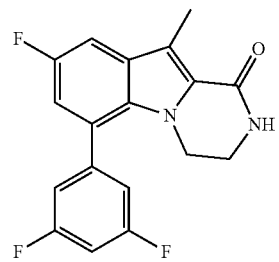 [SMILES: Cc1c2n(c3c(-c4cc(F)cc(F)c4)cc(F)cc13)CCNC2=O]

The title compound, white solid (69 mg, 84%), MS (ISP) m/z=331.5 [(M+H)⁺], mp 250° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 3,5-difluoro-phenylboronic acid (51.3 mg, 0.325 mmol).

Example 85

6-(4-Chloro-3-fluoro-phenyl)-8-fluoro-10-methyl-3,4-dihydro-2H-pyrazino[1,2-a]indol-1-one

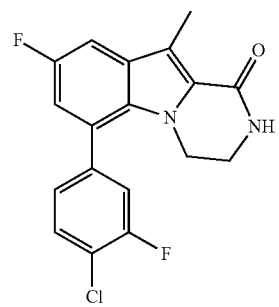 [SMILES: Cc1c2n(c3c(-c4ccc(Cl)c(F)c4)cc(F)cc13)CCNC2=O]

The title compound, white solid (57 mg, 66%), MS (ISP) m/z=347.5 [(M+H)⁺], mp 216° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-chloro-3-fluoro-phenylboronic acid (56.7 mg, 0.325 mmol).

Example 86

6-(3,4-Dichloro-phenyl)-8-fluoro-10-methyl-3,4-dihydro-2H-pyrazino[1,2-a]indol-1-one

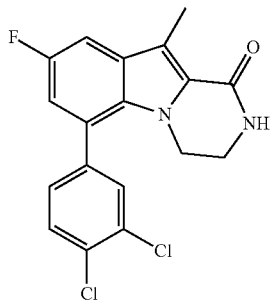

The title compound, light yellow solid (63 mg, 69%), MS (ISP) m/z=363.5 [(M+H)$^+$], mp 224° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 3,4-dichloro-phenylboronic acid (62.0 mg, 0.325 mmol).

Example 87

8-Fluoro-6-(3-fluoro-phenyl)-10-methyl-3,4-dihydro-2H-pyrazino[1,2-a]indol-1-one

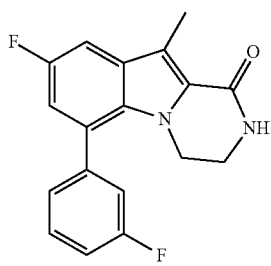

The title compound, white solid (61 mg, 78%), MS (ISP) m/z=313.6 [(M+H)$^+$], mp 222° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 3-fluoro-phenylboronic acid (45.5 mg, 0.325 mmol).

Example 88

8-Chloro-10-methyl-6-phenyl-3,4-dihydro-2H-pyrazino[1,2-a]indol-1-one

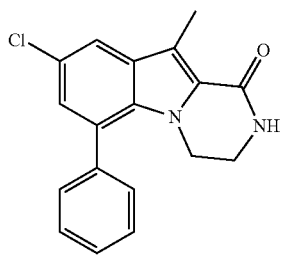 [SMILES: Cc1c2n(c3c(-c4ccccc4)cc(Cl)cc13)CCNC2=O]

The title compound, off-white solid (68 mg, 88%), MS (ISP) m/z=311.5 [(M+H)$^+$], mp 230.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available phenylboronic acid (39.6 mg, 0.325 mmol).

Example 89

8-Chloro-10-methyl-6-p-tolyl-3,4-dihydro-2H-pyrazino[1,2-a]indol-1-one

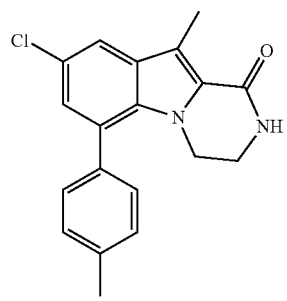 [SMILES: Cc1ccc(-c2cc(Cl)cc3c(C)c4n(c23)CCNC4=O)cc1]

The title compound, light brown solid (72 mg, 89%), MS (ISP) m/z=325.5 [(M+H)$^+$], mp 251.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available p-tolylboronic acid (44.2 mg, 0.325 mmol).

Example 90

8-Chloro-10-methyl-6-(4-trifluoromethyl-phenyl)-3,4-dihydro-2H-pyrazino[1,2-a]indol-1-one

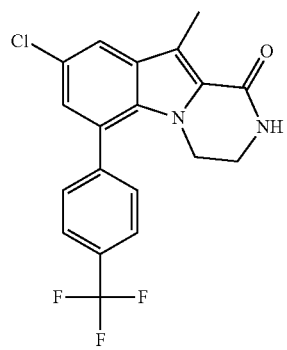 [SMILES: Cc1c2n(c3c(-c4ccc(C(F)(F)F)cc4)cc(Cl)cc13)CCNC2=O]

The title compound, light yellow solid (83 mg, 88%), MS (ISP) m/z=378.4 [(M+H)$^+$], mp 260.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-trifluoromethyl-phenylboronic acid (61.7 mg, 0.325 mmol).

Example 91

8-Chloro-10-methyl-6-pyridin-4-yl-3,4-dihydro-2H-pyrazino[1,2-a]indol-1-one

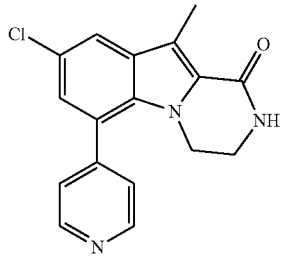 [SMILES: Cc1c2n(c3c(-c4ccncc4)cc(Cl)cc13)CCNC2=O]

The title compound, white solid (60 mg, 77%), MS (ISP) m/z=312.5 [(M+H)$^+$], mp 295° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available pyridine-4-ylboronic acid (39.9 mg, 0.325 mmol).

Example 92

1-Oxo-6-pyridin-4-yl-1,2,3,4-tetrahydro-pyrazino[1,2-a]indole-8-carbonitrile

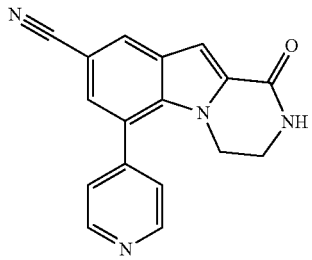

The title compound, off-white solid (64 mg, 89%), MS (ISP) m/z=289.5 [(M+H)$^+$], mp 315.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available pyridine-4-ylboronic acid (39.9 mg, 0.325 mmol).

Example 93

1-Oxo-6-phenyl-1,2,3,4-tetrahydro-pyrazino[1,2-a]indole-8-carbonitrile

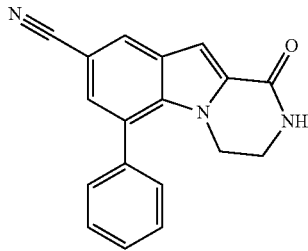 [SMILES: N#Cc1cc(-c2ccccc2)c2c(c1)cc1n2CCNC1=O]

The title compound, white solid (58 mg, 81%), MS (ISP) m/z=288.5 [(M+H)$^+$], mp 265.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available phenylboronic acid (39.6 mg, 0.325 mmol).

Example 94

1-Oxo-6-p-tolyl-1,2,3,4-tetrahydro-pyrazino[1,2-a]indole-8-carbonitrile

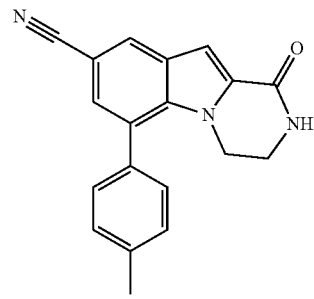 [SMILES: Cc1ccc(-c2cc(C#N)cc3cc4n(c23)CCNC4=O)cc1]

The title compound, white solid (61 mg, 81%), MS (ISP) m/z=302.5 [(M+H)$^+$], mp 285.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available p-tolylboronic acid (44.2 mg, 0.325 mmol).

Example 95

1-Oxo-6-(4-trifluoromethyl-phenyl)-1,2,3,4-tetrahydro-pyrazino[1,2-a]indole-8-carbonitrile

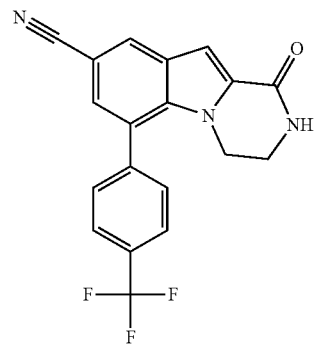 [SMILES: N#Cc1cc(-c2ccc(C(F)(F)F)cc2)c2c(c1)cc1n2CCNC1=O]

The title compound, off-white solid (76 mg, 86%), MS (ISP) m/z=356.5 [(M+H)$^+$], mp 359° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-trifluoromethyl-phenylboronic acid (61.7 mg, 0.325 mmol).

Example 96

8-Chloro-6-(3-fluoro-phenyl)-10-methyl-3,4-dihydro-2H-pyrazino[1,2-a]indol-1-one

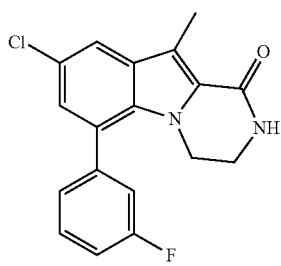

The title compound, white solid (73 mg, 89%), MS (ISP) m/z=329.5 [(M+H)$^+$], mp 239° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 3-fluoro-phenylboronic acid (45.5 mg, 0.325 mmol).

Example 97

8-Chloro-6-(3,4-dichloro-phenyl)-10-methyl-3,4-dihydro-2H-pyrazino[1,2-a]indol-1-one

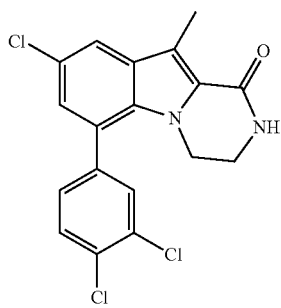 [SMILES: Cc1c2n(c3c(-c4ccc(Cl)c(Cl)c4)cc(Cl)cc13)CCNC2=O]

The title compound, white solid (77 mg, 81%), MS (ISP) m/z=379.6 [(M+H)$^+$], mp 240° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 3,4-dichloro-phenylboronic acid (62.0 mg, 0.325 mmol).

Example 98

8-Chloro-6-(4-chloro-3-fluoro-phenyl)-10-methyl-3,4-dihydro-2H-pyrazino[1,2-a]indol-1-one

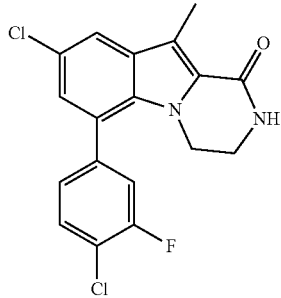 [SMILES: Cc1c2n(c3c(-c4ccc(Cl)c(F)c4)cc(Cl)cc13)CCNC2=O]

The title compound, light yellow solid (80 mg, 88%), MS (ISP) m/z=363.4 [(M+H)$^+$], mp 242.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-chloro-3-fluoro-phenylboronic acid (56.7 mg, 0.325 mmol).

Example 99

8-Chloro-6-(3,5-difluoro-phenyl)-10-methyl-3,4-dihydro-2H-pyrazino[1,2-a]indol-1-one

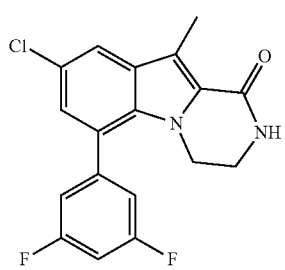 [SMILES: Cc1c2n(c3c(-c4cc(F)cc(F)c4)cc(Cl)cc13)CCNC2=O]

The title compound, off-white solid (76 mg, 88%), MS (ISP) m/z=347.5 [(M+H)$^+$], mp 241° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 3,5-difluoro-phenylboronic acid (51.3 mg, 0.325 mmol).

Example 100

8-Chloro-6-(2,4-difluoro-phenyl)-10-methyl-3,4-dihydro-2H-pyrazino[1,2-a]indol-1-one

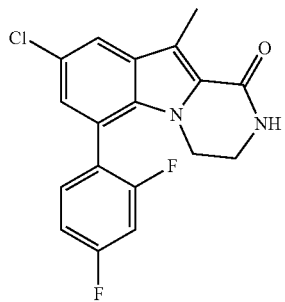 [SMILES: Cc1c2n(c3c(-c4ccc(F)cc4F)cc(Cl)cc13)CCNC2=O]

The title compound, white solid (64 mg, 74%), MS (ISP) m/z=347.5 [(M+H)$^+$], mp 238° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 2,4-difluoro-phenylboronic acid (51.3 mg, 0.325 mmol).

Example 101

8-Chloro-6-(4-chloro-2-fluoro-phenyl)-10-methyl-3,4-dihydro-2H-pyrazino[1,2-a]indol-1-one

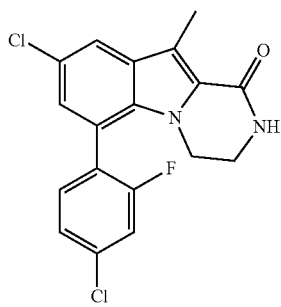

The title compound, white solid (55 mg, 61%), MS (ISP) m/z=363.4 [(M+H)$^+$], mp 251.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-chloro-2-fluoro-phenylboronic acid (56.7 mg, 0.325 mmol).

Example 102

8-Chloro-6-(2,4-dichloro-phenyl)-10-methyl-3,4-dihydro-2H-pyrazino[1,2-a]indol-1-one

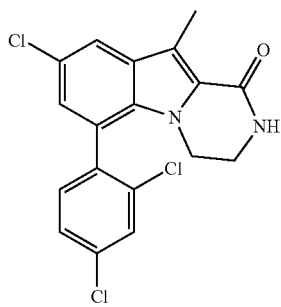 [SMILES: Cc1c2n(c3c(-c4ccc(Cl)cc4Cl)cc(Cl)cc13)CCNC2=O]

The title compound, white solid (63 mg, 66%), MS (ISP) m/z=379.4 [(M+H)$^+$], mp 213° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 2,4-dichloro-phenylboronic acid (62.0 mg, 0.325 mmol).

Example 103

6-Benzo[1,3]dioxol-5-yl-8-chloro-10-methyl-3,4-dihydro-2H-pyrazino[1,2-a]indol-1-one

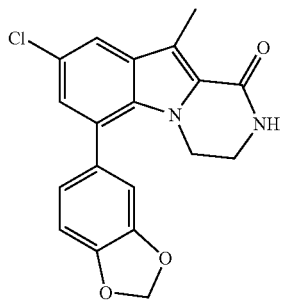 [SMILES: Cc1c2n(c3c(-c4ccc5c(c4)OCO5)cc(Cl)cc13)CCNC2=O]

The title compound, white solid (78 mg, 88%), MS (ISP) m/z=355.4 [(M+H)$^+$], mp 244.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available benzo[d][1,3]dioxol-5-ylboronic acid (53.9 mg, 0.325 mmol).

Example 104

4-(8-Chloro-10-methyl-1-oxo-1,2,3,4-tetrahydro-pyrazino[1,2-a]indol-6-yl)-benzonitrile

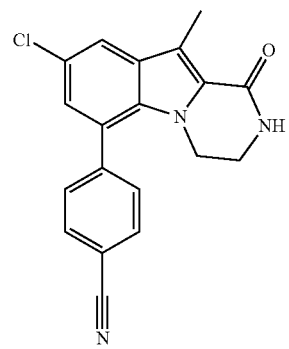 [SMILES: Cc1c2n(c3c(-c4ccc(C#N)cc4)cc(Cl)cc13)CCNC2=O]

The title compound, off-white solid (75 mg, 89%), MS (ISP) m/z=336.4 [(M+H)$^+$], mp 290° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-cyanophenylboronic acid (47.8 mg, 0.325 mmol).

Example 105

8-Chloro-6-(3-fluoro-4-methyl-phenyl)-10-methyl-3,4-dihydro-2H-pyrazino[1,2-a]indol-1-one

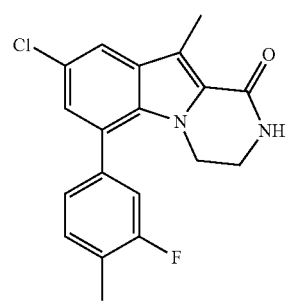 [SMILES: Cc1ccc(-c2cc(Cl)cc3c(C)c4n(c23)CCNC4=O)cc1F]

The title compound, off-white solid (69 mg, 81%), MS (ISP) m/z=343.4 [(M+H)$^+$], mp 225° C., was prepared in accordance with the general method of example 1 6-bromo-8-chloro-10-methyl-3,4-dihydro-2H-pyrazino[1,2-a]indol-1-one (intermediate 12) (78.4 mg, 0.25 mmol) and commercially available 3-fluoro-4-methyl-phenylboronic acid (50.0 mg, 0.325 mmol).

Example 106

8-Chloro-6-(4-isopropyl-phenyl)-10-methyl-3,4-dihydro-2H-pyrazino[1,2-a]indol-1-one

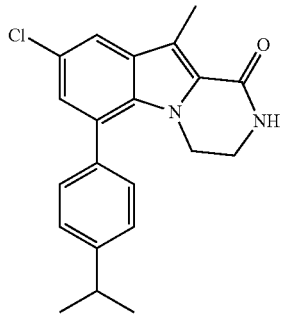

The title compound, off-white solid (76 mg, 86%), MS (ISP) m/z=353.5 [(M+H)+], mp 194.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-isopropyl-phenylboronic acid (53.3 mg, 0.325 mmol).

Example 107

8-Chloro-6-(4-methanesulfonyl-phenyl)-10-methyl-3,4-dihydro-2H-pyrazino[1,2-a]indol-1-one

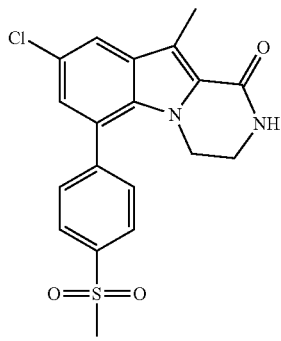 [SMILES: Cc1c2n(c3c(-c4ccc(S(C)(=O)=O)cc4)cc(Cl)cc13)CCNC2=O]

The title compound, white solid (23 mg, 24%), MS (ISP) m/z=389.6 [(M+H)+], mp 321.5° C., was prepared in accordance with the general method of example 1 from 6-bromo-8-chloro-10-methyl-3,4-dihydro-2H-pyrazino[1,2-a]indol1-one (intermediate 12) (78.4 mg, 0.25 mmol) and commercially available 4-methanesulfonyl-phenylboronic acid (65.0 mg, 0.325 mmol).

Example 108

8-Chloro-6-(2-fluoro-pyridin-4-yl)-10-methyl-3,4-dihydro-2H-pyrazino[1,2-a]indol-1-one

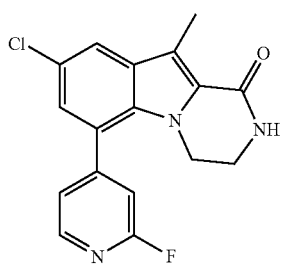 [SMILES: Cc1c2n(c3c(-c4ccnc(F)c4)cc(Cl)cc13)CCNC2=O]

The title compound, off-white solid (67 mg, 81%), MS (ISP) m/z=330.5 [(M+H)+], mp 290.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 2-fluoro-pyridin-4-ylboronic acid (45.8 mg, 0.325 mmol).

Example 109

8-Chloro-10-methyl-6-(4-nitro-phenyl)-3,4-dihydro-2H-pyrazino[1,2-a]indol-1-one

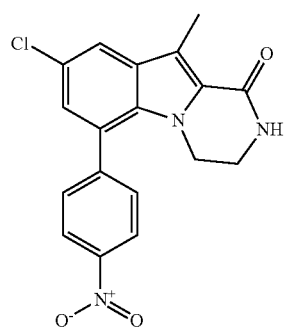 [SMILES: Cc1c2n(c3c(-c4ccc([N+](=O)[O-])cc4)cc(Cl)cc13)CCNC2=O]

The title compound, yellow solid (79 mg, 89%), MS (ISP) m/z=356.5 [(M+H)+], mp 313.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-nitro-phenylboronic acid (54.3 mg, 0.325 mmol).

Example 110

8-Chloro-6-(4-hydroxymethyl-phenyl)-10-methyl-3,4-dihydro-2H-pyrazino[1,2-a]indol-1-one

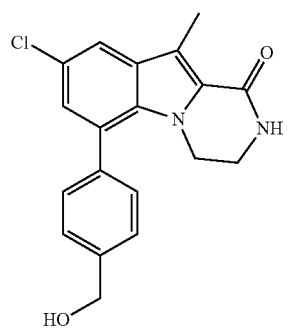 [SMILES: Cc1c2n(c3c(-c4ccc(CO)cc4)cc(Cl)cc13)CCNC2=O]

The title compound, off-white solid (78 mg, 92%), MS (ISP) m/z=341.5 [(M+H)+], mp 211° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-hydroxymethyl-phenylboronic acid (49.4 mg, 0.325 mmol).

Example 111

8-Chloro-6-(6-methoxy-pyridin-3-yl)-10-methyl-3,4-dihydro-2H-pyrazino[1,2-a]indol-1-one

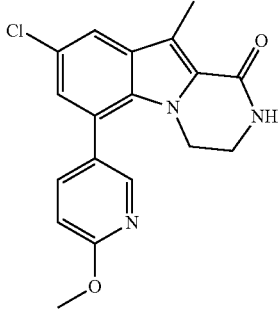 [SMILES: COc1ccc(-c2cc(Cl)cc3c(C)c4n(c23)CCNC4=O)cn1]

The title compound, off-white solid (68 mg, 80%), MS (ISP) m/z=342.5 [(M+H)$^+$], mp 196° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 6-methoxy-pyridin-3-ylphenylboronic acid (49.7 mg, 0.325 mmol).

Example 112

8-Chloro-6-(6-chloro-pyridin-3-yl)-10-methyl-3,4-dihydro-2H-pyrazino[1,2-a]indol-1-one

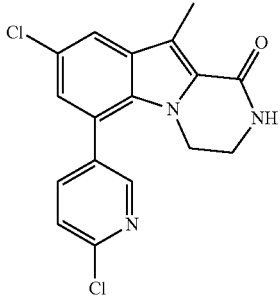

The title compound, light yellow solid (49 mg, 57%), MS (ISP) m/z=346.4 [(M+H)$^+$], mp 276° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) (78.4 mg, 0.25 mmol) and commercially available 6-chloro-pyridin-3-ylboronic acid (51.1 mg, 0.325 mmol).

Example 113

8-Chloro-6-(4-dimethylamino-phenyl)-10-methyl-3,4-dihydro-2H-pyrazino[1,2-a]indol-1-one

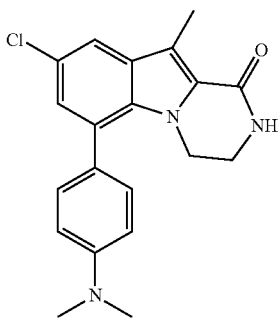 [SMILES: Cc1c2n(c3c(-c4ccc(N(C)C)cc4)cc(Cl)cc13)CCNC2=O]

The title compound, white solid (31 mg, 35%), MS (ISP) m/z=354.5 [(M+H)$^+$], mp 227° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-dimethylamino-phenylboronic acid (53.6 mg, 0.325 mmol).

Example 114

8-Chloro-6-(6-fluoro-pyridin-3-yl)-10-methyl-3,4-dihydro-2H-pyrazino[1,2-a]indol-1-one

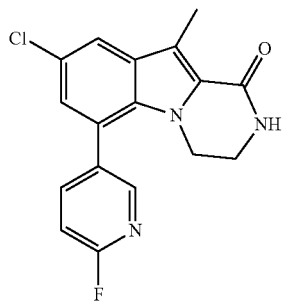 [SMILES: Cc1c2n(c3c(-c4ccc(F)nc4)cc(Cl)cc13)CCNC2=O]

The title compound, light yellow solid (74 mg, 90%), MS (ISP) m/z=330.5 [(M+H)$^+$], mp 270° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 6-fluoro-pyridin-3-ylboronic acid (45.8 mg, 0.325 mmol).

Example 115

8-Chloro-6-(3-chloro-phenyl)-10-methyl-3,4-dihydro-2H-pyrazino[1,2-a]indol-1-one

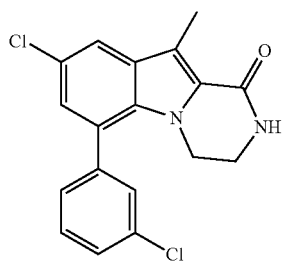 [SMILES: Cc1c2n(c3c(-c4cccc(Cl)c4)cc(Cl)cc13)CCNC2=O]

The title compound, off-white solid (66 mg, 77%), MS (ISP) m/z=345.4 [(M+H)$^+$], mp 218.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 3-chloro-phenylboronic acid (50.8 mg, 0.325 mmol).

Example 116

8-Chloro-6-(2,3-dihydro-benzofuran-5-yl)-10-methyl-3,4-dihydro-2H-pyrazino[1,2-a]indol-1-one

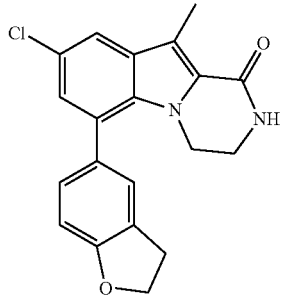 [SMILES: Cc1c2n(c3c(-c4ccc5c(c4)CCO5)cc(Cl)cc13)CCNC2=O]

The title compound, light brown solid (80 mg, 91%), MS (ISP) m/z=353.5 [(M+H)$^+$], mp 261° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 2,3-dihydro-benzofuran-5-ylboronic acid (53.3 mg, 0.325 mmol).

Example 117

3-(8-Chloro-10-methyl-1-oxo-1,2,3,4-tetrahydro-pyrazino[1,2-a]indol-6-yl)-benzonitrile

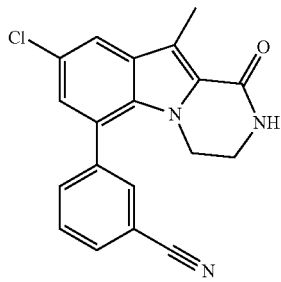 [SMILES: Cc1c2n(c3c(-c4cccc(C#N)c4)cc(Cl)cc13)CCNC2=O]

The title compound, white solid (76 mg, 91%), MS (ISP) m/z=336.5 [(M+H)$^+$], mp 199° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 3-cyano-phenylboronic acid (47.8 mg, 0.325 mmol).

Example 118

6-(4-tert-Butyl-phenyl)-8-chloro-10-methyl-3,4-dihydro-2H-pyrazino[1,2-a]indol-1-one

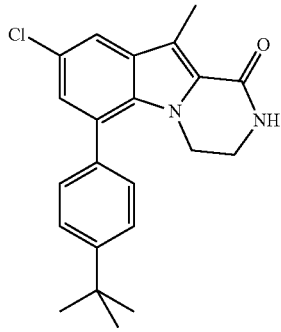 [SMILES: Cc1c2n(c3c(-c4ccc(C(C)(C)C)cc4)cc(Cl)cc13)CCNC2=O]

The title compound, white solid (77 mg, 84%), MS (ISP) m/z=367.5 [(M+H)$^+$], mp 252° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-tert-butyl-phenylboronic acid (57.9 mg, 0.325 mmol).

Example 119

8-Chloro-6-(2-chloro-pyridin-4-yl)-10-methyl-3,4-dihydro-2H-pyrazino[1,2-a]indol-1-one

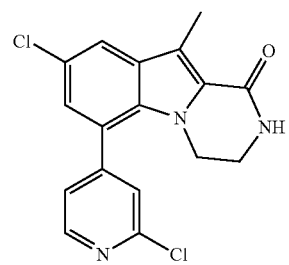 [SMILES: Cc1c2n(c3c(-c4ccnc(Cl)c4)cc(Cl)cc13)CCNC2=O]

The title compound, off-white solid (47 mg, 54%), MS (ISP) m/z=346.4 [(M+H)$^+$], mp 270° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 2-chloro-pyridin-4-ylboronic acid (51.1 mg, 0.325 mmol).

Example 120

6-(2,4-Dichloro-phenyl)-8-fluoro-10-methyl-3,4-dihydro-2H-pyrazino[1,2-a]indol-1-one

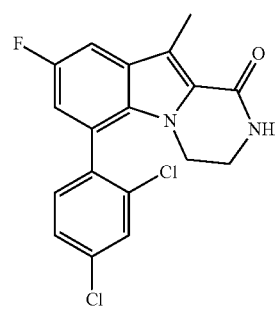 [SMILES: Cc1c2n(c3c(-c4ccc(Cl)cc4Cl)cc(F)cc13)CCNC2=O]

The title compound, white solid (50 mg, 55%), MS (ISP) m/z=363.5 [(M+H)$^+$], mp 214° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 2,4-dichloro-phenylboronic acid (62.0 mg, 0.325 mmol).

Example 121

6-(4-Chloro-2-fluoro-phenyl)-8-fluoro-10-methyl-3,4-dihydro-2H-pyrazino[1,2-a]indol-1-one

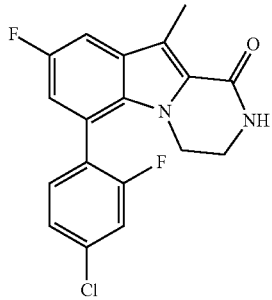 [SMILES: Cc1c2n(c3c(-c4ccc(Cl)cc4F)cc(F)cc13)CCNC2=O]

The title compound, white solid (29 mg, 33%), MS (ISP) m/z=347.5 [(M+H)$^+$], mp 221° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-chloro-2-fluoro-phenylboronic acid (56.7 mg, 0.325 mmol).

Example 122

6-(2,4-Difluoro-phenyl)-8-fluoro-10-methyl-3,4-dihydro-2H-pyrazino[1,2-a]indol-1-one

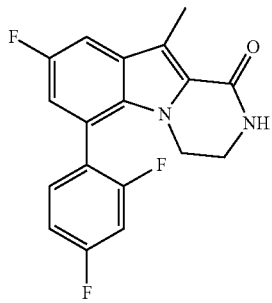 [SMILES: Cc1c2n(c3c(-c4ccc(F)cc4F)cc(F)cc13)CCNC2=O]

The title compound, white solid (32 mg, 39%), MS (ISP) m/z=331.4 [(M+H)$^+$], mp 204° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 2,4-difluoro-phenylboronic acid (51.3 mg, 0.325 mmol).

Example 123

6-Benzo[1,3]dioxol-5-yl-8-fluoro-10-methyl-3,4-dihydro-2H-pyrazino[1,2-a]indol-1-one

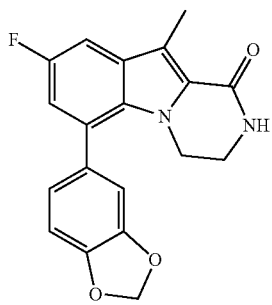 [SMILES: Cc1c2n(c3c(-c4ccc5c(c4)OCO5)cc(F)cc13)CCNC2=O]

The title compound, white solid (73 mg, 86%), MS (ISP) m/z=339.5 [(M+H)$^+$], mp 206° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available benzo[d][1,3]dioxol-5-ylboronic acid (53.9 mg, 0.325 mmol).

Example 124

4-(8-Fluoro-10-methyl-1-oxo-1,2,3,4-tetrahydro-pyrazino[1,2-a]indol-6-yl)-benzonitrile

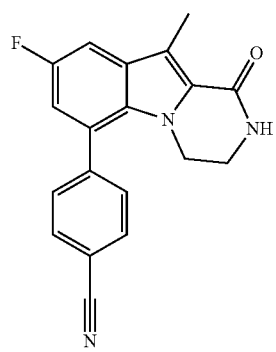 [SMILES: Cc1c2n(c3c(-c4ccc(C#N)cc4)cc(F)cc13)CCNC2=O]

The title compound, white solid (65 mg, 81%), MS (ISP) m/z=320.6 [(M+H)$^+$], mp 295° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-cyanophenylboronic acid (47.8 mg, 0.325 mmol).

Example 125

8-Fluoro-6-(4-methanesulfonyl-phenyl)-10-methyl-3,4-dihydro-2H-1-pyrazino[1,2-a]indol-1-one

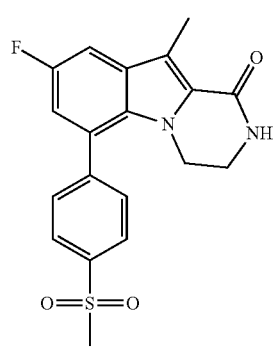 [SMILES: Cc1c2n(c3c(-c4ccc(S(C)(=O)=O)cc4)cc(F)cc13)CCNC2=O]

The title compound, white solid (42 mg, 45%), MS (ISP) m/z=373.5 [(M+H)$^+$], mp 292° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-methanesulfonyl-phenylboronic acid (65.0 mg, 0.325 mmol).

Example 126

8-Fluoro-10-methyl-6-(4-nitro-phenyl)-3,4-dihydro-2H-pyrazino[1,2-a]indol-1-one

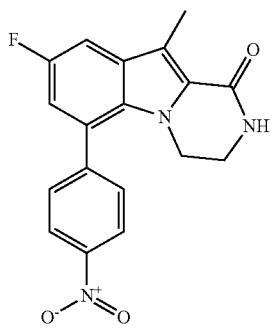 [SMILES: Cc1c2n(c3c(-c4ccc([N+](=O)[O-])cc4)cc(F)cc13)CCNC2=O]

The title compound, light brown solid (63 mg, 74%), MS (ISP) m/z=340.5 [(M+H)$^+$], mp 309° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-nitro-phenylboronic acid (54.3 mg, 0.325 mmol).

Example 127

8-Fluoro-6-(4-isopropyl-phenyl)-10-methyl-3,4-dihydro-2H-pyrazino[1,2-a]indol-1-one

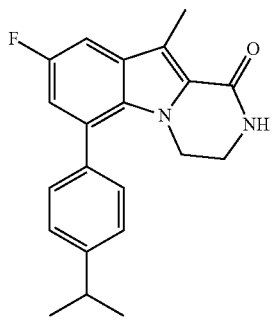 [SMILES: Cc1c2n(c3c(-c4ccc(C(C)C)cc4)cc(F)cc13)CCNC2=O]

The title compound, off-white solid (69 mg, 82%), MS (ISP) m/z=337.5 [(M+H)$^+$], mp 177° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-isopropyl-phenylboronic acid (53.3 mg, 0.325 mmol).

Example 128

6-(3-Chloro-phenyl)-8-fluoro-10-methyl-3,4-dihydro-2H-pyrazino[1,2-a]indol-1-one

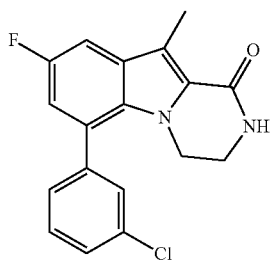 [SMILES: Cc1c2n(c3c(-c4cccc(Cl)c4)cc(F)cc13)CCNC2=O]

The title compound, off-white solid (59 mg, 72%), MS (ISP) m/z=329.4 [(M+H)$^+$], mp 182° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 3-chloro-phenylboronic acid (50.8 mg, 0.325 mmol).

Example 129

6-(2,3-Dihydro-benzofuran-5-yl)-8-fluoro-10-methyl-3,4-dihydro-2H-pyrazino[1,2-a]indol-1-one

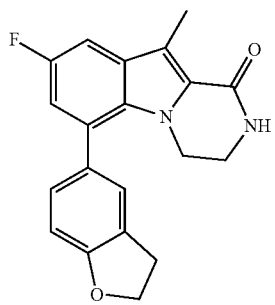 [SMILES: Cc1c2n(c3c(-c4ccc5c(c4)CCO5)cc(F)cc13)CCNC2=O]

The title compound, white solid (70 mg, 83%), MS (ISP) m/z=337.5 [(M+H)$^+$], mp 251° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 2,3-dihydro-benzofuran-5-ylboronic acid (53.3 mg, 0.325 mmol).

Example 130

8-Fluoro-6-(4-hydroxymethyl-phenyl)-10-methyl-3,4-dihydro-2H-pyrazino[1,2-a]indol-1-one

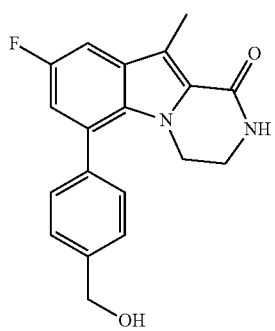

The title compound, white solid (59 mg, 73%), MS (ISP) m/z=325.5 [(M+H)$^+$], mp 220° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-hydroxymethyl-phenylboronic acid (49.4 mg, 0.325 mmol).

Example 131

3-(8-Fluoro-10-methyl-1-oxo-1,2,3,4-tetrahydro-pyrazino[1,2-a]indol-6-yl)-benzonitrile

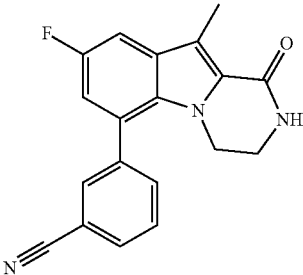 [SMILES: Cc1c2n(c3c(-c4cccc(C#N)c4)cc(F)cc13)CCNC2=O]

The title compound, white solid (69 mg, 86%), MS (ISP) m/z=320.5 [(M+H)$^+$], mp 192° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 3-cyano-phenylboronic acid (47.8 mg, 0.325 mmol).

Example 132

6-(4-tert-Butyl-phenyl)-8-fluoro-10-methyl-3,4-dihydro-2H-pyrazino[1,2-a]indol-1-one

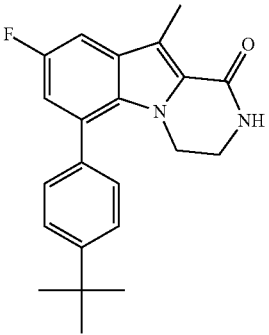 [SMILES: Cc1c2n(c3c(-c4ccc(C(C)(C)C)cc4)cc(F)cc13)CCNC2=O]

The title compound, white solid (71 mg, 81%), MS (ISP) m/z=351.5 [(M+H)$^+$], mp 216° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-tert-butyl-phenylboronic acid (57.9 mg, 0.325 mmol).

Example 133

8-Chloro-10-methyl-6-(4-trifluoromethoxy-phenyl)-3,4-dihydro-2H-pyrazino[1,2-a]indol-1-one

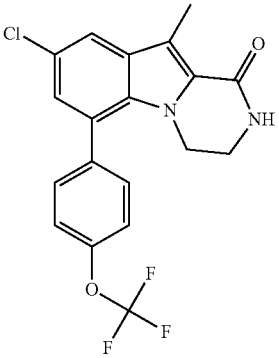 [SMILES: Cc1c2n(c3c(-c4ccc(OC(F)(F)F)cc4)cc(Cl)cc13)CCNC2=O]

The title compound, white solid (70 mg, 71%), MS (ISP) m/z=395.5 [(M+H)$^+$], mp 212° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-trifluoromethoxy-phenylboronic acid (66.9 mg, 0.325 mmol).

Example 134

8-Chloro-6-(4-fluoro-3-methyl-phenyl)-10-methyl-3,4-dihydro-2H-pyrazino[1,2-a]indol-1-one

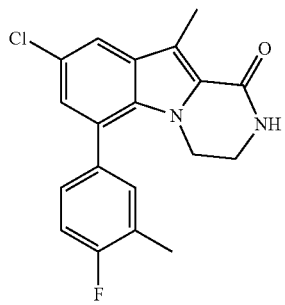 [SMILES: Cc1cc(-c2cc(Cl)cc3c(C)c4n(c23)CCNC4=O)ccc1F]

The title compound, off-white solid (73 mg, 85%), MS (ISP) m/z=343.5 [(M+H)$^+$], mp 235.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-fluoro-3-methyl-phenylboronic acid (50.0 mg, 0.325 mmol).

Example 135

8-Chloro-6-(4-chloro-3-trifluoromethyl-phenyl)-10-methyl-3,4-dihydro-2H-pyrazino[1,2-a]indol-1-one

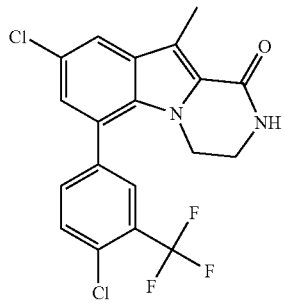 [SMILES: Cc1c2n(c3c(-c4ccc(Cl)c(C(F)(F)F)c4)cc(Cl)cc13)CCNC2=O]

The title compound, off-white solid (85 mg, 82%), MS (ISP) m/z=413.4 [(M+H)$^+$], mp 268° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 4-chloro-3-trifluoromethyl-phenylboronic acid (72.9 mg, 0.325 mmol).

Example 136

8-Chloro-10-methyl-6-(3,4,5-trifluoro-phenyl)-3,4-dihydro-2H-pyrazino[1,2-a]indol-1-one

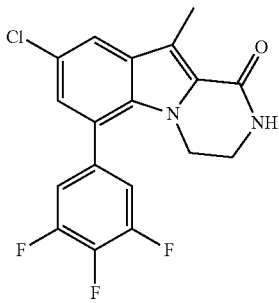 [SMILES: Cc1c2n(c3c(-c4cc(F)c(F)c(F)c4)cc(Cl)cc13)CCNC2=O]

The title compound, light brown solid (79 mg, 87%), MS (ISP) m/z=365.5 [(M+H)$^+$], mp 253° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 3,4,5-trifluoro-phenylboronic acid (57.2 mg, 0.325 mmol).

Example 137

8-Chloro-10-methyl-6-pyridin-3-yl-3,4-dihydro-2H-pyrazino[1,2-a]indol-1-one

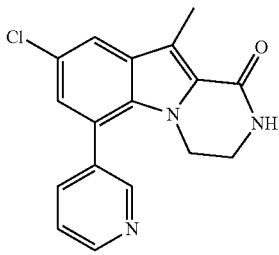

The title compound, white solid (60 mg, 77%), MS (ISP) m/z=312.5 [(M+H)$^+$], mp 252.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available pyridin-3-ylboronic acid (39.9 mg, 0.325 mmol).

Example 138

8-Chloro-10-methyl-6-pyrimidin-5-yl-3,4-dihydro-2H-pyrazino[1,2-a]indol-1-one

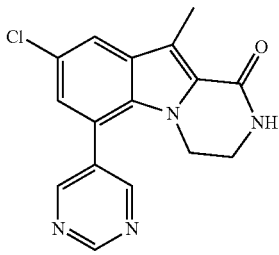 [SMILES: Cc1c2n(c3c(-c4cncnc4)cc(Cl)cc13)CCNC2=O]

The title compound, off-white solid (32 mg, 41%), MS (ISP) m/z=313.5 [(M+H)$^+$], mp 306° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available pyrimidin-5-ylboronic acid (40.3 mg, 0.325 mmol).

Example 139

8-Fluoro-6-(2-fluoro-pyridin-4-yl)-10-methyl-3,4-dihydro-2H-pyrazino[1,2-a]indol-1-one

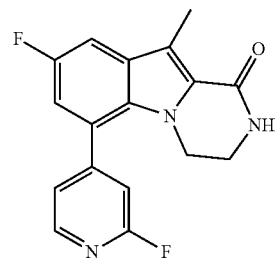 [SMILES: Cc1c2n(c3c(-c4ccnc(F)c4)cc(F)cc13)CCNC2=O]

The title compound, white solid (63 mg, 80%), MS (ISP) m/z=314.5 [(M+H)$^+$], mp 240° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 2-fluoro-pyridin-4-ylboronic acid (45.8 mg, 0.325 mmol).

Example 140

6-(2-Chloro-pyridin-4-yl)-8-fluoro-10-methyl-3,4-dihydro-2H-pyrazino[1,2-a]indol-1-one

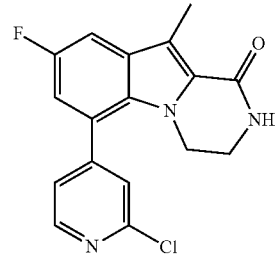 [SMILES: Cc1c2n(c3c(-c4ccnc(Cl)c4)cc(F)cc13)CCNC2=O]

The title compound, light yellow solid (53 mg, 64%), MS (ISP) m/z=330.5 [(M+H)$^+$], mp 254° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 2-chloro-pyridin-4-ylboronic acid (51.1 mg, 0.325 mmol).

Example 141

8-Fluoro-6-(6-fluoro-pyridin-3-yl)-10-methyl-3,4-dihydro-2H-pyrazino[1,2-a]indol-1-one

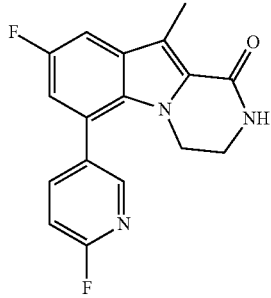

The title compound, off-white solid (59 mg, 75%), MS (ISP) m/z=314.5 [(M+H)$^+$], mp 247° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 6-fluoro-pyridin-3-ylboronic acid (45.8 mg, 0.325 mmol).

Example 142

8-Chloro-6-(2-methoxy-pyrimidin-5-yl)-10-methyl-3,4-dihydro-2H-pyrazino[1,2-a]indol-1-one

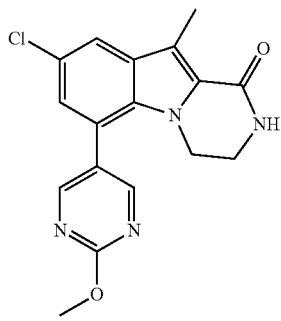 [SMILES: COc1ncc(-c2cc(Cl)cc3c(C)c4n(c23)CCNC4=O)cn1]

The title compound, white solid (68 mg, 79%), MS (ISP) m/z=343.5 [(M+H)$^+$], mp 270.5° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 2-methoxypyrimidin-5-ylboronic acid (50.0 mg, 0.325 mmol).

Example 143

6-(2-Amino-pyrimidin-5-yl)-8-chloro-10-methyl-3,4-dihydro-2H-pyrazino[1,2-a]indol-1-one

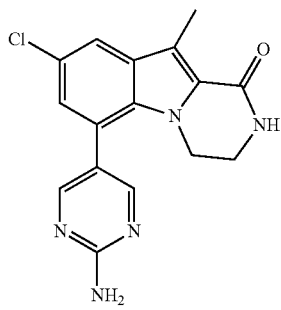 [SMILES: Cc1c2n(c3c(-c4cnc(N)nc4)cc(Cl)cc13)CCNC2=O]

The title compound, white solid (59 mg, 72%), MS (ISP) m/z=328.5 [(M+H)$^+$], mp 316° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 2-aminopyrimidin-5-ylboronic acid (45.1 mg, 0.325 mmol).

Example 144

6-(6-Chloro-pyridin-3-yl)-8-fluoro-10-methyl-3,4-dihydro-2H-pyrazino[1,2-a]indol-1-one

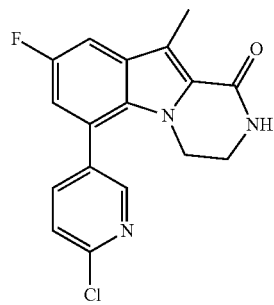 [SMILES: Cc1c2n(c3c(-c4ccc(Cl)nc4)cc(F)cc13)CCNC2=O]

The title compound, light yellow solid (62 mg, 75%), MS (ISP) m/z=314.5 [(M+H)$^+$], mp 232° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 6-chloro-pyridin-3-ylboronic acid (51.1 mg, 0.325 mmol).

Example 145

6-(4-Dimethylamino-phenyl)-8-fluoro-10-methyl-3,4-dihydro-2H-pyrazino[1,2-a]indol-1-one

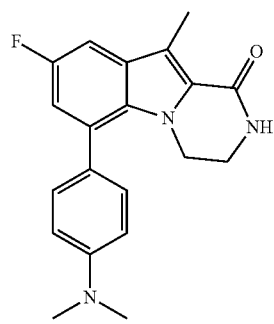 [SMILES: Cc1c2n(c3c(-c4ccc(N(C)C)cc4)cc(F)cc13)CCNC2=O]

The title compound, white solid (31 mg, 37%), MS (ISP) m/z=338.5 [(M+H)$^+$], mp 256° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-dimethylamino-phenylboronic acid (53.6 mg, 0.325 mmol).

Example 146

8-Fluoro-6-(6-methoxy-pyridin-3-yl)-10-methyl-3,4-dihydro-2H-pyrazino[1,2-a]indol-1-one

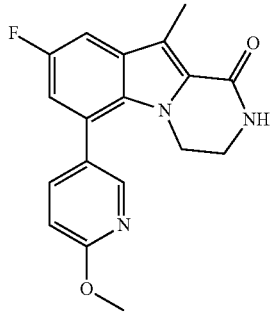

The title compound, off-white solid (67 mg, 82%), MS (ISP) m/z=326.4 [(M+H)$^+$], mp 226° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 6-methoxy-pyridin-3-ylboronic acid (49.7 mg, 0.325 mmol).

Example 147

8-Fluoro-6-(3-fluoro-4-methyl-phenyl)-10-methyl-3,4-dihydro-2H-pyrazino[1,2-a]indol-1-one

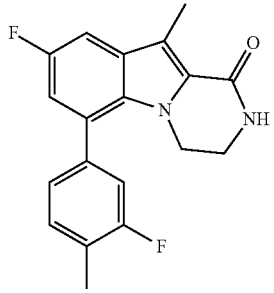 [SMILES: Cc1ccc(-c2cc(F)cc3c(C)c4n(c23)CCNC4=O)cc1F]

The title compound, light yellow solid (71 mg, 87%), MS (ISP) m/z=327.5 [(M+H)$^+$], mp 206° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 3-fluoro-4-methyl-phenylboronic acid (50.0 mg, 0.325 mmol).

Example 148

8-Fluoro-6-(4-fluoro-3-methyl-phenyl)-10-methyl-3,4-dihydro-2H-pyrazino[1,2-a]indol-1-one

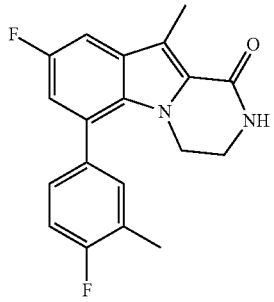 [SMILES: Cc1cc(-c2cc(F)cc3c(C)c4n(c23)CCNC4=O)ccc1F]

The title compound, light yellow solid (69 mg, 85%), MS (ISP) m/z=327.5 [(M+H)$^+$], mp 236° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-fluoro-3-methyl-phenylboronic acid (50.0 mg, 0.325 mmol).

Example 149

8-Fluoro-10-methyl-6-(4-trifluoromethoxy-phenyl)-3,4-dihydro-2H-pyrazino[1,2-a]indol-1-one

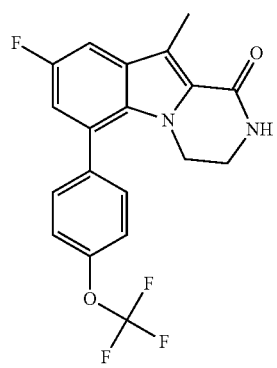 [SMILES: Cc1c2n(c3c(-c4ccc(OC(F)(F)F)cc4)cc(F)cc13)CCNC2=O]

The title compound, light yellow solid (76 mg, 80%), MS (ISP) m/z=379.5 [(M+H)$^+$], mp 162° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-trifluoromethoxy-phenylboronic acid (66.9 mg, 0.325 mmol).

Example 150

6-(4-Chloro-3-trifluoromethyl-phenyl)-8-fluoro-10-methyl-3,4-dihydro-2H-pyrazino[1,2-a]indol-1-one

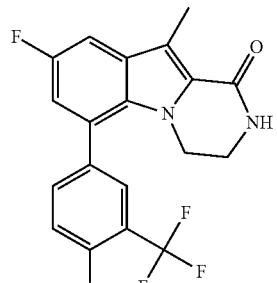

The title compound, light yellow solid (79 mg, 80%), MS (ISP) m/z=397.4 [(M+H)$^+$], mp 240° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 4-chloro-3-trifluoromethyl-phenyl-boronic acid (72.9 mg, 0.325 mmol).

Example 151

8-Fluoro-10-methyl-6-(2,3,4-trifluoro-phenyl)-3,4-dihydro-2H-pyrazino[1,2-a]indol-1-one

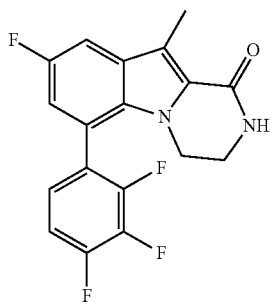 [SMILES: Cc1c2n(c3c(-c4ccc(F)c(F)c4F)cc(F)cc13)CCNC2=O]

The title compound, white solid (21 mg, 24%), MS (ISP) m/z=349.5 [(M+H)+], mp 130° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 2,3,4-trifluorophenylboronic acid (57.2 mg, 0.325 mmol).

Example 152

8-Fluoro-10-methyl-6-pyridin-3-yl-3,4-dihydro-2H-pyrazino[1,2-a]indol-1-one

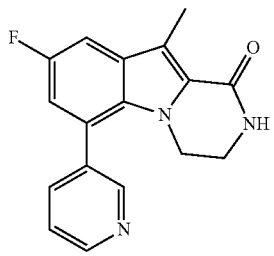 [SMILES: Cc1c2n(c3c(-c4cccnc4)cc(F)cc13)CCNC2=O]

The title compound, off-white solid (50 mg, 68%), MS (ISP) m/z=296.5 [(M+H)+], mp 239° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available pyridin-3-ylboronic acid (39.9 mg, 0.325 mmol).

Example 153

8-Chloro-10-methyl-6-(2,3,4-trifluoro-phenyl)-3,4-dihydro-2H-pyrazino[1,2-a]indol-1-one

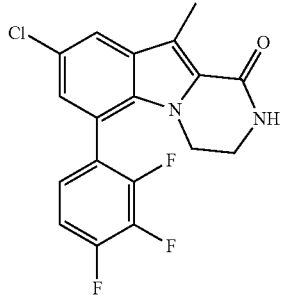 [SMILES: Cc1c2n(c3c(-c4ccc(F)c(F)c4F)cc(Cl)cc13)CCNC2=O]

The title compound, white solid (32 mg, 18%), MS (ISP) m/z=365.5 [(M+H)+], mp 205.5° C., was prepared in accordance with the general method of example 1 from 6-bromo-8-chloro-10-methyl-3,4-dihydro-2H-pyrazino[1,2-a]indol-1-one (intermediate 12) (157 mg, 0.5 mmol) and commercially available 2,3,4-trifluorophenylboronic acid (114 mg, 0.65 mmol).

Example 154

8-Chloro-6-(6-dimethylamino-pyridin-3-yl)-10-methyl-3,4-dihydro-2H-pyrazino[1,2-a]indol-1-one

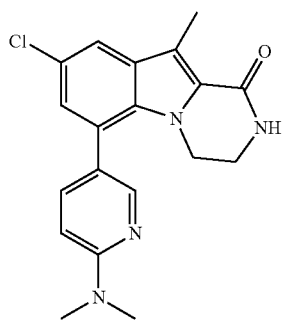 [SMILES: Cc1c2n(c3c(-c4ccc(N(C)C)nc4)cc(Cl)cc13)CCNC2=O]

The title compound, off-white solid (77 mg, 87%), MS (ISP) m/z=355.5 [(M+H)+], mp 248° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 6-dimethylamino-pyridin-3-ylboronic acid (53.9 mg, 0.325 mmol).

Example 155

8-Fluoro-10-methyl-6-pyrimidin-5-yl-3,4-dihydro-2H-pyrazino[1,2-a]indol-1-one

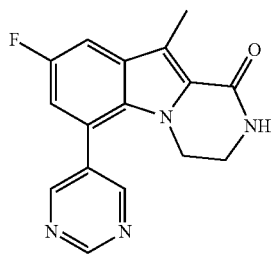 [SMILES: Cc1c2n(c3c(-c4cncnc4)cc(F)cc13)CCNC2=O]

The title compound, light yellow solid (39 mg, 53%), MS (ISP) m/z=297.5 [(M+H)+], mp 289° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available pyrimidin-5-ylboronic acid (40.3 mg, 0.325 mmol).

Example 156

8-Fluoro-6-(2-methoxy-pyrimidin-5-yl)-10-methyl-3,4-dihydro-2H-pyrazino[1,2-a]indol-1-one

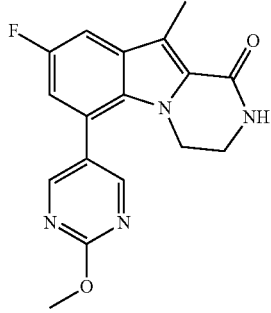 [SMILES: COc1ncc(-c2cc(F)cc3c(C)c4n(c23)CCNC4=O)cn1]

The title compound, white solid (50 mg, 61%), MS (ISP) m/z=327.5 [(M+H)⁺], mp 271° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 2-methoxy-pyrimidin-5-ylboronic acid (50.0 mg, 0.325 mmol).

Example 157

6-(2-Amino-pyrimidin-5-yl)-8-fluoro-10-methyl-3,4-dihydro-2H-pyrazino[1,2-a]indol-1-one

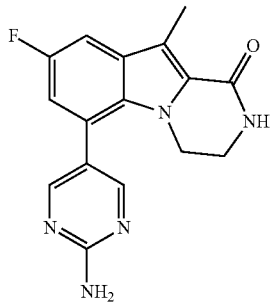 [SMILES: Cc1c2n(c3c(-c4cnc(N)nc4)cc(F)cc13)CCNC2=O]

The title compound, white solid (20 mg, 26%), MS (ISP) m/z=312.5 [(M+H)⁺], mp 310° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 2-amino-pyrimidin-5-ylboronic acid (45.1 mg, 0.325 mmol).

Example 158

6-(6-Dimethylamino-pyridin-3-yl)-8-fluoro-10-methyl-3,4-dihydro-2H-pyrazino[1,2-a]indol-1-one

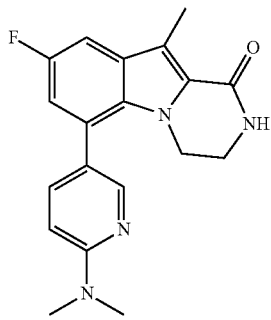

The title compound, grey solid (76 mg, 90%), MS (ISP) m/z=339.5 [(M+H)⁺], mp 259° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 6-dimethylamino-pyridin-3-ylboronic acid (53.9 mg, 0.325 mmol).

Example 159

8-Fluoro-10-methyl-6-(3,4,5-trifluoro-phenyl)-3,4-dihydro-2H-pyrazino[1,2-a]indol-1-one

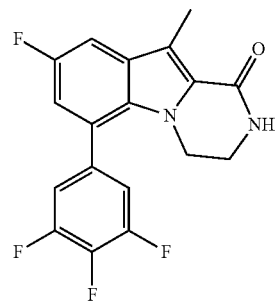 [SMILES: Cc1c2n(c3c(-c4cc(F)c(F)c(F)c4)cc(F)cc13)CCNC2=O]

The title compound, yellow solid (73 mg, 84%), MS (ISP) m/z=349.5 [(M+H)⁺], mp 250° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 3,4,5-trifluoro-phenylboronic acid (57.2 mg, 0.325 mmol).

Example 160

6-(6-Amino-pyridin-3-yl)-8-fluoro-10-methyl-3,4-dihydro-2H-pyrazino[1,2-a]indol-1-one

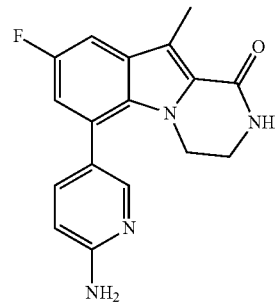 [SMILES: Cc1c2n(c3c(-c4ccc(N)nc4)cc(F)cc13)CCNC2=O]

The title compound, light grey solid (64 mg, 82%), MS (ISP) m/z=311.5 [(M+H)⁺], mp 254° C., was prepared in accordance with the general method of example 1 from 6-bromo-8-fluoro-10-methyl-3,4-dihydro-2H-pyrazino[1,2-a]indol-1-one (intermediate 14) (74.3 mg, 0.25 mmol) and commercially available 5-(4,4,5,5-tetramethyl-1,3,2-dioxaborolan-2-yl)pyridin-2-amine (71.5 mg, 0.325 mmol).

Example 161

6-(6-Amino-pyridin-3-yl)-8-chloro-10-methyl-3,4-dihydro-2H-pyrazino[1,2-a]indol-1-one

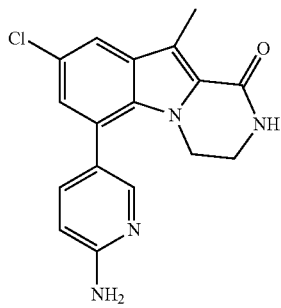 [SMILES: Cc1c2n(c3c(-c4ccc(N)nc4)cc(Cl)cc13)CCNC2=O]

The title compound, white solid (67 mg, 82%), MS (ISP) m/z=327.5 [(M+H)⁺], mp 250° C., was prepared in accordance with the general method of example 1 from 6-bromo-8-chloro-10-methyl-3,4-dihydro-2H-pyrazino[1,2-a]indol-1-one (intermediate 12) (78.4 mg, 0.25 mmol) and commercially available 5-(4,4,5,5-tetramethyl-1,3,2-dioxaborolan-2-yl)pyridin-2-amine (71.5 mg, 0.325 mmol).

Example 162

6-(4-Fluoro-phenyl)-10-methyl-1-oxo-1,2,3,4-tetrahydro-pyrazino[1,2-a]indole-8-carbonitrile

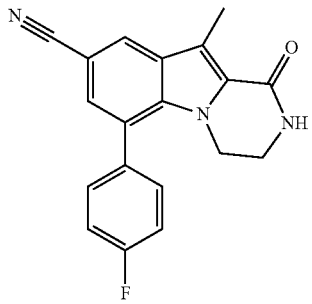

The title compound, light grey solid (70 mg, 88%), MS (ISP) m/z=320.5 [(M+H)⁺], mp 292° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-fluoro-phenylboronic acid (45.5 mg, 0.325 mmol).

Example 163

6-(4-Chloro-phenyl)-10-methyl-1-oxo-1,2,3,4-tetrahydro-pyrazino[1,2-a]indole-8-carbonitrile

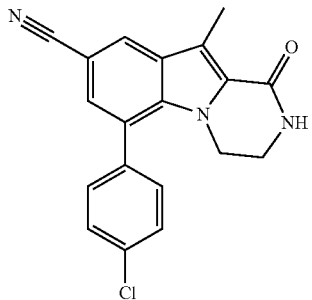 [SMILES: Cc1c2n(c3c(-c4ccc(F)cc4)cc(C#N)cc13)CCNC2=O]

The title compound, light grey solid (78 mg, 93%), MS (ISP) m/z=336.5 [(M+H)⁺], mp 298° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-chloro-phenylboronic acid (50.8 mg, 0.325 mmol).

Example 164

6-(3,4-Difluoro-phenyl)-10-methyl-1-oxo-1,2,3,4-tetrahydro-pyrazino[1,2-a]indole-8-carbonitrile

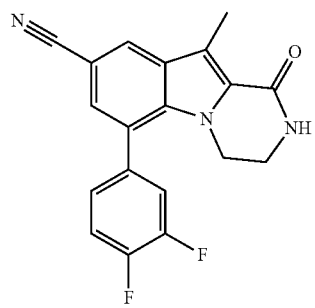 [SMILES: Cc1c2n(c3c(-c4ccc(F)c(F)c4)cc(C#N)cc13)CCNC2=O]

The title compound, light grey solid (73 mg, 87%), MS (ISP) m/z=338.5 [(M+H)⁺], mp 243° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 3,4-difluoro-phenylboronic acid (51.3 mg, 0.325 mmol).

Example 165

10-Methyl-1-oxo-6-(4-trifluoromethyl-phenyl)-1,2,3,4-tetrahydro-pyrazino[1,2-a]indole-8-carbonitrile

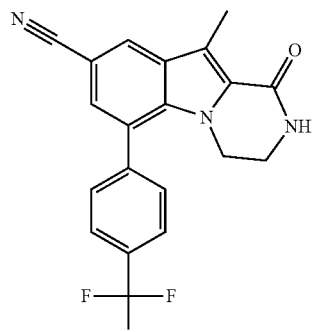

The title compound, light grey solid (78 mg, 85%), MS (ISP) m/z=370.5 [(M+H)⁺], mp 282° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-trifluoromethyl-phenylboronic acid (61.7 mg, 0.325 mmol).

Example 166

6-(4-Cyano-phenyl)-10-methyl-1-oxo-1,2,3,4-tetrahydro-pyrazino[1,2-a]indole-8-carbonitrile

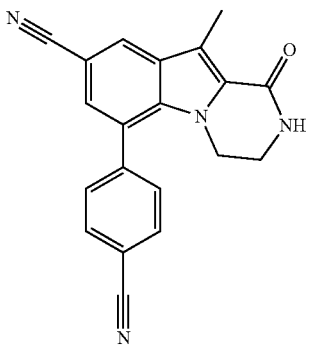 [SMILES: Cc1c2n(c3c(-c4ccc(C#N)cc4)cc(C#N)cc13)CCNC2=O]

The title compound, light grey solid (73 mg, 89%), MS (ISP) m/z=327.5 [(M+H)⁺], mp 323° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-cyanophenylboronic acid (47.8 mg, 0.325 mmol).

Example 167

6-(2,4-Dichloro-phenyl)-10-methyl-1-oxo-1,2,3,4-tetrahydro-pyrazino[1,2-a]indole-8-carbonitrile

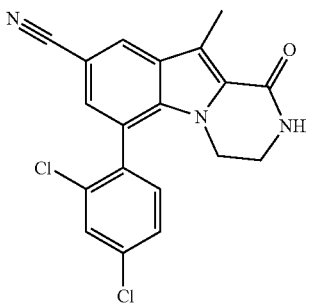 [SMILES: Cc1c2n(c3c(-c4ccc(Cl)cc4Cl)cc(C#N)cc13)CCNC2=O]

The title compound, light grey solid (70 mg, 76%), MS (ISP) m/z=370.4 [(M+H)⁺], mp 274° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 2,4-dichloro-phenylboronic acid (62.0 mg, 0.325 mmol).

Example 168

6-(2-Fluoro-pyridin-4-yl)-10-methyl-1-oxo-1,2,3,4-tetrahydro-pyrazino[1,2-a]indole-8-carbonitrile

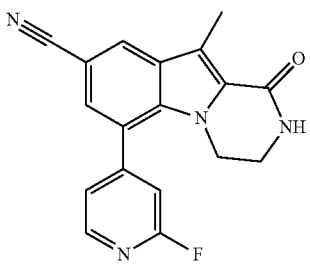

The title compound, light grey solid (33 mg, 41%), MS (ISP) m/z=321.4 [(M+H)⁺], mp 256° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 2-fluoro-pyridin-4-ylboronic acid (45.8 mg, 0.325 mmol).

Example 169

6-(6-Fluoro-pyridin-3-yl)-10-methyl-1-oxo-1,2,3,4-tetrahydro-pyrazino[1,2-a]indole-8-carbonitrile

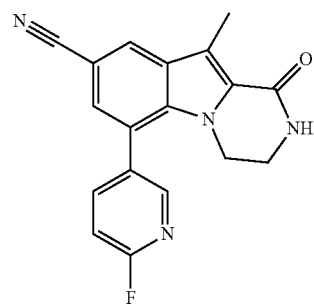 [SMILES: Cc1c2n(c3c(-c4ccc(F)nc4)cc(C#N)cc13)CCNC2=O]

The title compound, white solid (71 mg, 89%), MS (ISP) m/z=321.5 [(M+H)⁺], mp 272° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 6-fluoro-pyridin-3-ylboronic acid (45.8 mg, 0.325 mmol).

Example 170

10-Methyl-1-oxo-6-(4-trifluoromethoxy-phenyl)-1,2,3,4-tetrahydro-pyrazino[1,2-a]indole-8-carbonitrile

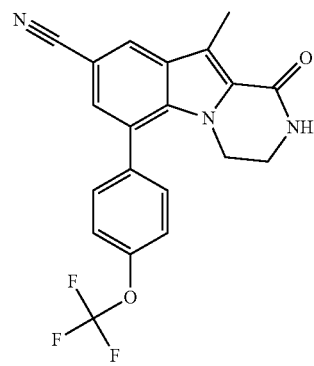 [SMILES: Cc1c2n(c3c(-c4ccc(OC(F)(F)F)cc4)cc(C#N)cc13)CCNC2=O]

The title compound, white solid (84 mg, 87%), MS (ISP) m/z=386.4 [(M+H)⁺], mp 239° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-trifluoromethoxy-phenylboronic acid (66.9 mg, 0.325 mmol).

Example 171

8-Fluoro-10-methyl-6-thiazol-2-yl-3,4-dihydro-2H-pyrazino[1,2-a]indol-1-one

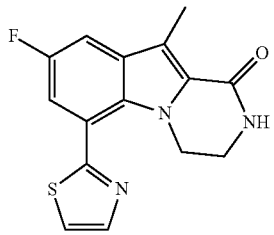 [SMILES: Cc1c2n(c3c(-c4nccs4)cc(F)cc13)CCNC2=O]

Step A

A mixture of 6-bromo-8-fluoro-10-methyl-3,4-dihydro-2H-pyrazino[1,2-a]indol-1-one (intermediate 14) (0.2 g, 0.67 mmol), 4,4,4',4',5,5,5',5'-octamethyl-2,2'-bi(1,3,2-dioxaborolane) (0.19 g, 0.74 mmol) and potassium acetate (0.2 g, 2.02 mmol) in dioxane (3.5 ml) was purged with argon in an ultrasonic bath during 5 min. Afterwards [1,1'-bis(diphenylphosphino)ferrocene]dichloropalladium(II) (24.6 mg, 33.7 µmol) was added and the reaction mixture was allowed to stir for 17 h at 80° C. The reaction mixture was cooled to room temperature, filtered (Dicalite), evaporated and purified by flash chromatography on silica gel (ethyl acetate) to yield 8-fluoro-10-methyl-6-(4,4,5,5-tetramethyl-[1,3,2]dioxaborolan-2-yl)-3,4-dihydro-2H-pyrazino[1,2-a]indol-1-one as an off-white solid (48 mg, 21%), MS (ISP) m/z=345.5 [(M+H)$^+$], mp 258° C.

Step B

To a mixture of 8-fluoro-10-methyl-6-(4,4,5,5-tetramethyl-[1,3,2]dioxaborolan-2-yl)-3,4-dihydro-2H-pyrazino[1,2-a]indol-1-one (Step A) (48 mg, 139 µmol) and 2-bromothiazole (34.3 mg, 18.6 µl, 209 µmol) in 1,2-dimethoxyethane (1 ml), 2M potassium carbonate solution (232 µl, 464 µmol) was added and the reaction mixture purged with argon in an ultrasonic bath during 5 min. Then triphenylphosphine (7.32 mg, 27.9 µmol) and palladium(II)acetate (3.13 mg, 13.9 µmol) were added and the reaction mixture was allowed to stir for 3 h under reflux conditions. The reaction mixture was cooled to room temperature, filtered (MgSO$_4$) and purified by flash chromatography on silica gel [dichloro methane/methanol (0-5%)] and subsequent trituration (diethyl ether) to yield the title compound as a light brown solid (6 mg, 15%), MS (ISP) m/z=302.5 [(M+H)$^+$], mp 268° C.

Example 172

6-(4-Chloro-3-fluoro-phenyl)-1-oxo-1,2,3,4-tetrahydro-pyrazino[1,2-a]indole-8-carbonitrile

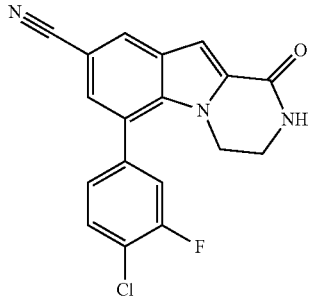 [SMILES: N#Cc1cc(-c2ccc(Cl)c(F)c2)c2c(c1)cc1n2CCNC1=O]

The title compound, light brown solid (64 mg, 75%), MS (ISP) m/z=340.3 [(M+H)$^+$], mp 309° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-chloro-3-fluoro-phenylboronic acid (56.7 mg, 0.325 mmol).

Example 173

6-(2,4-Difluoro-phenyl)-1-oxo-1,2,3,4-tetrahydro-pyrazino[1,2-a]indole-8-carbonitrile

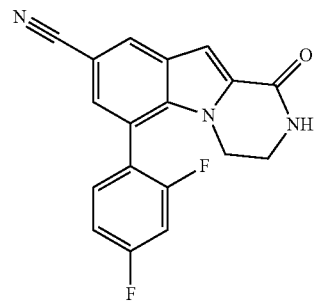 [SMILES: N#Cc1cc(-c2ccc(F)cc2F)c2c(c1)cc1n2CCNC1=O]

The title compound, light brown solid (59 mg, 73%), MS (ISP) m/z=324.4 [(M+H)$^+$], mp 292° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 2,4-difluoro-phenylboronic acid (51.3 mg, 0.325 mmol).

Example 174

6-(4-Chloro-2-fluoro-phenyl)-1-oxo-1,2,3,4-tetrahydro-pyrazino[1,2-a]indole-8-carbonitrile

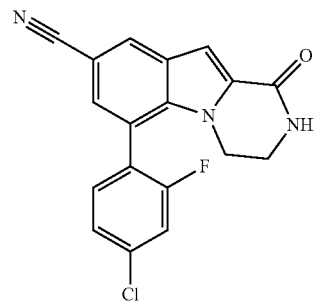 [SMILES: N#Cc1cc(-c2ccc(Cl)cc2F)c2c(c1)cc1n2CCNC1=O]

The title compound, light brown solid (65 mg, 77%), MS (ISP) m/z=340.3 [(M+H)$^+$], mp 278° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-chloro-2-fluoro-phenylboronic acid (56.7 mg, 0.325 mmol).

Example 175

6-(2,4-Dichloro-phenyl)-1-oxo-1,2,3,4-tetrahydro-pyrazino[1,2-a]indole-8-carbonitrile

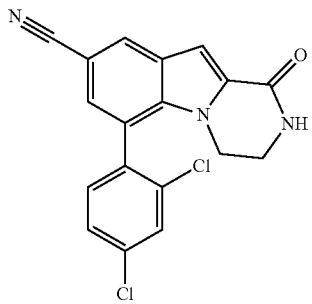 [SMILES: N#Cc1cc(-c2ccc(Cl)cc2Cl)c2c(c1)cc1n2CCNC1=O]

The title compound, light brown solid (46 mg, 52%), MS (ISP) m/z=356.4 [(M+H)$^+$], mp 284.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 2,4-dichloro-phenylboronic acid (62.0 mg, 0.325 mmol).

Example 176

6-(4-Cyano-phenyl)-1-oxo-1,2,3,4-tetrahydro-pyrazino[1,2-a]indole-8-carbonitrile

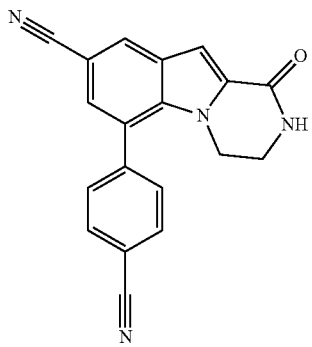 [SMILES: N#Cc1ccc(-c2cc(C#N)cc3cc4n(c23)CCNC4=O)cc1]

The title compound, light brown solid (49 mg, 63%), MS (ISP) m/z=313.4 [(M+H)$^+$], mp 363° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-cyanophenylboronic acid (47.8 mg, 0.325 mmol).

Example 177

6-(2-Fluoro-pyridin-4-yl)-1-oxo-1,2,3,4-tetrahydro-pyrazino[1,2-a]indole-8-carbonitrile

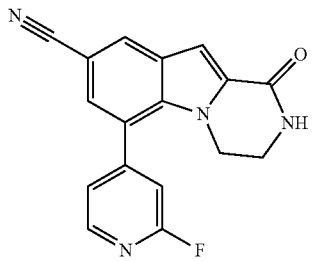 [SMILES: N#Cc1cc(-c2ccnc(F)c2)c2c(c1)cc1n2CCNC1=O]

The title compound, light brown solid (59 mg, 77%), MS (ISP) m/z=307.4 [(M+H)$^+$], mp 289° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 2-fluoro-pyridin-4-ylboronic acid (45.8 mg, 0.325 mmol).

Example 178

6-(4-Chloro-3-fluoro-phenyl)-10-methyl-1-oxo-1,2,3,4-tetrahydro-pyrazino[1,2-a]indole-8-carbonitrile

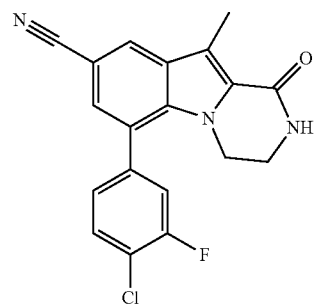 [SMILES: Cc1c2n(c3c(-c4ccc(Cl)c(F)c4)cc(C#N)cc13)CCNC2=O]

The title compound, off-white solid (63 mg, 71%), MS (ISP) m/z=354.5 [(M+H)$^+$], mp 260° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-chloro-3-fluoro-phenylboronic acid (56.7 mg, 0.325 mmol).

Example 179

6-(2,4-Difluoro-phenyl)-10-methyl-1-oxo-1,2,3,4-tetrahydro-pyrazino[1,2-a]indole-8-carbonitrile

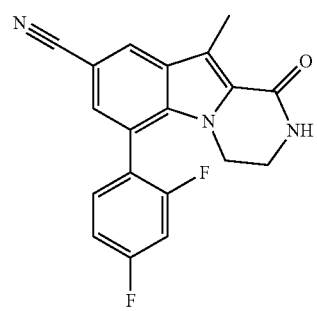 [SMILES: Cc1c2n(c3c(-c4ccc(F)cc4F)cc(C#N)cc13)CCNC2=O]

The title compound, off-white solid (49 mg, 58%), MS (ISP) m/z=338.5 [(M+H)$^+$], mp 237° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 2,4-difluoro-phenylboronic acid (51.3 mg, 0.325 mmol).

Example 180

6-(4-Chloro-2-fluoro-phenyl)-10-methyl-1-oxo-1,2,3,4-tetrahydro-pyrazino[1,2-a]indole-8-carbonitrile

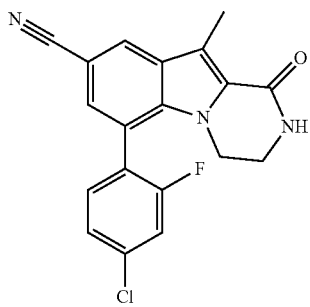 [SMILES: Cc1c2n(c3c(-c4ccc(Cl)cc4F)cc(C#N)cc13)CCNC2=O]

The title compound, off-white solid (66 mg, 75%), MS (ISP) m/z=354.5 [(M+H)⁺], mp 270° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-chloro-2-fluoro-phenylboronic acid (56.7 mg, 0.325 mmol).

Example 181

8-Fluoro-6-(4-fluoro-phenyl)-10-trifluoromethyl-3,4-dihydro-2H-pyrazino[1,2-a]indol-1-one

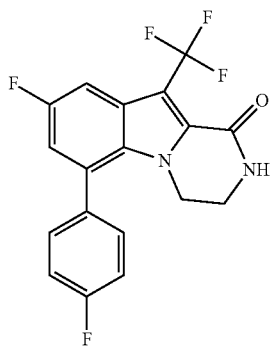 [SMILES: O=C1NCCn2c1c(C(F)(F)F)c1cc(F)cc(-c3ccc(F)cc3)c12]

To a solution of 8-fluoro-6-(4-fluoro-phenyl)-3,4-dihydro-2H-pyrazino[1,2-a]indol-1-one (example 18) (0.1 g, 0.335 mmol) in acetonitrile (1 ml) and DMF (1 ml), N,N,N',N'-tetra-methylethylenediamine (77.9 mg, 101 µl, 670 µmol) and tris(2,2'-biryridyl)ruthenium(II)-chloride hexahydrate (5.02 mg, 6.7 µmol) were added at room temperature. The vial was sealed, cooled to −78° C., and with the help of a needle trifluoroiodomethane (~0.5 ml) was condensed into the reaction tube. A high lumen (6500K) cool daylight lamp was positioned in front of the reaction vial and the reaction was allowed to stir for 40 h at room temperature. The reaction mixture was poured into water (30 ml) and extracted with ethyl acetate (2×40 ml). The combined organic layers were washed with brine (30 ml), dried (MgSO4) and evaporated. The crude product was further purified by flash chromatography on silica gel (heptane/ethyl acetate 20-80%) and trituration (diethyl ether/heptane) to yield the title compound as a white solid (42 mg, 34%), MS (ISP) m/z=367.4 [(M+H)⁺], mp 193° C.

Example 182

6-(3,4-Difluoro-phenyl)-1-oxo-10-trifluoromethyl-1,2,3,4-tetrahydro-pyrazino[1,2-a]indole-8-carbonitrile

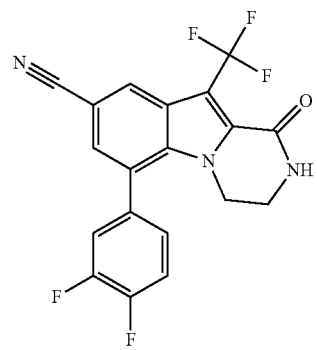 [SMILES: N#Cc1cc(-c2ccc(F)c(F)c2)c2c(c1)c(C(F)(F)F)c1n2CCNC1=O]

The title compound, off-white solid (29 mg, 24%), MS (ISP) m/z=392.5 [(M+H)⁺], mp 217° C., was prepared in accordance with the general method of example 181 from 6-(3,4-difluoro-phenyl)-1-oxo-1,2,3,4-tetrahydro-pyrazino[1,2-a]indole-8-carbonitrile (example 76) (0.1 g, 0.309 mmol).

Example 183

6-(5-Chloro-thiophen-2-yl)-8-fluoro-10-methyl-3,4-dihydro-2H-pyrazino[1,2-a]indol-1-one

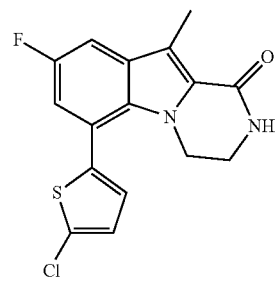 [SMILES: Cc1c2n(c3c(-c4ccc(Cl)s4)cc(F)cc13)CCNC2=O]

The title compound, light brown solid (15 mg, 22%), MS (ISP) m/z=335.4 [(M+H)⁺], mp 185° C., was prepared in accordance with the general method of example 171, step B from 8-fluoro-10-methyl-6-(4,4,5,5-tetramethyl-[1,3,2]dioxaborolan-2-yl)-3,4-dihydro-2H-pyrazino[1,2-a]indol-1- one (Example 171, step A) (68.8 mg, 0.2 mmol) and commercially available 2-bromo-5-chlorothiophene (59.2 mg, 0.3 mmol).

Example 184

8-Fluoro-10-methyl-6-[5-(trifluoromethyl)-1,3,4-thiadiazol-2-yl]-3,4-dihydro-2H-pyrazino[1,2-a]indol-1-one

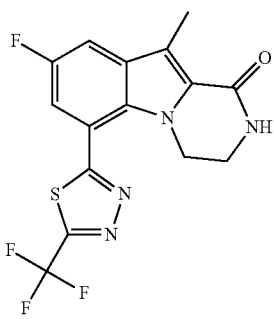 [SMILES: Cc1c2n(c3c(-c4nnc(C(F)(F)F)s4)cc(F)cc13)CCNC2=O]

The title compound, light yellow solid (10 mg, 14%), MS (ISP) m/z=371.5 [(M+H)+], mp 227° C., was prepared in accordance with the general method of example 171, step B from 8-fluoro-10-methyl-6-(4,4,5,5-tetramethyl-[1,3,2]dioxaborolan-2-yl)-3,4-dihydro-2H-pyrazino[1,2-a]indol-1-one (Example 171, step A) (68.8 mg, 0.2 mmol) and commercially available 2-bromo-5-trifluoromethyl-1,3,4-thiadiazole (69.9 mg, 0.3 mmol).

Example 185

5-(8-Fluoro-10-methyl-1-oxo-3,4-dihydro-2H-pyrazino[1,2-a]indol-6-yl)thiophene-2-carbonitrile

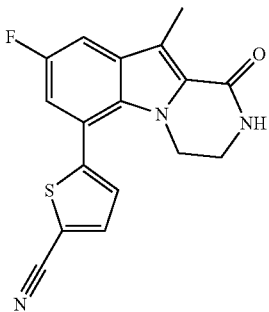 [SMILES: Cc1c2n(c3c(-c4ccc(C#N)s4)cc(F)cc13)CCNC2=O]

The title compound, light brown solid (25 mg, 38%), MS (ISP) m/z=326.5 [(M+H)+], mp 249° C., was prepared in accordance with the general method of example 171, step B from 8-fluoro-10-methyl-6-(4,4,5,5-tetramethyl-[1,3,2]dioxaborolan-2-yl)-3,4-dihydro-2H-pyrazino[1,2-a]indol-1-one (Example 171, step A) (68.8 mg, 0.2 mmol) and commercially available 5-bromothiophene-2-carbonitrile (56.4 mg, 0.3 mmol).

Example 186

8-Fluoro-10-methyl-6-[5-(trifluoromethyl)-1,3-thiazol-2-yl]-3,4-dihydro-2H-pyrazino[1,2-a]indol-1-one

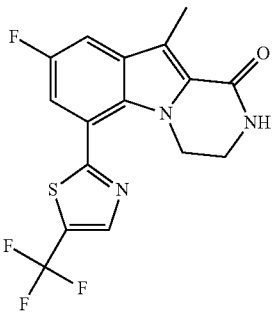 [SMILES: Cc1c2n(c3c(-c4ncc(C(F)(F)F)s4)cc(F)cc13)CCNC2=O]

The title compound, off-white solid (16 mg, 22%), MS (ISP) m/z=370.4 [(M+H)+], mp 263° C., was prepared in accordance with the general method of example 171, step B from 8-fluoro-10-methyl-6-(4,4,5,5-tetramethyl-[1,3,2]dioxaborolan-2-yl)-3,4-dihydro-2H-pyrazino[1,2-a]indol-1-one (Example 171, step A) (68.8 mg, 0.2 mmol) and commercially available 2-bromo-5-trifluoromethyl-thiazole (69.6 mg, 0.3 mmol).

Example 187

8-Chloro-6-(4-chlorophenyl)-10-(trifluoromethyl)-3,4-dihydro-2H-pyrazino[1,2-a]indol-1-one

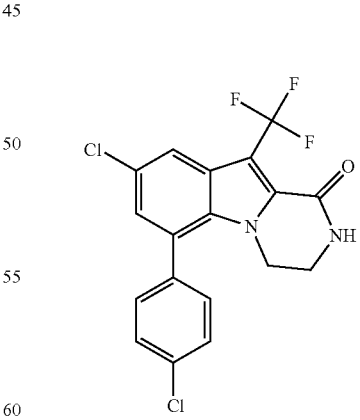

The title compound, light yellow solid (21 mg, %), MS (ISP) m/z=399.3 [(M+H)+], mp 214° C., was prepared in accordance with the general method of example 181 from 8-chloro-6-(4-chloro-phenyl)-3,4-dihydro-2H-pyrazino[1,2-a]indol-1-one (example 49) (0.1 g, 0.309 mmol).

Example 188

8-Fluoro-6-(furan-2-yl)-10-methyl-3,4-dihydro-2H-pyrazino[1,2-a]indol-1-one

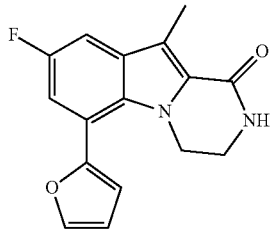 [SMILES: Cc1c2n(c3c(-c4ccco4)cc(F)cc13)CCNC2=O]

The title compound, off-white solid (21 mg, 37%), MS (ISP) m/z=285.5 [(M+H)⁺], mp 236° C., was prepared in accordance with the general method of example 171, step B from 8-fluoro-10-methyl-6-(4,4,5,5-tetramethyl-[1,3,2]dioxaborolan-2-yl)-3,4-dihydro-2H-pyrazino[1,2-a]indol-1-one (Example 171, step A) (68.8 mg, 0.2 mmol) and commercially available 2-bromofurane (44.1 mg, 0.3 mmol).

Example 189

1-Oxo-6-(3,4,5-trifluorophenyl)-3,4-dihydro-2H-pyrazino[1,2-a]indole-8-carbonitrile

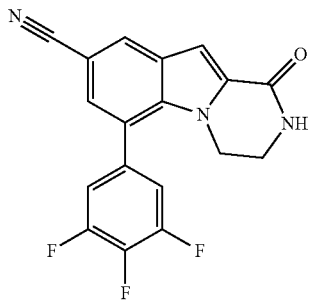 [SMILES: N#Cc1cc(-c2cc(F)c(F)c(F)c2)c2c(c1)cc1n2CCNC1=O]

The title compound, off-white solid (71 mg, 83%), MS (ISP) m/z=342.4 [(M+H)⁺], mp 304.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 3,4,5-trifluoro-phenylboronic acid (57.2 mg, 0.325 mmol).

Example 190

1-Oxo-6-[4-(trifluoromethoxy)phenyl]-3,4-dihydro-2H-pyrazino[1,2-a]indole-8-carbonitrile

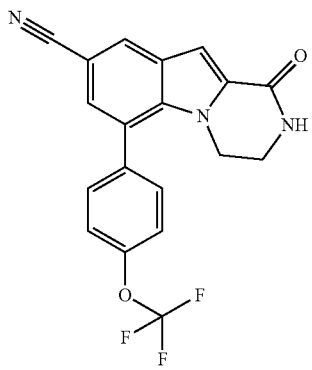 [SMILES: N#Cc1cc(-c2ccc(OC(F)(F)F)cc2)c2c(c1)cc1n2CCNC1=O]

The title compound, off-white solid (82 mg, 88%), MS (ISP) m/z=372.4 [(M+H)⁺], mp 311.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-trifluoromethoxy-phenylboronic acid (66.9 mg, 0.325 mmol).

Example 191

6-(4-Methylsulfonylphenyl)-1-oxo-3,4-dihydro-2H-pyrazino[1,2-a]indole-8-carbonitrile

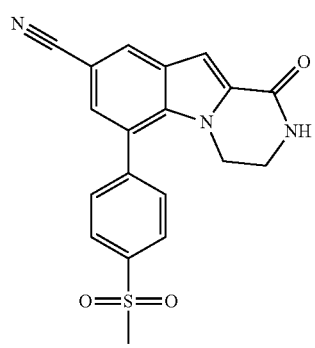 [SMILES: CS(=O)(=O)c1ccc(-c2cc(C#N)cc3cc4n(c23)CCNC4=O)cc1]

The title compound, light grey solid (90 mg, 99%), MS (ISP) m/z=366.4 [(M+H)⁺], mp 329° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-methanesulfonyl-phenylboronic acid (65.0 mg, 0.325 mmol).

Example 192

6-(3,4-Dichlorophenyl)-1-oxo-3,4-dihydro-2H-pyrazino[1,2-a]indole-8-carbonitrile

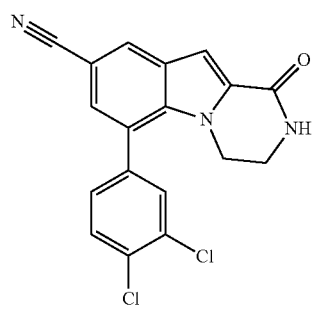 [SMILES: N#Cc1cc(-c2ccc(Cl)c(Cl)c2)c2c(c1)cc1n2CCNC1=O]

The title compound, off-white solid (80 mg, 90%), MS (ISP) m/z=356.3 [(M+H)⁺], mp 330.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 3,4-dichloro-phenylboronic acid (62.0 mg, 0.325 mmol).

Example 193

6-(3-Chlorophenyl)-1-oxo-3,4-dihydro-2H-pyrazino[1,2-a]indole-8-carbonitrile

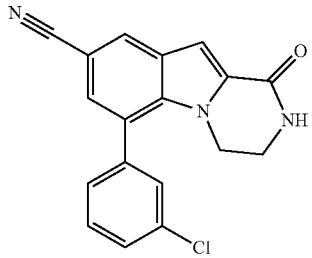 [SMILES: N#Cc1cc(-c2cccc(Cl)c2)c2c(c1)cc1n2CCNC1=O]

The title compound, off-white solid (73 mg, 91%), MS (ISP) m/z=322.4 [(M+H)⁺], mp 241.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 3-chloro-phenylboronic acid (50.8 mg, 0.325 mmol).

Example 194

6-(3-Cyanophenyl)-1-oxo-3,4-dihydro-2H-pyrazino[1,2-a]indole-8-carbonitrile

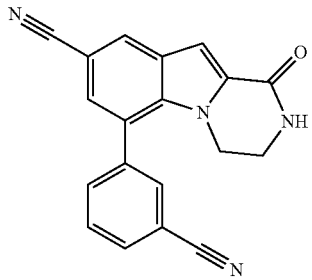 [SMILES: N#Cc1cccc(-c2cc(C#N)cc3cc4n(c23)CCNC4=O)c1]

The title compound, white solid (69 mg, 88%), MS (ISP) m/z=313.4 [(M+H)⁺], mp 253° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 3-cyanophenylboronic acid (47.8 mg, 0.325 mmol).

Example 195

1-Oxo-6-[3-(trifluoromethyl)phenyl]-3,4-dihydro-2H-pyrazino[1,2-a]indole-8-carbonitrile

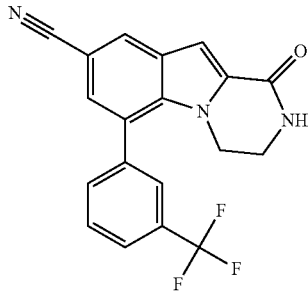 [SMILES: N#Cc1cc(-c2cccc(C(F)(F)F)c2)c2c(c1)cc1n2CCNC1=O]

The title compound, off-white solid (78 mg, 88%), MS (ISP) m/z=356.5 [(M+H)⁺], mp 279.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 3-trifluoromethyl-phenylboronic acid (61.7 mg, 0.325 mmol).

Example 196

7-(3,4-Difluorophenyl)-11-methyl-1-oxo-2,3,4,5-tetrahydro-[1,4]diazepino[1,2-a]indole-9-carbonitrile

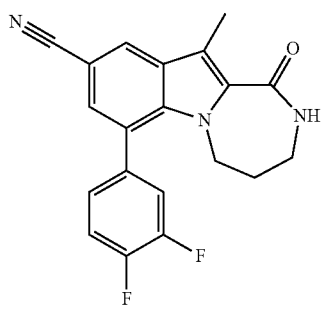 [SMILES: Cc1c2n(c3c(-c4ccc(F)c(F)c4)cc(C#N)cc13)CCCNC2=O]

The title compound, white solid (54 mg, 62%), MS (ISP) m/z=352.5 [(M+H)⁺], mp 278° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 3,4-difluoro-phenylboronic acid (51.3 mg, 0.325 mmol).

Example 197

11-Methyl-1-oxo-7-[4-(trifluoromethyl)phenyl]-2,3,4,5-tetrahydro-[1,4]diazepino[1,2-a]indole-9-carbonitrile

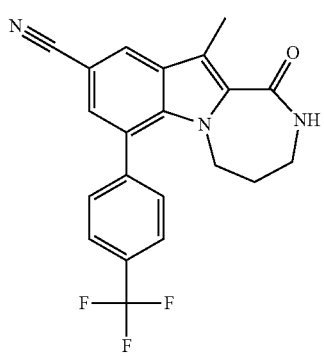 [SMILES: Cc1c2n(c3c(-c4ccc(C(F)(F)F)cc4)cc(C#N)cc13)CCCNC2=O]

The title compound, white solid (74 mg, 77%), MS (ISP) m/z=384.6 [(M+H)⁺], mp 252° C., was prepared in accordance with the general method of example 1 from 7-bromo-11-methyl-1-oxo-2,3,4,5-tetrahydro-[1,4]diazepino[1,2-a]

indole-9-carbonitrile (intermediate 17) (79.5 mg, 0.25 mmol) and commercially available 4-trifluoromethyl-phenylboronic acid (61.7 mg, 0.325 mmol).

Example 198

7-(4-Fluorophenyl)-11-methyl-1-oxo-2,3,4,5-tetrahydro-[1,4]diazepino[1,2-a]indole-9-carbonitrile

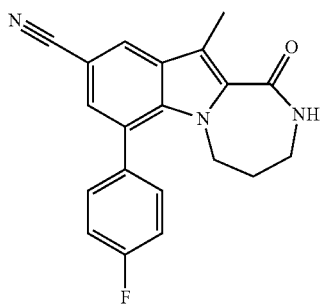

The title compound, white solid (66 mg, 79%), MS (ISP) m/z=334.5 [(M+H)$^+$], mp 278° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 4-fluoro-phenylboronic acid (45.5 mg, 0.325 mmol).

Example 199

7-(4-Chlorophenyl)-11-methyl-1-oxo-2,3,4,5-tetrahydro-[1,4]diazepino[1,2-a]indole-9-carbonitrile

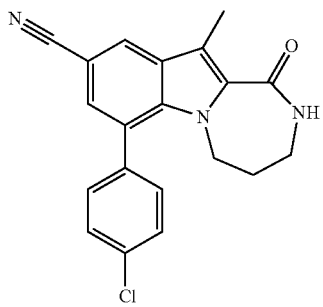

The title compound, light yellow solid (23 mg, 26%), MS (ISP) m/z=350.5 [(M+H)$^+$], mp 298° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 4-chloro-phenylboronic acid (50.8 mg, 0.325 mmol).

Example 200

7-(4-Cyanophenyl)-11-methyl-1-oxo-2,3,4,5-tetrahydro-[1,4]diazepino[1,2-a]indole-9-carbonitrile

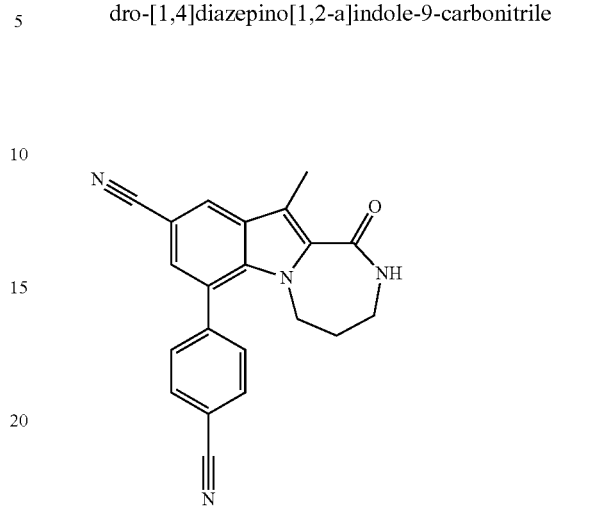

The title compound, white solid (30 mg, 35%), MS (ISP) m/z=341.6 [(M+H)$^+$], mp 314° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 4-cyanophenylboronic acid (47.8 mg, 0.325 mmol).

Example 201

11-Methyl-1-oxo-7-[4-(trifluoromethoxy)-phenyl]-2,3,4,5-tetrahydro-[1,4]diazepino[1,2-a]indole-9-carbonitrile

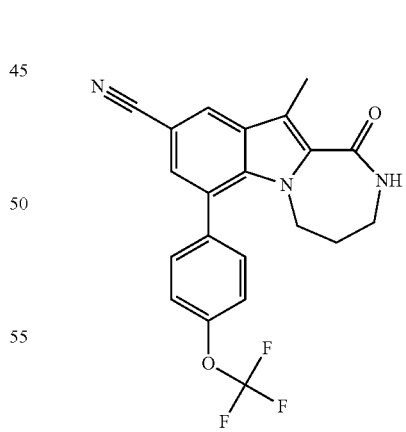

The title compound, light grey solid (81 mg, 81%), MS (ISP) m/z=400.6 [(M+H)$^+$], mp 218° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 4-trifluoromethoxy-phenylboronic acid (66.9 mg, 0.325 mmol).

Example 202

1-Oxo-6-(2,3,4-trifluorophenyl)-3,4-dihydro-2H-pyrazino[1,2-a]indole-8-carbonitrile

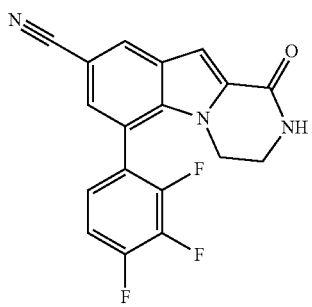 [SMILES: N#Cc1cc(-c2ccc(F)c(F)c2F)c2c(c1)cc1n2CCNC1=O]

The title compound, white solid (13 mg, 15%), MS (ISP) m/z=342.4 [(M+H)$^+$], mp 294° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 2,3,4-trifluoro-phenylboronic acid (57.2 mg, 0.325 mmol).

Example 203

6-(6-Fluoropyridin-3-yl)-1-oxo-3,4-dihydro-2H-pyrazino[1,2-a]indole-8-carbonitrile

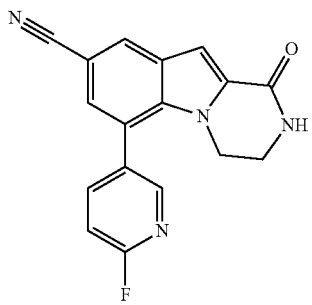

The title compound, off-white solid (68 mg, 89%), MS (ISP) m/z=307.4 [(M+H)$^+$], mp 268° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 6-fluoro-pyridin-3-ylboronic acid (45.8 mg, 0.325 mmol).

Example 204

6-[4-Chloro-3-(trifluoromethyl)phenyl]-1-oxo-3,4-dihydro-2H-pyrazino[1,2-a]indole-8-carbonitrile

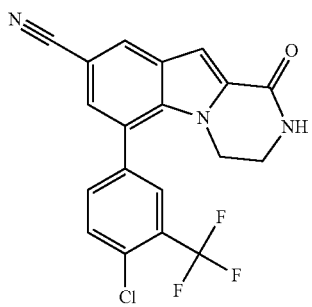 [SMILES: N#Cc1cc(-c2ccc(Cl)c(C(F)(F)F)c2)c2c(c1)cc1n2CCNC1=O]

The title compound, white solid (63 mg, 65%), MS (ISN) m/z=388.4 [(M−H)$^+$], mp 347° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-chloro-3-trifluoromethyl-phenylboronic acid (72.9 mg, 0.325 mmol).

Example 205

7-(2,4-Difluorophenyl)-11-methyl-1-oxo-2,3,4,5-tetrahydro-[1,4]diazepino[1,2-a]indole-9-carbonitrile

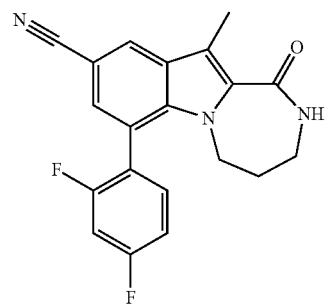 [SMILES: Cc1c2n(c3c(-c4ccc(F)cc4F)cc(C#N)cc13)CCCNC2=O]

The title compound, off-white solid (40 mg, 46%), MS (ISP) m/z=352.5 [(M+H)$^+$], mp 225° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 2,4-difluoro-phenylboronic acid (51.3 mg, 0.325 mmol).

Example 206

7-(2,4-Dichlorophenyl)-11-methyl-1-oxo-2,3,4,5-tetrahydro-[1,4]diazepino[1,2-a]indole-9-carbonitrile

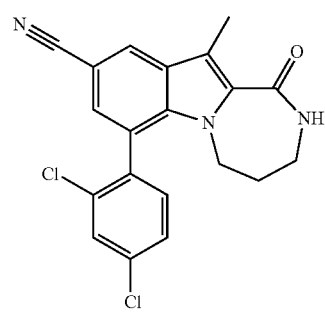 [SMILES: Cc1c2n(c3c(-c4ccc(Cl)cc4Cl)cc(C#N)cc13)CCCNC2=O]

The title compound, off-white solid (54 mg, 56%), MS (ISP) m/z=384.5 [(M+H)$^+$], mp 257° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 2,4-dichloro-phenylboronic acid (62.0 mg, 0.325 mmol).

Example 207

7-(4-Chloro-2-fluorophenyl)-11-methyl-1-oxo-2,3,4,5-tetrahydro-[1,4]diazepino[1,2-a]indole-9-carbonitrile

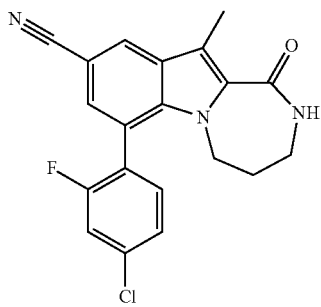 [SMILES: Cc1c2n(c3c(-c4ccc(Cl)cc4F)cc(C#N)cc13)CCCNC2=O]

The title compound, white solid (69 mg, 75%), MS (ISP) m/z=384.5 [(M+H)$^+$], mp 259° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 4-chloro-2-fluoro-phenylboronic acid (56.7 mg, 0.325 mmol).

Example 208

7-(2-Fluoropyridin-4-yl)-11-methyl-1-oxo-2,3,4,5-tetrahydro-[1,4]diazepino[1,2-a]indole-9-carbonitrile

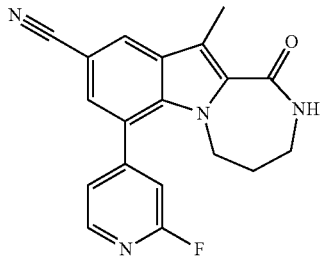 [SMILES: Cc1c2n(c3c(-c4ccnc(F)c4)cc(C#N)cc13)CCCNC2=O]

The title compound, white solid (59 mg, 71%), MS (ISP) m/z=335.5 [(M+H)$^+$], mp 264° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 2-fluoro-pyridin-4-ylboronic acid (45.8 mg, 0.325 mmol).

Example 209

7-(6-Fluoropyridin-3-yl)-11-methyl-1-oxo-2,3,4,5-tetrahydro-[1,4]diazepino[1,2-a]indole-9-carbonitrile

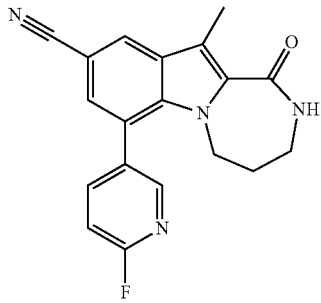 [SMILES: Cc1c2n(c3c(-c4ccc(F)nc4)cc(C#N)cc13)CCCNC2=O]

The title compound, off-white solid (41 mg, 49%), MS (ISP) m/z=335.5 [(M+H)$^+$], mp 280° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 6-fluoro-pyridin-3-ylboronic acid (45.8 mg, 0.325 mmol).

Example 210

6-(4-Fluorophenyl)-8-methoxy-3,4-dihydro-2H-pyrazino[1,2-a]indol-1-one

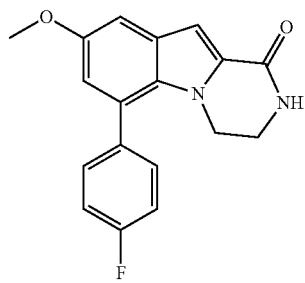 [SMILES: COc1cc(-c2ccc(F)cc2)c2c(c1)cc1n2CCNC1=O]

The title compound, white solid (61 mg, 79%), MS (ISP) m/z=311.5 [(M+H)$^+$], mp 220° C., was prepared in accordance with the general method of example 1 from 6-bromo-8-methoxy-3,4-dihydro-2H-pyrazino[1,2-a]indol-1-one (intermediate 18) (73.8 mg, 0.25 mmol) and commercially available 4-fluoro-phenylboronic acid (45.5 mg, 0.325 mmol).

Example 211

6-(4-Chlorophenyl)-8-methoxy-3,4-dihydro-2H-pyrazino[1,2-a]indol-1-one

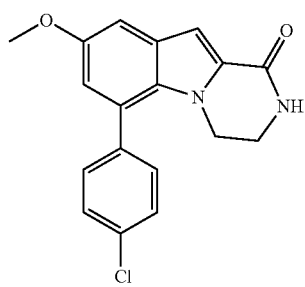 [SMILES: COc1cc(-c2ccc(Cl)cc2)c2c(c1)cc1n2CCNC1=O]

The title compound, white solid (64 mg, 78%), MS (ISP) m/z=327.5 [(M+H)$^+$], mp 246° C., was prepared in accordance with the general method of example 1 from 6-bromo-8-methoxy-3,4-dihydro-2H-pyrazino[1,2-a]indol-1-one (intermediate 18) (73.8 mg, 0.25 mmol) and commercially available 4-chloro-phenylboronic acid (50.8 mg, 0.325 mmol).

Example 212

6-(3,4-Difluorophenyl)-8-methoxy-3,4-dihydro-2H-pyrazino[1,2-a]indol-1-one

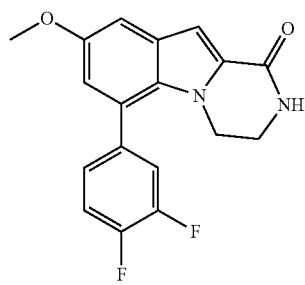 [SMILES: COc1cc(-c2ccc(F)c(F)c2)c2c(c1)cc1n2CCNC1=O]

The title compound, off-white solid (66 mg, 80%), MS (ISP) m/z=329.4 [(M+H)$^+$], mp 216° C., was prepared in accordance with the general method of example 1 from 6-bromo-8-methoxy-3,4-dihydro-2H-pyrazino[1,2-a]indol-1-one (intermediate 18) (73.8 mg, 0.25 mmol) and commercially available 3,4-difluoro-phenylboronic acid (51.3 mg, 0.325 mmol).

Example 213

8-Methoxy-6-[4-(trifluoromethyl)-phenyl]-3,4-dihydro-2H-pyrazino[1,2-a]indol-1-one

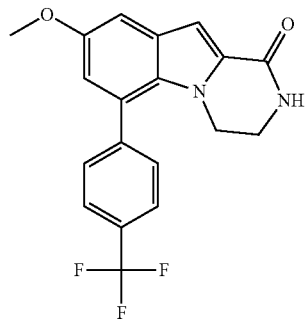 [SMILES: COc1cc(-c2ccc(C(F)(F)F)cc2)c2c(c1)cc1n2CCNC1=O]

The title compound, white solid (77 mg, 81%), MS (ISP) m/z=361.4 [(M+H)$^+$], mp 276° C., was prepared in accordance with the general method of example 1 from 6-bromo-8-methoxy-3,4-dihydro-2H-pyrazino[1,2-a]indol-1-one (intermediate 18) (73.8 mg, 0.25 mmol) and commercially available 4-trifluoromethyl-phenylboronic acid (61.7 mg, 0.325 mmol).

Example 214

7-(4-Chlorophenyl)-1-oxo-2,3,4,5-tetrahydro-[1,4]diazepino[1,2-a]indole-9-carbonitrile

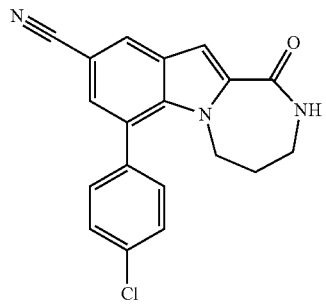 [SMILES: N#Cc1cc(-c2ccc(Cl)cc2)c2c(c1)cc1n2CCCNC1=O]

The title compound, light grey solid (76 mg, 91%), MS (ISP) m/z=336.4 [(M+H)$^+$], mp 245.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-chloro-phenylboronic acid (50.8 mg, 0.325 mmol).

Example 215

7-(4-Fluorophenyl)-1-oxo-2,3,4,5-tetrahydro-[1,4]diazepino[1,2-a]indole-9-carbonitrile

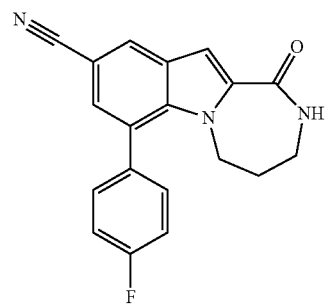

The title compound, light grey solid (75 mg, 94%), MS (ISP) m/z=320.4 [(M+H)$^+$], mp 230° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-fluoro-phenylboronic acid (45.5 mg, 0.325 mmol).

Example 216

8-(Trifluoromethoxy)-6-[4-(trifluoromethyl)-phenyl]-3,4-dihydro-2H-pyrazino[1,2-a]indol-1-one

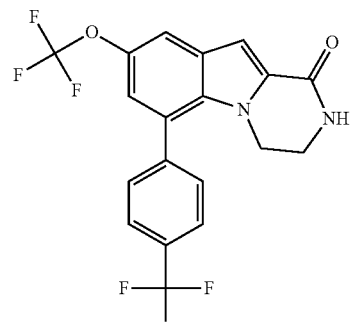

The title compound, white solid (87 mg, 84%), MS (ISP) m/z=415.4 [(M+H)$^+$], mp 243° C., was prepared in accordance with the general method of example 1 from 6-bromo-8-(trifluoromethoxy)-3,4-dihydro-2H-pyrazino[1,2-a]indol-1-one (intermediate 19) (87.3 mg, 0.25 mmol) and commercially available 4-trifluoromethyl-phenylboronic acid (61.7 mg, 0.325 mmol).

Example 217

7-(3,4-Difluorophenyl)-1-oxo-2,3,4,5-tetrahydro-[1,4]diazepino[1,2-a]indole-9-carbonitrile

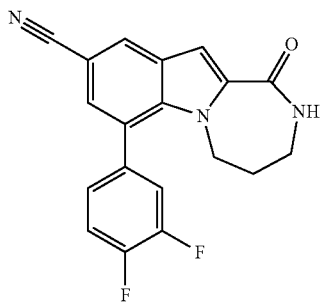

The title compound, light grey solid (72 mg, 85%), MS (ISP) m/z=338.4 [(M+H)$^+$], mp 224.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 3,4-difluoro-phenylboronic acid (51.3 mg, 0.325 mmol).

Example 218

1-Oxo-7-[4-(trifluoromethyl)-phenyl]-2,3,4,5-tetrahydro-[1,4]diazepino[1,2-a]indole-9-carbonitrile

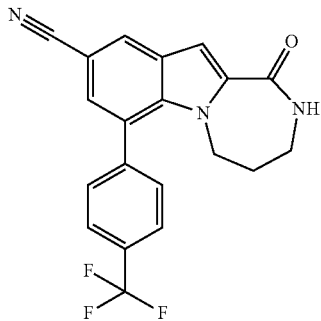 [SMILES: N#Cc1cc(-c2ccc(C(F)(F)F)cc2)c2c(c1)cc1n2CCCNC1=O]

The title compound, light grey solid (83 mg, 90%), MS (ISP) m/z=370.4 [(M+H)$^+$], mp 241.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-trifluoromethyl-phenylboronic acid (61.7 mg, 0.325 mmol).

Example 219

7-(4-Chloro-2-fluorophenyl)-1-oxo-2,3,4,5-tetrahydro-[1,4]diazepino[1,2-a]indole-9-carbonitrile

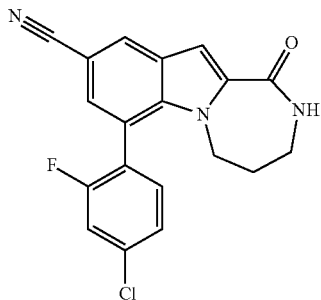 [SMILES: N#Cc1cc(-c2ccc(Cl)cc2F)c2c(c1)cc1n2CCCNC1=O]

The title compound, white solid (83 mg, 94%), MS (ISP) m/z=354.4 [(M+H)$^+$], mp 217.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-chloro-2-fluoro-phenylboronic acid (56.7 mg, 0.325 mmol).

Example 220

7-(2-Fluoropyridin-4-yl)-1-oxo-2,3,4,5-tetrahydro-[1,4]diazepino[1,2-a]indole-9-carbonitrile

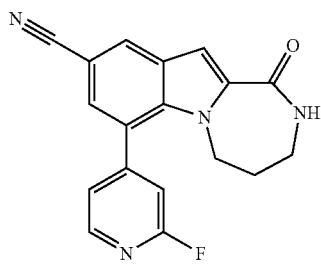

The title compound, white solid (51 mg, 64%), MS (ISP) m/z=321.4 [(M+H)$^+$], mp 275° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 2-fluoro-pyridin-4-ylboronic acid (45.8 mg, 0.325 mmol).

Example 221

7-(2,4-Difluorophenyl)-1-oxo-2,3,4,5-tetrahydro-[1,4]diazepino[1,2-a]indole-9-carbonitrile

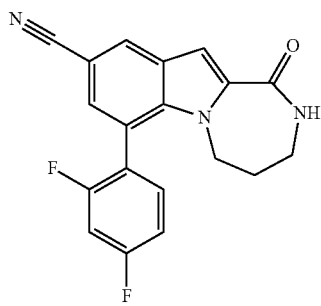 [SMILES: N#Cc1cc(-c2ccc(F)cc2F)c2c(c1)cc1n2CCCNC1=O]

The title compound, white solid (53 mg, 53%), MS (ISP) m/z=338.4 [(M+H)$^+$], mp 216.5° C., was prepared in accordance with the general method of example 1 from 7-bromo-1-oxo-2,3,4,5-tetrahydro-[1,4]diazepino[1,2-a]indole-9-carbonitrile (intermediate 20) (90 mg, 0.296 mmol) and commercially available 2,4-difluoro-phenylboronic acid (60.7 mg, 0.385 mmol).

Example 222

6-(3,5-Difluorophenyl)-1-oxo-3,4-dihydro-2H-pyrazino[1,2-a]indole-8-carbonitrile

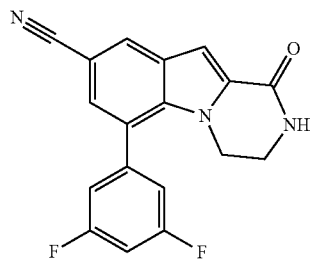 [SMILES: N#Cc1cc(-c2cc(F)cc(F)c2)c2c(c1)cc1n2CCNC1=O]

The title compound, off-white solid (66 mg, 82%), MS (ISN) m/z=324.5 [(M+H)+], mp 264° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 3,5-difluoro-phenylboronic acid (51.3 mg, 0.325 mmol).

Example 223

6-(3-Fluorophenyl)-1-oxo-3,4-dihydro-2H-pyrazino[1,2-a]indole-8-carbonitrile

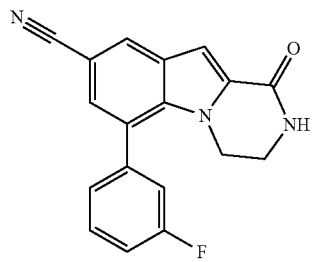 [SMILES: N#Cc1cc(-c2cccc(F)c2)c2c(c1)cc1n2CCNC1=O]

The title compound, light grey solid (67 mg, 88%), MS (ISN) m/z=306.5 [(M+H)+], mp 248.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 3-fluoro-phenylboronic acid (45.5 mg, 0.325 mmol).

Example 224

6-(6-Aminopyridin-3-yl)-1-oxo-3,4-dihydro-2H-pyrazino[1,2-a]indole-8-carbonitrile

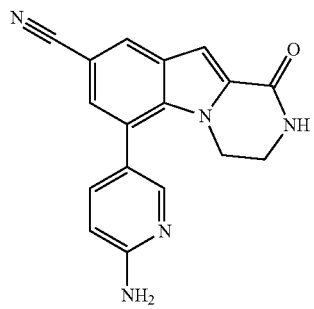 [SMILES: N#Cc1cc(-c2ccc(N)nc2)c2c(c1)cc1n2CCNC1=O]

The title compound, light brown solid (46 mg, 61%), MS (ISN) m/z=304.5 [(M+H)+], mp 305° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 5-(4,4,5,5-tetramethyl-1,3,2-dioxaborolan-2-yl)pyridin-2-amine (71.5 mg, 0.325 mmol).

Example 225

1-Oxo-6-pyrimidin-5-yl-3,4-dihydro-2H-pyrazino[1,2-a]indole-8-carbonitrile

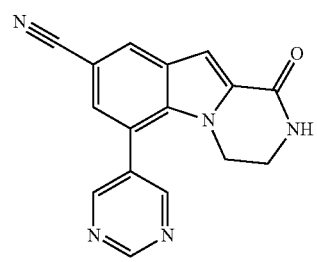

The title compound, off-white solid (16 mg, 22%), MS (ISN) m/z=290.5 [(M+H)+], mp 323.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available pyrimidin-5-ylboronic acid (40.3 mg, 0.325 mmol).

Example 226

6-(6-Chloropyridin-3-yl)-1-oxo-3,4-dihydro-2H-pyrazino[1,2-a]indole-8-carbonitrile

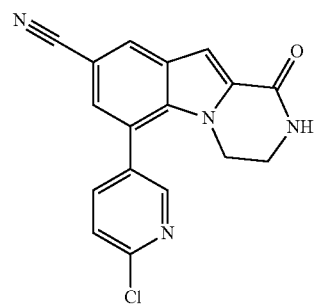 [SMILES: N#Cc1cc(-c2ccc(Cl)nc2)c2c(c1)cc1n2CCNC1=O]

The title compound, off-white solid (62 mg, 77%), MS (ISN) m/z=323.5 [(M+H)+], mp 300.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 6-chloro-pyridin-3-ylboronic acid (51.1 mg, 0.325 mmol).

Example 227

6-(2-Chloropyridin-4-yl)-1-oxo-3,4-dihydro-2H-pyrazino[1,2-a]indole-8-carbonitrile

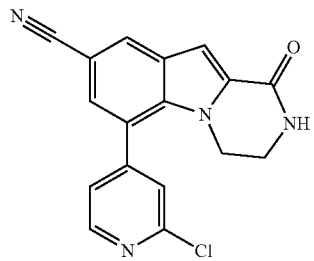 [SMILES: N#Cc1cc(-c2ccnc(Cl)c2)c2c(c1)cc1n2CCNC1=O]

The title compound, off-white solid (68 mg, 84%), MS (ISN) m/z=323.5 [(M+H)$^+$], mp 286° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 2-chloro-pyridin-4-ylboronic acid (51.1 mg, 0.325 mmol).

Example 228

6-[4-(Hydroxymethyl)-phenyl]-1-oxo-3,4-dihydro-2H-pyrazino[1,2-a]indole-8-carbonitrile

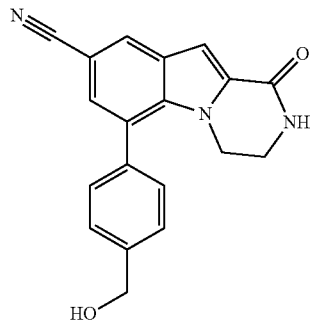 [SMILES: N#Cc1cc(-c2ccc(CO)cc2)c2c(c1)cc1n2CCNC1=O]

The title compound, light brown solid (18 mg, 23%), MS (ISN) m/z=318.5 [(M+H)$^+$], mp 257.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-hydroxymethyl-phenylboronic acid (49.4 mg, 0.325 mmol).

Example 229

1-Oxo-6-pyridin-3-yl-3,4-dihydro-2H-pyrazino[1,2-a]indole-8-carbonitrile

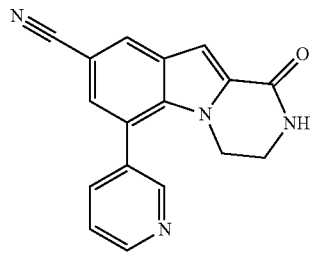 [SMILES: N#Cc1cc(-c2cccnc2)c2c(c1)cc1n2CCNC1=O]

The title compound, off-white solid (50 mg, 69%), MS (ISN) m/z=289.4 [(M+H)$^+$], mp 272.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available pyridin-3-ylboronic acid (39.9 mg, 0.325 mmol).

Example 230

6-(4-tert-Butylphenyl)-1-oxo-3,4-dihydro-2H-pyrazino[1,2-a]indole-8-carbonitrile

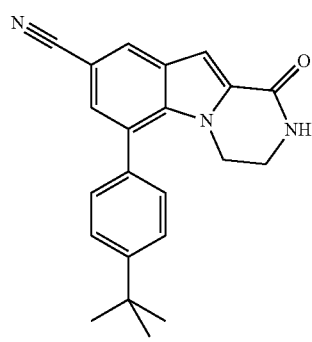 [SMILES: CC(C)(C)c1ccc(-c2cc(C#N)cc3cc4n(c23)CCNC4=O)cc1]

The title compound, off-white solid (76 mg, 89%), MS (ISN) m/z=344.5 [(M+H)$^+$], mp 300° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-tert-butyl-phenylboronic acid (57.9 mg, 0.325 mmol).

Example 231

6-(4-Fluoro-3-methylphenyl)-1-oxo-3,4-dihydro-2H-pyrazino[1,2-a]indole-8-carbonitrile

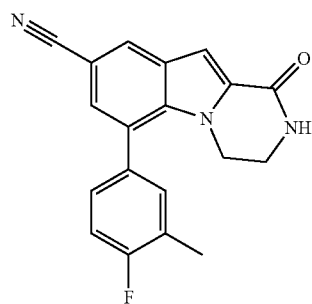 [SMILES: Cc1cc(-c2cc(C#N)cc3cc4n(c23)CCNC4=O)ccc1F]

The title compound, off-white solid (69 mg, 86%), MS (ISN) m/z=320.4 [(M+H)$^+$], mp 290° C., was prepared in accordance with the general method of example 1 from 6-bromo-1-oxo-1,2,3,4-tetrahydro-pyrazino[1,2-a]indole-8- carbonitrile (intermediate 15) (72.5 mg, 0.25 mmol) and commercially available 4-fluoro-3-methyl-phenylboronic acid (50.0 mg, 0.325 mmol).

Example 232

6-(4-Nitrophenyl)-1-oxo-3,4-dihydro-2H-pyrazino[1,2-a]indole-8-carbonitrile

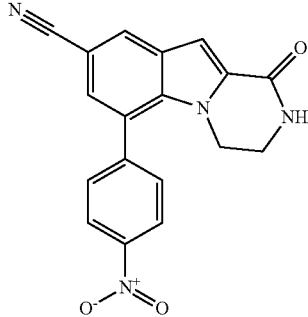 [SMILES: N#Cc1cc(-c2ccc([N+](=O)[O-])cc2)c2c(c1)cc1n2CCNC1=O]

The title compound, yellow solid (16 mg, 19%), MS (ISN) m/z=333.4 [(M+H)$^+$], mp 369.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 4-nitro-phenylboronic acid (54.3 mg, 0.325 mmol).

Example 233

6-(3-Fluoro-4-methylphenyl)-1-oxo-3,4-dihydro-2H-pyrazino[1,2-a]indole-8-carbonitrile

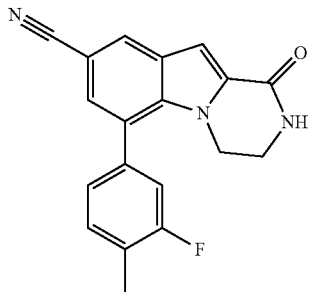 [SMILES: Cc1ccc(-c2cc(C#N)cc3cc4n(c23)CCNC4=O)cc1F]

The title compound, off-white solid (72 mg, 90%), MS (ISN) m/z=320.4 [(M+H)$^+$], mp 278.5° C., was prepared in accordance with the general method of example 1 from 6-bromo-1-oxo-1,2,3,4-tetrahydro-pyrazino[1,2-a]indole-8-carbonitrile (intermediate 15) (72.5 mg, 0.25 mmol) and commercially available 3-fluoro-4-methyl-phenylboronic acid (50.0 mg, 0.325 mmol).

Example 234

7-(4-Nitrophenyl)-1-oxo-2,3,4,5-tetrahydro-[1,4]diazepino[1,2-a]indole-9-carbonitrile

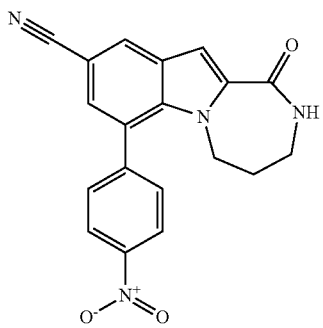 [SMILES: N#Cc1cc(-c2ccc([N+](=O)[O-])cc2)c2c(c1)cc1n2CCCNC1=O]

The title compound, yellow solid (69 mg, 80%), MS (ISP) m/z=347.5 [(M+H)$^+$], mp 193.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-nitro-phenylboronic acid (54.3 mg, 0.325 mmol).

Example 235

7-(4-Fluoro-3-methylphenyl)-1-oxo-2,3,4,5-tetrahydro-[1,4]diazepino[1,2-a]indole-9-carbonitrile

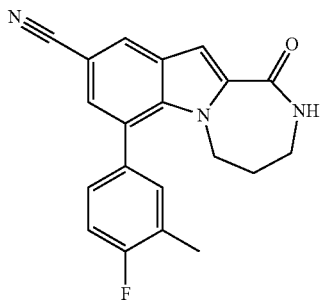

The title compound, white solid (76 mg, 91%), MS (ISP) m/z=334.5 [(M+H)$^+$], mp 223.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-fluoro-3-methyl-phenylboronic acid (50.0 mg, 0.325 mmol).

Example 236

7-(2,4-Dichlorophenyl)-1-oxo-2,3,4,5-tetrahydro-[1,4]diazepino[1,2-a]indole-9-carbonitrile

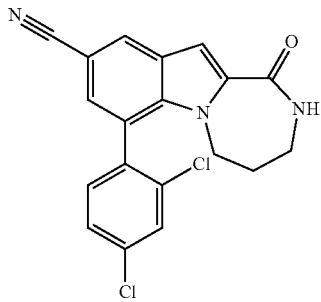 [SMILES: N#Cc1cc(-c2ccc(Cl)cc2Cl)c2c(c1)cc1n2CCCNC1=O]

The title compound, white solid (84 mg, 91%), MS (ISP) m/z=370.4 [(M+H)$^+$], mp 253° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 2,4-dichloro-phenylboronic acid (62.0 mg, 0.325 mmol).

Example 237

7-(4-Cyanophenyl)-1-oxo-2,3,4,5-tetrahydro-[1,4]diazepino[1,2-a]indole-9-carbonitrile

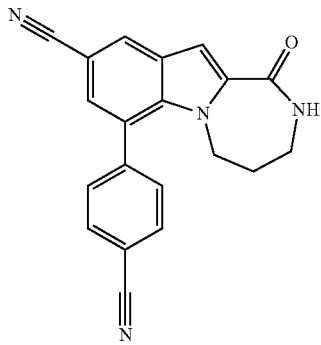 [SMILES: N#Cc1ccc(-c2cc(C#N)cc3cc4n(c23)CCCNC4=O)cc1]

The title compound, light grey solid (75 mg, 92%), MS (ISP) m/z=327.4 [(M+H)$^+$], mp 257° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-cyanophenylboronic acid (47.8 mg, 0.325 mmol).

Example 238

7-(3,5-Difluorophenyl)-1-oxo-2,3,4,5-tetrahydro-[1,4]diazepino[1,2-a]indole-9-carbonitrile

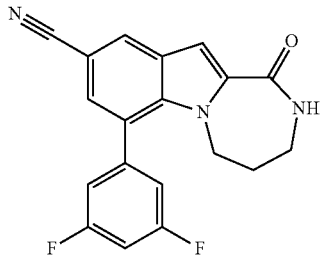

The title compound, light grey solid (65 mg, 77%), MS (ISP) m/z=338.6 [(M+H)$^+$], mp 211° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 3,5-difluoro-phenylboronic acid (51.3 mg, 0.325 mmol).

Example 239

7-(3-Fluorophenyl)-1-oxo-2,3,4,5-tetrahydro-[1,4]diazepino[1,2-a]indole-9-carbonitrile

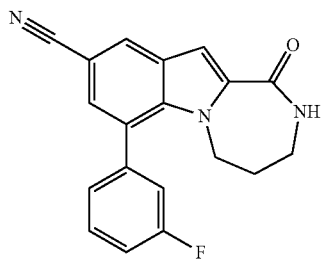

The title compound, white solid (76 mg, 95%), MS (ISP) m/z=320.5 [(M+H)$^+$], mp 210.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 3-fluoro-phenylboronic acid (45.5 mg, 0.325 mmol).

Example 240

10-Methyl-1-oxo-6-(3,4,5-trifluorophenyl)-3,4-dihydro-2H-pyrazino[1,2-a]indole-8-carbonitrile

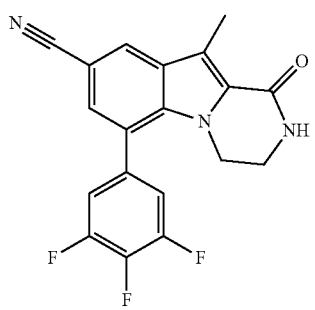 [SMILES: Cc1c2n(c3c(-c4cc(F)c(F)c(F)c4)cc(C#N)cc13)CCNC2=O]

The title compound, grey solid (45 mg, 51%), MS (ISP) m/z=356.6 [(M+H)$^+$], mp 253° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 3,4,5-trifluoro-phenylboronic acid (57.2 mg, 0.325 mmol).

Example 241

10-Methyl-1-oxo-6-phenyl-3,4-dihydro-2H-pyrazino[1,2-a]indole-8-carbonitrile

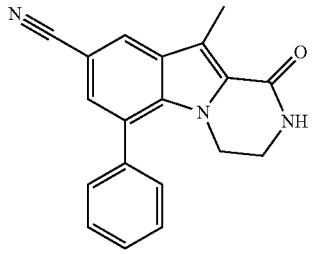 [SMILES: Cc1c2n(c3c(-c4ccccc4)cc(C#N)cc13)CCNC2=O]

The title compound, light yellow solid (62 mg, 82%), MS (ISP) m/z=302.6 [(M+H)$^+$], mp 253° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available phenylboronic acid (39.6 mg, 0.325 mmol).

Example 242

6-(6-Aminopyridin-3-yl)-10-methyl-1-oxo-3,4-dihydro-2H-pyrazino[1,2-a]indole-8-carbonitrile

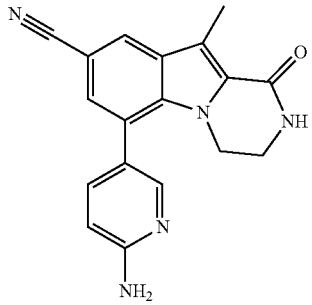 [SMILES: Cc1c2n(c3c(-c4ccc(N)nc4)cc(C#N)cc13)CCNC2=O]

The title compound, light brown solid (13 mg, 16%), MS (ISP) m/z=318.5 [(M+H)$^+$], mp 332° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 5-(4,4,5,5-tetramethyl-1,3,2-dioxaborolan-2-yl)-pyridin-2-amine (71.5 mg, 0.325 mmol).

Example 243

10-Methyl-1-oxo-6-pyridin-4-yl-3,4-dihydro-2H-pyrazino[1,2-a]indole-8-carbonitrile

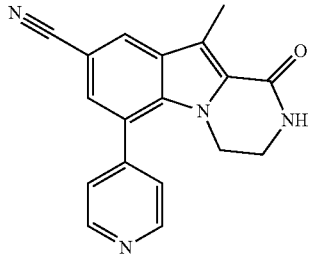 [SMILES: Cc1c2n(c3c(-c4ccncc4)cc(C#N)cc13)CCNC2=O]

The title compound, white solid (29 mg, 38%), MS (ISP) m/z=303.5 [(M+H)$^+$], mp 307° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available pyridin-4-ylboronic acid (39.9 mg, 0.325 mmol).

Example 244

11-Methyl-1-oxo-7-(3,4,5-trifluorophenyl)-2,3,4,5-tetrahydro-[1,4]diazepino[1,2-a]indole-9-carbonitrile

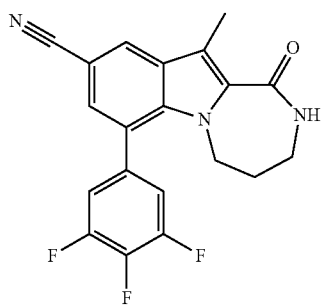 [SMILES: Cc1c2n(c3c(-c4cc(F)c(F)c(F)c4)cc(C#N)cc13)CCCNC2=O]

The title compound, off-white solid (37 mg, 40%), MS (ISP) m/z=370.4 [(M+H)$^+$], mp 306° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 3,4,5-trifluorophenylboronic acid (57.2 mg, 0.325 mmol).

Example 245

11-Methyl-1-oxo-7-phenyl-2,3,4,5-tetrahydro-[1,4]diazepino[1,2-a]indole-9-carbonitrile

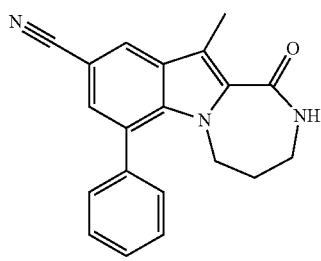 [SMILES: Cc1c2n(c3c(-c4ccccc4)cc(C#N)cc13)CCCNC2=O]

The title compound, off-white solid (60 mg, 76%), MS (ISP) m/z=316.5 [(M+H)$^+$], mp 258° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available phenylboronic acid (39.6 mg, 0.325 mmol).

Example 246

10-Methyl-1-oxo-6-(2,3,4-trifluorophenyl)-3,4-dihydro-2H-pyrazino[1,2-a]indole-8-carbonitrile

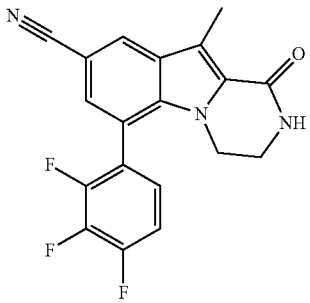 [SMILES: Cc1c2n(c3c(-c4ccc(F)c(F)c4F)cc(C#N)cc13)CCNC2=O]

The title compound, white solid (17 mg, 19%), MS (ISP) m/z=356.5 [(M+H)$^+$], mp 238° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 2,3,4-trifluoro-phenylboronic acid (57.2 mg, 0.325 mmol).

Example 247

6-(4-Methoxyphenyl)-10-methyl-1-oxo-3,4-dihydro-2H-pyrazino[1,2-a]indole-8-carbonitrile

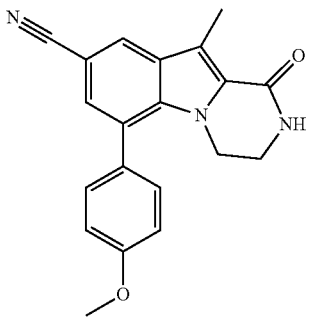 [SMILES: COc1ccc(-c2cc(C#N)cc3c(C)c4n(c23)CCNC4=O)cc1]

The title compound, light grey solid (34 mg, 41%), MS (ISP) m/z=332.6 [(M+H)$^+$], mp 285° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-methoxy-phenylboronic acid (49.4 mg, 0.325 mmol).

Example 248

1-Oxo-7-(3,4,5-trifluorophenyl)-2,3,4,5-tetrahydro-[1,4]diazepino[1,2-a]indole-9-carbonitrile

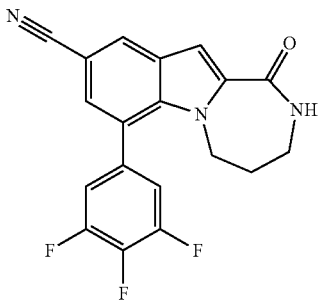 [SMILES: N#Cc1cc(-c2cc(F)c(F)c(F)c2)c2c(c1)cc1n2CCCNC1=O]

The title compound, light grey solid (72 mg, 81%), MS (ISP) m/z=356.4 [(M+H)$^+$], mp 248.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 3,4,5-trifluoro-phenylboronic acid (57.2 mg, 0.325 mmol).

Example 249

7-(3,4-Dichlorophenyl)-1-oxo-2,3,4,5-tetrahydro-[1,4]diazepino[1,2-a]indole-9-carbonitrile

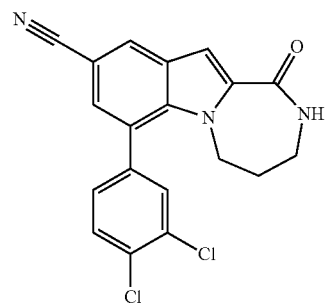 [SMILES: N#Cc1cc(-c2ccc(Cl)c(Cl)c2)c2c(c1)cc1n2CCCNC1=O]

The title compound, off-white solid (80 mg, 86%), MS (ISP) m/z=370.4 [(M+H)$^+$], mp 217.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 3,4-dichloro-phenylboronic acid (62.0 mg, 0.325 mmol).

Example 250

11-Methyl-1-oxo-7-pyridin-4-yl-2,3,4,5-tetrahydro-[1,4]diazepino[1,2-a]indole-9-carbonitrile

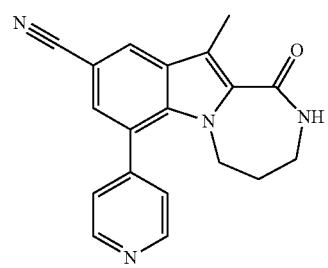 [SMILES: Cc1c2n(c3c(-c4ccncc4)cc(C#N)cc13)CCCNC2=O]

The title compound, white solid (64 mg, 81%), MS (ISP) m/z=317.5 [(M+H)$^+$], mp 285° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available pyridin-4-ylboronic acid (39.9 mg, 0.325 mmol).

Example 251

7-(6-Aminopyridin-3-yl)-11-methyl-1-oxo-2,3,4,5-tetrahydro-[1,4]diazepino[1,2-a]indole-9-carbonitrile

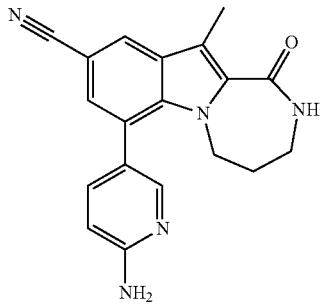 [SMILES: Cc1c2n(c3c(-c4ccc(N)nc4)cc(C#N)cc13)CCCNC2=O]

The title compound, off-white solid (28 mg, 34%), MS (ISP) m/z=332.4 [(M+H)$^+$], mp 306° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 5-(4,4,5,5-tetramethyl-1,3,2-dioxaborolan-2-yl)-pyridin-2-amine (71.5 mg, 0.325 mmol).

Example 252

7-(4-Chloro-3-fluorophenyl)-1-oxo-2,3,4,5-tetrahydro-[1,4]diazepino[1,2-a]indole-9-carbonitrile

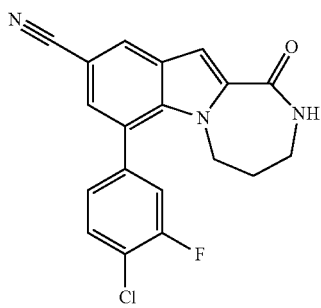 [SMILES: N#Cc1cc(-c2ccc(Cl)c(F)c2)c2c(c1)cc1n2CCCNC1=O]

The title compound, white solid (74 mg, 84%), MS (ISP) m/z=354.3 [(M+H)$^+$], mp 221.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-chloro-3-fluoro-phenylboronic acid (56.7 mg, 0.325 mmol).

Example 253

7-(3-Fluoro-4-methylphenyl)-1-oxo-2,3,4,5-tetrahydro-[1,4]diazepino[1,2-a]indole-9-carbonitrile

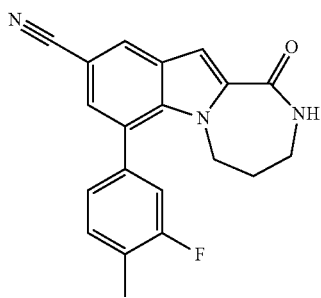 [SMILES: Cc1ccc(-c2cc(C#N)cc3cc4n(c23)CCCNC4=O)cc1F]

The title compound, light grey solid (75 mg, 90%), MS (ISP) m/z=334.5 [(M+H)$^+$], mp 250.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 3-fluoro-4-methyl-phenylboronic acid (50.0 mg, 0.325 mmol).

Example 254

7-[4-Chloro-3-(trifluoromethyl)phenyl]-1-oxo-2,3,4,5-tetrahydro-[1,4]diazepino[1,2-a]indole-9-carbonitrile

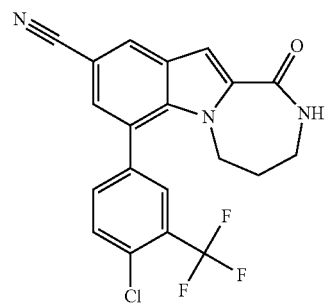 [SMILES: N#Cc1cc(-c2ccc(Cl)c(C(F)(F)F)c2)c2c(c1)cc1n2CCCNC1=O]

The title compound, light grey solid (89 mg, 88%), MS (ISP) m/z=404.3 [(M+H)$^+$], mp 224.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-chloro-3-trifluoromethyl-phenylboronic acid (72.9 mg, 0.325 mmol).

Example 255

1-Oxo-7-[4-(trifluoromethoxy)phenyl]-2,3,4,5-tetrahydro-[1,4]diazepino[1,2-a]indole-9-carbonitrile

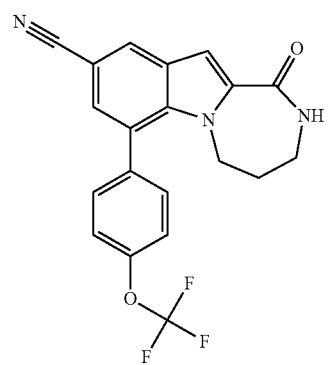 [SMILES: N#Cc1cc(-c2ccc(OC(F)(F)F)cc2)c2c(c1)cc1n2CCCNC1=O]

The title compound, off-white solid (83 mg, 86%), MS (ISP) m/z=386.4 [(M+H)$^+$], mp 230.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-trifluoromethoxy-phenylboronic acid (66.9 mg, 0.325 mmol).

Example 256

7-(4-Methylsulfonylphenyl)-1-oxo-2,3,4,5-tetrahydro-[1,4]diazepino[1,2-a]indole-9-carbonitrile

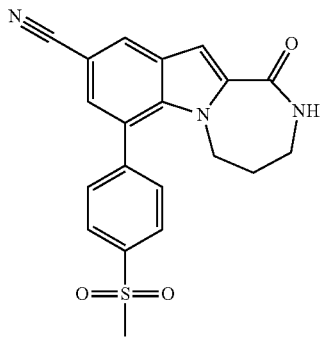 [SMILES: CS(=O)(=O)c1ccc(-c2cc(C#N)cc3cc4n(c23)CCCNC4=O)cc1]

The title compound, light grey solid (93 mg, 98%), MS (ISP) m/z=380.3 [(M+H)+], mp 305.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-methanesulfonyl-phenylboronic acid (65.0 mg, 0.325 mmol).

Example 257

7-(2-Chloropyridin-4-yl)-1-oxo-2,3,4,5-tetrahydro-[1,4]diazepino[1,2-a]indole-9-carbonitrile

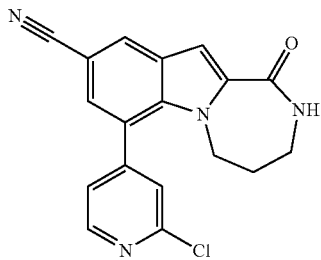 [SMILES: N#Cc1cc(-c2ccnc(Cl)c2)c2c(c1)cc1n2CCCNC1=O]

The title compound, light yellow solid (72 mg, 86%), MS (ISP) m/z=337.3 [(M+H)+], mp 286.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 2-chloro-pyridin-4-ylboronic acid (51.1 mg, 0.325 mmol).

Example 258

10-Methyl-6-(4-methylphenyl)-1-oxo-3,4-dihydro-2H-pyrazino[1,2-a]indole-8-carbonitrile

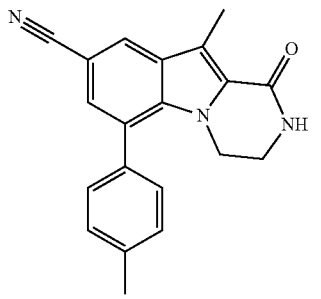 [SMILES: Cc1ccc(-c2cc(C#N)cc3c(C)c4n(c23)CCNC4=O)cc1]

The title compound, light yellow solid (67 mg, 85%), MS (ISP) m/z=316.6 [(M+H)+], mp 277° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available p-tolylboronic acid (44.2 mg, 0.325 mmol).

Example 259

6-(3-Fluorophenyl)-10-methyl-1-oxo-3,4-dihydro-2H-pyrazino[1,2-a]indole-8-carbonitrile

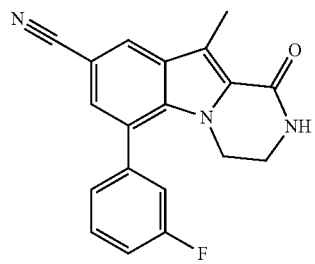 [SMILES: Cc1c2n(c3c(-c4cccc(F)c4)cc(C#N)cc13)CCNC2=O]

The title compound, grey solid (61 mg, 76%), MS (ISP) m/z=320.5 [(M+H)+], mp 226° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 3-fluoro-phenylboronic acid (45.5 mg, 0.325 mmol).

Example 260

6-(3,4-Dichlorophenyl)-10-methyl-1-oxo-3,4-dihydro-2H-pyrazino[1,2-a]indole-8-carbonitrile

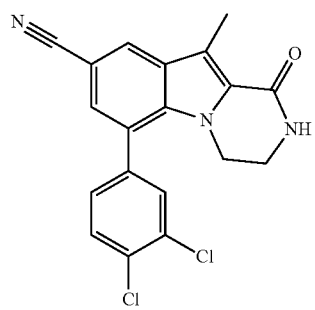 [SMILES: Cc1c2n(c3c(-c4ccc(Cl)c(Cl)c4)cc(C#N)cc13)CCNC2=O]

The title compound, grey solid (46 mg, 50%), MS (ISP) m/z=370.3 [(M+H)+], mp 245° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 3,4-dichloro-phenylboronic acid (62.0 mg, 0.325 mmol).

Example 261

6-(3,5-Difluorophenyl)-10-methyl-1-oxo-3,4-dihydro-2H-pyrazino[1,2-a]indole-8-carbonitrile

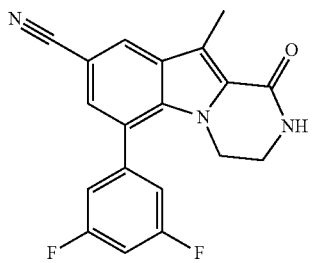 [SMILES: Cc1c2n(c3c(-c4cc(F)cc(F)c4)cc(C#N)cc13)CCNC2=O]

The title compound, grey solid (43 mg, 51%), MS (ISP) m/z=338.5 [(M+H)+], mp 303° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 3,5-difluoro-phenylboronic acid (51.3 mg, 0.325 mmol).

Example 262

7-(4-Methoxyphenyl)-11-methyl-1-oxo-2,3,4,5-tetrahydro-[1,4]diazepino[1,2-a]indole-9-carbonitrile

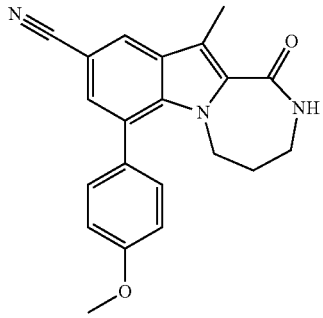 [SMILES: COc1ccc(-c2cc(C#N)cc3c(C)c4n(c23)CCCNC4=O)cc1]

The title compound, white solid (55 mg, 64%), MS (ISP) m/z=346.5 [(M+H)+], mp 277° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 4-methoxy-phenylboronic acid (49.4 mg, 0.325 mmol).

Example 263

1-Oxo-7-pyridin-3-yl-2,3,4,5-tetrahydro-[1,4]diazepino[1,2-a]indole-9-carbonitrile

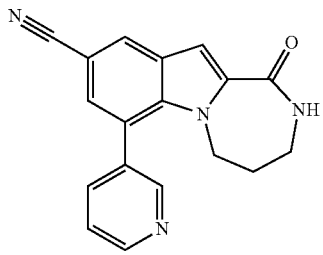 [SMILES: N#Cc1cc(-c2cccnc2)c2c(c1)cc1n2CCCNC1=O]

The title compound, white solid (38 mg, 50%), MS (ISP) m/z=303.5 [(M+H)+], mp 252° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available pyridin-3-ylboronic acid (39.9 mg, 0.325 mmol).

Example 264

7-(6-Aminopyridin-3-yl)-1-oxo-2,3,4,5-tetrahydro-[1,4]diazepino[1,2-a]indole-9-carbonitrile

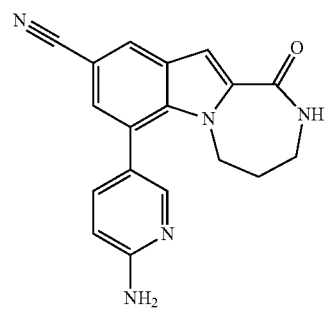

The title compound, brown solid (46 mg, 58%), MS (ISP) m/z=318.5 [(M+H)+], mp 314.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 5-(4,4,5,5-tetramethyl-1,3,2-dioxaborolan-2-yl)-pyridin-2-amine (71.5 mg, 0.325 mmol).

Example 265

7-(6-Chloropyridin-3-yl)-1-oxo-2,3,4,5-tetrahydro-[1,4]diazepino[1,2-a]indole-9-carbonitrile

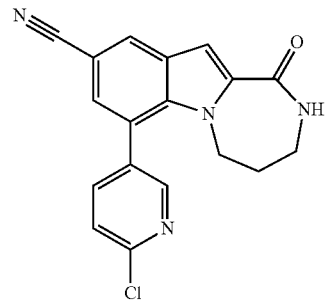

The title compound, off-white solid (73 mg, 87%), MS (ISP) m/z=337.4 [(M+H)+], mp 204° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 6-chloro-pyridin-3-ylboronic acid (51.1 mg, 0.325 mmol).

Example 266

7-[4-(Hydroxymethyl)phenyl]-1-oxo-2,3,4,5-tetrahydro-[1,4]diazepino[1,2-a]indole-9-carbonitrile

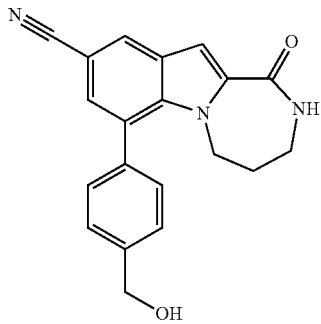 [SMILES: N#Cc1cc(-c2ccc(CO)cc2)c2c(c1)cc1n2CCCNC1=O]

The title compound, light yellow solid (75 mg, 91%), MS (ISP) m/z=332.5 [(M+H)$^+$], mp 256.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-hydroxymethyl-phenylboronic acid (49.4 mg, 0.325 mmol).

Example 267

6-(3-Fluoro-4-methylphenyl)-10-methyl-1-oxo-3,4-dihydro-2H-pyrazino[1,2-a]indole-8-carbonitrile

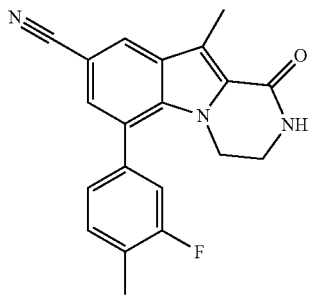 [SMILES: Cc1ccc(-c2cc(C#N)cc3c(C)c4n(c23)CCNC4=O)cc1F]

The title compound, light yellow solid (53 mg, 64%), MS (ISP) m/z=334.6 [(M+H)$^+$], mp 255° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 3-fluoro-4-methyl-phenylboronic acid (50.0 mg, 0.325 mmol).

Example 268

6-(3-Chlorophenyl)-10-methyl-1-oxo-3,4-dihydro-2H-pyrazino[1,2-a]indole-8-carbonitrile

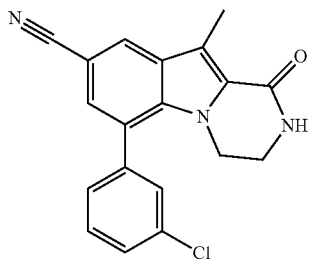 [SMILES: Cc1c2n(c3c(-c4cccc(Cl)c4)cc(C#N)cc13)CCNC2=O]

The title compound, off-white solid (70 mg, 83%), MS (ISP) m/z=336.5 [(M+H)$^+$], mp 254° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-chloro-phenylboronic acid (50.8 mg, 0.325 mmol).

Example 269

7-(3-Cyanophenyl)-1-oxo-2,3,4,5-tetrahydro-[1,4]diazepino[1,2-a]indole-9-carbonitrile

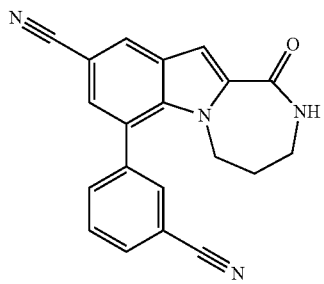 [SMILES: N#Cc1cccc(-c2cc(C#N)cc3cc4n(c23)CCCNC4=O)c1]

The title compound, light grey solid (78 mg, 96%), MS (ISP) m/z=327.5 [(M+H)$^+$], mp 225.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 3-cyanophenylboronic acid (47.8 mg, 0.325 mmol).

Example 270

7-(4-tert-Butylphenyl)-1-oxo-2,3,4,5-tetrahydro-[1,4]diazepino[1,2-a]indole-9-carbonitrile

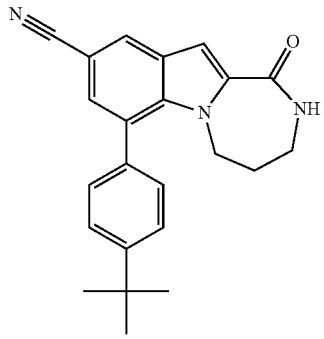 [SMILES: CC(C)(C)c1ccc(-c2cc(C#N)cc3cc4n(c23)CCCNC4=O)cc1]

The title compound, white solid (61 mg, 68%), MS (ISP) m/z=358.5 [(M+H)$^+$], mp 215° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-tert-butyl-phenylboronic acid (57.9 mg, 0.325 mmol).

Example 271

1-Oxo-7-pyridin-4-yl-2,3,4,5-tetrahydro-[1,4]diazepino[1,2-a]indole-9-carbonitrile

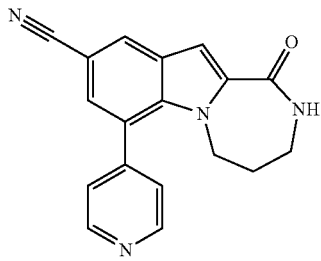 [SMILES: N#Cc1cc(-c2ccncc2)c2c(c1)cc1n2CCCNC1=O]

The title compound, white solid (64 mg, 85%), MS (ISP) m/z=303.5 [(M+H)⁺], mp 278.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available pyridin-4-ylboronic acid (39.9 mg, 0.325 mmol).

Example 272

7-(6-Fluoropyridin-3-yl)-1-oxo-2,3,4,5-tetrahydro-[1,4]diazepino[1,2-a]indole-9-carbonitrile

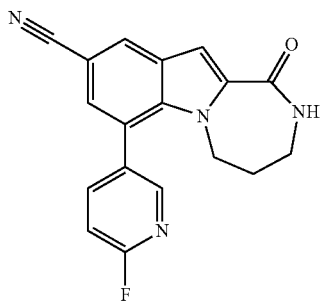 [SMILES: N#Cc1cc(-c2ccc(F)nc2)c2c(c1)cc1n2CCCNC1=O]

The title compound, white solid (55 mg, 69%), MS (ISP) m/z=321.5 [(M+H)⁺], mp 264.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 6-fluoro-pyridin-3-ylboronic acid (45.8 mg, 0.325 mmol).

Example 273

1-Oxo-7-pyrimidin-5-yl-2,3,4,5-tetrahydro-[1,4]diazepino[1,2-a]indole-9-carbonitrile

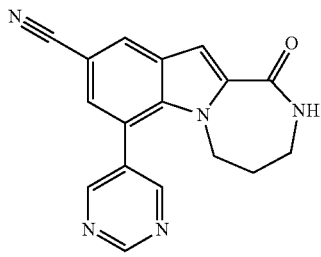 [SMILES: N#Cc1cc(-c2cncnc2)c2c(c1)cc1n2CCCNC1=O]

The title compound, off-white solid (13 mg, 17%), MS (ISP) m/z=304.5 [(M+H)⁺], mp 277° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available pyrimidin-5-ylboronic acid (40.3 mg, 0.325 mmol).

Example 274

1-Oxo-7-phenyl-2,3,4,5-tetrahydro-[1,4]diazepino[1,2-a]indole-9-carbonitrile

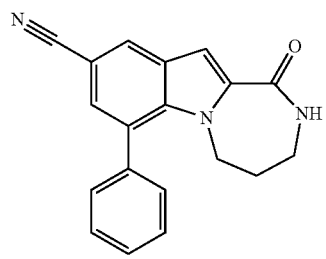 [SMILES: N#Cc1cc(-c2ccccc2)c2c(c1)cc1n2CCCNC1=O]

The title compound, light grey solid (66 mg, 88%), MS (ISP) m/z=302.5 [(M+H)⁺], mp 237.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available phenylboronic acid (39.6 mg, 0.325 mmol).

Example 275

7-(4-Methoxyphenyl)-1-oxo-2,3,4,5-tetrahydro-[1,4]diazepino[1,2-a]indole-9-carbonitrile

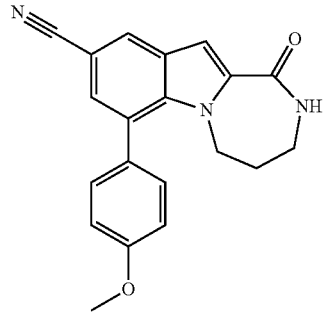 [SMILES: COc1ccc(-c2cc(C#N)cc3cc4n(c23)CCCNC4=O)cc1]

The title compound, light grey solid (73 mg, 88%), MS (ISP) m/z=332.5 [(M+H)⁺], mp 260.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-methoxy-phenylboronic acid (49.4 mg, 0.325 mmol).

Example 276

10-Methyl-6-(4-nitrophenyl)-1-oxo-3,4-dihydro-2H-pyrazino[1,2-a]indole-8-carbonitrile

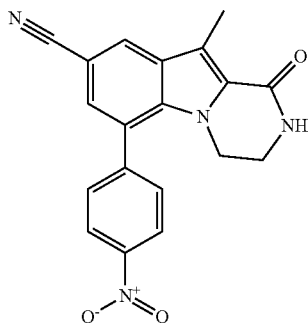 [SMILES: Cc1c2n(c3c(-c4ccc([N+](=O)[O-])cc4)cc(C#N)cc13)CCNC2=O]

The title compound, yellow solid (41 mg, 47%), MS (ISP) m/z=347.5 [(M+H)+], mp 312° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-nitro-phenylboronic acid (54.3 mg, 0.325 mmol).

Example 277

6-[4-(Hydroxymethyl)phenyl]-10-methyl-1-oxo-3,4-dihydro-2H-pyrazino[1,2-a]indole-8-carbonitrile

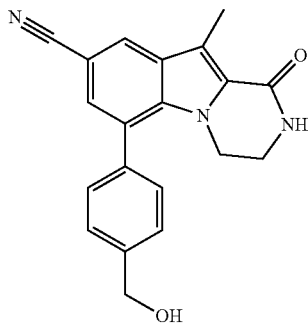 [SMILES: Cc1c2n(c3c(-c4ccc(CO)cc4)cc(C#N)cc13)CCNC2=O]

The title compound, grey solid (68 mg, 82%), MS (ISP) m/z=332.5 [(M+H)+], mp 265° C., was prepared in accordance with the general method of example 1 from 6-bromo-10-methyl-1-oxo-1,2,3,4-tetrahydro-pyrazino[1,2-a]indole8-carbonitrile (intermediate 16) (76 mg, 0.25 mmol) and commercially available 4-hydroxymethyl-phenylboronic acid (49.4 mg, 0.325 mmol).

Example 278

6-(6-Chloropyridin-3-yl)-10-methyl-1-oxo-3,4-dihydro-2H-pyrazino[1,2-a]indole-8-carbonitrile

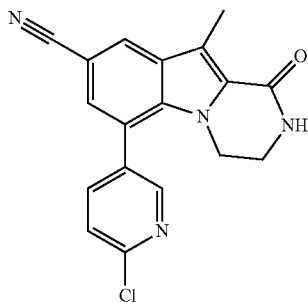

The title compound, light yellow solid (66 mg, 78%), MS (ISP) m/z=335.5 [(M+H)+], mp 318° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 6-chloro-pyridin-3-ylboronic acid (51.1 mg, 0.325 mmol).

Example 279

6-(3-Cyanophenyl)-10-methyl-1-oxo-3,4-dihydro-2H-pyrazino[1,2-a]indole-8-carbonitrile

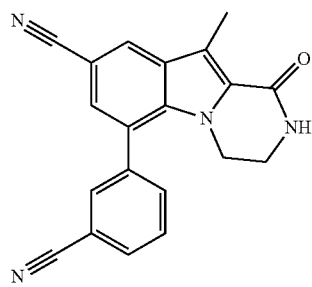 [SMILES: Cc1c2n(c3c(-c4cccc(C#N)c4)cc(C#N)cc13)CCNC2=O]

The title compound, white solid (63 mg, 77%), MS (ISP) m/z=325.6 [(M+H)+], mp 266° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 3-cyanophenylboronic acid (47.8 mg, 0.325 mmol).

Example 280

6-(4-tert-Butylphenyl)-10-methyl-1-oxo-3,4-dihydro-2H-pyrazino[1,2-a]indole-8-carbonitrile

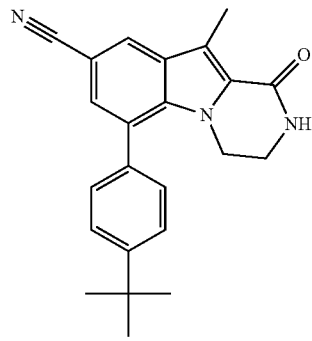 [SMILES: Cc1c2n(c3c(-c4ccc(C(C)(C)C)cc4)cc(C#N)cc13)CCNC2=O]

The title compound, off-white solid (72 mg, 81%), MS (ISP) m/z=358.5 [(M+H)+], mp 292° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-tert-butyl-phenylboronic acid (57.9 mg, 0.325 mmol).

Example 281

6-(2-Chloropyridin-4-yl)-10-methyl-1-oxo-3,4-dihydro-2H-pyrazino[1,2-a]indole-8-carbonitrile

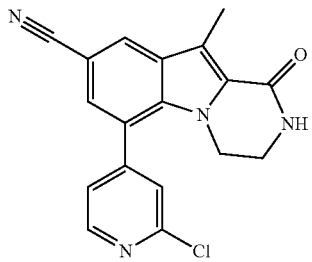

The title compound, off-white solid (50 mg, 59%), MS (ISP) m/z=335.4 [(M+H)$^+$], mp 281° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 2-chloro-pyridin-4-ylboronic acid (51.1 mg, 0.325 mmol).

Example 282

10-Methyl-1-oxo-6-pyridin-3-yl-3,4-dihydro-2H-pyrazino[1,2-a]indole-8-carbonitrile

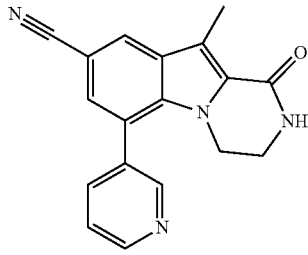 [SMILES: Cc1c2n(c3c(-c4cccnc4)cc(C#N)cc13)CCNC2=O]

The title compound, white solid (60 mg, 79%), MS (ISN) m/z=301.4 [(M−H)$^+$], mp 273° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available pyridin-3-ylboronic acid (39.9 mg, 0.325 mmol).

Example 283

10-Methyl-1-oxo-6-pyrimidin-5-yl-3,4-dihydro-2H-pyrazino[1,2-a]indole-8-carbonitrile

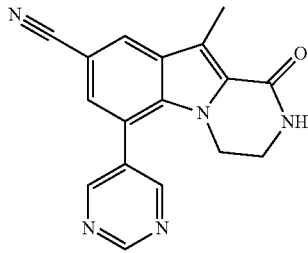

The title compound, off-white solid (25 mg, 33%), MS (ISN) m/z=302.4 [(M−H)$^+$], mp 325° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available pyrimidin-5-ylboronic acid (40.3 mg, 0.325 mmol).

Example 284

1-Oxo-7-(2,3,4-trifluorophenyl)-2,3,4,5-tetrahydro-[1,4]diazepino[1,2-a]indole-9-carbonitrile

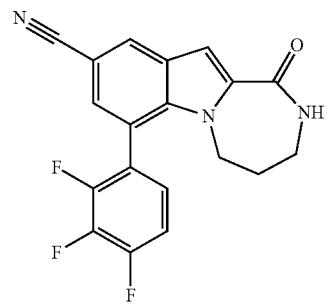 [SMILES: N#Cc1cc(-c2ccc(F)c(F)c2F)c2c(c1)cc1n2CCCNC1=O]

The title compound, white solid (18 mg, 20%), MS (ISP) m/z=356.5 [(M+H)$^+$], mp 187° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 2,3,4-trifluoro-phenylboronic acid (57.2 mg, 0.325 mmol).

Example 285

7-(3-Chlorophenyl)-1-oxo-2,3,4,5-tetrahydro-[1,4]diazepino[1,2-a]indole-9-carbonitrile

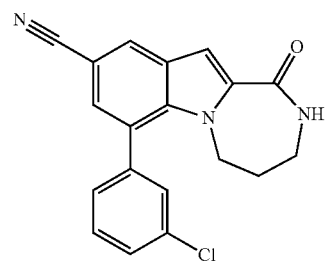 [SMILES: N#Cc1cc(-c2cccc(Cl)c2)c2c(c1)cc1n2CCCNC1=O]

The title compound, off-white solid (72 mg, 86%), MS (ISP) m/z=336.4 [(M+H)$^+$], mp 209° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 4-chloro-phenylboronic acid (50.8 mg, 0.325 mmol).

Example 286

7-(3,5-Dichlorophenyl)-1-oxo-2,3,4,5-tetrahydro-[1,4]diazepino[1,2-a]indole-9-carbonitrile

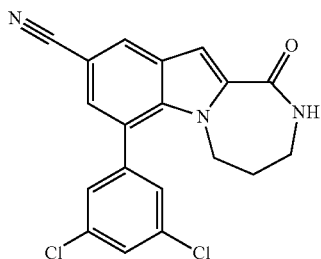 [SMILES: N#Cc1cc(-c2cc(Cl)cc(Cl)c2)c2c(c1)cc1n2CCCNC1=O]

The title compound, off-white solid (75 mg, 81%), MS (ISP) m/z=372.4 [(M+H)⁺], mp 244° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available 3,5-dichloro-phenylboronic acid (62.0 mg, 0.325 mmol).

Example 287

7-(4-Methylphenyl)-1-oxo-2,3,4,5-tetrahydro-[1,4]diazepino[1,2-a]indole-9-carbonitrile

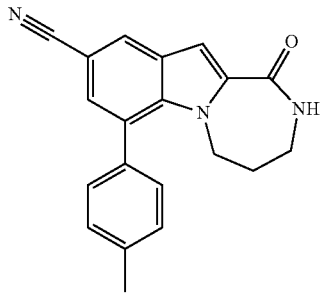 [SMILES: Cc1ccc(-c2cc(C#N)cc3cc4n(c23)CCCNC4=O)cc1]

The title compound, white solid (74 mg, 94%), MS (ISP) m/z=316.5 [(M+H)⁺], mp 240.5° C., was prepared in accordance with the general method of example 1 from 7-bromo-1-oxo-2,3,4,5-tetrahydro-[1,4]diazepino[1,2-a]indole-9-carbonitrile (intermediate 20) (76.0 mg, 0.25 mmol) and commercially available p-tolylboronic acid (44.2 mg, 0.325 mmol).

Example 288

11-Methyl-7-(4-methylphenyl)-1-oxo-2,3,4,5-tetrahydro-[1,4]diazepino[1,2-a]indole-9-carbonitrile

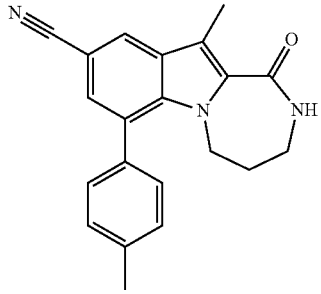 [SMILES: Cc1ccc(-c2cc(C#N)cc3c(C)c4n(c23)CCCNC4=O)cc1]

The title compound, grey solid (20 mg, 24%), MS (ISP) m/z=330.6 [(M+H)⁺], mp 287° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available p-tolylboronic acid (44.2 mg, 0.325 mmol).

Example 289

7-(3-Fluorophenyl)-11-methyl-1-oxo-2,3,4,5-tetrahydro-[1,4]diazepino[1,2-a]indole-9-carbonitrile

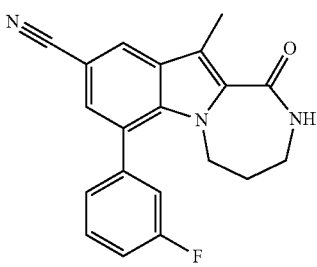 [SMILES: Cc1c2n(c3c(-c4cccc(F)c4)cc(C#N)cc13)CCCNC2=O]

The title compound, off-white solid (64 mg, 77%), MS (ISP) m/z=334.6 [(M+H)⁺], mp 261° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 3-fluoro-phenylboronic acid (45.5 mg, 0.325 mmol).

Example 290

7-(3,5-Difluorophenyl)-11-methyl-1-oxo-2,3,4,5-tetrahydro-[1,4]diazepino[1,2-a]indole-9-carbonitrile

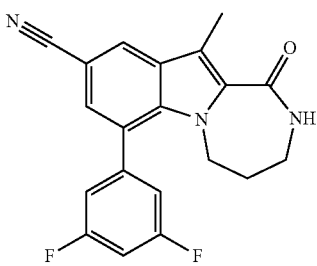 [SMILES: Cc1c2n(c3c(-c4cc(F)cc(F)c4)cc(C#N)cc13)CCCNC2=O]

The title compound, grey solid (45 mg, 51%), MS (ISP) m/z=352.6 [(M+H)⁺], mp 265° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 3,5-difluoro-phenylboronic acid (51.3 mg, 0.325 mmol).

Example 291

7-(3-Fluoro-4-methylphenyl)-11-methyl-1-oxo-2,3,4,5-tetrahydro-[1,4]diazepino[1,2-a]indole-9-carbonitrile

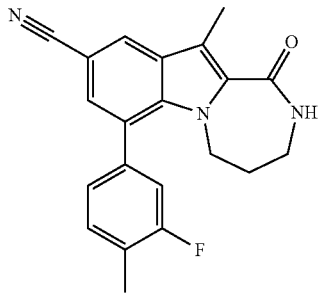 [SMILES: Cc1ccc(-c2cc(C#N)cc3c(C)c4n(c23)CCCNC4=O)cc1F]

The title compound, off-white solid (66 mg, 76%), MS (ISP) m/z=348.6 [(M+H)⁺], mp 265° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 3-fluoro-4-methyl-phenylboronic acid (50.0 mg, 0.325 mmol).

Example 292

6-(4-Fluoro-3-methylphenyl)-10-methyl-1-oxo-3,4-dihydro-2H-pyrazino[1,2-a]indole-8-carbonitrile

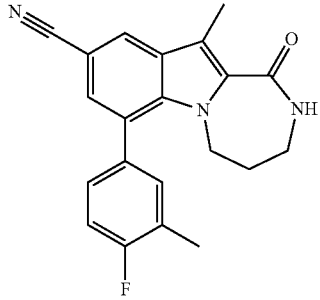

The title compound, light yellow solid (73 mg, 88%), MS (ISP) m/z=334.6 [(M+H)⁺], mp 232° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-fluoro-3-methyl-phenylboronic acid (50.0 mg, 0.325 mmol).

Example 293

6-(3,5-Dichlorophenyl)-10-methyl-1-oxo-3,4-dihydro-2H-pyrazino[1,2-a]indole-8-carbonitrile

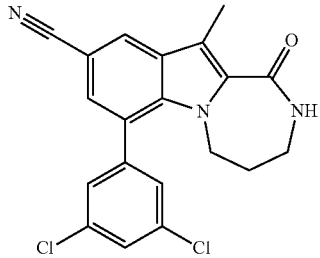 [SMILES: Cc1c2n(c3c(-c4cc(Cl)cc(Cl)c4)cc(C#N)cc13)CCCNC2=O]

The title compound, light grey solid (58 mg, 62%), MS (ISN) m/z=368.4 [(M−H)⁺], mp 347° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 3,5-dichloro-phenylboronic acid (62.0 mg, 0.325 mmol).

Example 294

10-Methyl-6-(4-methylsulfonylphenyl)-1-oxo-3,4-dihydro-2H-pyrazino[1,2-a]indole-8-carbonitrile

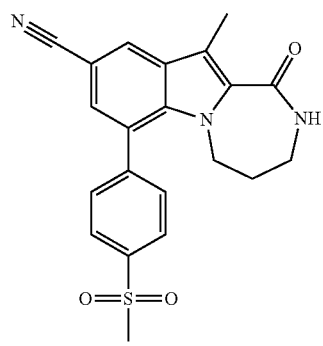 [SMILES: Cc1c2n(c3c(-c4ccc(S(C)(=O)=O)cc4)cc(C#N)cc13)CCCNC2=O]

The title compound, light grey solid (58 mg, 61%), MS (ISN) m/z=378.4 [(M−H)⁺], mp 332° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-methanesulfonyl-phenylboronic acid (65.0 mg, 0.325 mmol).

Example 295

6-[4-Chloro-3-(trifluoromethyl)phenyl]-10-methyl-1-oxo-3,4-dihydro-2H-pyrazino[1,2-a]indole-8-carbonitrile

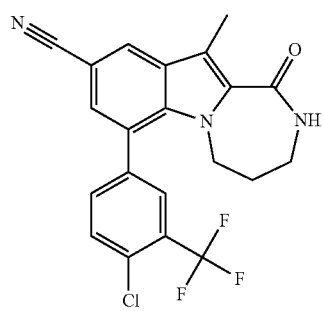 [SMILES: Cc1c2n(c3c(-c4ccc(Cl)c(C(F)(F)F)c4)cc(C#N)cc13)CCCNC2=O]

The title compound, light yellow solid (77 mg, 76%), MS (ISP) m/z=404.4 [(M+H)⁺], mp 278° C., was prepared in accordance with the general method of example 1 from 6-bromo-10-methyl-1-oxo-1,2,3,4-tetrahydro-pyrazino[1,2-a]indole-8-carbonitrile (intermediate 16) (76 mg, 0.25 mmol) and commercially available 4-chloro-3-trifluoromethyl-phenylboronic acid (72.9 mg, 0.325 mmol).

Example 296

7-(3,4-Dichlorophenyl)-11-methyl-1-oxo-2,3,4,5-tetrahydro-[1,4]diazepino[1,2-a]indole-9-carbonitrile

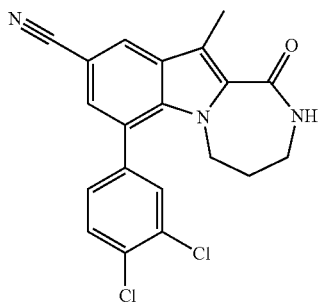 [SMILES: Cc1c2n(c3c(-c4ccc(Cl)c(Cl)c4)cc(C#N)cc13)CCCNC2=O]

The title compound, white solid (88 mg, 92%), MS (ISP) m/z=384.4 [(M+H)⁺], mp 254° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 3,4-dichloro-phenylboronic acid (62.0 mg, 0.325 mmol).

Example 297

7-(4-Chloro-3-fluorophenyl)-11-methyl-1-oxo-2,3,4,5-tetrahydro-[1,4]diazepino[1,2-a]indole-9-carbonitrile

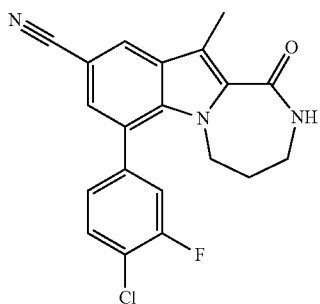 [SMILES: Cc1c2n(c3c(-c4ccc(Cl)c(F)c4)cc(C#N)cc13)CCCNC2=O]

The title compound, off-white solid (85 mg, 92%), MS (ISP) m/z=368.4 [(M+H)⁺], mp 247.5° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available 4-chloro-3-fluoro-phenylboronic acid (56.7 mg, 0.325 mmol).

Example 298

11-Methyl-1-oxo-7-pyridin-3-yl-2,3,4,5-tetrahydro-[1,4]diazepino[1,2-a]indole-9-carbonitrile

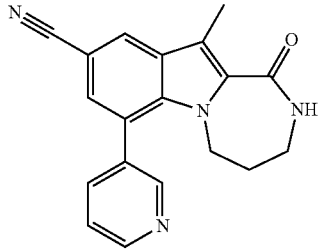 [SMILES: Cc1c2n(c3c(-c4cccnc4)cc(C#N)cc13)CCCNC2=O]

The title compound, off-white solid (42 mg, 53%), MS (ISP) m/z=317.6 [(M+H)⁺], mp 260° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available pyridin-3-ylboronic acid (39.9 mg, 0.325 mmol).

Example 299

11-Methyl-1-oxo-7-pyrimidin-5-yl-2,3,4,5-tetrahydro-[1,4]diazepino[1,2-a]indole-9-carbonitrile

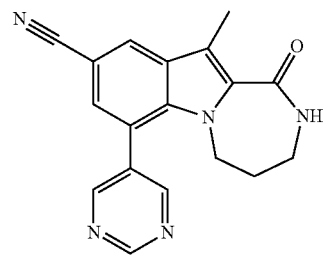 [SMILES: Cc1c2n(c3c(-c4cncnc4)cc(C#N)cc13)CCCNC2=O]

The title compound, light yellow solid (19 mg, 24%), MS (ISP) m/z=318.6 [(M+H)⁺], mp 304° C., was prepared in accordance with the general method of example 1 from 7-bromo-11-methyl-1-oxo-2,3,4,5-tetrahydro-[1,4]diazepino[1,2-a]indole-9-carbonitrile (intermediate 17) (79.5 mg, 0.25 mmol) and commercially available pyrimidin-5-ylboronic acid (40.3 mg, 0.325 mmol).

The invention claimed is:
1. A compound of formula I

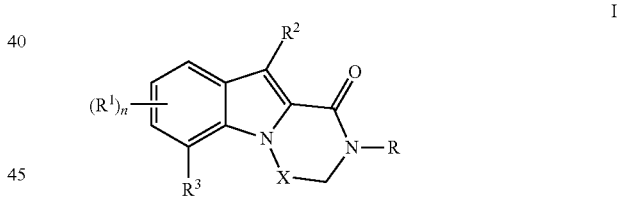

wherein
$R^1$ is hydrogen, halogen, lower alkyl, lower alkoxy, lower alkoxy substituted by halogen or cyano;
$R^2$ is hydrogen, lower alkyl or lower alkyl substituted by halogen;
$R^3$ is phenyl, benzo[1,3]dioxolyl, 2,3-dihydro-benzofuran-5-yl or a 5- and 6-membered heteroaryl, wherein phenyl and the 5- and 6-membered heteroaryl groups may be substituted by one or more substituents, selected from cyano, nitro, amino and lower di-alkylamino, lower alkyl sulfonyl, lower alkoxy, lower alkoxy substituted by halogen, halogen, lower alkyl, lower alkyl substituted by halogen or lower alkyl substituted by hydroxyl;
X is —CH(lower alkyl)-, —CH₂—, —CH₂CH₂— or —CH(lower alkyl)CH₂—;
R is hydrogen or lower alkyl;
n is 1 or 2;
or a pharmaceutically acceptable acid addition salt, a racemic mixture or its corresponding enantiomer and/or optical isomers thereof.

2. The compound of claim 1,
wherein
R³ is phenyl, which may be substituted by one or more substituents, selected from cyano, nitro, amino and lower di-alkylamino, lower alkyl sulfonyl, lower alkoxy, lower alkoxy substituted by halogen, halogen, lower alkyl, lower alkyl substituted by halogen or lower alkyl substituted by hydroxyl.

3. The compound of claim 2, wherein the compound is selected from:
  (R)-4-Methyl-6-phenyl-3,4-dihydro-2H-pyrazino[1,2-a]indol-1-one
  (R)-6-(4-Methoxy-phenyl)-4-methyl-3,4-dihydro-2H-pyrazino[1,2-a]indol-1-one
  (R)-8-Fluoro-4-methyl-6-phenyl-3,4-dihydro-2H-pyrazino[1,2-a]indol-1-one
  (R)-8-Fluoro-6-(4-methoxy-phenyl)-4-methyl-3,4-dihydro-2H-pyrazino[1,2-a]indol-1-one
  (R)-8-Fluoro-6-(4-fluoro-phenyl)-4-methyl-3,4-dihydro-2H-pyrazino[1,2-a]indol-1-one
  (R)-8-Fluoro-4-methyl-6-p-tolyl-3,4-dihydro-2H-pyrazino[1,2-a]indol-1-one
  (R)-6-(3,5-Difluoro-phenyl)-8-fluoro-4-methyl-3,4-dihydro-2H-pyrazino[1,2-a]indol-1-one
  (R)-6-(3,4-Difluoro-phenyl)-8-fluoro-4-methyl-3,4-dihydro-2H-pyrazino[1,2-a]indol-1-one
  (R)-6-(4-Chloro-phenyl)-8-fluoro-4-methyl-3,4-dihydro-2H-pyrazino[1,2-a]indol-1-one
  8-Fluoro-6-phenyl-3,4-dihydro-2H-pyrazino[1,2-a]indol-1-one
  (R)-8-Fluoro-4-methyl-6-(4-trifluoromethyl-phenyl)-3,4-dihydro-2H-pyrazino[1,2-a]indol-1-one
  (R)-8-Fluoro-6-(3-fluoro-phenyl)-4-methyl-3,4-dihydro-2H-pyrazino[1,2-a]indol-1-one
  9-Fluoro-7-phenyl-2,3,4,5-tetrahydro-[1,4]diazepino[1,2-a]indol-1-one
  9-Fluoro-7-(4-methoxy-phenyl)-2,3,4,5-tetrahydro-[1,4]diazepino[1,2-a]indol-1-one
  9-Fluoro-7-(4-fluoro-phenyl)-2,3,4,5-tetrahydro-[1,4]diazepino[1,2-a]indol-1-one
  8-Fluoro-6-(4-fluoro-phenyl)-3,4-dihydro-2H-pyrazino[1,2-a]indol-1-one
  8-Fluoro-6-(4-methoxy-phenyl)-3,4-dihydro-2H-pyrazino[1,2-a]indol-1-one
  6-(3,4-Difluoro-phenyl)-8-fluoro-3,4-dihydro-2H-pyrazino[1,2-a]indol-1-one
  6-(4-Chloro-phenyl)-8-fluoro-3,4-dihydro-2H-pyrazino[1,2-a]indol-1-one
  8-Fluoro-6-p-tolyl-3,4-dihydro-2H-pyrazino[1,2-a]indol-1-one
  8-Fluoro-6-(4-trifluoromethyl-phenyl)-3,4-dihydro-2H-pyrazino[1,2-a]indol-1-one
  (RS)-9-Fluoro-5-methyl-7-phenyl-2,3,4,5-tetrahydro-[1,4]diazepino[1,2-a]indol-1-one
  (RS)-9-Fluoro-7-(4-fluoro-phenyl)-5-methyl-2,3,4,5-tetrahydro-[1,4]diazepino[1,2-a]indol-1-one
  7-(3,4-Difluoro-phenyl)-9-fluoro-2,3,4,5-tetrahydro-[1,4]diazepino[1,2-a]indol-1-one
  7-(4-Chloro-phenyl)-9-fluoro-2,3,4,5-tetrahydro-[1,4]diazepino[1,2-a]indol-1-one
  9-Fluoro-7-p-tolyl-2,3,4,5-tetrahydro-[1,4]diazepino[1,2-a]indol-1-one
  9-Fluoro-7-(4-trifluoromethyl-phenyl)-2,3,4,5-tetrahydro-[1,4]diazepino[1,2-a]indol-1-one
  8,9-Difluoro-6-(4-fluoro-phenyl)-3,4-dihydro-2H-pyrazino[1,2-a]indol-1-one
  8,9-Difluoro-6-(4-methoxy-phenyl)-3,4-dihydro-2H-pyrazino[1,2-a]indol-1-one
  6-(4-Chloro-phenyl)-8,9-difluoro-3,4-dihydro-2H-pyrazino[1,2-a]indol-1-one
  6-(3,4-Difluoro-phenyl)-8,9-difluoro-3,4-dihydro-2H-pyrazino[1,2-a]indol-1-one
  9,10-Difluoro-7-(4-fluoro-phenyl)-2,3,4,5-tetrahydro-[1,4]diazepino[1,2-a]indol-1-one
  9,10-Difluoro-7-(4-methoxy-phenyl)-2,3,4,5-tetrahydro-[1,4]diazepino[1,2-a]indol-1-one
  7,8-Difluoro-6-(4-fluoro-phenyl)-3,4-dihydro-2H-pyrazino[1,2-a]indol-1-one
  7,8-Difluoro-6-(4-methoxy-phenyl)-3,4-dihydro-2H-pyrazino[1,2-a]indol-1-one
  8,9-Difluoro-7-(4-fluoro-phenyl)-2,3,4,5-tetrahydro-[1,4]diazepino[1,2-a]indol-1-one
  8,9-Difluoro-7-(4-methoxy-phenyl)-2,3,4,5-tetrahydro-[1,4]diazepino[1,2-a]indol-1-one
  7-(3,4-Difluoro-phenyl)-8,9-difluoro-2,3,4,5-tetrahydro-[1,4]diazepino[1,2-a]indol-1-one
  7-(4-Chloro-phenyl)-8,9-difluoro-2,3,4,5-tetrahydro-[1,4]diazepino[1,2-a]indol-1-one
  6-(3,4-Difluoro-phenyl)-7,8-difluoro-3,4-dihydro-2H-pyrazino[1,2-a]indol-1-one
  6-(4-Chloro-phenyl)-7,8-difluoro-3,4-dihydro-2H-pyrazino[1,2-a]indol-1-one
  9-Chloro-7-(3,4-difluoro-phenyl)-2,3,4,5-tetrahydro-[1,4]diazepino[1,2-a]indol-1-one
  9-Chloro-7-p-tolyl-2,3,4,5-tetrahydro-[1,4]diazepino[1,2-a]indol-1-one
  9-Chloro-7-(4-fluoro-phenyl)-2,3,4,5-tetrahydro-[1,4]diazepino[1,2-a]indol-1-one
  8-Chloro-6-(4-chloro-phenyl)-3,4-dihydro-2H-pyrazino[1,2-a]indol-1-one
  8-Chloro-6-(3,4-difluoro-phenyl)-3,4-dihydro-2H-pyrazino[1,2-a]indol-1-one
  8-Chloro-6-(4-fluoro-phenyl)-3,4-dihydro-2H-pyrazino[1,2-a]indol-1-one
  8-Chloro-6-(4-methoxy-phenyl)-3,4-dihydro-2H-pyrazino[1,2-a]indol-1-one
  9-Chloro-7-(4-chloro-phenyl)-2,3,4,5-tetrahydro-[1,4]diazepino[1,2-a]indol-1-one
  9-Chloro-7-(4-methoxy-phenyl)-2,3,4,5-tetrahydro-[1,4]diazepino[1,2-a]indol-1-one
  7-(3,4-Difluoro-phenyl)-9-methyl-2,3,4,5-tetrahydro-[1,4]diazepino[1,2-a]indol-1-one
  7-(4-Methoxy-phenyl)-9-methyl-2,3,4,5-tetrahydro-[1,4]diazepino[1,2-a]indol-1-one
  7-(4-Fluoro-phenyl)-9-methyl-2,3,4,5-tetrahydro-[1,4]diazepino[1,2-a]indol-1-one
  7-(4-Chloro-phenyl)-9-methyl-2,3,4,5-tetrahydro-[1,4]diazepino[1,2-a]indol-1-one
  6-(4-Chloro-phenyl)-8-methyl-3,4-dihydro-2H-pyrazino[1,2-a]indol-1-one
  6-(3,4-Difluoro-phenyl)-8-methyl-3,4-dihydro-2H-pyrazino[1,2-a]indol-1-one
  6-(4-Methoxy-phenyl)-8-methyl-3,4-dihydro-2H-pyrazino[1,2-a]indol-1-one
  6-(4-Fluoro-phenyl)-8-methyl-3,4-dihydro-2H-pyrazino[1,2-a]indol-1-one
  8-Fluoro-6-(4-fluoro-phenyl)-2-methyl-3,4-dihydro-2H-pyrazino[1,2-a]indol-1-one
  8-Chloro-6-(3,4-difluoro-phenyl)-10-methyl-3,4-dihydro-2H-pyrazino[1,2-a]indol-1-one
  8-Chloro-6-(4-chloro-phenyl)-10-methyl-3,4-dihydro-2H-pyrazino[1,2-a]indol-1-one 8-Chloro-6-(4-fluoro-phenyl)-10-methyl-3,4-dihydro-2H-pyrazino[1,2-a]indol-1-one 8-Chloro-6-(4-methoxy-phenyl)-10-methyl-3,4-dihydro-2H-pyrazino[1,2-a]indol-1-one 9-Chloro-7-(3,4-difluoro-phenyl)-11-methyl-2,3,4,5-tetrahydro-[1,4]diazepino[1,2-a]indol-1-one 9-Chloro-7-(4-chloro-phenyl)-11-methyl-2,3,4,5-tetrahydro-[1,4]diazepino[1,2-a]indol-1-one 9-Chloro-7-(4-fluoro-phenyl)-11-methyl-2,3,4,5-tetrahydro-[1,4]diazepino[1,2-a]indol-1-one 9-Chloro-7-(4-methoxy-phenyl)-11-methyl-2,3,4,5-tetrahydro-[1,4]diazepino[1,2-a]indol-1-one 6-(3,4-Difluoro-phenyl)-8-fluoro-10-methyl-3,4-dihydro-2H-pyrazino[1,2-a]indol-1-one 6-(4-Chloro-phenyl)-8-fluoro-10-methyl-3,4-dihydro-2H-pyrazino[1,2-a]indol-1-one 8-Fluoro-6-(4-fluoro-phenyl)-10-methyl-3,4-dihydro-2H-pyrazino[1,2-a]indol-1-one 8-Fluoro-6-(4-methoxy-phenyl)-10-methyl-3,4-dihydro-2H-pyrazino[1,2-a]indol-1-one 8-Fluoro-10-methyl-6-phenyl-3,4-dihydro-2H-pyrazino[1,2-a]indol-1-one 6-(4-Chloro-phenyl)-1-oxo-1,2,3,4-tetrahydro-pyrazino[1,2-a]indole-8-carbonitrile 6-(4-Fluoro-phenyl)-1-oxo-1,2,3,4-tetrahydro-pyrazino[1,2-a]indole-8-carbonitrile 6-(4-Methoxy-phenyl)-1-oxo-1,2,3,4-tetrahydro-pyrazino[1,2-a]indole-8-carbonitrile 6-(3,4-Difluoro-phenyl)-1-oxo-1,2,3,4-tetrahydro-pyrazino[1,2-a]indole-8-carbonitrile 8-Fluoro-10-methyl-6-p-tolyl-3,4-dihydro-2H-pyrazino[1,2-a]indol-1-one 8-Fluoro-10-methyl-6-(4-trifluoromethyl-phenyl)-3,4-dihydro-2H-pyrazino[1,2-a]indol-1-one 6-(3,5-Difluoro-phenyl)-8-fluoro-10-methyl-3,4-dihydro-2H-pyrazino[1,2-a]indol-1-one 6-(4-Chloro-3-fluoro-phenyl)-8-fluoro-10-methyl-3,4-dihydro-2H-pyrazino[1,2-a]indol-1-one 6-(3,4-Dichloro-phenyl)-8-fluoro-10-methyl-3,4-dihydro-2H-pyrazino[1,2-a]indol-1-one 8-Fluoro-6-(3-fluoro-phenyl)-10-methyl-3,4-dihydro-2H-pyrazino[1,2-a]indol-1-one 8-Chloro-10-methyl-6-phenyl-3,4-dihydro-2H-pyrazino[1,2-a]indol-1-one 8-Chloro-10-methyl-6-p-tolyl-3,4-dihydro-2H-pyrazino[1,2-a]indol-1-one 8-Chloro-10-methyl-6-(4-trifluoromethyl-phenyl)-3,4-dihydro-2H-pyrazino[1,2-a]indol-1-one 1-Oxo-6-phenyl-1,2,3,4-tetrahydro-pyrazino[1,2-a]indole-8-carbonitrile 1-Oxo-6-p-tolyl-1,2,3,4-tetrahydro-pyrazino[1,2-a]indole-8-carbonitrile 1-Oxo-6-(4-trifluoromethyl-phenyl)-1,2,3,4-tetrahydro-pyrazino[1,2-a]indole-8-carbonitrile 8-Chloro-6-(3-fluoro-phenyl)-10-methyl-3,4-dihydro-2H-pyrazino[1,2-a]indol-1-one 8-Chloro-6-(3,4-dichloro-phenyl)-10-methyl-3,4-dihydro-2H-pyrazino[1,2-a]indol-1-one 8-Chloro-6-(4-chloro-3-fluoro-phenyl)-10-methyl-3,4-dihydro-2H-pyrazino[1,2-a]indol-1-one 8-Chloro-6-(3,5-difluoro-phenyl)-10-methyl-3,4-dihydro-2H-pyrazino[1,2-a]indol-1-one 8-Chloro-6-(2,4-difluoro-phenyl)-10-methyl-3,4-dihydro-2H-pyrazino[1,2-a]indol-1-one 8-Chloro-6-(4-chloro-2-fluoro-phenyl)-10-methyl-3,4-dihydro-2H-pyrazino[1,2-a]indol-1-one 8-Chloro-6-(2,4-dichloro-phenyl)-10-methyl-3,4-dihydro-2H-pyrazino[1,2-a]indol-1-one 4-(8-Chloro-10-methyl-1-oxo-1,2,3,4-tetrahydro-pyrazino[1,2-a]indol-6-yl)-benzonitrile 8-Chloro-6-(3-fluoro-4-methyl-phenyl)-10-methyl-3,4-dihydro-2H-pyrazino[1,2-a]indol-1-one 8-Chloro-6-(4-isopropyl-phenyl)-10-methyl-3,4-dihydro-2H-pyrazino[1,2-a]indol-1-one 8-Chloro-6-(4-methanesulfonyl-phenyl)-10-methyl-3,4-dihydro-2H-pyrazino[1,2-a]indol-1-one 8-Chloro-10-methyl-6-(4-nitro-phenyl)-3,4-dihydro-2H-pyrazino[1,2-a]indol-1-one 8-Chloro-6-(4-hydroxymethyl-phenyl)-10-methyl-3,4-dihydro-2H-pyrazino[1,2-a]indol-1-one 8-Chloro-6-(4-dimethylamino-phenyl)-10-methyl-3,4-dihydro-2H-pyrazino[1,2-c]indol-1-one 8-Chloro-6-(3-chloro-phenyl)-10-methyl-3,4-dihydro-2H-pyrazino[1,2-c]indol-1-one 3-(8-Chloro-10-methyl-1-oxo-1,2,3,4-tetrahydro-pyrazino[1,2-c]indol-6-yl)-benzonitrile 6-(4-tert-Butyl-phenyl)-8-chloro-10-methyl-3,4-dihydro-2H-pyrazino[1,2-c]indol-1-one 6-(2,4-Dichloro-phenyl)-8-fluoro-10-methyl-3,4-dihydro-2H-pyrazino[1,2-c]indol-1-one 6-(4-Chloro-2-fluoro-phenyl)-8-fluoro-10-methyl-3,4-dihydro-2H-pyrazino[1,2-c]indol-1-one 6-(2,4-Difluoro-phenyl)-8-fluoro-10-methyl-3,4-dihydro-2H-pyrazino[1,2-c]indol-1-one 4-(8-Fluoro-10-methyl-1-oxo-1,2,3,4-tetrahydro-pyrazino[1,2-c]indol-6-yl)-benzonitrile 8-Fluoro-6-(4-methanesulfonyl-phenyl)-10-methyl-3,4-dihydro-2H-pyrazino[1,2-c]indol-1-one 8-Fluoro-10-methyl-6-(4-nitro-phenyl)-3,4-dihydro-2H-pyrazino[1,2-c]indol-1-one 8-Fluoro-6-(4-isopropyl-phenyl)-10-methyl-3,4-dihydro-2H-pyrazino[1,2-c]indol-1-one 6-(3-Chloro-phenyl)-8-fluoro-10-methyl-3,4-dihydro-2H-pyrazino[1,2-c]indol-1-one 8-Fluoro-6-(4-hydroxymethyl-phenyl)-10-methyl-3,4-dihydro-2H-pyrazino[1,2-c]indol-1-one 3-(8-Fluoro-10-methyl-1-oxo-1,2,3,4-tetrahydro-pyrazino[1,2-c]indol-6-yl)-benzonitrile 6-(4-tert-Butyl-phenyl)-8-fluoro-10-methyl-3,4-dihydro-2H-pyrazino[1,2-c]indol-1-one 8-Chloro-10-methyl-6-(4-trifluoromethoxy-phenyl)-3,4-dihydro-2H-pyrazino[1,2-c]indol-1-one 8-Chloro-6-(4-fluoro-3-methyl-phenyl)-10-methyl-3,4-dihydro-2H-pyrazino[1,2-c]indol-1-one 8-Chloro-6-(4-chloro-3-trifluoromethyl-phenyl)-10-methyl-3,4-dihydro-2H-pyrazino[1,2-c]indol-1-one 8-Chloro-10-methyl-6-(3,4,5-trifluoro-phenyl)-3,4-dihydro-2H-pyrazino[1,2-c]indol-1-one 6-(4-Dimethylamino-phenyl)-8-fluoro-10-methyl-3,4-dihydro-2H-pyrazino[1,2-c]indol-1-one 8-Fluoro-6-(3-fluoro-4-methyl-phenyl)-10-methyl-3,4-dihydro-2H-pyrazino[1,2-c]indol-1-one 8-Fluoro-6-(4-fluoro-3-methyl-phenyl)-10-methyl-3,4-dihydro-2H-pyrazino[1,2-c]indol-1-one 8-Fluoro-10-methyl-6-(4-trifluoromethoxy-phenyl)-3,4-dihydro-2H-pyrazino[1,2-a]indol-1-one 6-(4-Chloro-3-trifluoromethyl-phenyl)-8-fluoro-10-methyl-3,4-dihydro-2H-pyrazino[1,2-a]indol-1-one 8-Fluoro-10-methyl-6-(2,3,4-trifluoro-phenyl)-3,4-dihydro-2H-pyrazino[1,2-c]indol-1-one 8-Fluoro-10-methyl-6-(3,4,5-trifluoro-phenyl)-3,4-dihydro-2H-pyrazino[1,2-c]indol-1-one 6-(4-Fluoro-phenyl)-10-methyl-1-oxo-1,2,3,4-tetrahydro-pyrazino[1,2-c]indole-8-carbonitrile
6-(4-Chloro-phenyl)-10-methyl-1-oxo-1,2,3,4-tetrahydro-pyrazino[1,2-c]indole-8-carbonitrile
6-(3,4-Difluoro-phenyl)-10-methyl-1-oxo-1,2,3,4-tetrahydro-pyrazino[1,2-c]indole-8-carbonitrile
10-Methyl-1-oxo-6-(4-trifluoromethyl-phenyl)-1,2,3,4-tetrahydro-pyrazino[1,2-c]indole-8-carbonitrile
6-(4-Cyano-phenyl)-10-methyl-1-oxo-1,2,3,4-tetrahydro-pyrazino[1,2-c]indole-8-carbonitrile
6-(2,4-Dichloro-phenyl)-10-methyl-1-oxo-1,2,3,4-tetrahydro-pyrazino[1,2-c]indole-8-carbonitrile
10-Methyl-1-oxo-6-(4-trifluoromethoxy-phenyl)-1,2,3,4-tetrahydro-pyrazino[1,2-a]indole-8-carbonitrile
6-(4-Chloro-3-fluoro-phenyl)-1-oxo-1,2,3,4-tetrahydro-pyrazino[1,2-c]indole-8-carbonitrile
6-(2,4-Difluoro-phenyl)-1-oxo-1,2,3,4-tetrahydro-pyrazino[1,2-a]indole-8-carbonitrile
6-(4-Chloro-2-fluoro-phenyl)-1-oxo-1,2,3,4-tetrahydro-pyrazino[1,2-a]indole-8-carbonitrile
6-(2,4-Dichloro-phenyl)-1-oxo-1,2,3,4-tetrahydro-pyrazino[1,2-a]indole-8-carbonitrile
6-(4-Cyano-phenyl)-1-oxo-1,2,3,4-tetrahydro-pyrazino[1,2-a]indole-8-carbonitrile
6-(4-Chloro-3-fluoro-phenyl)-10-methyl-1-oxo-1,2,3,4-tetrahydro-pyrazino[1,2-a]indole-8-carbonitrile
6-(2,4-Difluoro-phenyl)-10-methyl-1-oxo-1,2,3,4-tetrahydro-pyrazino[1,2-a]indole-8-carbonitrile
6-(4-Chloro-2-fluoro-phenyl)-10-methyl-1-oxo-1,2,3,4-tetrahydro-pyrazino[1,2-a]indole-8-carbonitrile
8-Fluoro-6-(4-fluoro-phenyl)-10-trifluoromethyl-3,4-dihydro-2H-pyrazino[1,2-a]indol-1-one
6-(3,4-Difluoro-phenyl)-1-oxo-10-trifluoromethyl-1,2,3,4-tetrahydro-pyrazino[1,2-a]indole-8-carbonitrile
8-Chloro-6-(4-chlorophenyl)-10-(trifluoromethyl)-3,4-dihydro-2H-pyrazino[1,2-a]indol-1-one
1-Oxo-6-(3,4,5-trifluorophenyl)-3,4-dihydro-2H-pyrazino[1,2-a]indole-8-carbonitrile
1-Oxo-6-[4-(trifluoromethoxy)phenyl]-3,4-dihydro-2H-pyrazino[1,2-a]indole-8-carbonitrile
6-(4-Methylsulfonylphenyl)-1-oxo-3,4-dihydro-2H-pyrazino[1,2-a]indole-8-carbonitrile
6-(3,4-Dichlorophenyl)-1-oxo-3,4-dihydro-2H-pyrazino[1,2-a]indole-8-carbonitrile
6-(3-Chlorophenyl)-1-oxo-3,4-dihydro-2H-pyrazino[1,2-a]indole-8-carbonitrile
6-(3-Cyanophenyl)-1-oxo-3,4-dihydro-2H-pyrazino[1,2-a]indole-8-carbonitrile
1-Oxo-6-[3-(trifluoromethyl)phenyl]-3,4-dihydro-2H-pyrazino[1,2-a]indole-8-carbonitrile
7-(3,4-Difluorophenyl)-11-methyl-1-oxo-2,3,4,5-tetrahydro-[1,4]diazepino[1,2-a]indole-9-carbonitrile
11-Methyl-1-oxo-7-[4-(trifluoromethyl)phenyl]-2,3,4,5-tetrahydro-[1,4]diazepino[1,2-a]indole-9-carbonitrile
7-(4-Fluorophenyl)-11-methyl-1-oxo-2,3,4,5-tetrahydro-[1,4]diazepino[1,2-a]indole-9-carbonitrile
7-(4-Chlorophenyl)-11-methyl-1-oxo-2,3,4,5-tetrahydro-[1,4]diazepino[1,2-a]indole-9-carbonitrile
7-(4-Cyanophenyl)-11-methyl-1-oxo-2,3,4,5-tetrahydro-[1,4]diazepino[1,2-a]indole-9-carbonitrile
11-Methyl-1-oxo-7-[4-(trifluoromethoxy)-phenyl]-2,3,4,5-tetrahydro-[1,4]diazepino[1,2-a]indole-9-carbonitrile
1-Oxo-6-(2,3,4-trifluorophenyl)-3,4-dihydro-2H-pyrazino[1,2-a]indole-8-carbonitrile
6-[4-Chloro-3-(trifluoromethyl)phenyl]-1-oxo-3,4-dihydro-2H-pyrazino[1,2-a]indole-8-carbonitrile
7-(2,4-Difluorophenyl)-11-methyl-1-oxo-2,3,4,5-tetrahydro-[1,4]diazepino[1,2-a]indole-9-carbonitrile
7-(2,4-Dichlorophenyl)-11-methyl-1-oxo-2,3,4,5-tetrahydro-[1,4]diazepino[1,2-a]indole-9-carbonitrile
7-(4-Chloro-2-fluorophenyl)-11-methyl-1-oxo-2,3,4,5-tetrahydro-[1,4]diazepino[1,2-a]indole-9-carbonitrile
6-(4-Fluorophenyl)-8-methoxy-3,4-dihydro-2H-pyrazino[1,2-a]indol-1-one
6-(4-Chlorophenyl)-8-methoxy-3,4-dihydro-2H-pyrazino[1,2-a]indol-1-one
6-(3,4-Difluorophenyl)-8-methoxy-3,4-dihydro-2H-pyrazino[1,2-a]indol-1-one
8-Methoxy-6-[4-(trifluoromethyl)-phenyl]-3,4-dihydro-2H-pyrazino[1,2-a]indol-1-one
7-(4-Chlorophenyl)-1-oxo-2,3,4,5-tetrahydro-[1,4]diazepino[1,2-a]indole-9-carbonitrile
7-(4-Fluorophenyl)-1-oxo-2,3,4,5-tetrahydro-[1,4]diazepino[1,2-a]indole-9-carbonitrile
8-(Trifluoromethoxy)-6-[4-(trifluoromethyl)-phenyl]-3,4-dihydro-2H-pyrazino[1,2-a]indol-1-one
7-(3,4-Difluorophenyl)-1-oxo-2,3,4,5-tetrahydro-[1,4]diazepino[1,2-a]indole-9-carbonitrile
1-Oxo-7-[4-(trifluoromethyl)-phenyl]-2,3,4,5-tetrahydro-[1,4]diazepino[1,2-a]indole-9-carbonitrile
7-(4-Chloro-2-fluorophenyl)-1-oxo-2,3,4,5-tetrahydro-[1,4]diazepino[1,2-a]indole-9-carbonitrile
7-(2,4-Difluorophenyl)-1-oxo-2,3,4,5-tetrahydro-[1,4]diazepino[1,2-a]indole-9-carbonitrile
6-(3,5-Difluorophenyl)-1-oxo-3,4-dihydro-2H-pyrazino[1,2-a]indole-8-carbonitrile
6-(3-Fluorophenyl)-1-oxo-3,4-dihydro-2H-pyrazino[1,2-a]indole-8-carbonitrile
6-[4-(Hydroxymethyl)-phenyl]-1-oxo-3,4-dihydro-2H-pyrazino[1,2-a]indole-8-carbonitrile
6-(4-tert-Butylphenyl)-1-oxo-3,4-dihydro-2H-pyrazino[1,2-a]indole-8-carbonitrile
6-(4-Fluoro-3-methylphenyl)-1-oxo-3,4-dihydro-2H-pyrazino[1,2-a]indole-8-carbonitrile
6-(4-Nitrophenyl)-1-oxo-3,4-dihydro-2H-pyrazino[1,2-a]indole-8-carbonitrile
6-(3-Fluoro-4-methylphenyl)-1-oxo-3,4-dihydro-2H-pyrazino[1,2-a]indole-8-carbonitrile
7-(4-Nitrophenyl)-1-oxo-2,3,4,5-tetrahydro-[1,4]diazepino[1,2-a]indole-9-carbonitrile
7-(4-Fluoro-3-methylphenyl)-1-oxo-2,3,4,5-tetrahydro-[1,4]diazepino[1,2-a]indole-9-carbonitrile
7-(2,4-Dichlorophenyl)-1-oxo-2,3,4,5-tetrahydro-[1,4]diazepino[1,2-a]indole-9-carbonitrile
7-(4-Cyanophenyl)-1-oxo-2,3,4,5-tetrahydro-[1,4]diazepino[1,2-a]indole-9-carbonitrile
7-(3,5-Difluorophenyl)-1-oxo-2,3,4,5-tetrahydro-[1,4]diazepino[1,2-a]indole-9-carbonitrile
7-(3-Fluorophenyl)-1-oxo-2,3,4,5-tetrahydro-[1,4]diazepino[1,2-a]indole-9-carbonitrile
10-Methyl-1-oxo-6-(3,4,5-trifluorophenyl)-3,4-dihydro-2H-pyrazino[1,2-a]indole-8-carbonitrile
10-Methyl-1-oxo-6-phenyl-3,4-dihydro-2H-pyrazino[1,2-a]indole-8-carbonitrile
11-Methyl-1-oxo-7-(3,4,5-trifluorophenyl)-2,3,4,5-tetrahydro-[1,4]diazepino[1,2-a]indole-9-carbonitrile
11-Methyl-1-oxo-7-phenyl-2,3,4,5-tetrahydro-[1,4]diazepino[1,2-a]indole-9-carbonitrile
10-Methyl-1-oxo-6-(2,3,4-trifluorophenyl)-3,4-dihydro-2H-pyrazino[1,2-a]indole-8-carbonitrile
6-(4-Methoxyphenyl)-10-methyl-1-oxo-3,4-dihydro-2H-pyrazino[1,2-a]indole-8-carbonitrile 1-Oxo-7-(3,4,5-trifluorophenyl)-2,3,4,5-tetrahydro-[1,4]
diazepino[1,2-a]indole-9-carbonitrile
7-(3,4-Dichlorophenyl)-1-oxo-2,3,4,5-tetrahydro-[1,4]di-
azepino[1,2-a]indole-9-carbonitrile
7-(4-Chloro-3-fluorophenyl)-1-oxo-2,3,4,5-tetrahydro-
[1,4]diazepino[1,2-a]indole-9-carbonitrile
7-(3-Fluoro-4-methylphenyl)-1-oxo-2,3,4,5-tetrahydro-
[1,4]diazepino[1,2-a]indole-9-carbonitrile
7-[4-Chloro-3-(trifluoromethyl)phenyl]-1-oxo-2,3,4,5-
tetrahydro-[1,4]diazepino[1,2-a]indole-9-carbonitrile
1-Oxo-7-[4-(trifluoromethoxy)phenyl]-2,3,4,5-tetrahy-
dro-[1,4]diazepino[1,2-a]indole-9-carbonitrile
7-(4-Methylsulfonylphenyl)-1-oxo-2,3,4,5-tetrahydro-[1,
4]diazepino[1,2-a]indole-9-carbonitrile
10-Methyl-6-(4-methylphenyl)-1-oxo-3,4-dihydro-2H-
pyrazino[1,2-a]indole-8-carbonitrile
6-(3-Fluorophenyl)-10-methyl-1-oxo-3,4-dihydro-2H-
pyrazino[1,2-a]indole-8-carbonitrile
6-(3,4-Dichlorophenyl)-10-methyl-1-oxo-3,4-dihydro-
2H-pyrazino[1,2-a]indole-8-carbonitrile
6-(3,5-Difluorophenyl)-10-methyl-1-oxo-3,4-dihydro-
2H-pyrazino[1,2-a]indole-8-carbonitrile
7-(4-Methoxyphenyl)-11-methyl-1-oxo-2,3,4,5-tetrahy-
dro-[1,4]diazepino[1,2-a]indole-9-carbonitrile
7-[4-(Hydroxymethyl)phenyl]-1-oxo-2,3,4,5-tetrahydro-
[1,4]diazepino[1,2-a]indole-9-carbonitrile
6-(3-Fluoro-4-methylphenyl)-10-methyl-1-oxo-3,4-dihy-
dro-2H-pyrazino[1,2-a]indole-8-carbonitrile
6-(3-Chlorophenyl)-10-methyl-1-oxo-3,4-dihydro-2H-
pyrazino[1,2-a]indole-8-carbonitrile
7-(3-Cyanophenyl)-1-oxo-2,3,4,5-tetrahydro-[1,4]diaz-
epino[1,2-a]indole-9-carbonitrile
7-(4-tert-Butylphenyl)-1-oxo-2,3,4,5-tetrahydro-[1,4]di-
azepino[1,2-a]indole-9-carbonitrile
1-Oxo-7-phenyl-2,3,4,5-tetrahydro-[1,4]diazepino[1,2-a]
indole-9-carbonitrile
7-(4-Methoxyphenyl)-1-oxo-2,3,4,5-tetrahydro-[1,4]di-
azepino[1,2-a]indole-9-carbonitrile
10-Methyl-6-(4-nitrophenyl)-1-oxo-3,4-dihydro-2H-
pyrazino[1,2-a]indole-8-carbonitrile
6-[4-(Hydroxymethyl)phenyl]-10-methyl-1-oxo-3,4-di-
hydro-2H-pyrazino[1,2-a]indole-8-carbonitrile
6-(3-Cyanophenyl)-10-methyl-1-oxo-3,4-dihydro-2H-
pyrazino[1,2-a]indole-8-carbonitrile
6-(4-tert-Butylphenyl)-10-methyl-1-oxo-3,4-dihydro-2H-
pyrazino[1,2-a]indole-8-carbonitrile
1-Oxo-7-(2,3,4-trifluorophenyl)-2,3,4,5-tetrahydro-[1,4]
diazepino[1,2-a]indole-9-carbonitrile
7-(3-Chlorophenyl)-1-oxo-2,3,4,5-tetrahydro-[1,4]diaz-
epino[1,2-a]indole-9-carbonitrile
7-(3,5-Dichlorophenyl)-1-oxo-2,3,4,5-tetrahydro-[1,4]di-
azepino[1,2-a]indole-9-carbonitrile
7-(4-Methylphenyl)-1-oxo-2,3,4,5-tetrahydro-[1,4]diaz-
epino[1,2-a]indole-9-carbonitrile
11-Methyl-7-(4-methylphenyl)-1-oxo-2,3,4,5-tetrahydro-
[1,4]diazepino[1,2-a]indole-9-carbonitrile
7-(3-Fluorophenyl)-11-methyl-1-oxo-2,3,4,5-tetrahydro-
[1,4]diazepino[1,2-a]indole-9-carbonitrile
7-(3,5-Difluorophenyl)-11-methyl-1-oxo-2,3,4,5-tetrahy-
dro-[1,4]diazepino[1,2-a]indole-9-carbonitrile
7-(3-Fluoro-4-methylphenyl)-11-methyl-1-oxo-2,3,4,5-
tetrahydro-[1,4]diazepino[1,2-a]indole-9-carbonitrile
6-(4-Fluoro-3-methylphenyl)-10-methyl-1-oxo-3,4-dihy-
dro-2H-pyrazino[1,2-a]indole-8-carbonitrile
6-(3,5-Dichlorophenyl)-10-methyl-1-oxo-3,4-dihydro-
2H-pyrazino[1,2-a]indole-8-carbonitrile
10-Methyl-6-(4-methylsulfonylphenyl)-1-oxo-3,4-dihydro-2H-pyrazino[1,2-a]indole-8-carbonitrile
6-[4-Chloro-3-(trifluoromethyl)phenyl]-10-methyl-1-
oxo-3,4-dihydro-2H-pyrazino[1,2-a]indole-8-carboni-
trile
7-(3,4-Dichlorophenyl)-11-methyl-1-oxo-2,3,4,5-tetrahy-
dro-[1,4]diazepino[1,2-a]indole-9-carbonitrile of and
7-(4-Chloro-3-fluorophenyl)-11-methyl-1-oxo-2,3,4,5-
tetrahydro-[1,4]diazepino[1,2-a]indole-9-carbonitrile.

4. The compound of claim 1
wherein
$R^3$ is pyridinyl or pyrimidinyl, which may be substituted by one or more substituents, selected from cyano, nitro, amino and lower di-alkylamino, lower alkyl sulfonyl, lower alkoxy, lower alkoxy substituted by halogen, halogen, lower alkyl, lower alkyl substituted by halogen or lower alkyl substituted by hydroxyl.

5. The compound of claim 4, wherein the compound is selected from:
(R)-4-Methyl-6-pyridin-4-yl-3,4-dihydro-2H-pyrazino[1,
2-a]indol-1-one
(R)-8-Fluoro-4-methyl-6-pyridin-4-yl-3,4-dihydro-2H-
pyrazino[1,2-a]indol-1-one
9-Fluoro-7-pyridin-4-yl-2,3,4,5-tetrahydro-[1,4]diaz-
epino[1,2-a]indol-1-one
8-Fluoro-6-pyridin-4-yl-3,4-dihydro-2H-pyrazino[1,2-a]
indol-1-one
8-Fluoro-10-methyl-6-pyridin-4-yl-3,4-dihydro-2H-
pyrazino[1,2-a]indol-1-one
8-Chloro-10-methyl-6-pyridin-4-yl-3,4-dihydro-2H-
pyrazino[1,2-a]indol-1-one
1-Oxo-6-pyridin-4-yl-1,2,3,4-tetrahydro-pyrazino[1,2-a]
indole-8-carbonitrile
8-Chloro-6-(2-fluoro-pyridin-4-yl)-10-methyl-3,4-dihy-
dro-2H-pyrazino[1,2-a]indol-1-one
8-Chloro-6-(6-methoxy-pyridin-3-yl)-10-methyl-3,4-di-
hydro-2H-pyrazino[1,2-a]indol-1-one
8-Chloro-6-(6-chloro-pyridin-3-yl)-10-methyl-3,4-dihy-
dro-2H-pyrazino[1,2-a]indol-1-one
8-Chloro-6-(6-fluoro-pyridin-3-yl)-10-methyl-3,4-dihy-
dro-2H-pyrazino[1,2-a]indol-1-one
8-Chloro-6-(2-chloro-pyridin-4-yl)-10-methyl-3,4-dihy-
dro-2H-pyrazino[1,2-a]indol-1-one
8-Chloro-10-methyl-6-pyridin-3-yl-3,4-dihydro-2H-
pyrazino[1,2-a]indol-1-one
8-Fluoro-6-(2-fluoro-pyridin-4-yl)-10-methyl-3,4-dihy-
dro-2H-pyrazino[1,2-a]indol-1-one
6-(2-Chloro-pyridin-4-yl)-8-fluoro-10-methyl-3,4-dihy-
dro-2H-pyrazino[1,2-a]indol-1-one
8-Fluoro-6-(6-fluoro-pyridin-3-yl)-10-methyl-3,4-dihy-
dro-2H-pyrazino[1,2-a]indol-1-one
6-(6-Chloro-pyridin-3-yl)-8-fluoro-10-methyl-3,4-dihy-
dro-2H-pyrazino[1,2-a]indol-1-one
8-Fluoro-6-(6-methoxy-pyridin-3-yl)-10-methyl-3,4-di-
hydro-2H-pyrazino[1,2-a]indol-1-one
8-Fluoro-10-methyl-6-pyridin-3-yl-3,4-dihydro-2H-
pyrazino[1,2-a]indol-1-one
8-Chloro-6-(6-dimethylamino-pyridin-3-yl)-10-methyl-3,
4-dihydro-2H-pyrazino[1,2-a]indol-1-one
6-(6-Dimethylamino-pyridin-3-yl)-8-fluoro-10-methyl-3,
4-dihydro-2H-pyrazino[1,2-a]indol-1-one
6-(6-Amino-pyridin-3-yl)-8-fluoro-10-methyl-3,4-dihy-
dro-2H-pyrazino[1,2-a]indol-1-one
6-(6-Amino-pyridin-3-yl)-8-chloro-10-methyl-3,4-dihy-
dro-2H-pyrazino[1,2-a]indol-1-one
6-(2-Fluoro-pyridin-4-yl)-10-methyl-1-oxo-1,2,3,4-tet-
rahydro-pyrazino[1,2-a]indole-8-carbonitrile 6-(6-Fluoro-pyridin-3-yl)-10-methyl-1-oxo-1,2,3,4-tetrahydro-pyrazino[1,2-a]indole-8-carbonitrile
6-(2-Fluoro-pyridin-4-yl)-1-oxo-1,2,3,4-tetrahydro-pyrazino[1,2-a]indole-8-carbonitrile
6-(6-Fluoropyridin-3-yl)-1-oxo-3,4-dihydro-2H-pyrazino[1,2-a]indole-8-carbonitrile
7-(2-Fluoropyridin-4-yl)-11-methyl-1-oxo-2,3,4,5-tetrahydro-[1,4]diazepino[1,2-a]indole-9-carbonitrile
7-(6-Fluoropyridin-3-yl)-11-methyl-1-oxo-2,3,4,5-tetrahydro-[1,4]diazepino[1,2-a]indole-9-carbonitrile
7-(2-Fluoropyridin-4-yl)-1-oxo-2,3,4,5-tetrahydro-[1,4]diazepino[1,2-a]indole-9-carbonitrile
6-(6-Aminopyridin-3-yl)-1-oxo-3,4-dihydro-2H-pyrazino[1,2-a]indole-8-carbonitrile
6-(6-Chloropyridin-3-yl)-1-oxo-3,4-dihydro-2H-pyrazino[1,2-a]indole-8-carbonitrile
6-(2-Chloropyridin-4-yl)-1-oxo-3,4-dihydro-2H-pyrazino[1,2-a]indole-8-carbonitrile
1-Oxo-6-pyridin-3-yl-3,4-dihydro-2H-pyrazino[1,2-a]indole-8-carbonitrile
6-(6-Aminopyridin-3-yl)-10-methyl-1-oxo-3,4-dihydro-2H-pyrazino[1,2-a]indole-8-carbonitrile
10-Methyl-1-oxo-6-pyridin-4-yl-3,4-dihydro-2H-pyrazino[1,2-a]indole-8-carbonitrile
11-Methyl-1-oxo-7-pyridin-4-yl-2,3,4,5-tetrahydro-[1,4]diazepino[1,2-a]indole-9-carbonitrile
7-(6-Aminopyridin-3-yl)-11-methyl-1-oxo-2,3,4,5-tetrahydro-[1,4]diazepino[1,2-a]indole-9-carbonitrile
7-(2-Chloropyridin-4-yl)-1-oxo-2,3,4,5-tetrahydro-[1,4]diazepino[1,2-a]indole-9-carbonitrile
1-Oxo-7-pyridin-3-yl-2,3,4,5-tetrahydro-[1,4]diazepino[1,2-a]indole-9-carbonitrile
7-(6-Aminopyridin-3-yl)-1-oxo-2,3,4,5-tetrahydro-[1,4]diazepino[1,2-a]indole-9-carbonitrile
7-(6-Chloropyridin-3-yl)-1-oxo-2,3,4,5-tetrahydro-[1,4]diazepino[1,2-a]indole-9-carbonitrile
1-Oxo-7-pyridin-4-yl-2,3,4,5-tetrahydro-[1,4]diazepino[1,2-a]indole-9-carbonitrile
7-(6-Fluoropyridin-3-yl)-1-oxo-2,3,4,5-tetrahydro-[1,4]diazepino[1,2-a]indole-9-carbonitrile
6-(6-Chloropyridin-3-yl)-10-methyl-1-oxo-3,4-dihydro-2H-pyrazino[1,2-a]indole-8-carbonitrile
10-Methyl-1-oxo-6-pyridin-3-yl-3,4-dihydro-2H-pyrazino[1,2-a]indole-8-carbonitrile
11-Methyl-1-oxo-7-pyridin-3-yl-2,3,4,5-tetrahydro-[1,4]diazepino[1,2-a]indole-9-carbonitrile
8-Chloro-10-methyl-6-pyrimidin-5-yl-3,4-dihydro-2H-pyrazino[1,2-a]indol-1-one
8-Chloro-6-(2-methoxy-pyrimidin-5-yl)-10-methyl-3,4-dihydro-2H-pyrazino[1,2-a]indol-1-one
6-(2-Amino-pyrimidin-5-yl)-8-chloro-10-methyl-3,4-dihydro-2H-pyrazino[1,2-a]indol-1-one
8-Fluoro-10-methyl-6-pyrimidin-5-yl-3,4-dihydro-2H-pyrazino[1,2-a]indol-1-one
8-Fluoro-6-(2-methoxy-pyrimidin-5-yl)-10-methyl-3,4-dihydro-2H-pyrazino[1,2-a]indol-1-one
6-(2-Amino-pyrimidin-5-yl)-8-fluoro-10-methyl-3,4-dihydro-2H-pyrazino[1,2-a]indol-1-one
1-Oxo-6-pyrimidin-5-yl-3,4-dihydro-2H-pyrazino[1,2-a]indole-8-carbonitrile
1-Oxo-7-pyrimidin-5-yl-2,3,4,5-tetrahydro-[1,4]diazepino[1,2-a]indole-9-carbonitrile
10-Methyl-1-oxo-6-pyrimidin-5-yl-3,4-dihydro-2H-pyrazino[1,2-a]indole-8-carbonitrile and
11-Methyl-1-oxo-7-pyrimidin-5-yl-2,3,4,5-tetrahydro-[1,4]diazepino[1,2-a]indole-9-carbonitrile.

6. The compound of claim 1,
wherein
R$^3$ is benzo[1,3]dioxolyl or 2,3-dihydro-benzofuranyl.

7. The compound of claim 6, wherein the compound is selected from
6-Benzo[1,3]dioxol-5-yl-8-chloro-10-methyl-3,4-dihydro-2H-pyrazino[1,2-a]indol-1-one
6-Benzo[1,3]dioxol-5-yl-8-fluoro-10-methyl-3,4-dihydro-2H-pyrazino[1,2-a]indol-1-one
8-Chloro-6-(2,3-dihydro-benzofuran-5-yl)-10-methyl-3,4-dihydro-2H-pyrazino[1,2-a]indol-1-one and
6-(2,3-Dihydro-benzofuran-5-yl)-8-fluoro-10-methyl-3,4-dihydro-2H-pyrazino[1,2-a]indol-1-one.

8. The compound of claim 1,
wherein
R$^3$ is a 5-membered heteroaryl, which may be substituted by one or more substituents, selected from cyano, nitro, amino and lower di-alkylamino, lower alkyl sulfonyl, lower alkoxy, lower alkoxy substituted by halogen, halogen, lower alkyl, lower alkyl substituted by halogen or lower alkyl substituted by hydroxyl.

9. The compound of claim 8, wherein the compound is selected from:
8-Fluoro-10-methyl-6-thiazol-2-yl-3,4-dihydro-2H-pyrazino[1,2-c]indol-1-one
6-(5-Chloro-thiophen-2-yl)-8-fluoro-10-methyl-3,4-dihydro-2H-pyrazino[1,2-c]indol-1-one
8-Fluoro-10-methyl-6-[5-(trifluoromethyl)-1,3,4-thiadiazol-2-yl]-3,4-dihydro-2H-pyrazino[1,2-a]indol-1-one
5-(8-Fluoro-10-methyl-1-oxo-3,4-dihydro-2H-pyrazino[1,2-a]indol-6-yl)thiophene-2-carbonitrile
8-Fluoro-10-methyl-6-[5-(trifluoromethyl)-1,3-thiazol-2-yl]-3,4-dihydro-2H-pyrazino[1,2-a]indol-1-one and
8-Fluoro-6-(furan-2-yl)-10-methyl-3,4-dihydro-2H-pyrazino[1,2-a]indol-1-one.

10. The compound of claim 1, wherein X is —CH(lower alkyl)-.

11. The compound of claim 1, wherein X is —CH$_2$—.

12. The compound of claim 1, wherein X is —CH$_2$CH$_2$—.

13. The compound of claim 1, wherein X is —CH(lower alkyl)CH$_2$—.

14. A Pharmaceutical composition comprising a compound of claim 1 and a pharmaceutical acceptable carrier and/or adjuvant.

\* \* \* \* \*